US008058445B2

(12) United States Patent
Tasker

(10) Patent No.: US 8,058,445 B2
(45) Date of Patent: *Nov. 15, 2011

(54) SUBSTITUTED PYRIDINECARBOXAMIDES FOR THE TREATMENT OF CANCER

(75) Inventor: Andrew Tasker, Simi Valley, CA (US)

(73) Assignee: Amgen Inc., Thousand Oaks, CA (US)

( * ) Notice: Subject to any disclaimer, the term of this patent is extended or adjusted under 35 U.S.C. 154(b) by 1437 days.

This patent is subject to a terminal disclaimer.

(21) Appl. No.: 11/234,713

(22) Filed: Sep. 23, 2005

(65) Prior Publication Data
US 2006/0040956 A1 Feb. 23, 2006

Related U.S. Application Data

(62) Division of application No. 10/046,681, filed on Jan. 10, 2002, now Pat. No. 6,995,162.

(60) Provisional application No. 60/323,764, filed on Sep. 19, 2001, provisional application No. 60/261,339, filed on Jan. 12, 2001.

(51) Int. Cl.
C07D 213/00 (2006.01)
(52) U.S. Cl. ........................................ 546/264; 548/490
(58) Field of Classification Search .................. 546/264; 548/490
See application file for complete search history.

(56) References Cited

U.S. PATENT DOCUMENTS

| 3,226,394 | A | 12/1965 | Schipper |
| 3,406,168 | A | 10/1968 | Schmidt |
| 3,822,277 | A | 7/1974 | Dufour |
| 4,321,371 | A | 3/1982 | Parg et al. |
| 4,816,485 | A | 3/1989 | Satzinger et al. |
| 4,857,662 | A | 8/1989 | Satzinger et al. |
| 5,532,358 | A | 7/1996 | Kelly |
| 5,559,135 | A | 9/1996 | Ashton et al. |
| 5,571,912 | A | 11/1996 | Grozinger et al. |
| 5,674,876 | A | 10/1997 | Gilbert et al. |
| 5,770,613 | A | 6/1998 | Gaeta et al. |
| 6,008,234 | A | 12/1999 | Kochanny et al. |
| 6,051,713 | A | 4/2000 | Teng et al. |
| 6,140,351 | A | 10/2000 | Arnaiz et al. |
| 6,156,766 | A | 12/2000 | Arita et al. |
| 6,251,917 | B1 | 6/2001 | Lubisch et al. |
| 6,271,237 | B1 | 8/2001 | Galemmo, Jr. et al. |
| 6,313,122 | B1 | 11/2001 | Beight et al. |
| 6,313,151 | B1 | 11/2001 | Beight et al. |
| 6,372,759 | B1 | 4/2002 | Beight et al. |
| 6,417,200 | B1 | 7/2002 | Beight et al. |
| 6,448,290 | B1 | 9/2002 | Ohuchida et al. |
| 6,562,827 | B1 | 5/2003 | Lubisch et al. |
| 6,593,352 | B2 | 7/2003 | Weichert et al. |
| 6,605,626 | B2 | 8/2003 | Beight et al. |
| 6,610,704 | B1 | 8/2003 | Beight et al. |
| 6,635,657 | B1 | 10/2003 | Beight et al. |
| 6,660,755 | B2 | 12/2003 | Song et al. |
| 6,794,397 | B2 | 9/2004 | Cai et al. |
| 6,878,714 | B2 * | 4/2005 | Askew et al. .................. 514/256 |
| 7,101,868 | B2 | 9/2006 | Elbaum et al. |
| 7,102,009 | B2 | 9/2006 | Patel et al. |
| 7,514,564 | B2 | 4/2009 | Chen et al. |
| 2003/0069250 | A1 | 4/2003 | Zhu et al. |
| 2003/0195192 | A1 | 10/2003 | Haviv et al. |
| 2003/0195195 | A1 | 10/2003 | Haviv et al. |
| 2004/0063775 | A1 | 4/2004 | Momose et al. |
| 2004/0102441 | A1 | 5/2004 | Krueger et al. |
| 2004/0254185 | A1 | 12/2004 | Ernst et al. |
| 2005/0032816 | A1 | 2/2005 | Ernst et al. |
| 2005/0054654 | A1 | 3/2005 | Huth et al. |

FOREIGN PATENT DOCUMENTS

| EP | 0 393 529 A1 | 10/1990 |
| EP | 0 410 148 A1 | 1/1991 |
| EP | 0 429 987 A2 | 6/1991 |
| EP | 0 393 529 B1 | 6/1993 |
| EP | 0 947 500 A1 | 10/1999 |
| EP | 1219609 A1 | 7/2002 |
| FR | 2 168 227 | 8/1973 |
| JP | P2000 256358 A | 9/2000 |
| WO | WO 96/41795 | 12/1996 |
| WO | WO 97/30035 | 8/1997 |
| WO | WO 98/24771 | 6/1998 |
| WO | WO 98/45268 | 10/1998 |
| WO | WO 99/32477 | 7/1999 |
| WO | WO 99/62885 | 12/1999 |
| WO | WO 00/02851 | 1/2000 |
| WO | WO 00/27819 | 5/2000 |
| WO | WO 00/27820 | 5/2000 |

(Continued)

OTHER PUBLICATIONS

Stein, Jay H., Ed. Internal Medicine, Mosby-Year Book, Inc., 1994, 4th ed., 699-727.*
Bertino, Joseph R. and Salmon, Sydney E. Principles of Cancer Therapy, Oncology XIV, 2000, 21st ed., vol. 1, 1060-1074.*
Hackam, et al. JAMA, 296(14), 2006, 1731-1732.*
Jordan, V. C. Nature Reviews: Drug Discovery, 2, 2003, 205-213.*
Konshin et al., "Synthesis and antimicrobial activity of arylamides of N-(4-pyridyl)anthranilc acid." (1981) Chem Abstr. 97:109837.
Singh et al., "Substituted Imidazolines and their CNS Activity" (1992) Ind. J. Het. Chem. 2:129-132.

(Continued)

Primary Examiner — James O Wilson
Assistant Examiner — Douglas M Willis
(74) Attorney, Agent, or Firm — Joseph W. Bulock

(57) ABSTRACT

Selected pyridine carboxamide compounds of Formula XI

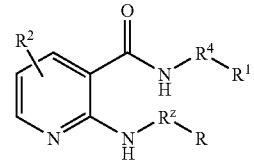

XI are effective for treatment of diseases and other maladies or conditions involving, cancer and the like.

4 Claims, No Drawings

FOREIGN PATENT DOCUMENTS

| WO | WO 00/39111 | 7/2000 |
| --- | --- | --- |
| WO | WO 00/39117 | 7/2000 |
| WO | WO 00/47212 | 8/2000 |
| WO | WO 01/29009 A1 | 4/2001 |
| WO | WO 01/30745 A1 | 5/2001 |
| WO | WO 01/55114 A1 | 8/2001 |
| WO | WO 01/55115 A1 | 8/2001 |
| WO | WO 01/81311 A1 | 11/2001 |
| WO | WO 01/85671 A2 | 11/2001 |
| WO | WO 01/85691 A1 | 11/2001 |
| WO | WO 01/85715 A2 | 11/2001 |
| WO | WO 02/055501 A2 | 7/2002 |
| WO | WO 02/066470 A1 | 8/2002 |
| WO | WO 03/068232 A1 | 8/2003 |
| WO | WO 03/068235 A1 | 8/2003 |

OTHER PUBLICATIONS

Seto et al., "Molecular Self-Assembly through Hydrogen Bonding: Supramolecular Aggregates Based on the Cyanuric Acid•Melamine Lattice." (1993) J. Amer. Chem. Soc. 115:905-916.

Breier et al., "The role of vascular endothelial growth factor in blood vessel formation" (1996) Trends in Cell Biology 6:454-456.

Connell et al., "Patent focus on cancer chemotherapeutics. II Angiogenesis agents: Apr. 2000-Sep. 2000" (2001) Exp. Opin. Ther. Patents 11:77-114.

Bold et al., "New Anilinophthalazines as Potent and Orally Well Absorbed Inhibitors of the VEGF Receptor Tyrosine Kinases Useful as Antagonists of Tumor-Driven Angiogenesis." (2000) J. Med. Chem. 43:2310-2323.

Hennequin et al., "Design and Structure-Activity Relationship of a New Class of Potent VEGF Receptor Tyrosine Kinase Inhibitor." (1999) J. Med. Chem. 42: 5369-5389.

Sun et al., "Design, Synthesis, and Evaluations of substituted 3-[(3- or 4-Carboxyethylpyrrol-2-yl)methylidenyl]indolin-2-ones as Inhibitors of VEGF, FGF, PDGF Receptor Tyrosine Kinases." (1999) J. Med. Chem. 42: 5120-5130.

Proudfoot et al., "Novel Non-nucleoside Inhibitors or HIV-1 Reverse Transcriptase. 3. Dipyrido[2,3-$b$:2',3'-e]diazepinones", J. Med. Chem., 38:1406-1410 (1995).

Smrckova-Voltrova et al., "Structure and Properties of Quaternized 2- and 4-aminonicotinamides", Collect. Czech. Chem. Commun., 50:1009-1015 (1995).

Samvelyan et al., "Discussion of Some New Amino Acid Derivatives of Nicotinic Acid and Their Antisoporific Properties", Farmakologiia I Toksikologiia, 49(3):35-37 (1986).

Hargrave et al., "Novel Non-Nucleoside Inhibitors of HIV-1 Reverse Transcriptase. 1. Tricyclic Pyridobenzo-0 and Dipyridodiazepinones", J. Med. Chem., 34:2231-2241 (1991).

Adams et al., "Discovery and Development of a Non-nucleoside Reverse Transcriptase Inhibitor", Royal Society of Chemistry, Recent Advances in the Chemistry of Anti-infective Agents, 19:282-296 (1993).

Jarzemsky, M. (Mar. 30, 2011). Amgen, Takeda's Motesanib Misses Primary Goal In Late-Stage Study. The Wall Street Journal, http://online.wsj.com/article/BT-CO-20110330-706623.html.

* cited by examiner

SUBSTITUTED PYRIDINECARBOXAMIDES FOR THE TREATMENT OF CANCER

This application is a divisional of U.S. patent application Ser. No. 10/046,681 filed Jan. 10, 2002 now U.S. Pat. No. 6,995,162 which claims benefit of U.S. Provisional Application Nos. 60/261,339, filed Jan. 12, 2001, and 60/323,764 filed Sep. 19, 2001 which are hereby incorporated by reference.

FIELD OF THE INVENTION

This invention is in the field of pharmaceutical agents and specifically relates to compounds, compositions, uses and methods for treating cancer and angiogenesis-related disorders.

BACKGROUND OF THE INVENTION

Protein kinases represent a large family of proteins which play a central role in the regulation of a wide variety of cellular processes, maintaining control over cellular function. A partial list of such kinases includes ab1, Atk, bcr-ab1, Blk, Brk, Btk, c-kit, c-met, c-src, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as Vascular Endothelial Growth Factor"(VEGF; originally termed 'Vascular Permeability Factor", VPF), along with its cellular receptors (see G. Breier et al., Trends in Cell Biology, 6, 454-6 (1996)).

VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor"(PlGF) and VEGF-C.

VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors which grow beyond a diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11, 77-114 (2001).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic target.

Schipper U.S. Pat. No. 3,226,394, issued Dec. 28, 1965, describes anthranilamides as CNS depressants. Japanese patent JP2000256358 describes pyrazole derivatives that block the calcium release-activated calcium channel. EP application 9475000, published 6 Oct. 1999, describes compounds as $PGE_2$ antagonists. PCT publication WO96/41795, published 27 Dec. 1996, describes benzamides as vasopressin antagonists. WO01/29009 describes aminopyridines as KDR inhibitors. WO01/30745 describes anthranilic acids as CGMP phosphodiesterase inhibitors. WO00/02851, published 20 Jan. 2000 describes arylsulfonylamnoaryl amides as guanylate cyclase activators. WO98/45268 describes nicotinamide derivatives as PDE4 inhibitors. WO98/24771 describes benzamides as vasopressin antagonists.

U.S. Pat. No. 5,532,358, issued Jul. 2, 1996, describes the preparation of 2-(cyclopropylamino)-N-(2-methoxy-4-methyl-3-pyridinyl)-3-pyridinecarboxamide as an intermediate for HIV inhibitors. Triazine-substituted amines are described for their aggregating ability (J. Amer. Chem. Soc., 115, 905-16 (1993). Substituted imidazolines were tested for their antidepressant activity in Ind. J. Het. Chem., 2, 129-32 (1992). N-(4-Pyridyl)anthranilic amides were described in Chem Abstr. 97:109837 (1981). PCT publication WO99/32477, published 1 Jul. 1999, describes anthranilamides as anti-coagulants. U.S. Pat. No. 6,140,351 describes anthranilamides as anti-coagulants. PCT publication WO99/62885, published 9 Dec. 1999, describes 1-(4-aminophenyl)pyrazoles as anti-inflammatories. PCT publication WO00/39111, published 6 Jul. 2000, describes amides as factor Xa inhibitors. PCT publication WO00/39117, published 6 Jul. 2000, describes heteroaromatic amides as factor Xa inhibitors. PCT publication WO0/27819, published 18 May 2000, describes anthranilic acid amides as VEGF inhibitors. PCT publication WO00/27820 published 18 May 2000, describes N-aryl anthranilic acid amides as VEGF inhibitors. 7-Chloroquinolinylamines are described in FR2168227 as antiinflammatories. WO01/55114, published 2 Aug. 2001, describes nicotinamides for the treatment of cancer. WO01/55115, published 2 Aug. 2001, describes nicotinamides as inducers of apoptosis. WO01/85715, published 15 Nov. 2001, describes substituted pyridines and pyrimidines as anti-angiogenesis agents. PCT publication WO01/85691 published 15 Nov. 2001, describes anthranilic amides as VEGF inhibitors. PCT publication WO01/85671 published 15 Nov. 2001, describes anthranyl amides as VEGF inhibitors. PCT publication WO01/81311 published 1 Nov. 2001, describes anthranilic amides as VEGF inhibitors. However, compounds of the current invention have not been described as inhibitors of angiogenesis such as for the treatment of cancer.

DESCRIPTION OF THE INVENTION

A class of compounds useful in treating cancer and angiogenesis is defined by Formula I

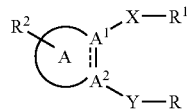

I wherein each of $A^1$ and $A^2$ is independently C, CH or N;
wherein ring A is selected from
  a) 5- or 6-membered partially saturated heterocyclyl,
     preferably dihydropyran, dihydrothienyl, dihydrofuryl, oxo-dihydrofuryl, pyrrolinyl, dihydrothiazolyl, dihydro-oxazolyl, dihydro-isothiazolyl, dihydro-isoxazolyl, imidazolinyl and pyrazolinyl,
  b) 5- or 6-membered heteroaryl,
     preferably
       I) 5-membered heteroaryl selected from thienyl, furanyl, pyrrolyl, thiazolyl, oxazolyl, imidazolyl, pyrazolyl, isoxazolyl, triazolyl and isothiazolyl,
         even more preferably 5-membered heteroaryl selected from

A)

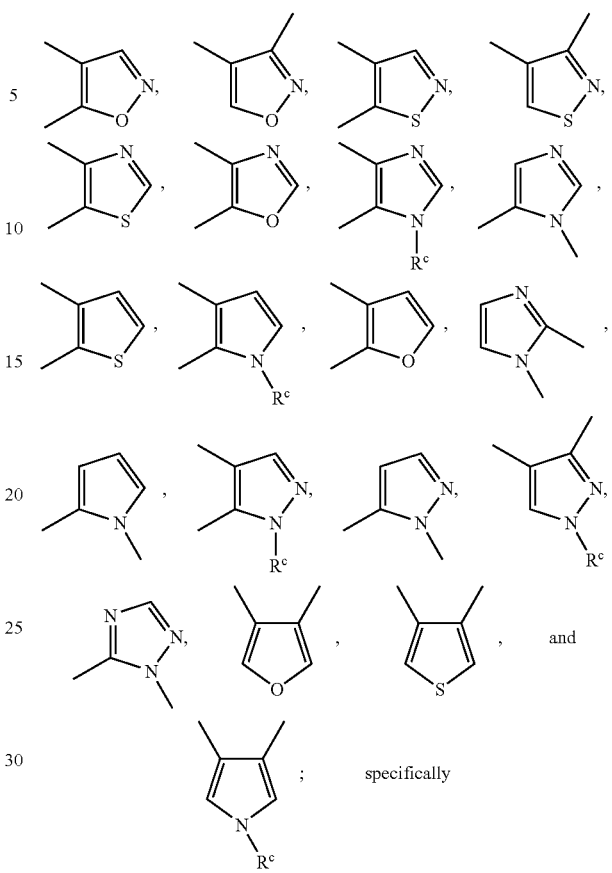

specifically

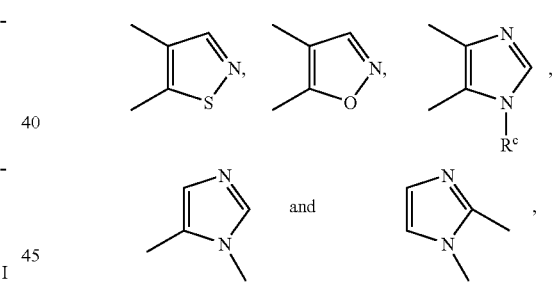

and

B)

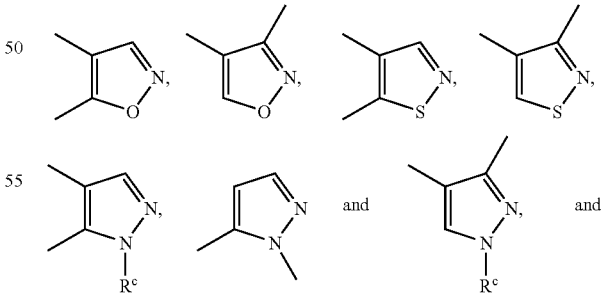

C)

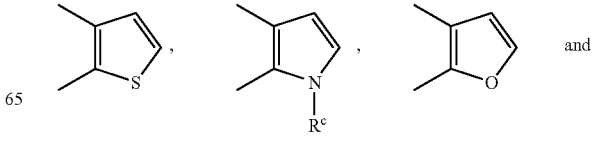

-continued

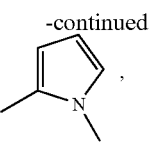, and

II) preferably 6-membered heteroaryl selected from pyridyl, pyrazinyl, pyrimidinyl, pyridazinyl, and triazinyl, even more preferably 6-membered heteroaryl selected from

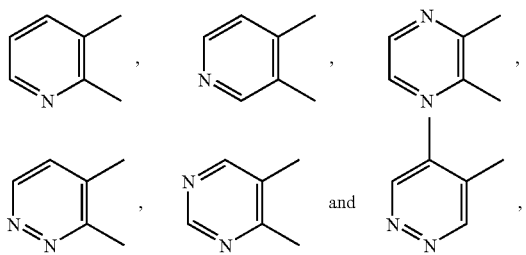

more specifically

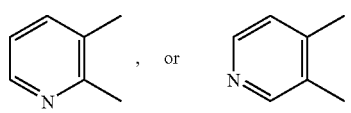, c) 9-, 10- or 11-membered fused partially saturated heterocyclyl
preferably tetrahydroquinolinyl,
d) 9- or 10-membered fused heteroaryl,
preferably
  i) fused 9-membered fused heteroaryl selected from benzothienyl, benzothiazolyl, indolyl, benzimidazolyl, benzoxazolyl, benzofuryl, indazolyl and isoindolyl, and
  ii) fused 10-membered heteroaryl selected from quinolyl, isoquinolyl, naphthpyridinyl, quinoxalinyl and quinazolinyl,
e) naphthyl, and
f) 4-, 5- or 6-membered cycloalkenyl,
  preferably 5-membered cycloalkenyl,
    more preferably cyclopentadienyl or cyclopentenyl;
wherein X is selected from

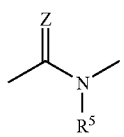 and 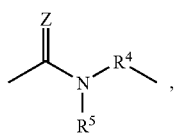, preferably X is selected from

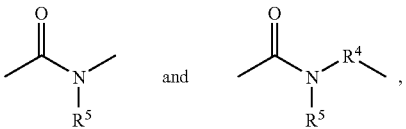

more preferably X is

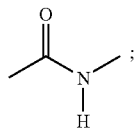;

wherein Z is oxygen or sulfur;
wherein Y is selected from

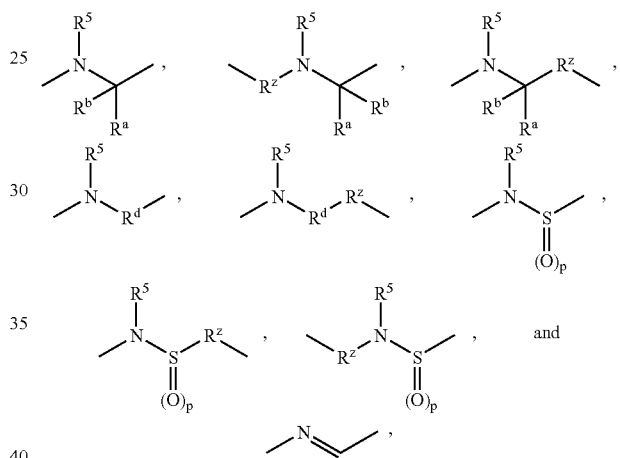

preferably Y is selected from

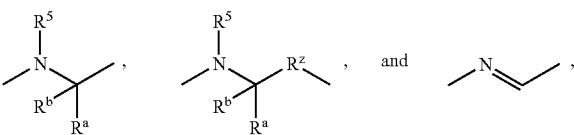

more preferably Y is selected from

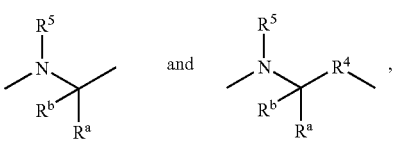

even more preferably Y is —NH—CH$_2$—;
wherein $R^a$ and $R^b$ are independently selected from H, halo, cyano and C$_{1-4}$-alkyl substituted with $R^2$, or wherein $R^a$ and $R^b$ together form C$_3$-C$_4$ cycloalkyl,
preferably H, halo, cyano and C$_{1-2}$-alkyl substituted with $R^2$, or wherein $R^a$ and $R^b$ together form C$_3$-C$_4$ cycloalkyl, more preferably H, halo and C$_{1-2}$-alkyl, even more preferably H;
wherein $R^z$ is selected from $C_1$-$C_4$ alkylenyl, where one of the $CH_2$ groups may be substituted with an oxygen atom or an —NH—,
  preferably $C_1$-$C_2$ alkylenyl, where one of the $CH_2$ groups may be substituted with an oxygen atom or an —NH—
  more preferably $C_1$-$C_2$ alkylenyl;
wherein $R^d$ is cycloalkyl,
  preferably $C_3$-$C_6$ cycloalkyl;
wherein R is selected from
  a) substituted or unsubstituted 5-6 membered heterocyclyl,
    preferably substituted or unsubstituted 5-6 membered heteroaryl comprising one or more nitrogen atoms,
      more preferably 4-pyrazolyl, triazolyl, 4-pyridyl, 4-pyrimidinyl, 5-pyrimidinyl, 6-pyrimidinyl, 4-pyridazinyl, or 6-pyridazinyl,
        even more preferably 4-pyridyl, 4-pyrimidinyl and 4-pyridazinyl,
        even more preferably 4-pyridyl, and
  b) substituted or unsubstituted fused 9-, 10- or 11-membered heterocyclyl,
    preferably substituted or unsubstituted 9-10 membered fused heteroaryl comprising one or more nitrogen atoms,
      more preferably indazolyl, quinolinyl, isoquinolinyl, or quinazolinyl,
        even more preferably indazolyl, 4-quinolyl, 5-quinolyl, 6-quinolyl, 4-isoquinolyl, 5-isoquinolyl, and 6-isoquinolyl,
      wherein substituted R is substituted with one or more substituents independently selected from halo, —$OR^3$, —$SR^3$, —$SO_2R^3$, —$CO_2R^3$, —$CONR^3R^3$, —$COR^3$, —$NR^3R^3$, —$SO_2NR^3R^3$, —$NR^3C(O)OR^3$, —$NR^3C(O)R^3$, cycloalkyl, optionally substituted 5-6 membered heterocyclyl, optionally substituted phenyl, lower alkyl substituted with $R^2$, cyano, nitro, lower alkenyl and lower alkynyl;
        preferably halo, —$OR^3$, —$SR^3$, —$CO_2R^3$, —$CONR^3R^3$, —$COR^3$, —$NR^3R^3$, —$SO_2NR^3R^3$, —$NR^3C(O)OR^3$—$NR^3C(O)R^3$, —$NR^3C(O)NR^3R^3$, cycloalkyl, optionally substituted 5-6 membered heterocyclyl, optionally substituted phenyl, $C_{1-2}$-alkyl, cyano, $C_{1-2}$-hydroxyalkyl, nitro and $C_{1-2}$-haloalkyl;
wherein $R^1$ is selected from
  a) substituted or unsubstituted 6-10 membered aryl,
    preferably phenyl, naphthyl, indenyl, or tetrahydronaphthyl,
      more preferably phenyl,
  b) substituted or unsubstituted 5-6 membered heterocyclyl,
    preferably 5-6 membered heteroaryl,
      more preferably thienyl, pyridyl, pyrimidinyl, pyridazinyl, pyrazolyl, imidazolyl, oxazolyl, thiazolyl, thiadiazolyl, furyl, or pyrrolyl,
  c) substituted or unsubstituted 9-10 membered fused heterocyclyl,
    preferably 9-10 membered fused heteroaryl,
      more preferably indazolyl, indolyl, 2,1,3-benzothiadiazolyl, isoquinolyl, quinolyl, tetrahydroquinolyl, benzodioxanyl, or quinazolinyl,
  d) cycloalkyl, and
  e) cycloalkenyl
    wherein substituted $R^1$ is substituted with one or more substituents independently selected from halo, —$OR^3$, —$SR^3$, —$CO_2R^3$, —$CONR^3R^3$, —$COR^3$, —$NR^3R^3$, —$NH(C_1$-$C_4$ alkylenyl$R^{14}$), —$SO_2R^3$, —$SO_2NR^3R^3$, —$NR^3C(O)OR^3$, —$NR^3C(O)R^3$, optionally substituted cycloalkyl, optionally substituted 5-6 membered heterocyclyl, optionally substituted phenyl, lower alkyl substituted with $R^2$, cyano, nitro, lower alkenyl and lower alkynyl,
      preferably $R^1$ is unsubstituted or substituted with one or more substituents independently selected from halo, —$OR^3$, —$SR^3$, —$SO_2R^3$, —$CO_2R^3$, —$CONR^3R^3$, —$COR^3$, —$NR^3R^3$, —$NH(C_1$-$C_2$ alkylenyl$R^3$), —$(C_1$-$C_2$ alkylenyl)$NR^3R^3$, —$SO_2NR^3R^3$, —$NR^3C(O)OR^3$, —$NR^3C(O)R^3$, optionally substituted cycloalkyl, optionally substituted 5-6 membered heterocyclyl, optionally substituted phenyl, optionally substituted phenyl-$C_{1-2}$-alkylenyl, optionally substituted 5-6 membered heterocyclyl-$C_1$-$C_2$-alkylenyl, $C_{1-2}$-alkyl, cyano, $C_{1-2}$-hydroxyalkyl, nitro and $C_{1-2}$-haloalkyl,
        more preferably $R^1$ is unsubstituted or substituted with one or more substituents selected from chloro, fluoro, bromo, methoxy, phenyloxy, benzyl, methylthio, methyl, ethyl, trifluoromethyl, difluoromethyl, pentafluoroethyl, hydroxymethyl, cyano, carboxy, aminocarbonyl, methylcarbonyl, amino, methylamino, cyclopropyl, cyclohexyl, piperidinyl, morpholinyl, N-methylpiperazinyl, N-ethylpiperazinyl, morpholinylmethyl, methylpiperdinylmethyl, methylpiperazinylmethyl, methylaminothiocarbonyl, N-methylamino-methylenyl, optionally substituted phenyl, N,N-diethylamino, or N,N-dimethylamino;
wherein $R^2$ is one or more substituents independently selected from H, halo, —$OR^3$, oxo, —$SR^3$, —$CO_2R^3$, —$COR^3$, —$CONR^3R^3$, —$NR^3R^3$, —$SO_2NR^3R^3$—$NR^3C(O)OR^3$, —$NR^3C(O)R^3$, cycloalkyl, optionally substituted phenylalkylenyl, optionally substituted 5-6 membered heterocyclyl, optionally substituted heteroarylalkylenyl, optionally substituted phenyl, lower alkyl, cyano, lower hydroxyalkyl, lower carboxyalkyl, nitro, lower alkenyl, lower alkynyl, lower aminoalkyl, lower alkylaminoalkyl and lower haloalkyl,
  preferably $R^2$ is one or more substituents independently selected from H, halo, —$OR^3$, oxo, —$SR^3$, —$CO_2R^3$, —$CONR^3R^3$—$COR^3$, —$NR^3R^3$, —$SO_2NR^3R^3$, —$NR^3C(O)OR^3$, —$NR^3C(O)R^3$, cycloalkyl, optionally substituted 5-6 membered heterocyclyl, optionally substituted phenyl, $C_{1-2}$-alkyl, cyano, $C_{1-2}$-hydroxyalkyl, $C_{1-3}$-carboxyalkyl, nitro, $C_{2-3}$-alkenyl, $C_{2-3}$-alkynyl and $C_{1-2}$-haloalkyl;
wherein $R^3$ is selected from H, lower alkyl, phenyl, 5-6 membered heterocyclyl, $C_3$-$C_6$ cycloalkyl, and lower haloalkyl,
  preferably H, $C_{1-2}$-alkyl, phenyl, $C_3$-$C_6$ cycloalkyl, and $C_{1-2}$-haloalkyl,
    more preferably H, methyl, phenyl, cyclopropyl, cyclohexyl, and trifluoromethyl;
wherein $R^4$ is independently selected from $C_{2-4}$-alkylenyl, $C_{2-4}$-alkenylenyl and $C_{2-4}$-alkynylenyl, where one of the $CH_2$ groups may be substituted with an oxygen atom or an —NH—,
  preferably $C_{2-3}$-alkylenyl where one of the $CH_2$ groups may be substituted with an oxygen atom or an —NH—,
    more preferably $C_2$-$C_3$ alkylenyl;
wherein $R^5$ is selected from H, lower alkyl, phenyl and lower aralkyl,
  preferably H, methyl or ethyl;
wherein $R^6$ is selected from H or $C_{1-6}$-alkyl,
  preferably H or $C_{1-2}$ alkyl; and wherein $R^c$ is selected from H, methyl and optionally substituted phenyl;
wherein $R^{14}$ is selected from H, phenyl, 5-6 membered heterocyclyl and $C_3$-$C_6$ cycloalkyl;
wherein p is 0 to 2, preferably p is 2;
and pharmaceutically acceptable salts thereof;
provided A is not naphthyl when X is —C(O)NH— and when $R^1$ is phenyl when Y is —NHCH$_2$— and when R is 4-pyridyl; further provided A is not pyridyl when X is —C(O)NH— and when $R^1$ is 4-[3,5-bis(trifluoromethyl)-1H-pyrazol-1-yl]phenyl when Y is —N(CH$_3$)— and when R is 4-methylpiperidinyl; further provided A is not pyridyl when X is —C(O)NH— and when Y is —NHCH$_2$— and when R is 4-pyridylpiperidin-4-yl, 1-tertbutylpiperidin-4-yl, 1-isopropylpiperidin-4-yl or 1-cycloalkylpiperidin-4-yl; further provided A is not pyridyl when X is —C(O)NH— and when $R^1$ is 4-[3-(3-pyridyl)-5-(trifluoromethyl)-1H-pyrazol-1-yl]phenyl when Y is —NHCH$_2$— and when R is 4-pyridyl; and further provided R is not unsubstituted 2-thienyl, 2-pyridyl or 3-pyridyl.

The invention also relates to compounds of Formula II

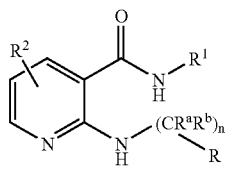

II wherein $R^a$ and $R^b$ are independently selected from H, halo, $C_{1-4}$-alkyl and —N(R$^6$)$_2$,
  preferably H;
wherein n is 0-2;
  preferably 1-2;
wherein R is selected from
  a) unsubstituted or substituted 5- or 6-membered nitrogen-containing heteroaryl, and
  b) unsubstituted or substituted 9- or 10-membered fused nitrogen-containing heteroaryl,
    preferably 4-pyridyl, pyrimidinyl, triazolyl, pyridazinyl, indolyl, isoindolyl, indazolyl, quinolyl, isoquinolyl, naphthyridinyl or quinozalinyl,
    where R is substituted with one or more substituents selected from halo, amino, hydroxy, $C_{1-6}$-alkyl, $C_{1-6}$-haloalkyl and $C_{1-6}$-alkoxy,
      preferably substituted with one or more substituents selected from chloro, fluoro, amino, hydroxy, methyl, ethyl, propyl, trifluoromethyl, methoxy and ethoxy;
wherein $R^1$ is selected from unsubstituted or substituted aryl, 5-6-membered heteroaryl and 9-10 membered fused heteroaryl,
  preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
    wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5-6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy,
      preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;
wherein $R^2$ is one or more substituents independently selected from
  H,
  halo,
  $C_{1-6}$-alkyl,
  $C_{1-6}$-haloalkyl,
  $C_{1-6}$-alkoxy,
  $C_{1-6}$-haloalkoxy,
  $C_{1-6}$-carboxyalkyl,
  unsubstituted or substituted aryl and
  unsubstituted or substituted 5-6 membered heteroaryl;
preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected from thienyl, furanyl, pyridyl, imidazolyl, and pyrazolyl; and
wherein $R^6$ is H or $C_{1-2}$-alkyl;
and pharmaceutically acceptable isomers and salts thereof.

The invention also relates to compounds of Formula III

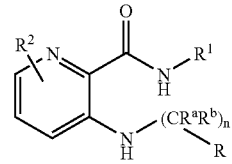

III wherein $R^a$ and $R^b$ are independently selected from H, halo, $C_{1-4}$-alkyl and —N(R$^6$)$_2$,
  preferably H;
wherein n is 0-2;
  preferably 1-2;
wherein R is selected from
  a) unsubstituted or substituted 5- or 6-membered nitrogen-containing heteroaryl, and
  b) unsubstituted or substituted 9- or 10-membered fused nitrogen-containing heteroaryl,
    preferably 4-pyridyl, pyrimidinyl, pyridazinyl, indolyl, isoindolyl, indazolyl, quinolyl, isoquinolyl, naphthyridinyl or quinozalinyl,
    where R is substituted with one or more substituents selected from halo, amino, hydroxy, $C_{1-6}$-alkyl, $C_{1-6}$-haloalkyl and $C_{1-6}$-alkoxy, preferably substituted with one or more
      substituents selected from chloro, fluoro, amino, hydroxy, methyl, ethyl, propyl, trifluoromethyl, methoxy and ethoxy;
wherein $R^1$ is selected from unsubstituted or substituted aryl, 5-6-membered heteroaryl and 9-10 membered fused heteroaryl,
  preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl, wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5-6 membered heterocyclyl-$C_{1-2}$-alkylenyl, optionally substituted heteroaryl, optionally substituted heteroaryloxy, $C_{1-6}$-haloalkyl, and $C_{1-6}$-alkoxy, preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;

wherein $R^2$ is one or more substituents independently selected from
H,
halo,
$C_{1-6}$-alkyl,
$C_{1-6}$-haloalkyl,
$C_{1-6}$-alkoxy,
$C_{1-6}$-haloalkoxy,
$C_{1-6}$-carboxyalkyl,
unsubstituted or substituted aryl and
unsubstituted or substituted 5-6 membered heteroaryl;
preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected from thienyl, furanyl, pyridyl, imidazolyl, and pyrazolyl; and wherein $R^6$ is H or $C_{1-2}$-alkyl;

and pharmaceutically acceptable isomers and salts thereof.

The invention also relates to compounds of Formula IV

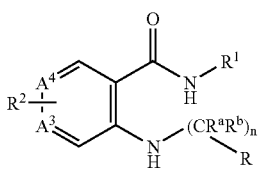

IV wherein $A^3$ is selected from $CR^2$ and N;
wherein $A^4$ is selected from $CR^2$ and N; provided one of $A^3$ and $A^4$ is not $CR^2$;
wherein $R^a$ and $R^b$ are independently selected from H, halo, $C_{1-4}$-alkyl and $-N(R^6)_2$,
preferably H;
wherein n is 0-2;
preferably 1-2;
wherein R is selected from
a) unsubstituted or substituted 5- or 6-membered nitrogen-containing heteroaryl, and
b) unsubstituted or substituted 9- or 10-membered fused nitrogen-containing heteroaryl,
preferably 4-pyridyl, pyrimidinyl, pyridazinyl, indolyl, isoindolyl, indazolyl, quinolyl, isoquinolyl, naphthyridinyl or quinozalinyl,
where R is substituted with one or more substituents selected from halo, amino, hydroxy, $C_{1-6}$-alkyl, $C_{1-6}$-haloalkyl and $C_{1-6}$-alkoxy, preferably substituted with one or more substituents selected from chloro, fluoro, amino, hydroxy, methyl, ethyl, propyl, trifluoromethyl, methoxy and ethoxy;

wherein $R^1$ is selected from unsubstituted or substituted aryl, 5-6-membered heteroaryl and 9-10 membered fused heteroaryl, preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl, wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5-6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy, preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;

wherein $R^2$ is one or more substituents independently selected from
H,
halo,
$C_{1-6}$-alkyl,
$C_{1-6}$-haloalkyl,
$C_{1-6}$-alkoxy,
$C_{1-6}$-haloalkoxy,
$C_{1-6}$-carboxyalkyl,
unsubstituted or substituted aryl and
unsubstituted or substituted 5-6 membered heteroaryl;
preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected
from thienyl, furanyl, pyridyl, imidazolyl, and pyrazolyl; and wherein $R^6$ is H or $C_{1-2}$-alkyl;
and pharmaceutically acceptable isomers and salts thereof.

The invention also relates to compounds of Formula V

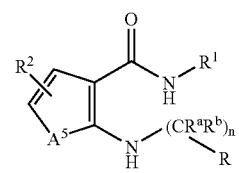

V wherein $A^5$ is selected from S, O and $NR^6$;
wherein $R^a$ and $R^b$ are independently selected from H, halo, $C_{1-4}$-alkyl and $-N(R^6)_2$,
preferably H;
wherein n is 0-2;
preferably 1-2;
wherein R is selected from
a) unsubstituted or substituted 5- or 6-membered nitrogen-containing heteroaryl, and b) unsubstituted or substituted 9- or 10-membered fused nitrogen-containing heteroaryl,
preferably 4-pyridyl, pyrimidinyl, pyridazinyl, indolyl, isoindolyl, indazolyl, quinolyl, isoquinolyl, naphthyridinyl or quinozalinyl,
where R is substituted with one or more substituents selected from halo, amino, hydroxy, $C_{1-6}$-alkyl, $C_{1-6}$-haloalkyl and $C_{1-6}$-alkoxy,
preferably substituted with one or more substituents selected from chloro, fluoro, amino, hydroxy, methyl, ethyl, propyl, trifluoromethyl, methoxy and ethoxy;
wherein $R^1$ is selected from unsubstituted or substituted aryl, 5-6-membered heteroaryl and 9-10 membered fused heteroaryl,
preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5-6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy,
preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;
wherein $R^2$ is one or more substituents independently selected from
H,
halo,
$C_{1-6}$-alkyl,
$C_{1-6}$-haloalkyl,
$C_{1-6}$-alkoxy,
$C_{1-6}$-haloalkoxy,
$C_{1-6}$-carboxyalkyl,
unsubstituted or substituted aryl and
unsubstituted or substituted 5-6 membered heteroaryl;
preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected from thienyl, furanyl, pyridyl, imidazolyl, and pyrazolyl; and
wherein $R^6$ is H or $C_{1-2}$-alkyl;
and pharmaceutically acceptable isomers and salts thereof.

The invention also relates to compounds of Formula VI

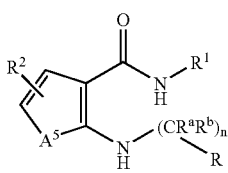

VI wherein $A^5$ is selected from S, O and $NR^6$;
wherein $R^a$ and $R^b$ are independently selected from H, halo, $C_{1-4}$-alkyl and —$N(R^6)_2$,
preferably H;

wherein n is 0-2;
preferably 1-2;
wherein R is selected from
a) unsubstituted or substituted 5- or 6-membered nitrogen-containing heteroaryl, and
b) unsubstituted or substituted 9- or 10-membered fused nitrogen-containing heteroaryl,
preferably 4-pyridyl, pyrimidinyl, pyridazinyl, indolyl, isoindolyl, indazolyl, quinolyl, isoquinolyl, naphthyridinyl or quinozalinyl,
where R is substituted with one or more substituents selected from halo, amino, hydroxy, $C_{1-6}$-alkyl, $C_{1-6}$-haloalkyl and $C_{1-6}$-alkoxy,
preferably substituted with one or more substituents selected from chloro, fluoro, amino, hydroxy, methyl, ethyl, propyl, trifluoromethyl, methoxy and ethoxy;
wherein $R^1$ is selected from unsubstituted or substituted aryl, 5-6-membered heteroaryl and 9-10 membered fused heteroaryl,
preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5-6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy,
preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;
wherein $R^2$ is one or more substituents independently selected from
H,
halo,
$C_{1-6}$-alkyl,
$C_{1-6}$-haloalkyl,
$C_{1-6}$-alkoxy,
$C_{1-6}$-haloalkoxy,
$C_{1-6}$-carboxyalkyl,
unsubstituted or substituted aryl and
unsubstituted or substituted 5-6 membered heteroaryl;
preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected
from thienyl, furanyl, pyridyl, imidazolyl, and pyrazolyl; and
wherein $R^6$ is H or $C_{1-2}$-alkyl;
and pharmaceutically acceptable isomers and salts thereof.

The invention also relates to compounds of Formula VII

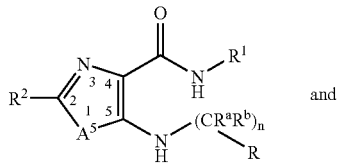

VII

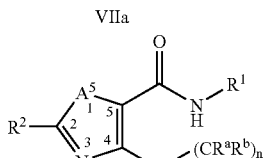

VIIa

VIIb wherein $A^5$ is selected from S, O and $NR^6$;
wherein $R^a$ and $R^b$ are independently selected from H, halo, $C_{1-4}$-alkyl and $—N(R^6)_2$,
  preferably H;
wherein n is 0-2;
  preferably 1-2;
wherein R is selected from
  a) unsubstituted or substituted 5- or 6-membered nitrogen-containing heteroaryl, and
  b) unsubstituted or substituted 9- or 10-membered fused nitrogen-containing heteroaryl,
    preferably 4-pyridyl, pyrimidinyl, pyridazinyl, indolyl, isoindolyl, indazolyl, quinolyl, isoquinolyl, naphthyridinyl or quinozalinyl,
    where R is substituted with one or more substituents selected from halo, amino, hydroxy, $C_{1-6}$-alkyl, $C_{1-6}$-haloalkyl and $C_{1-6}$-alkoxy,
      preferably substituted with one or more substituents selected from chloro, fluoro, amino, hydroxy, methyl, ethyl, propyl, trifluoromethyl, methoxy and ethoxy;
wherein $R^1$ is selected from unsubstituted or substituted aryl, 5-6-membered heteroaryl and 9-10 membered fused heteroaryl,
  preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
    wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5-6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy,
      preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;
wherein $R^2$ is one or more substituents independently selected from
H,
halo,
$C_{1-6}$-alkyl,
$C_{1-6}$-haloalkyl,
$C_{1-6}$-alkoxy,
$C_{1-6}$-haloalkoxy,
$C_{1-6}$-carboxyalkyl,
unsubstituted or substituted aryl and
unsubstituted or substituted 5-6 membered heteroaryl;
preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected from thienyl, furanyl, pyridyl, imidazolyl, and pyrazolyl; and
wherein $R^6$ is H or $C_{1-2}$-alkyl;
and pharmaceutically acceptable isomers and salts thereof.

The invention also relates to compounds of Formula VIII

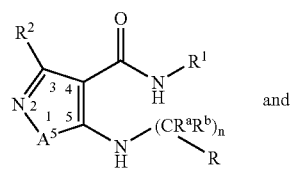

VIIIa

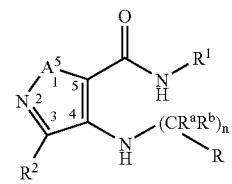

VIIIb wherein $A^5$ is selected from S, O and $NR^6$;
wherein $R^a$ and $R^b$ are independently selected from H, halo, $C_{1-4}$-alkyl and $—N(R^6)_2$,
  preferably H;
wherein n is 0-2;
  preferably 1-2;
wherein R is selected from
  a) unsubstituted or substituted 5- or 6-membered nitrogen-containing heteroaryl, and
  b) unsubstituted or substituted 9- or 10-membered fused nitrogen-containing heteroaryl,
    preferably 4-pyridyl, pyrimidinyl, pyridazinyl, indolyl, isoindolyl, indazolyl, quinolyl, isoquinolyl, naphthyridinyl or quinozalinyl,
    where R is substituted with one or more substituents selected from halo, amino, hydroxy, $C_{1-6}$-alkyl, $C_{1-6}$-haloalkyl and $C_{1-6}$-alkoxy,
      preferably substituted with one or more substituents selected from chloro, fluoro, amino, hydroxy, methyl, ethyl, propyl, trifluoromethyl, methoxy and ethoxy;
wherein $R^1$ is selected from unsubstituted or substituted aryl, 5-6-membered heteroaryl and 9-10 membered fused heteroaryl,
  preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
    wherein $R^1$ is substituted with one or more substituents selected from halo, $C_{1-6}$-alkyl, optionally substituted $C_{3-6}$-cycloalkyl, optionally substituted phenyl, $C_{1-6}$- haloalkoxy, optionally substituted phenyloxy, benzyl, optionally substituted 5-6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy, preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;

wherein $R^2$ is one or more substituents independently selected from
H,
halo,
$C_{1-6}$-alkyl,
$C_{1-6}$-haloalkyl,
$C_{1-6}$-alkoxy,
$C_{1-6}$-haloalkoxy,
$C_{1-6}$-carboxyalkyl,
unsubstituted or substituted aryl and
unsubstituted or substituted 5-6 membered heteroaryl;
preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected from thienyl, furanyl, pyridyl, imidazolyl, and pyrazolyl; and wherein $R^6$ is H or $C_{1-2}$-alkyl;
and pharmaceutically acceptable isomers and salts thereof.

The invention also relates to compounds of Formula IX

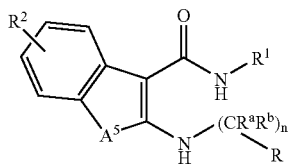

wherein $A^5$ is selected from S, O and $NR^6$;
wherein $R^a$ and $R^b$ are independently selected from H, halo, $C_{1-4}$-alkyl and $-N(R^6)_2$,
preferably H;
wherein n is 0-2;
preferably 1-2;
wherein R is selected from
a) unsubstituted or substituted 5- or 6-membered nitrogen-containing heteroaryl, and
b) unsubstituted or substituted 9- or 10-membered fused nitrogen-containing heteroaryl,
preferably 4-pyridyl, pyrimidinyl, pyridazinyl, indolyl, isoindolyl, indazolyl, quinolyl, isoquinolyl, naphthyridinyl or quinozalinyl,
where R is substituted with one or more substituents selected from halo, amino, hydroxy, $C_{1-6}$-alkyl, $C_{1-6}$-haloalkyl and $C_{1-6}$-alkoxy,
preferably substituted with one or more substituents selected from chloro, fluoro, amino, hydroxy, methyl, ethyl, propyl, trifluoromethyl, methoxy and ethoxy;

wherein $R^1$ is selected from unsubstituted or substituted aryl, 5-6-membered heteroaryl and 9-10 membered fused heteroaryl,
preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl, wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5-6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy, preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;

wherein $R^2$ is one or more substituents independently selected from
H,
halo,
$C_{1-6}$-alkyl,
$C_{1-6}$-haloalkyl,
$C_{1-6}$-alkoxy,
$C_{1-6}$-haloalkoxy,
$C_{1-6}$-carboxyalkyl,
unsubstituted or substituted aryl and
unsubstituted or substituted 5-6 membered heteroaryl;
preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected
from thienyl, furanyl, pyridyl, imidazolyl, and pyrazolyl; and wherein $R^6$ is H or $C_{1-2}$-alkyl;
and pharmaceutically acceptable isomers and salts thereof.

The invention also relates to compounds of Formula X

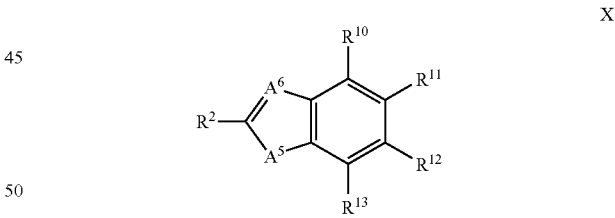

wherein $A^5$ is selected from S, O and $NR^6$;
wherein $A^6$ is selected from N and $CR^2$;
wherein $R^a$ and $R^b$ are independently selected from H, halo, $C_{1-4}$-alkyl and $-N(R^6)_2$,
preferably H;
wherein n is 0-2;
preferably 1-2;
wherein R is selected from
a) unsubstituted or substituted 5- or 6-membered nitrogen-containing heteroaryl, and
b) unsubstituted or substituted 9- or 10-membered fused nitrogen-containing heteroaryl,
preferably 4-pyridyl, pyrimidinyl, pyridazinyl, indolyl, isoindolyl, indazolyl, quinolyl, isoquinolyl, naphthyridinyl or quinozalinyl, where R is substituted with one or more substituents selected from halo, amino, hydroxy, C$_{1-6}$-alkyl, C$_{1-6}$-haloalkyl and C$_{1-6}$-alkoxy,
preferably substituted with one or more substituents selected from chloro, fluoro, amino, hydroxy, methyl, ethyl, propyl, trifluoromethyl, methoxy and ethoxy;
wherein R$^1$ is selected from unsubstituted or substituted aryl, 5-6-membered heteroaryl and 9-10 membered fused heteroaryl,
preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
wherein R$^1$ is substituted with one or more substituents selected from halo, C$_{1-6}$-alkyl, optionally substituted C$_{3-6}$-cycloalkyl, optionally substituted phenyl, C$_{1-6}$-haloalkoxy, optionally substituted phenyloxy, benzyl, optionally substituted 5-6 membered heterocyclyl-C$_{1-2}$-alkylenyl, optionally substituted heteroaryl, optionally substituted heteroaryloxy, C$_{1-6}$-haloalkyl, and C$_{1-6}$-alkoxy,
preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;
wherein R$^2$ is one or more substituents independently selected from
H,
halo,
C$_{1-6}$-alkyl,
C$_{1-6}$-haloalkyl,
C$_{1-6}$-alkoxy,
C$_{1-6}$-haloalkoxy,
C$_{1-6}$-carboxyalkyl,
unsubstituted or substituted aryl and
unsubstituted or substituted 5-6 membered heteroaryl;
preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected
from thienyl, furanyl, pyridyl, imidazolyl, and pyrazolyl;
wherein

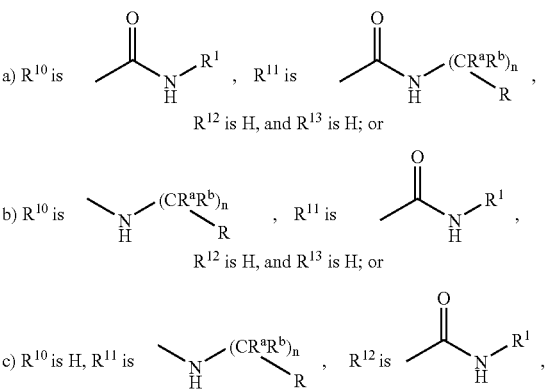

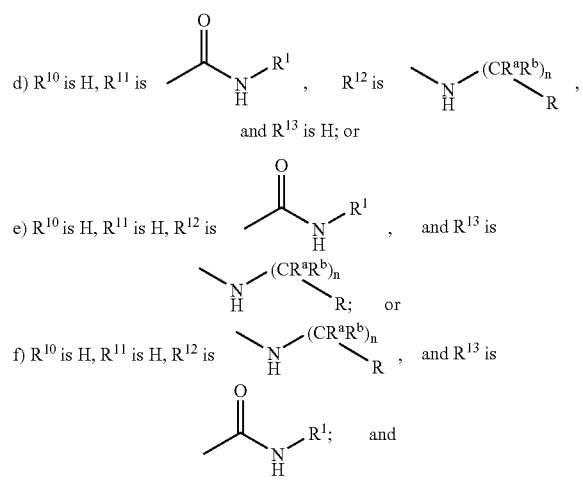

wherein R$^6$ is H or C$_{1-2}$-alkyl;
and pharmaceutically acceptable isomers and salts thereof.
The invention also relates to compounds of Formula II'

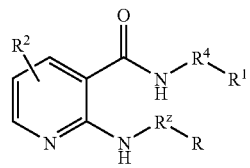

II' wherein R is selected from
a) unsubstituted or substituted 5- or 6-membered nitrogen-containing heteroaryl,
preferably 4-pyridyl, 3-pyridyl, 2-pyridyl, pyrimidinyl, triazolyl, and pyridazinyl,
more preferably 4-pyridyl, and
b) unsubstituted or substituted 9- or 10-membered fused heterocyclyl
preferably indolyl, isoindolyl, indazolyl, quinolyl, isoquinolyl, benzotriazolyl, 2,3-dihydrobenzofuryl, 2-oxo-1,2-dihydroquinol-7-yl, naphthyridinyl and quinozalinyl,
where substituted R is substituted with one or more substituents selected from halo, amino, hydroxy, oxo, C$_{1-6}$-alkyl, C$_{1-6}$-haloalkyl, C$_{1-6}$-alkoxy, optionally substituted heterocyclyl-C$_{1-6}$-alkoxy, optionally substituted heterocyclyl-C$_{1-6}$-alkylamino, optionally substituted heterocyclyl-C$_{1-6}$-alkyl, C$_{1-6}$-alkylamino-C$_{2-4}$-alkynyl, C$_{1-6}$-alkylamino-C$_{1-6}$-alkoxy, C$_{1-6}$-alkylamino-C$_{1-6}$-alkoxy-C$_{1-6}$-alkoxy, and optionally substituted heterocyclyl-C$_{2-4}$-alkynyl,
preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;
wherein R$^1$ is selected from unsubstituted or substituted aryl, preferably phenyl, tetrahydronaphthyl, indanyl, indenyl, and naphthyl,
cycloalkyl, preferably cyclohexyl,
5-6 membered heteroaryl, preferably isoxazolyl, pyrazolyl, thiazolyl, thiadiazolyl, thienyl, pyridyl, pyrimidinyl, and pyridazinyl, and 9-10 membered bicyclic and 13-14 membered tricyclic heterocyclyl, preferably 1,2-dihydroquinolyl, 1,2,3,4-tetrahydro-isoquinolyl, isoquinolyl, quinolyl, indolyl, isoindolyl, 2,3-dihydro-1H-indolyl, naphthyridinyl, quinozalinyl, benzo[d]isothiazolyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3-benzothiadiazolyl, benzodioxanyl, benzothienyl, benzofuryl, dihydro-benzimidazolyl, benzimidazolyl, benzoxazolyl and benzthiazolyl;

wherein substituted $R^1$ is substituted with one or more substituents selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted 4-6 membered heterocyclyl-$C_1$-$C_4$-alkylenyl, optionally substituted 4-6 membered heterocyclyl-$C_2$-$C_4$-alkenylenyl, optionally substituted 4-6 membered heterocyclyl, optionally substituted phenyloxy, optionally substituted 4-6 membered heterocyclyloxy, optionally substituted 4-6 membered heterocyclyl-$C_{1-4}$-alkyloxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-$C_{1-4}$-alkylcarbonyl, $C_{1-2}$-haloalkyl, $C_{1-4}$-aminoalkyl, nitro, amino, —NHC(O)NH$_2$, alkylcarbonylamino, hydroxy, oxo, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

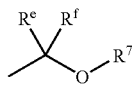

and $C_{1-4}$-alkoxy, preferably bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylcarbonyl, Boc, piperidin-1-ylmethylcarbonyl, 4-methylpiperazin-1-ylcarbonylethyl, methoxycarbonyl, aminomethylcarbonyl, dimethylaminomethylcarbonyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperdin-4-ylmethoxy, piperdin-4-ylmethoxy, 1-methylpiperdin-4-yloxy, isopropoxy, methoxy and ethoxy;

wherein $R^2$ is one or more substituents independently selected from

H,
halo,
hydroxy,
amino,
$C_{1-6}$-alkyl,
$C_{1-6}$-haloalkyl,
$C_{1-6}$-alkoxy,
$C_{1-2}$-alkylamino,
aminosulfonyl,
$C_{3-6}$-cycloalkyl,
cyano,
$C_{1-2}$-hydroxyalkyl,
nitro,
$C_{2-3}$-alkenyl,
$C_{2-3}$-alkynyl,
$C_{1-6}$-haloalkoxy,
$C_{1-6}$-carboxyalkyl,
5-6-membered heterocyclyl-$C_{1-6}$-alkylamino,
unsubstituted or substituted phenyl and
unsubstituted or substituted 5-6 membered heterocyclyl;
preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from thienyl, furanyl, pyridyl, imidazolyl, and pyrazolyl;

wherein $R^4$ is selected from a direct bond, $C_{1-4}$-alkyl, and

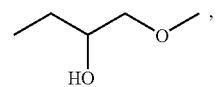

preferably a direct bond, ethyl, butyl, and

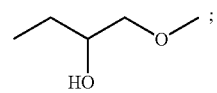

wherein $R^z$ is selected from $C_{1-2}$-alkyl, $C_{2-6}$-branched alkyl, $C_{2-4}$-branched haloalkyl, amino-$C_{1-4}$-alkyl and $C_{1-2}$-alkylamino-$C_{1-2}$-alkyl, preferably methylenyl, ethylenyl,

and aminoethylenyl;
wherein $R^e$ and $R^f$ are independently selected from H and $C_{1-2}$-haloalkyl,
preferably trifluoromethyl; and
wherein $R^7$ is selected from H, $C_{1-3}$-alkyl, optionally substituted phenyl, optionally substituted phenyl-$C_{1-3}$-alkyl, optionally substituted 4-6 membered heterocyclyl, optionally substituted 4-6 membered heterocyclyl-$C_1$-$C_3$-alkyl, $C_{1-3}$-alkylamino-$C_{1-3}$-alkyl, $C_{1-3}$-alkoxy-$C_{1-2}$-alkyl and $C_{1-3}$-alkoxy-$C_{1-3}$-alkoxy-$C_{1-3}$-alkyl;
provided $R^2$ is not H, or provided $R^1$ is not heteroaryl or aryl or provided R is substituted with optionally substituted heterocyclyl-$C_{1-6}$-alkoxy, optionally substituted heterocyclyl-$C_{1-6}$-alkylamino, optionally substituted heterocyclyl-$C_{1-6}$-alkyl, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, or optionally substituted heterocyclyl-$C_{2-4}$-alkynyl, or $R^1$ is substituted with optionally substituted phenyloxy, optionally substituted 5-6 membered heterocyclyloxy, optionally substituted 5-6 membered heterocyclylsulfonyl, optionally substituted 5-6 membered heterocyclylamino, optionally substituted 5-6 membered heterocyclylcarbonyl, optionally substituted 5-6 membered heterocyclyl-$C_{1-4}$-alkylcarbonyl, $C_{1-3}$-alkylamino-$C_{1-3}$-alkoxy, or $C_{1-3}$-alkylamino-$C_{1-3}$-alkoxy-$C_{1-3}$-alkoxy; further provided R is not 3-pyridyl when $R^z$ is $CH_2$;
and pharmaceutically acceptable isomers and derivatives thereof.

The invention also relates to compounds of Formula XI

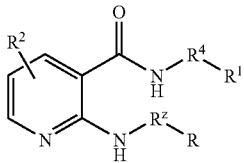

wherein R is selected from
a) unsubstituted or substituted 5- or 6-membered nitrogen-containing heteroaryl,
preferably 4-pyridyl, 3-pyridyl, 2-pyridyl, pyrimidinyl, triazolyl, and pyridazinyl, more preferably 4-pyridyl, and
b) unsubstituted or substituted 9- or 10-membered fused heteroaryl
preferably indolyl, isoindolyl, indazolyl, quinolyl, isoquinolyl, benzotriazolyl, naphthyridinyl and quinozalinyl,
where substituted R is substituted with one or more substituents selected from halo, amino, hydroxy, $C_{1-6}$-alkyl, $C_{1-6}$-haloalkyl, $C_{1-6}$-alkoxy, optionally substituted heterocyclyl-$C_{1-6}$-alkoxy, optionally substituted heterocyclyl-$C_{1-6}$-alkylamino, optionally substituted heterocyclyl-$C_{1-6}$-alkyl, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, and optionally substituted heterocyclyl-$C_{2-4}$-alkynyl,
preferably chloro, fluoro, amino, methyl, ethyl, propyl, trifluoromethyl, dimethylaminopropynyl, 1-methylpiperdinylmethoxy, dimethylaminoethoxyethoxy, methoxy and ethoxy;
wherein $R^1$ is selected from unsubstituted or substituted aryl, cycloalkyl,
5-6 membered heteroaryl and
9-10 membered bicyclic and 13-14 membered tricyclic heterocyclyl,
preferably phenyl, tetrahydronaphthyl, indanyl, indenyl, naphthyl, cyclohexyl, isoxazolyl, pyrazolyl, thiazolyl, thiadiazolyl, thienyl, pyridyl, pyrimidinyl, pyridazinyl, 1,2-dihydroquinolyl, 1,2,3,4-tetrahydro-isoquinolyl, isoquinolyl, quinolyl, indolyl, isoindolyl, 2,3-dihydro-1H-indolyl, naphthyridinyl, quinozalinyl, benzo[d]isothiazolyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3-benzothiadiazolyl, benzodioxanyl, benzothienyl, benzofuryl, dihydro-benzimidazolyl, benzimidazolyl, benzoxazolyl and benzthiazolyl,
specifically 4-6 membered saturated or partially un-saturated monocyclic heterocyclyl,
9-10 membered saturated or partially un-saturated bicyclic heterocyclyl, and
13-14 membered saturated or partially un-saturated tricyclic heterocyclyl,
more specifically 1,2-dihydroquinolyl, 1,2,3,4-tetrahydro-isoquinolyl, 2,3-dihydro-1H-indolyl, benzo[d]isothiazolyl, dihydro-benzimidazolyl, 2,3,4,4a,9,9a-hexahydro-1H-3-aza-fluorenyl, 5,6,7-trihydro-1,2,4-triazolo[3,4-a]isoquinolyl, and tetrahydroquinolinyl,
wherein substituted $R^1$ is substituted with one or more substituents selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted 4-6 membered heterocyclyl-$C_1$-$C_4$-alkyl, optionally substituted 4-6 membered heterocyclyl-$C_2$-$C_4$-alkenyl, optionally substituted 4-6 membered heterocyclyl, optionally substituted phenyloxy, optionally substituted 4-6 membered heterocyclyloxy, optionally substituted 4-6 membered heterocyclyl-$C_1$-$C_4$-alkoxy, optionally substituted 4-6 membered heterocyclylsulfonyl, optionally substituted 4-6 membered heterocyclylamino, optionally substituted 4-6 membered heterocyclylcarbonyl, optionally substituted 5-6 membered heterocyclyl-$C_{1-4}$-alkylcarbonyl, $C_{1-2}$-haloalkyl, $C_{1-4}$-aminoalkyl, nitro, amino, hydroxy, oxo, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

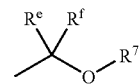

and $C_{1-4}$-alkoxy,
preferably bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4- ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylcarbonyl, Boc, piperidin-1-ylmethylcarbonyl, 4-methylpiperazin-1-ylcarbonylethyl, methoxycarbonyl, aminomethylcarbonyl, dimethylaminomethylcarbonyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperdin-4-ylmethoxy, piperdin-4-ylmethoxy, 1-methylpiperdin-4-yloxy, isopropoxy, methoxy and ethoxy;

wherein $R^2$ is one or more substituents independently selected from
H,
halo,
hydroxy,
amino,
$C_{1-6}$-alkyl,
$C_{1-6}$-haloalkyl,
$C_{1-6}$-alkoxy,
$C_{1-2}$-alkylamino,
aminosulfonyl,
$C_{3-6}$-cycloalkyl,
cyano,
$C_{1-2}$-hydroxyalkyl,
nitro,
$C_{2-3}$-alkenyl,
$C_{2-3}$-alkynyl,
$C_{1-6}$-haloalkoxy,
$C_{1-6}$-carboxyalkyl,
5-6-membered heterocyclyl-$C_{1-6}$-alkylamino,
unsubstituted or substituted phenyl and
unsubstituted or substituted 5-6 membered heterocyclyl,
preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from thienyl, furanyl, pyridyl, imidazolyl, and pyrazolyl,
specifically chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from thienyl, furanyl, pyridyl, imidazolyl, and pyrazolyl;

wherein $R^4$ is selected from a direct bond, $C_{1-4}$-alkyl, and

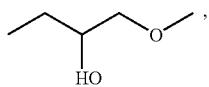

preferably a direct bond, ethyl, butyl, and

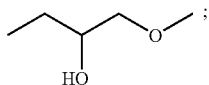

wherein $R^z$ is selected from $C_{1-2}$-alkyl, $C_{2-6}$-branched alkyl, $C_{2-4}$-branched haloalkyl, amino-$C_{1-4}$-alkyl and $C_{1-2}$-alkylamino-$C_{1-2}$-alkyl,
preferably methylenyl, ethylenyl,

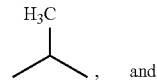

aminoethylenyl;
wherein $R^e$ and $R^f$ are independently selected from H and $C_{1-2}$-haloalkyl,
preferably trifluoromethyl; and
wherein $R^7$ is selected from H, $C_{1-3}$-alkyl, optionally substituted phenyl, optionally substituted phenyl-$C_{1-3}$-alkyl, optionally substituted 4-6 membered heterocyclyl, optionally substituted 4-6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl;
provided $R^1$ is substituted with optionally substituted phenyloxy, optionally substituted 4-6 membered heterocycyloxy, optionally substituted 4-6 membered heterocyclyl-$C_{1-4}$-alkoxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-$C_{1-4}$-alkylcarbonyl, $C_{1-3}$-alkylamino-$C_{1-3}$-alkoxy, or $C_{1-3}$-alkylamino-$C_{1-3}$-alkoxy-$C_{1-3}$-alkoxy; further provided R is not 3-pyridyl when $R^5$ is $CH_2$;
and pharmaceutically acceptable isomers and derivatives thereof.

The invention also relates to compounds of Formula XII

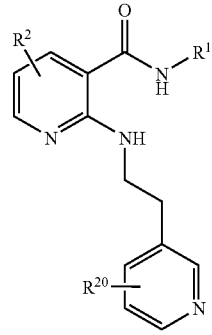

XII wherein $R^1$ is selected from unsubstituted or substituted aryl, preferably phenyl, tetrahydronaphthyl, indanyl, indenyl, and naphthyl, cycloalkyl, preferably cyclohexyl, 5-6 membered heteroaryl, preferably isoxazolyl, pyrazolyl, thiazolyl, thiadiazolyl, thienyl, pyridyl, pyrimidinyl, and pyridazinyl, and 9-10 membered bicyclic and 13-14 membered tricyclic heterocyclyl, preferably 1,2-dihydroquinolyl, 1,2,3,4-tetrahydro-isoquinolyl, isoquinolyl, quinolyl, indolyl, isoindolyl, 2,3-dihydro-1H-indolyl, naphthyridinyl, quinozalinyl, benzo[d]isothiazolyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3-benzothiadiazolyl, benzodioxanyl, benzothienyl, benzofuryl, benzimidazolyl, benzoxazolyl and benzthiazolyl;

wherein substituted $R^1$ is substituted with one or more substituents selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted 4-6 membered heterocyclyl-$C_1$-$C_4$-alkyl, optionally substituted 4-6 membered heterocyclyl-$C_2$-$C_4$-alkenyl, optionally substituted 4-6 membered heterocyclyl, optionally substituted phenyloxy, optionally substituted 4-6 membered heterocyclyloxy, optionally substituted 4-6 membered heterocyclyl-$C_1$-$C_4$-alkoxy, optionally substituted 4-6 membered heterocyclylsulfonyl, optionally substituted 4-6 membered heterocyclylamino, optionally substituted 4-6 membered heterocyclylcarbonyl, optionally substituted 5-6 membered heterocyclyl-$C_{1-4}$-alkylcarbonyl, $C_{1-2}$-haloalkyl, $C_{1-4}$-aminoalkyl, nitro, amino, hydroxy, oxo, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

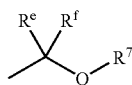

and $C_{1-4}$-alkoxy, preferably bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylcarbonyl, Boc, piperidin-1-ylmethylcarbonyl, 4-methylpiperazin-1-ylcarbonylethyl, methoxycarbonyl, aminomethylcarbonyl, dimethylaminomethylcarbonyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperdin-4-ylmethoxy, piperdin-4-ylmethoxy, 1-methylpiperdin-4-yloxy, isopropoxy, methoxy and ethoxy;

wherein $R^2$ is one or more substituents independently selected from
H,
halo,
hydroxy,
amino,
$C_{1-6}$-alkyl,
$C_{1-6}$-haloalkyl,
$C_{1-6}$-alkoxy,
$C_{1-2}$-alkylamino,
aminosulfonyl,
$C_{3-6}$-cycloalkyl,
cyano,
$C_{1-2}$-hydroxyalkyl,
nitro,
$C_{2-3}$-alkenyl,
$C_{2-3}$-alkynyl,
$C_{1-6}$-haloalkoxy,
$C_{1-6}$-carboxyalkyl,
5-6-membered heterocyclyl-$C_{1-6}$-alkylamino,
unsubstituted or substituted phenyl and
unsubstituted or substituted 5-6 membered heterocyclyl,
preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from thienyl, fury, pyridyl, imidazolyl, and pyrazolyl;

wherein $R^e$ and $R^f$ are independently selected from H and $C_{1-2}$-haloalkyl, preferably trifluoromethyl;

wherein $R^7$ is selected from H, $C_{1-3}$-alkyl, optionally substituted phenyl, optionally substituted phenyl-$C_{1-3}$-alkyl, optionally substituted 4-6 membered heterocyclyl, optionally substituted 4-6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl; and wherein $R^{20}$ is one or more substituents selected from halo, amino, hydroxy, $C_{1-6}$-alkyl, $C_{1-6}$-haloalkyl, $C_{1-6}$-alkoxy, optionally substituted heterocyclyl-$C_{1-6}$-alkoxy, optionally substituted heterocyclyl-$C_{1-6}$-alkylamino, optionally substituted heterocyclyl-$C_{1-6}$-alkyl, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, and optionally substituted heterocyclyl-$C_{2-4}$-alkynyl,
preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;

and pharmaceutically acceptable isomers and derivatives thereof.

A family of specific compounds of particular interest within Formula I consists of compounds and pharmaceutically-acceptable derivatives thereof as follows:

N-(4-Isopropylphenyl) {2-[(4-pyridylmethyl)amino](3-pyridyl)}carboxamide;

N-[3-(Isopropyl)phenyl]{2-[(4-pyridylmethyl)amino](3-pyridyl)}carboxamide;

N-(3-Isoquinolyl){2-[(4-pyridylmethyl)amino](3-pyridyl)}carboxamide;

N-[4-Isopropylphenyl]{2-[(2-(3-pyridyl)ethyl)amino](3-pyridyl)}carboxamide;

N-[4-(tert-Butyl)phenyl]{2-[(2-(3-pyridyl)ethyl)amino](3-pyridyl)}carboxamide;

N-[4-(Methylpropyl)phenyl]{2-[(2-(3-pyridyl)ethyl)amino](3-pyridyl)}carboxamide;

{2-[(2-(3-Pyridyl)ethyl)amino](3-pyridyl)}-N-[3-(trifluoromethyl)phenyl]carboxamide;

{2-[(4-Pyridylmethyl)amino](3-pyridyl)}-N-{4-[2,2,2-trifluoro-1-hydroxy-1-(trifluoromethyl)ethyl]phenyl}carboxamide;

N-[5-(tert-Butyl)isoxazol-3-yl]{2-[(4-pyridylmethyl)amino](3-pyridyl)}carboxamide;

N-[5-(tert-Butyl)-1-methylpyrazol-3-yl]{2-[(4-pyridylmethyl)amino](3-pyridyl)}carboxamide;

N-[4-(tert-Butyl)(1,3-thiazol-2-yl)]{2-[(4-pyridylmethyl)amino](3-pyridyl)}carboxamide;

N-[5-(tert-Butyl)(1,3,4-thiadiazol-2-yl)]{2-[(4-pyridylmethyl)amino](3-pyridyl)}carboxamide;

N-[4-(4-Hydroxybutyl)phenyl]{2-[(4-pyridylmethyl)amino](3-pyridyl)}carboxamide;

N-[2-(4-Chlorophenyl)ethyl]-2-[(pyridin-4-ylmethyl)amino](3-pyridyl)carboxamide;

5-Bromo-N-[2-(4-chlorophenyl)ethyl]-2-[(pyridin-4-ylmethyl)amino](3-pyridyl)carboxamide;

N-[2-(4-Phenoxyphenyl)ethyl]-2-[(pyridin-4-ylmethyl)amino](3-pyridyl)carboxamide;

N-[2-(4-Methoxyphenyl)ethyl]-2-[(pyridin-4-ylmethyl)amino](3-pyridyl)carboxamide;

N-[2-(3,4-Dimethoxyphenyl)ethyl]-2-[(pyridin-4-ylmethyl)amino](3-pyridyl)carboxamide;

N-[2-(4-Hydroxy-3-ethoxyphenyl)ethyl]-2-[(pyridin-4-ylmethyl)amino](3-pyridyl)carboxamide;

N-[2-(4-Fluorophenyl)ethyl]-2-[(pyridin-4-ylmethyl)amino](3-pyridyl)carboxamide;

N-[2-(4-(tert-Butyl)phenyl)ethyl]-2-[(pyridin-4-ylmethyl)amino](3-pyridyl)carboxamide;

N-[2-(3-Fluorophenyl)ethyl]-2-[(pyridin-4-ylmethyl)amino](3-pyridyl)carboxamide;

N-[2-(3-Chlorophenyl)ethyl]-2-[(pyridin-4-ylmethyl)amino](3-pyridyl)carboxamide;

N-[2-(3-(Trifluoromethyl)phenyl)ethyl]-2-[(pyridin-4-ylmethyl)amino](3-pyridyl)carboxamide;

N-[2-(3-Ethoxyphenyl)ethyl]-2-[(pyridin-4-ylmethyl)amino](3-pyridyl)carboxamide;

N-[2-(3,4-Dimethylphenyl)ethyl]-2-[(pyridin-4-ylmethyl)amino](3-pyridyl)carboxamide;

N-[2-(1,3-Benzodioxol-5-yl)ethyl]-2-[(pyridin-4-ylmethyl)amino](3-pyridyl)carboxamide;

N-[2-(4-Methylphenyl)ethyl]-2-[(pyridin-4-ylmethyl)amino](3-pyridyl)carboxamide;

N-[2-(4-Hydroxyphenyl)ethyl]-2-[(pyridin-4-ylmethyl)amino](3-pyridyl)carboxamide;

N-[2-(3,4-Dimethoxyphenyl)ethyl]-2-[(pyridin-4-ylmethyl)amino](3-pyridyl)carboxamide;

N-[2-(4-Bromophenyl)ethyl]-2-[(pyridin-4-ylmethyl)amino](3-pyridyl)carboxamide;

N-[2-(3,4-Dichlorophenyl)ethyl]-2-[(pyridin-4-ylmethyl)amino](3-pyridyl)carboxamide;

N-[2-(4-(Fluorosulfonyl)phenyl)ethyl]-2-[(pyridin-4-ylmethyl)amino](3-pyridyl)carboxamide;

N-[2-(3,5-(Dimethoxy)phenyl)ethyl]-2-[(pyridin-4-ylmethyl)amino](3-pyridyl)carboxamide;

N-[2-(2,4-Dichlorophenyl)ethyl]-2-[(pyridin-4-ylmethyl)amino](3-pyridyl)carboxamide;

N-[2-(2-Fluorophenyl)ethyl]-2-[(pyridin-4-ylmethyl)amino](3-pyridyl)carboxamide;

N-[2-(2-Chlorophenyl)ethyl]-2-[(pyridin-4-ylmethyl)amino](3-pyridyl)carboxamide;

N-[2-(4-(Aminosulphonyl)phenyl)ethyl]-2-[(pyridin-4-ylmethyl)amino](3-pyridyl)carboxamide;

N-[2-(2-Thienyl)ethyl]-2-[(pyridin-4-ylmethyl)amino](3-pyridyl)carboxamide;

N-[2-(Pyridin-2-yl)ethyl]-2-[(pyridin-4-ylmethyl)amino](3-pyridyl)carboxamide;

N-[2-(Pyridin-3-yl)ethyl]-2-[(pyridin-4-ylmethyl)amino](3-pyridyl)carboxamide;

N-[2-(Pyridin-4-yl)ethyl]-2-[(pyridin-4-ylmethyl)amino](3-pyridyl)carboxamide;

N-(4-Phenylbutyl)-2-[(pyridin-4-ylmethyl)amino](3-pyridyl)carboxamide;

N-(2-Hydroxy-3-phenoxypropyl)-2-[(pyridin-4-ylmethyl)amino](3-pyridyl)carboxamide;

{6-Chloro-5-fluoro-2-[(4-pyridylmethyl)amino](3-pyridyl)}-N-[4-(isopropyl)phenyl]carboxamide;

{5-Fluoro-2-[(4-pyridylmethyl)amino](3-pyridyl)}-N-[4-(isopropyl)phenyl]carboxamide;

2-[(Pyridin-4-ylmethyl)amino]-N-[4-tert-butyl-3-(1,2,3,6-tetrahydropyridin-4-yl)phenyl](3-pyridyl)carboxamide;

N-(3,4-Dichlorophenyl){6-[(2-morpholin-4-ylethyl)amino]-2-[(4-pyridylmethyl)amino](3-pyridyl)}carboxamide;

N-[4-(Morpholin-4-ylmethyl)phenyl]{2-[(4-pyridylmethyl)amino](3-pyridyl)}carboxamide;

N-(4-{2-[(tert-Butoxy)carbonylamino]ethyl}phenyl){2-[(4-pyridylmethyl)amino](3-pyridyl)}carboxamide;

N-[4-(2-Aminoethyl)phenyl]{2-[(4-pyridylmethyl)amino](3-pyridyl)}carboxamide;

N-[4-(tert-Butyl)-3-nitrophenyl]{2-[(2-pyridylmethyl)amino](3-pyridyl)}carboxamide;

N-[3-Amino-4-(tert-butyl)phenyl]{2-[(2-pyridylmethyl)amino](3-pyridyl)}carboxamide;

N-[4-(Isopropyl)phenyl]{2-[(2-pyridylmethyl)amino](3-pyridyl)}carboxamide;

N-(3-Aminosulfonyl-4-chlorophenyl){2-[(4-pyridylmethyl)amino](3-pyridyl)}carboxamide;

N-{3-[(4-Methylpiperazinyl)sulfonyl]phenyl}{2-[(4-pyridylmethyl)amino](3-pyridyl)}carboxamide;

N-[4-(1,1,2,2,2-Pentafluoroethyl)phenyl]{2-[(4-pyridylmethyl)amino](3-pyridyl)}carboxamide;

N-[4-(1,1,2,2,3,3,4,4,4-Nonafluorobutyl)phenyl]{2-[(4-pyridylmethyl)amino](3-pyridyl)}carboxamide;

N-[4-(Isopropyl)phenyl]{2-[(2-(1,2,4-triazolyl)ethyl)amino](3-pyridyl)}carboxamide;

(2-{[2-(2-Pyridylamino)ethyl]amino}(3-pyridyl))-N-[3-(trifluoromethyl)phenyl]carboxamide;

{2-[(1-(2-Pyridyl)pyrrolidin-3-yl)amino](3-pyridyl)}-N-[3-(trifluoromethyl)phenyl]carboxamide;

2-[(Pyridin-4-ylmethyl)-amino]-N-(3-trifluoromethyl-phenyl)-nicotinamide {2-[(4-Pyridylmethyl)amino](3-pyridyl)}-N-(8-quinolyl)carboxamide hydrochloride;

N-[4-(4-Chlorophenoxy)phenyl]{2-[(4-pyridylmethyl)amino](3-pyridyl)}carboxamide hydrochloride;

{2-[(4-Pyridylmethyl)amino](3-pyridyl)}-N-(2,3,4-trifluorophenyl)carboxamide hydrochloride;

N-(2-Naphthyl){2-[(4-pyridylmethyl)amino](3-pyridyl)}carboxamide hydrochloride;
N-(2-Phenoxyphenyl){2-[(4-pyridylmethyl)amino](3-pyridyl)}carboxamide hydrochloride;
{2-[(4-Pyridylmethyl)amino](3-pyridyl)}-N-(5,6,7,8-tetrahydronaphthyl) carboxamide hydrochloride;
N-(2H-Benzo[3,4-d]1,3-dioxolen-5-yl){2-[(4-pyridylmethyl)amino](3-pyridyl)}carboxamide hydrochloride;
N-Naphthyl{2-[(4-pyridylmethyl)amino](3-pyridyl)}carboxamide hydrochloride;
N-[3-Benzylphenyl]{2-[(4-pyridylmethyl)amino](3-pyridyl)}carboxamide hydrochloride;
N-(Cyclohexylethyl){2-[(4-pyridylmethyl)amino](3-pyridyl)}carboxamide hydrochloride;
N-(Cyclohexylethyl){2-[(4-pyridylmethyl)amino](3-pyridyl)}carboxamide hydrochloride;
N-Indan-2-yl{2-[(4-pyridylmethyl)amino](3-pyridyl)}carboxamide hydrochloride;
N-[4-(tert-Butyl)phenyl]{2-[(4-pyridylmethyl)amino](3-pyridyl)}carboxamide;
N-(4-sec-Butyl-phenyl)-2-[(pyridin-4-ylmethyl)-amino]-nicotinamide;
N-(4-Methylphenyl){2-[(4-pyridylmethyl)amino](3-pyridyl)}carboxamide;
{2-[(4-Pyridylmethyl)amino](3-pyridyl)}-N-[4-trifluoromethoxy)phenyl]carboxamide;
N-(4-Ethylphenyl){2-[(4-pyridylmethyl)amino](3-pyridyl)}carboxamide;
N-(4-Butylphenyl){2-[(4-pyridylmethyl)amino](3-pyridyl)}carboxamide;
N-(4-Iodophenyl){2-[(4-pyridylmethyl)amino](3-pyridyl)}carboxamide;
N-(3-(Hydroxyethyl)phenyl){2-[(4-pyridylmethyl)amino](3-pyridyl)}carboxamide;
N-(3-Ethylphenyl){2-[(4-pyridylmethyl)amino](3-pyridyl)}carboxamide;
Ethyl 2-methyl-5-[3-({2-[(4-pyridylmethyl)amino](3-pyridyl)}carbonylamino)phenyl]furan-3-carboxylate;
N-(3-Phenylphenyl){2-[(4-pyridylmethyl)amino](3-pyridyl)}carboxamide;
N-(4-Benzylphenyl){2-[(4-pyridylmethyl)amino](3-pyridyl)}carboxamide;
N-(6-Ethyl(2-pyridyl)){2-[(4-pyridylmethyl)amino](3-pyridyl)}carboxamide;
N-(6-Propyl(2-pyridyl)){2-[(4-pyridylmethyl)amino](3-pyridyl)}carboxamide;
N-[4-(tert-Butyl)(2-pyridyl)]{2-[(4-pyridylmethyl)amino](3-pyridyl)}carboxamide;
N-(3-Hydroxyphenyl){2-[(4-pyridylmethyl)amino](3-pyridyl)}carboxamide;
N-[4-(Methylethyl)(2-pyridyl)]{2-[(4-pyridylmethyl)amino](3-pyridyl)}carboxamide;
N-[3,5-bis(Trifluoromethyl)phenyl]{2-[(4-pyridylmethyl)amino](3-pyridyl)}carboxamide hydrochloride;
N-[4-Chloro-3-(trifluoromethyl)phenyl]{2-[(4-pyridylmethyl)amino](3-pyridyl)}carboxamide hydrochloride;
N-(3-Chlorophenyl){2-[(2-(4-pyridyl)ethyl)amino](3-pyridyl)}carboxamide hydrochloride;
N-(4-Phenoxyphenyl){2-[(2-(2-pyridyl)ethyl)amino](3-pyridyl)}carboxamide;
2-[(Benzo[b]thiophen-3-ylmethyl)amino](3-pyridyl)}-N-(4-phenoxyphenyl)carboxamide;
N-(4-Phenoxyphenyl){2-[(2-(3-pyridyl)ethyl)amino](3-pyridyl)}carboxamide;
N-[4-(Methylsulfonyl)phenyl]{2-[(4-pyridylmethyl)amino](3-pyridyl)}carboxamide;
N-(1-Acetylindolin-6-yl){2-[(4-pyridylmethyl)amino](3-pyridyl)}carboxamide;
N-Indolin-6-yl{2-[(4-pyridylmethyl)amino](3-pyridyl)}carboxamide;
N-Indol-6-yl{2-[(4-pyridylmethyl)amino](3-pyridyl)}carboxamide;
N-Indol-5-yl{2-[(4-pyridylmethyl)amino](3-pyridyl)}carboxamide;
N-Indol-7-yl{2-[(4-pyridylmethyl)amino](3-pyridyl)}carboxamide;
N-[3-(tert-Butyl)pyrazol-5-yl]{2-[(4-pyridylmethyl)amino](3-pyridyl)}carboxamide;
N-(3-Phenylpyrazol-5-yl){2-[(4-pyridylmethyl)amino](3-pyridyl)}carboxamide;
N-{2-[2-(dimethylamino)ethoxy]-5-(tert-butyl)phenyl}{2-[(4-pyridylmethyl)amino](3-pyridyl)}carboxamide;
N-[4-(tert-Butyl)-3-(4-methylpiperazinyl)phenyl]{2-[(4-pyridylmethyl)amino](3-pyridyl)}carboxamide;
N-[3-(4-Methylpiperazinyl)phenyl]{2-[(4-pyridylmethyl)amino](3-pyridyl)}carboxamide;
N-[4-(4-Methylpiperazinyl)phenyl]{2-[(4-pyridylmethyl)amino](3-pyridyl)}formamide;
N-[1-(1-Methyl-(4-piperidyl))indolin-6-yl]{2-[(4-pyridylmethyl)amino](3-pyridyl)}carboxamide;
N-[1-(1-Methyl-(4-piperidyl))indolin-6-yl]{2-[(2-(3-pyridyl)ethyl)amino](3-pyridyl)}carboxamide;
N-[1-(2-Piperidylethyl)indolin-6-yl]{2-[(4-pyridylmethyl)amino](3-pyridyl)}carboxamide;
N-[1-(2-Piperidylacetyl)indolin-6-yl]{2-[(4-pyridylmethyl)amino](3-pyridyl)}carboxamide;
N-[3,3-Dimethyl-1-(1-methyl(4-piperidyl))indolin-6-yl]{2-[(4-pyridylmethyl)amino](3-pyridyl)}carboxamide;
N-(3,3-Dimethylindolin-6-yl){2-[(4-pyridylmethyl)amino](3-pyridyl)}carboxamide;
N-[3-(1-Methyl-(4-piperidyl))indol-5-yl]{2-[(4-pyridylmethyl)amino](3-pyridyl)}carboxamide;
N-[4-(1,1-Dimethyl-3-morpholin-4-ylpropyl)phenyl]{2-[(4-pyridylmethyl)amino](3-pyridyl)}carboxamide;
N-[4-(tert-Butyl)phenyl]{2-[({2-[(1-methyl(4-piperidyl))methoxy](4-pyridyl)}methyl)amino](3-pyridyl)}carboxamide;
N-(4-Bromo-2-fluorophenyl){2-[(4-pyridylmethyl)amino](3-pyridyl)}carboxamide;
N-[4-(tert-Butyl)phenyl](2-{[(2-chloro(4-pyridyl))methyl]amino}(3-pyridyl))carboxamide;
{2-[({2-[3-(Dimethylamino)prop-1-ynyl](4-pyridyl)}methyl)amino](3-pyridyl)}-N-[4-(tert-butyl)phenyl]carboxamide;
(2-{[(2-Methoxy(4-pyridyl))methyl]amino}(3-pyridyl))-N-[4-(methylethyl)phenyl]carboxamide;
N-{3-[3-(Dimethylamino)propyl]-5-(trifluoromethyl)phenyl}-{2-[(4-pyridylmethyl)amino](3-pyridyl)}carboxamide;
N-[4-(tert-Butyl)-3-(3-piperid-1-ylpropyl)phenyl]{2-[(4-pyridylmethyl)amino](3-pyridyl)}carboxamide;
N-[4-(tert-Butyl)-3-(3-pyrrolidin-1-ylpropyl)phenyl]{2-[(4-pyridylmethyl)amino](3-pyridyl)}carboxamide;
N-[3-((1E)-4-Pyrrolidin-1-ylbut-1-enyl)-4-(tert-butyl)phenyl]{2-[(4-pyridylmethyl)amino](3-pyridyl)}carboxamide;
N-[4-(tert-Butyl)-3-(3-morpholin-4-ylpropyl)phenyl]{2-[(4-pyridylmethyl)amino](3-pyridyl)}carboxamide;
N-[1-(2-Morpholin-4-ylethyl)indol-6-yl]{2-[(4-pyridylmethyl)amino](3-pyridyl)}carboxamide;
N-[4-(tert-Butyl)phenyl]{2-[(pyrimidin-4-ylmethyl)amino](3-pyridyl)}carboxamide;

N-(4-Chlorophenyl){2-[(pyrimidin-4-ylmethyl)amino](3-pyridyl)}carboxamide;

{2-[(Pyrimidin-4-ylmethyl)amino](3-pyridyl)}-N-[3-(trifluoromethyl)phenyl]carboxamide;

N-[4-(Isopropyl)phenyl]{4-[(4-pyridylmethyl)amino]pyrimidin-5-yl}carboxamide;

(2-{[(2-{2-[2-(Dimethylamino)ethoxy]ethoxy}(4-pyridyl))methyl]amino}(3-pyridyl))-N-[4-(tert-butyl)phenyl]carboxamide;

{2-[(4-Pyridylmethyl)amino](3-pyridyl)}-N-{4-[2,2,2-trifluoro-1-(2-piperidylethoxy)-1-(trifluoromethyl)ethyl]phenyl}carboxamide;

(2-{[(2-{2-[2-(Dimethylamino)ethoxy]ethoxy}(4-pyridyl))methyl]amino}-6-fluoro(3-pyridyl))-N-[3-(trifluoromethyl)phenyl]carboxamide;

N-[4-(tert-Butyl)phenyl]{6-fluoro-2-[(4-pyridylmethyl)amino](3-pyridyl)}carboxamide;

{6-Fluoro-2-[(4-pyridylmethyl)amino](3-pyridyl)}-N-[4-(isopropyl)phenyl]carboxamide;

{6-Fluoro-2-[(4-pyridylmethyl)amino](3-pyridyl)}-N-[3-(trifluoromethyl)phenyl]carboxamide;

N-(1-Bromo(3-isoquinolyl)){6-fluoro-2-[(4-pyridylmethyl)amino](3-pyridyl)}-carboxamide;

N-(4-Phenoxyphenyl){2-[(4-pyridylmethyl)amino](3-pyridyl)}carboxamide hydrochloride;

N-(4-Phenylphenyl){2-[(4-pyridylmethyl)amino](3-pyridyl)}carboxamide hydrochloride;

N-(3-Phenoxyphenyl){2-[(4-pyridylmethyl)amino](3-pyridyl)}carboxamide hydrochloride;

N-(4-Cyclohexylphenyl){2-[(4-pyridylmethyl)amino](3-pyridyl)}carboxamide hydrochloride;

N-(4-Imidazol-1-ylphenyl){2-[(4-pyridylmethyl)amino](3-pyridyl)}carboxamide;

N-(4-Morpholin-4-ylphenyl){2-[(4-pyridylmethyl)amino](3-pyridyl)}carboxamide hydrochloride;

N-(4-Cyanonaphthyl){2-[(4-pyridylmethyl)amino](3-pyridyl)}carboxamide hydrochloride;

{2-[(4-Pyridylmethyl)amino](3-pyridyl)}-N-[4-(trifluoromethyl)phenyl]carboxamide hydrochloride;

Methyl-4-({2-[(4-pyridylmethyl)amino]-3-pyridyl}carbonylamino)benzoate hydrochloride;

N-[4-(Isopropyl)phenyl]{2-[(4-quinolylmethyl)amino](3-pyridyl)}carboxamide;

N-[4-(tert-Butyl)phenyl]{2-[(6-quinolylmethyl)amino](3-pyridyl)}carboxamide;

{2-[(6-Quinolylmethyl)amino](3-pyridyl)}-N-[3-(trifluoromethyl)phenyl]carboxamide;

N-(4-chlorophenyl){3-[(4-pyridylmethyl)amino](2-thienyl)}carboxamide;

N-phenyl{3-[(4-pyridylmethyl)amino](2-thienyl)}carboxamide;

N-(4-chlorophenyl)-3-[(4-pyridinylmethylene)amino]-4-pyridinecarboxamide;

N-(4-chlorophenyl){2-[(4-pyridylmethyl)amino](3-pyridyl)}carboxamide;

N-(3,4-dichlorophenyl){2-[(4-pyridylmethyl)amino](3-pyridyl)}-carboxamide;

N-(3-chlorophenyl){2-[(4-pyridylmethyl)amino](3-pyridyl)}carboxamide;

N-(4-chlorophenyl){3-[(4-pyridylmethyl)amino](2-pyridyl)}carboxamide;

N-(4-chlorophenyl){3-[(6-quinolylmethyl)amino](2-pyridyl)}carboxamide;

N-(3,4-dichlorophenyl){2-[(6-quinolylmethyl)amino](3-pyridyl)}-carboxamide;

N-(4-chlorophenyl){6-methyl-2-[(4-pyridylmethyl)amino](3-pyridyl)}carboxamide;

N-(3,4-dichlorophenyl){6-methyl-2-[(4-pyridylmethyl)amino](3-pyridyl)}carboxamide;

N-(3-fluoro-4-methylphenyl){6-methyl-2-[(4-pyridylmethyl)amino](3-pyridyl)}carboxamide;

N-(3,4-dichlorophenyl){6-chloro-2-[(4-pyridylmethyl)amino](3-pyridyl)}carboxamide;

N-(4-chlorophenyl){6-chloro-2-[(4-pyridylmethyl)amino](3-pyridyl)}carboxamide;

{6-chloro-2-[(4-pyridylmethyl)amino](3-pyridyl)}-N-(3-fluorophenyl)carboxamide;

N-(3-chlorophenyl){6-chloro-2-[(4-pyridylmethyl)amino](3-pyridyl)}carboxamide;

N-(4-chlorophenyl){3-[(4-pyridylmethyl)amino](4-pyridyl)}carboxamide;

N-(3-fluoro-4-methylphenyl){2-[(4-pyridylmethyl)amino](3-pyridyl)}carboxamide;

N-(4-chlorophenyl){2-[(4-quinolylmethyl)amino](3-pyridyl)}carboxamide;

N-(4-chlorophenyl){2-[(5-quinolylmethyl)amino](3-pyridyl)}carboxamide;

N-(4-chlorophenyl){2-[(4-pyridylethyl)amino]-5-(3-thienyl)-(3-pyridyl)}carboxamide;

N-(4-chlorophenyl){5-(4-methoxyphenyl)-2-[(4-pyridylmethyl)amino]-(3-pyridyl)}carboxamide; and N-(4-chlorophenyl){5-bromo-2-[(4-pyridylmethyl)amino]-(3-pyridyl)}carboxamide.

A family of specific compounds of particular interest within Formula II' consists of compounds and pharmaceutically-acceptable derivatives thereof as follows:

2-{[2-(1-Isopropyl-azetidin-3-ylmethoxy)-pyridin-4-ylmethyl]-amino}-N-(4-trifluoromethyl-phenyl)-nicotinamide;

N-(4-tert-Butyl-phenyl)-2-{[2-(1-isopropyl-azetidin-3-ylmethoxy)-pyridin-4-ylmethyl]-amino}-nicotinamide;

2-[(2,3-Dihydro-benzofuran-5-ylmethyl)-amino]-N-{4-[1-methyl-1-(1-methyl-piperidin-4-yl)-ethyl]-phenyl}-nicotinamide;

N-(1-Acetyl-3,3-dimethyl-2,3-dihydro-1H-indol-6-yl)-2-[(2,3-dihydro-benzofuran-5-ylmethyl)-amino]-nicotinamide;

2-[(2,3-Dihydro-benzofuran-5-ylmethyl)-amino]-N-[3,3-dimethyl-1-(1-Boc-piperidin-4-ylmethyl)-2,3-dihydro-1H-indol-6-yl]-nicotinamide;

2-[(2,3-Dihydro-benzofuran-5-ylmethyl)-amino]-N-[3,3-dimethyl-1-(1-methylpiperidin-4-ylmethyl)-2,3-dihydro-1H-indol-6-yl]-nicotinamide;

N-(1-Acetyl-3,3-dimethyl-2,3-dihydro-1H-indol-6-yl)-2-({2-[2-(1-methyl-piperidin-4-yl)-ethoxy]-pyridin-4-ylmethyl}-amino)-nicotinamide;

2-({2-[2-(1-Methyl-piperidin-4-yl)-ethoxy]-pyridin-4-ylmethyl}-amino)-N-(3-trifluoromethyl-phenyl)-nicotinamide;

N-(4-tert-Butyl-phenyl)-2-{[2-ethylpyridin-4-ylmethyl]-amino}-nicotinamide;

N-(4-tert-Butyl-phenyl)-2-({2-[2-(1-methyl-pyrrolidin-2-yl)-ethoxy]-pyridin-4-ylmethyl}-amino)-nicotinamide;

2-({2-[2-(1-Methyl-pyrrolidin-2-yl)-ethoxy]-pyridin-4-ylmethyl}-amino)-N-(4-pentafluoroethyl-phenyl)-nicotinamide;

N-(4-Pentafluoroethyl-phenyl)-2-{[2-(2-pyrrolidin-1-yl-ethoxy)-pyridin-4-ylmethyl]-amino}-nicotinamide;

N-(4-tert-Butyl-phenyl)-2-{[2-(2-pyrrolidin-1-yl-ethoxy)-pyridin-4-ylmethyl]-amino}-nicotinamide;

N-[3-(4-Boc-piperazin-1-ylmethyl)-5-trifluoromethyl-phenyl]-2-[(pyridin-4-ylmethyl)-amino]-nicotinamide;

N-[3-(4-Boc-piperazine-1-carbonyl)-5-trifluoromethyl-phenyl]-2-[(pyridin-4-ylmethyl)-amino]-nicotinamide;

N-[3-(4-Boc-piperazine-1-carbonyl)-5-trifluoromethyl-phenyl]-2-(2-pyridin-4-yl-ethylamino)-nicotinamide;
N-[3-(4-Methyl-piperazin-1-ylmethyl)-4-pentafluoroethyl-phenyl]-2-[(pyridin-4-ylmethyl)-amino]-nicotinamide;
N-[3-(4-Boc-piperazin-1-ylmethyl)-4-pentafluoroethyl-phenyl]-2-[(pyridin-4-ylmethyl)-amino]-nicotinamide;
2-{[2-(1-Methyl-piperidin-4-ylmethoxy)-pyridin-4-ylmethyl]-amino}-N-(4-trifluoromethyl-phenyl)-nicotinamide;
N-(4-tert-Butyl-phenyl)-2-{[2-(1-methyl-piperidin-4-ylmethoxy)-pyridin-4-ylmethyl]-amino}-nicotinamide;
2-({2-[3-(1-Methyl-piperidin-4-yl)-propoxy]-pyridin-4-ylmethyl}-amino)-N-(4-pentafluoroethyl-phenyl)-nicotinamide;
N-(1-Acetyl-3,3-dimethyl-2,3-dihydro-1H-indol-6-yl)-2-[(2-methoxy-pyridin-4-ylmethyl)-amino]-nicotinamide;
N-[3,3-Dimethyl-1-(1-methyl-piperidin-4-yl)-2,3-dihydro-1H-indol-6-yl]-2-[(2-methoxy-pyridin-4-ylmethyl)-amino]-nicotinamide;
N-(1-Boc-3,3-dimethyl-2,3-dihydro-1H-indol-6-yl)-2-[(2-methoxy-pyridin-4-ylmethyl)-amino]-nicotinamide;
N-[3,3-Dimethyl-1-(1-Boc-piperidin-4-ylmethyl)-2,3-dihydro-1H-indol-6-yl]-2-[(2-methoxy-pyridin-4-ylmethyl)-amino]-nicotinamide;
N-[3,3-Dimethyl-1-(1-methyl-piperidin-4-yl)-2,3-dihydro-1H-indol-6-yl]-2-[(2-methoxy-pyridin-4-ylmethyl)-amino]-nicotinamide;
N-[1-(2-Dimethylamino-acetyl)-3,3-dimethyl-2,3-dihydro-1H-indol-6-yl]-2-[(2-methoxy-pyridin-4-ylmethyl)-amino]-nicotinamide;
N-[1-(2-Dimethylamino-acetyl)-3,3-dimethyl-2,3-dihydro-1H-indol-6-yl]-2-[(pyridin-4-ylmethyl)-amino]-nicotinamide;
2-[(2-Methoxy-pyridin-4-ylmethyl)-amino]-N-[3-(1-Boc-piperidin-4-ylmethoxy)-5-trifluoromethyl-phenyl]-nicotinamide;
N-[3,3-Dimethyl-1-(1-Boc-pyrrolidin-2-ylmethoxy)-2,3-dihydro-1H-indol-6-yl]-2-[(2-methoxy-pyridin-4-ylmethyl)-amino]-nicotinamide;
N-[3,3-Dimethyl-1-(2-Boc-amino-acetyl)-2,3-dihydro-1H-indol-6-yl]-2-[(2-methoxy-pyridin-4-ylmethyl)-amino]-nicotinamide;
N-[3,3-Dimethyl-1-(2-Boc-amino-acetyl)-2,3-dihydro-1H-indol-6-yl]-2-[(pyridin-4-ylmethyl)-amino]-nicotinamide;
2-[(2-Methoxy-pyridin-4-ylmethyl)-amino]-N-[3-(1-methyl-pyrrolidin-2-ylmethoxy)-5-trifluoromethyl-phenyl]-nicotinamide;
2-[(2-Methoxy-pyridin-4-ylmethyl)-amino]-N-[3-(1-Boc-piperidin-4-ylmethyl)-5-trifluoromethyl-phenyl]-nicotinamide;
2-[(2-Methoxy-pyridin-4-ylmethyl)-amino]-N-[3-(4-Boc-piperazin-1-ylmethyl)-5-trifluoromethyl-phenyl]-nicotinamide;
2-{[2-(3-Morpholin-4-yl-propoxy)-pyridin-4-ylmethyl]-amino}-N-(4-pentafluoroethyl-phenyl)-nicotinamide;
(S) 2-{[2-(1-Methyl-pyrrolidin-2-ylmethoxy)-pyridin-4-ylmethyl]-amino}-N-(4-pentafluoroethyl-phenyl)-nicotinamide;
N-(3-tert-Butyl-isoxazol-5-yl)-2-{[2-(3-morpholin-4-yl-propoxy)-pyridin-4-ylmethyl]-amino}-nicotinamide;
N-(1-Acetyl-3,3-dimethyl-2,3-dihydro-1H-indol-6-yl)-2-{[2-(3-morpholin-4-yl-propylamino)-pyridin-4-ylmethyl]-amino}-nicotinamide;
N-(4-tert-Butyl-phenyl)-2-{[2-(3-morpholin-4-yl-propoxy)-pyridin-4-ylmethyl]-amino}-nicotinamide;
N-(4-tert-Butyl-phenyl)-2-{[2-(2-morpholin-4-yl-ethoxy)-pyridin-4-ylmethyl]-amino}-nicotinamide;
2-{[2-(2-Morpholin-4-yl-ethoxy)-pyridin-4-ylmethyl]-amino}-N-(4-trifluoromethyl-phenyl)-nicotinamide;
2-{[2-(2-Morpholin-4-yl-ethoxy)-pyridin-4-ylmethyl]-amino}-N-(3-trifluoromethyl-phenyl)-nicotinamide;
2-{[2-(2-Morpholin-4-yl-ethoxy)-pyridin-4-ylmethyl]-amino}-N-(4-pentafluoroethyl-phenyl)-nicotinamide;
N-(3-tert-Butyl-isoxazol-5-yl)-2-{[2-(2-morpholin-4-yl-ethoxy)-pyridin-4-ylmethyl]-amino}-nicotinamide;
N-(1-Acetyl-3,3-dimethyl-2,3-dihydro-1H-indol-6-yl)-2-{[2-(2-morpholin-4-yl-ethoxy)-pyridin-4-ylmethyl]-amino}-nicotinamide;
N-(1-Acetyl-3,3-dimethyl-2,3-dihydro-1H-indol-6-yl)-2-{[2-(1-methyl-piperidin-4-yloxy)-pyridin-4-ylmethyl]-amino}-nicotinamide;
2-{[2-(1-Methyl-piperidin-4-yloxy)-pyridin-4-ylmethyl]-amino}-N-(4-trifluoromethyl-phenyl)-nicotinamide;
2-{[2-(1-Methyl-piperidin-4-yloxy)-pyridin-4-ylmethyl]-amino}-N-(4-pentafluoroethyl-phenyl)-nicotinamide;
2-{[2-(1-Methyl-piperidin-4-yloxy)-pyridin-4-ylmethyl]-amino}-N-(4-tert-butyl-phenyl)-nicotinamide;
(R)N-(4-tert-Butyl-phenyl)-2-{[2-(1-methyl-pyrrolidin-2-ylmethoxy)-pyridin-4-ylmethyl]-amino}-nicotinamide;
(R)N-[3-(1-Boc-pyrrolidin-2-ylmethoxy)-5-trifluoromethyl-phenyl]-2-[(pyridin-4-ylmethyl)-amino]-nicotinamide;
(R)N-[3-(1-Methyl-pyrrolidin-2-ylmethoxy)-5-trifluoromethyl-phenyl]-2-[(pyridin-4-ylmethyl)-amino]-nicotinamide;
N-[3-(1-Methyl-piperidin-4-yloxy)-5-trifluoromethyl-phenyl]-2-[(pyridin-4-ylmethyl)-amino]-nicotinamide;
N-[3-(1-Methyl-piperidin-4-ylmethyl)-5-trifluoromethyl-phenyl]-2-[(pyridin-4-ylmethyl)-amino]-nicotinamide;
N-[3-tert-Butyl-4-(1-Boc-pyrrolidin-2-ylmethoxy)-phenyl]-2-[(pyridin-4-ylmethyl)-amino]-nicotinamide;
N-(3,3-Dimethyl-2,3-dihydro-benzofuran-6-yl)-2-{[2-(1-methyl-piperidin-4-ylmethoxy)-pyridin-4-ylmethyl]-amino}-nicotinamide;
2-({2-[3-(1-Methyl-piperidin-4-yl)-propoxy]-pyridin-4-ylmethyl}-amino)-N-(4-trifluoromethyl-phenyl)-nicotinamide;
2-({2-[3-(1-Methyl-piperidin-4-yl)-propoxy]-pyridin-4-ylmethyl}-amino)-N-(3-trifluoromethyl-phenyl)-nicotinamide;
2-({2-[3-(1-Methyl-piperidin-4-yl)-propoxy]-pyridin-4-ylmethyl}-amino)-N-(4-tert-butyl-phenyl)-nicotinamide;
2-({2-[3-(1-Methyl-piperidin-4-yl)-propoxy]-pyridin-4-ylmethyl}-amino)-N-(3-tert-butyl-isoxazol-5-yl)-nicotinamide;
N-(3,3-Dimethyl-2,3-dihydro-1H-indol-6-yl)-2-({2-[3-(1-methyl-piperidin-4-yl)-propoxy]-pyridin-4-ylmethyl}-amino)-nicotinamide;
2-[(Pyridin-4-ylmethyl)-amino]-N-(3,9,9-trimethyl-2,3,4,4a,9,9a-hexahydro-1H-3-aza-fluoren-6-yl)-nicotinamide;
N-[3,3-Dimethyl-1-(1-Boc-piperidin-4-ylmethyl)-2,3-dihydro-1H-indol-6-yl]-2-[(pyridin-4-ylmethyl)-amino]-nicotinamide;
N-(4-Imidazol-1-ylphenyl){2-[(4-pyridylmethyl)amino](3-pyridyl)}carboxamide hydrochloride;
N-[3,3-Dimethyl-1-(1-methyl-piperidin-4-ylmethyl)-2,3-dihydro-1H-indol-6-yl]-2-[(pyridin-4-ylmethyl)-amino]-nicotinamide;
2-{[2-(1-Methyl-piperidin-4-ylmethoxy)-pyridin-4-ylmethyl]-amino}-N-(4-pentafluoroethyl-phenyl)-nicotinamide;

N-(3-tert-Butyl-isoxazol-5-yl)-2-{[2-(1-methyl-piperidin-4-ylmethoxy)-pyridin-4-ylmethyl]-amino}-nicotinamide;
N-(1-Acetyl-3,3-dimethyl-2,3-dihydro-1H-indol-6-yl)-2-{[2-(1-methyl-piperidin-4-ylmethoxy)-pyridin-4-ylmethyl]-amino}-nicotinamide;
N-(4-tert-Butyl-phenyl)-2-{[2-(3-morpholin-4-yl-propylamino)-pyrimidin-4-ylmethyl]-amino}-nicotinamide;
2-{[2-(3-Morpholin-4-yl-propylamino)-pyrimidin-4-ylmethyl]-amino}-N-(4-pentafluoroethyl-phenyl)-nicotinamide;
2-{[2-(3-Morpholin-4-yl-propylamino)-pyrimidin-4-ylmethyl]-amino}-N-(3-trifluoromethyl-phenyl)-nicotinamide;
N-(4-tert-Butyl-phenyl)-2-({2-[2-(1-methyl-pyrrolidin-2-yl)-ethylamino]-pyrimidin-4-ylmethyl}-amino)-nicotinamide;
N-(1-Acetyl-3,3-dimethyl-2,3-dihydro-1H-indol-6-yl)-2-({2-[2-(1-methyl-pyrrolidin-2-yl)-ethylamino]-pyrimidin-4-ylmethyl}-amino)-nicotinamide;
N-(4-Phenoxyphenyl){2-[(4-pyridylmethyl)amino](3-pyridyl)}carboxamide hydrochloride;
2-{[2-(1-Methyl-piperidin-4-ylmethoxy)-pyridin-4-ylmethyl]-amino}-N-[3-(1-methyl-piperidin-4-yl)-5-trifluoromethyl-phenyl]-nicotinamide;
N-(3-tert-Butyl-isoxazol-5-yl)-2-{[2-(1-methyl-piperidin-4-ylmethoxy)-pyridin-4-ylmethyl]-amino}-nicotinamide;
N-[3-(1-Boc-azetidin-3-ylmethoxy)-5-trifluoromethyl-phenyl]-2-[(pyridin-4-ylmethyl)-amino]-nicotinamide;
2-[(2-Methoxy-pyridin-4-ylmethyl)-amino]-N-[3-(1-Boc-azetidin-3-ylmethoxy)-5-trifluoromethyl-phenyl]-nicotinamide;
N-(3,3-Dimethylindolin-6-yl){2-[(4-pyridylmethyl)amino](3-pyridyl)}carboxamide phosphate salt;
N-(4-Morpholin-4-ylphenyl){2-[(4-pyridylmethyl)amino](3-pyridyl)}carboxamide hydrochloride;
N-(4-Cyanonaphthyl){2-[(4-pyridylmethyl)amino](3-pyridyl)}carboxamide, hydrochloride;
{2-[(4-Pyridylmethyl)amino](3-pyridyl)}-N-[4-(trifluoromethyl)phenyl]carboxamide hydrochloride;
Methyl-({2-[(4-pyridylmethyl)amino]-3-pyridyl}carbonylamino)benzoate, hydrochloride;
2-[(Pyridin-4-ylmethyl)-amino]-N-(2,2,4-trimethyl-3,4-dihydro-2H-benzo[1,4]oxazin-6-yl)-nicotinamide;
N-(4-Acetyl-2,2-dimethyl-3,4-dihydro-2H-benzo[1,4]oxazin-6-yl)-2-[(pyridin-4-ylmethyl)-amino]-nicotinamide;
N-(2,2-Dimethyl-3-oxo-3,4-dihydro-2H-benzo[1,4]oxazin-6-yl)-2-[(pyridin-4-ylmethyl)-amino]-nicotinamide;
2-{[2-(1-Benzhydryl-azetidin-3-yloxy)-pyridin-4-ylmethyl]-amino}-N-(4-tert-butyl-phenyl)-nicotinamide;
N-(4,4-Dimethyl-1-oxo-1,2,3,4-tetrahydro-isoquinolin-7-yl)-2-[(pyridin-4-ylmethyl)-amino]-nicotinamide;
N-(4-tert-Butyl-phenyl)-2-({2-[2-(1-methyl-piperidin-4-yl)-ethoxy]-pyridin-4-ylmethyl}-amino)-nicotinamide;
N-(3-tert-Butyl-isoxazol-5-yl)-2-({2-[2-(1-methyl-piperidin-4-yl)-ethoxy]-pyridin-4-ylmethyl}-amino)-nicotinamide;
N-(3-trifluoromethylphenyl)-2-({2-[2-(1-methyl-piperidin-4-yl)-ethoxy]-pyridin-4-ylmethyl}-amino)-nicotinamide;
2-[(2,3-Dihydro-benzofuran-6-ylmethyl)-amino]-N-[3-(1-Boc-pyrrolidin-2-ylmethoxy)-4-pentafluoroethyl-phenyl]-nicotinamide;
N-[3-(1-Methyl-piperidin-4-ylmethoxy)-4-pentafluoroethyl-phenyl]-2-[(pyridin-4-ylmethyl)-amino]-nicotinamide hydrochloride;
(R)N-[3-(2-Hydroxy-3-pyrrolidin-1-yl-propoxy)-4-pentafluoroethyl-phenyl]-2-[(pyridin-4-ylmethyl)-amino]-nicotinamide;
(S)N-[3-(2-Hydroxy-3-pyrrolidin-1-yl-propoxy)-4-pentafluoroethyl-phenyl]-2-[(pyridin-4-ylmethyl)-amino]-nicotinamide;
N-[4-tert-Butyl-3-(1-methyl-piperidin-4-ylmethoxy)-phenyl]-2-[(pyridin-4-ylmethyl)-amino]-nicotinamide;
N-[3-(1-Methyl-piperidin-4-ylmethoxy)-4-pentafluoroethyl-phenyl]-2-[(pyridin-4-ylmethyl)-amino]-nicotinamide;
N-[4-Pentafluoroethyl-3-(2-piperidin-1-yl-ethoxy)-phenyl]-2-[(pyridin-4-ylmethyl)-amino]-nicotinamide;
2-[(Pyridin-4-ylmethyl)-amino]-N-(3-trifluoromethyl-phenyl)-nicotinamide hydrochloride;
N-(4-Imidazol-1-ylphenyl){2-[(4-pyridylmethyl)amino](3-pyridyl)}carboxamide hydrochloride;
N-(3,3-Dimethyl-2,3-dihydro-benzofuran-6-yl)-2-[(pyridin-4-ylmethyl)-amino]-nicotinamide hydrochloride;
2-[(Pyridin-4-ylmethyl)-amino]-N-(4-tert-butyl-phenyl)-nicotinamide hydrochloride;
N-[4-Trifluoromethyl-3-(2-piperidin-1-yl-ethoxy)-phenyl]-2-[(pyridin-4-ylmethyl)-amino]-nicotinamide;
(S)N-[3-(1-Boc-pyrrolidin-2-ylmethoxy)-4-pentafluoroethyl-phenyl]-2-[(pyridin-4-ylmethyl)-amino]-nicotinamide;
(R)N-[3-(1-Boc-pyrrolidin-2-ylmethoxy)-4-trifluoromethyl-phenyl]-2-[(pyridin-4-ylmethyl)-amino]-nicotinamide;
(R)N-[3-(1-Boc-pyrrolidin-2-ylmethoxy)-4-pentafluoroethyl-phenyl]-2-[(pyridin-4-ylmethyl)-amino]-nicotinamide;
N-(4-tert-Butyl-phenyl)-2-{[2-(1-methyl-piperidin-4-yloxy)-pyridin-4-ylmethyl]-amino}-nicotinamide;
N-(3-Trifluoromethyl-phenyl)-2-{[2-(1-methyl-piperidin-4-yloxy)-pyridin-4-ylmethyl]-amino}-nicotinamide;
N-(3-tert-Butyl-isoxazol-5-yl)-2-{[2-(1-methyl-piperidin-4-yloxy)-pyridin-4-ylmethyl]-amino}-nicotinamide;
N-[3-(3-Piperidin-1-yl-propyl)-5-trifluoromethyl-phenyl]-2-[(pyridin-4-ylmethyl)-amino]-nicotinamide;
N-[3-(3-Morpholin-4-yl-propyl)-5-trifluoromethyl-phenyl]-2-[(pyridin-4-ylmethyl)-amino]-nicotinamide;
2-[(2-Methoxy-pyridin-4-ylmethyl)-amino]-N-[3-(1-Boc-piperidin-4-yloxy)-5-trifluoromethyl-phenyl]-nicotinamide;
N-(3,3-Dimethylindolin-6-yl){2-[(4-pyridylmethyl)amino](3-pyridyl)}carboxamide edisylate;
N-{4-tert-Butyl-3-[2-(1-Boc-piperidin-4-yl)-ethyl]-phenyl}-2-[(pyridin-4-ylmethyl)-amino]-nicotinamide N-[4-tert-Butyl-3-(1-methyl-azetidin-3-ylmethoxy)-phenyl]-2-[(pyridin-4-ylmethyl)-amino]-nicotinamide;
N-(3,3-Dimethyl-1,1-dioxo-2,3-dihydro-1H-1λ-benzo[d]isothiazol-6-yl)-2-[(pyridin-4-ylmethyl)-amino]-nicotinamide;
N-[1,1,4,4-Tetramethyl-1,2,3,4-tetrahydro-naphth-6-yl]-2-[(pyridin-4-ylmethyl)-amino]-nicotinamide;
N-{4-[1-Methyl-1-(1-methyl-piperidin-4-yl)-ethyl]-phenyl}-2-[(pyridin-4-ylmethyl)-amino]-nicotinamide;
2-[(2-Methoxy-pyridin-4-ylmethyl)-amino]-N-{4-[1-methyl-1-(1-methyl-piperidin-4-yl)-ethyl]-phenyl}-nicotinamide;
N-(3,3-Dimethyl-2,3-dihydro-benzofuran-6-yl)-2-[(pyridin-4-ylmethyl)-amino]-nicotinamide;
N-(3,3-Dimethyl-2,3-dihydro-1H-indol-6-yl)-2-({2-[2-(1-methyl-piperidin-4-yl)-ethoxy]-pyridin-4-ylmethyl}-amino)-nicotinamide;
2-[(Pyridin-4-ylmethyl)-amino]-N-[3-(2-pyrrolidin-1-yl-ethoxy)-4-trifluoromethyl-phenyl]-nicotinamide hydrochloride;

N-(2,2-Dimethyl-3,4-dihydro-2H-benzo[1,4]oxazin-6-yl)-2-[(pyridin-4-ylmethyl)-amino]-nicotinamide;
N-(4,4-Dimethyl-1,2,3,4-tetrahydro-isoquinolin-7-yl)-2-[(pyridin-4-ylmethyl)-amino]-nicotinamide;
N-(3,3-Dimethyl-2,3-dihydro-1H-indol-6-yl)-2-{[2-(1-methyl-piperidin-4-ylmethoxy)-pyridin-4-ylmethyl]-amino}-nicotinamide;
N-(3,3-Dimethylindolin-6-yl){2-[(4-pyridylmethyl)amino](3-pyridyl)}carboxamide hydrochloride;
N-(3,3-Dimethyl-1-piperidin-4-yl-2,3-dihydro-1H-indol-6-yl)-2-[(pyridin-4-ylmethyl)-amino]-nicotinamide;
N-(3,3-dimethyl-2,3-dihydro-1H-indol-6-yl)-2-({2-[2-(1-methyl-pyrrolidin-2-yl)-ethylamino]-pyrimidin-4-ylmethyl}-amino)-nicotinamide;
N-(3,3-dimethyl-2,3-dihydro-1H-indol-6-yl)-2-[(2-methoxy-pyridin-4-ylmethyl)-amino]-nicotinamide;
N-[3,3-Dimethyl-1-(piperidin-4-ylmethyl)-2,3-dihydro-1H-indol-6-yl]-2-[(2-methoxy-pyridin-4-ylmethyl)-amino]-nicotinamide;
N-(3,3-Dimethyl-1-piperidin-4-yl-2,3-dihydro-1H-indol-6-yl)-2-[(2-methoxy-pyridin-4-ylmethyl)-amino]-nicotinamide;
2-[(2-Methoxy-pyridin-4-ylmethyl)-amino]-N-[3-(piperidin-4-ylmethoxy)-5-trifluoromethyl-phenyl]-nicotinamide;
N-[3,3-Dimethyl-1-(pyrrolidin-2-ylmethoxy)-2,3-dihydro-1H-indol-6-yl]-2-[(2-methoxy-pyridin-4-ylmethyl)-amino]-nicotinamide;
2-[(2-Methoxy-pyridin-4-ylmethyl)-amino]-N-[3-(piperazin-1-ylmethyl)-5-trifluoromethyl-phenyl]-nicotinamide;
N-(3,3-dimethyl-2,3-dihydro-1H-indol-6-yl)-2-{[2-(2-morpholin-4-yl-ethoxy)-pyridin-4-ylmethyl]-amino}-nicotinamide;
N-(3,3-dimethyl-2,3-dihydro-1H-indol-6-yl)-2-{[2-(2-morpholin-4-yl-propylamino)-pyridin-4-ylmethyl]-amino}-nicotinamide hydrochloride;
N-(3,3-dimethyl-2,3-dihydro-1H-indol-6-yl)-2-{[2-(1-methyl-piperidin-4-yloxy)-pyridin-4-ylmethyl]-amino}-nicotinamide;
N-(3,3-dimethyl-2,3-dihydro-1H-indol-6-yl)-2-{[2-(2-morpholin-4-yl-propoxy)-pyridin-4-ylmethyl]-amino}-nicotinamide;
N-(4-Pentafluoroethyl-phenyl)-2-[(pyrimidin-4-ylmethyl)-amino]-nicotinamide;
2-{[2-(Azetidin-3-yloxy)-pyridin-4-ylmethyl]-amino}-N-(4-tert-butyl-phenyl)nicotinamide;
N-(2,3,3-Trimethyl-1,1-dioxo-2,3-dihydro-1H-1λ-benzo[d]isothiazol-6-yl)-2-[(pyridin-4-ylmethyl)-amino]-benzamide;
N-(4,4-Dimethyl-1-oxo-1,2,3,4-tetrahydro-isoquinolin-7-yl)-2-[(pyridin-4-ylmethyl)-amino]-nicotinamide hydrochloride;
N-[3,3-Dimethyl-1,1-dioxo-2-(2-piperidin-1-yl-ethyl)-2,3-dihydro-1H-1λ'-benzo[d]isothiazol-6-yl]-2-[(pyridin-4-ylmethyl)-amino]-nicotinamide; and
N-[2-(2-Dimethylamino-ethyl)-3,3-dimethyl-1,1-dioxo-2,3-dihydro-1H-1λ'-benzo[d]isothiazol-6-yl]-2-[(pyridin-4-ylmethyl)-amino]-nicotinamide.

Indications

Compounds of the present invention would be useful for, but not limited to, the prevention or treatment of angiogenesis related diseases. The compounds of the invention have kinase inhibitory activity, such as VEGFR/KDR inhibitory activity. The compounds of the invention are useful in therapy as antineoplasia agents or to minimize deleterious effects of VEGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemagimomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anaemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

The compounds of this invention may also act as inhibitors of other protein kinases, e.g. p38, EGFR, CDK-2, CDK-5, IKK, JNK3, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Definitions

The term "treatment" includes therapeutic treatment as well as prophylactic treatment (either preventing the onset of disorders altogether or delaying the onset of a preclinically evident stage of disorders in individuals).

The term "prevention" includes either preventing the onset of disorders altogether or delaying the onset of a preclinically evident stage of disorders in individuals. This includes prophylactic treatment of those at risk of developing a disease, such as a cancer, for example. "Prophylaxis" is another term for prevention.

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]

dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —$SO_2$—.

The terms "sulfamyl," "aminosulfonyl" and "sulfonamidyl," denotes a sulfonyl radical substituted with an amine radical, forming a sulfonamide (—$SO_2NH_2$)

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The term "aminocarbonyl" denotes an amide group of the formula —C(=O)$NH_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The term "heterocyclylalkylenyl" embraces heterocyclic-substituted alkyl radicals. More preferred heterocyclylalkylenyl radicals are "5- or 6-membered heteroarylalkylenyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—)

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are substituted with one alkyl radical and with two independent alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The arylamino radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups which have been substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The phrase "Formula I-XII" includes sub formulas such as II'.

The compounds of the invention are endowed with kinase inhibitory activity, such as KDR inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of KDR.

The present invention comprises a pharmaceutical composition comprising a therapeutically-effective amount of a compound of Formulas I-XII in association with a least one pharmaceutically-acceptable carrier, adjuvant or diluent.

The present invention also comprises a method of treating angiogenesis related disorders in a subject having or susceptible to such disorder, the method comprising treating the subject with a therapeutically-effective amount of a compound of Formula I

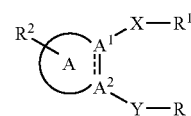

wherein each of $A^1$ and $A^2$ is independently C, CH or N;
wherein ring A is selected from
  a) 5- or 6-membered partially saturated heterocyclyl,
  b) 5- or 6-membered heteroaryl,
  c) 9-, 10- or 11-membered fused partially saturated heterocyclyl,
  d) 9-, 10- or 11-membered fused heteroaryl;
  e) naphthyl, and
  f) 4-, 5- or 6-membered cycloalkenyl;
wherein X is

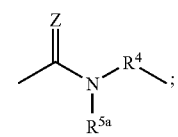

wherein Z is oxygen or sulfur;
wherein Y is selected from

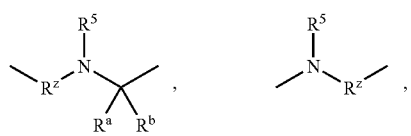

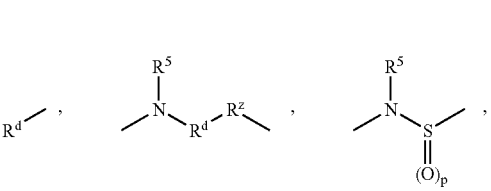

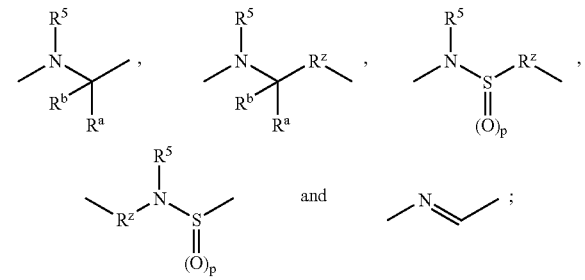

wherein p is 0 to 2,
wherein $R^a$ and $R^b$ are independently selected from H, halo, cyano, —$NHR^6$ and $C_{1-4}$-alkyl substituted with $R^2$, or wherein $R^a$ and $R^b$ together form $C_3$-$C_6$ cycloalkyl;
wherein $R^z$ is selected from $C_2$-$C_6$-alkylenyl, where one of the $CH_2$ groups may be replaced with an oxygen atom or an —NH—; wherein one of the $CH_2$ groups may be substituted with one or two radicals selected from halo, cyano, —$NHR^6$ and $C_{1-4}$-alkyl substituted with $R^2$;

wherein $R^d$ is cycloalkyl;
wherein R is selected from
  a) substituted or unsubstituted 5-6 membered heterocyclyl,
  b) substituted aryl, and
  c) substituted or unsubstituted fused 9-14-membered bicyclic or tricyclic heterocyclyl;
    wherein substituted R is substituted with one or more substituents independently selected from halo, —$OR^3$, —$SR^3$, —$SO_2R^3$, —$CO_2R^3$, —$CONR^3R^3$, —$COR^3$, —$NR^3R^3$—$SO_2NR^3R^3$, —$NR^3C(O)OR^3$, —$NR^3C(O)R^3$, cycloalkyl, optionally substituted 5-6 membered heterocyclyl, optionally substituted phenyl, nitro, alkylaminoalkoxyalkoxy, cyano, alkylaminoalkoxy, lower alkyl substituted with $R^2$, lower alkenyl substituted with $R^2$, and lower alkynyl substituted with $R^2$;
wherein $R^1$ is selected from
  a) substituted or unsubstituted 6-10 membered aryl,
  b) substituted or unsubstituted 5-6 membered heterocyclyl,
  c) substituted or unsubstituted 9-14 membered bicyclic or tricyclic heterocyclyl,
  d) cycloalkyl, and
  e) cycloalkenyl,
    wherein substituted $R^1$ is substituted with one or more substituents independently selected from halo, —$OR^3$, —$SR^1$, —$CO_2R^3$, —$CONR^3R^3$, —$COR^3$, —$NR^3R^3$, —$NH(C_1$-$C_4$ alkylenyl$R^{14}$), —$SO_2R^3$, —$SO_2NR^3R^3$, —$NR^3C(O)OR^3$, —$NR^3C(O)R^3$, optionally substituted cycloalkyl, optionally substituted 5-6 membered heterocyclyl, optionally substituted phenyl, halosulfonyl, cyano, alkylaminoalkoxy, alkylaminoalkoxyalkoxy, nitro, lower alkyl substituted with $R^2$, lower alkenyl substituted with $R^2$, and lower alkynyl substituted with $R^2$;
wherein $R^2$ is one or more substituents independently selected from H, halo, —$OR^3$, oxo, —$SR^3$, —$CO_2R^3$, —$COR^3$, —$CONR^3R^3$, —$NR^3R^3$, —$SO_2NR^3R^3$, —$NR^3C(O)OR^3$, —$NR^3C(O)R^3$, cycloalkyl, optionally substituted phenylalkylenyl, optionally substituted 5-6 membered heterocyclyl, optionally substituted heteroarylalkylenyl, optionally substituted phenyl, lower alkyl, cyano, lower hydroxyalkyl, lower carboxyalkyl, nitro, lower alkenyl, lower alkynyl, lower aminoalkyl, lower alkylaminoalkyl and lower haloalkyl;
wherein $R^3$ is selected from H, lower alkyl, phenyl, heterocyclyl, $C_3$-$C_6$-cycloalkyl, phenylalkyl, heterocyclylalkyl, $C_3$-$C_6$ cycloalkylalkyl, and lower haloalkyl;
wherein $R^4$ is selected from a direct bond, $C_{2-4}$-alkylenyl, $C_{2-4}$-alkenylenyl and $C_{2-4}$-alkynylenyl, where one of the $CH_2$ groups may be substituted with an oxygen atom or an —NH—, wherein $R^4$ is optionally substituted with hydroxy;
wherein $R^5$ is selected from H, lower alkyl, phenyl and lower aralkyl;
wherein $R^{5a}$ is selected from H, lower alkyl, phenyl and lower aralkyl;
wherein $R^6$ is selected from H or $C_{1-6}$-alkyl; and
wherein $R^{14}$ is selected from H, phenyl, 5-6 membered heterocyclyl and $C_3$-$C_6$ cycloalkyl;
and pharmaceutically acceptable derivatives thereof; provided A is not naphthyl when X is —C(O)NH— and when $R^1$ is phenyl when Y is —$NCH_2$— and when R is 4-pyridyl; and further provided R is not unsubstituted 2-thienyl, 2-pyridyl or 3-pyridyl when Y is —$NHCH_2$—.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneously with, or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other anti-neoplastic agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The present invention comprises processes for the preparation of a compound of Formula I-XII.

Also included in the family of compounds of Formula I-XII are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I-XII may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I-XII include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I-XII.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases. Preferred salts include hydrochloride, phosphate and edisylate.

Additional examples of such salts can be found in Berge et al., J. Pharm. Sci., 66, 1 (1977).

General Synthetic Procedures

The compounds of the invention can be synthesized according to the following procedures of Schemes 1-48, wherein the substituents are as defined for Formulas I-XII, above, except where further noted.

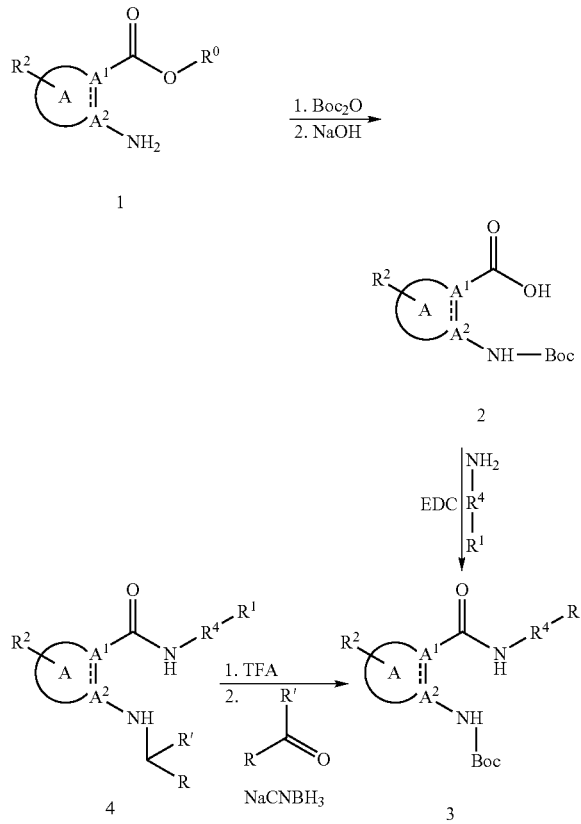

Scheme 1

Cyclic amides can be prepared according to the method set out in Scheme 1. The amino group of compound 1 (where $R^0$ is alkyl, aryl, and the like) is protected, such as with Boc anhydride, followed by treatment, to remove the ester, such as with base, forming the protected amine/free acid 2. Alternatively, other amino protecting groups known in the art can be used. Substituted amines are coupled with the free acid, such as with EDC, to form the protected amine/amide 3. The protected amine moiety is deprotected, such as with acid, and reacted via one step reductive alkylation with carbonyl-containing compounds (where R is H, halo, cyano, —NHR$^6$ and $C_{1-4}$ alkyl) to form the 1-amido-2-substituted amino-compounds 4. Preferably the amination is in an alcohol, such as MeOH, EtOH or propanol, and at a temperature between about 0-50° C., such as RT. Aldehydes or ketones are preferred carbonyl-containing compounds. Alternative carbonyl-containing compounds are, for example, bisulfite adducts or hemiacetals, acetals, hemiketals or ketals of compounds with alcohols, for example lower hydroxyalkyl compounds; or thioacetals or thioketals of compounds with mercaptans, for example lower alkylthio compounds. The reductive alkylation is preferably carried out with hydrogenation in the presence of a catalyst, such as platinum or especially palladium, which is preferably bonded to a carrier material, such as carbon, or a heavy metal catalyst, such as Raney nickel, at normal pressure or at pressures of from 0.1 to 10 MegaPascal (MPa), or with reduction by means of complex hydrides, such as borohydrides, especially alkali metal cyanoborohydrides, for example sodium cyanoborohydride, in the presence of a suitable acid, preferably relatively weak acids, such as lower alkylcarboxylic acids, especially acetic acid, or a sulfonic acid, such as p-toluenesulfonic acid; in customary solvents, for example alcohols, such as MeOH or EtOH, or ethers, for example cyclic ethers, such as THF, in the presence or absence of water.

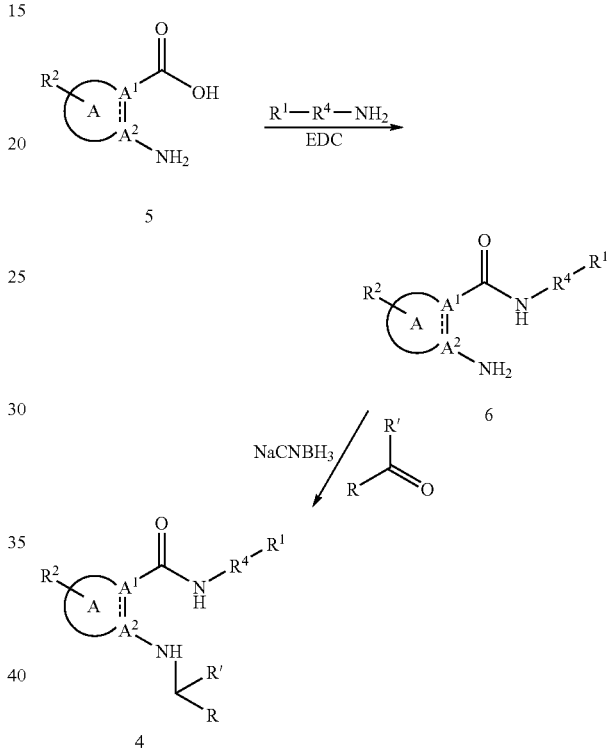

Scheme 2

Alternatively, compounds 4 can be prepared from mixed acid/amines 5 as shown in Scheme 2. Substituted amines are coupled with the mixed acid/amines 5 such as with a coupling reagent, for example EDC, to form the mixed amine/amide 6. Substituted carbonyl compounds, such as acid halides, anhydrides, carboxylic acids, esters, ketones, aldehydes and the like, are added to the mixed amine/amide 6 followed with reduction to give the substituted amide/substituted amine compounds 4.

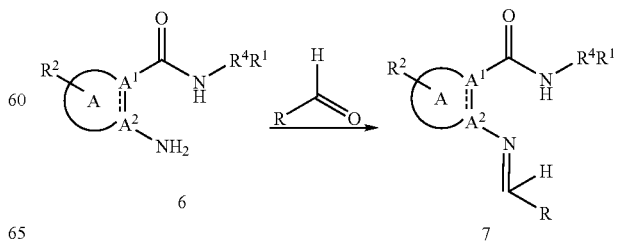

Scheme 3

Imino compounds 7 can be formed from the mixed amine/amides 6, such as by reacting with a substituted carbonyl compound.

Scheme 4

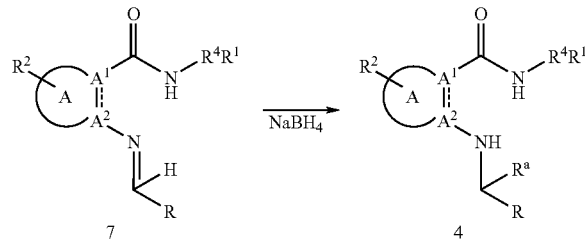

Substituted cyclic carboxamides can be prepared from the corresponding imino analogs by the process outlined in Scheme 4. Treatment of the imino compound 7 with a reducing agent yields compound 4. Reagents which can be used to add hydrogen to an imine double bond include borane in THF, LiAlH$_4$, NaBH$_4$, sodium in EtOH and hydrogen in the presence of a catalyst, and others.

Scheme 5

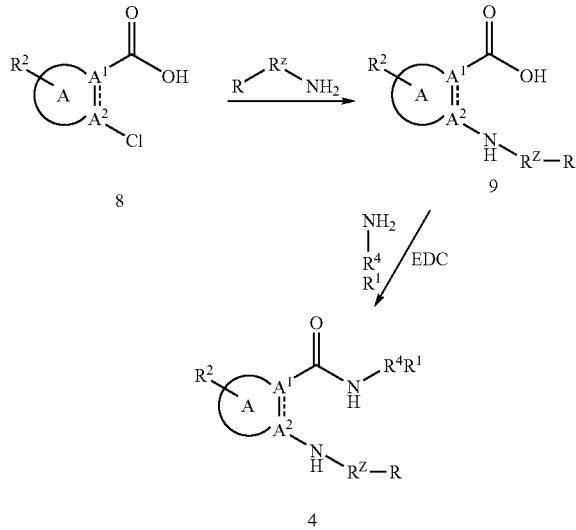

Substituted carboxamides 4 can be prepared from the corresponding halo analogs 8 by the process outlined in Scheme 5. Substituted amino acids 9 are prepared from the corresponding chloro compounds 8 such as by reacting with an amine at a suitable temperature, such as about 80° C. The acid 9 is coupled with an amine, preferably in the presence of a coupling agent such as EDC, to form the corresponding amide 4.

The amination process can be carried out as an Ullmann type reaction using a copper catalyst, such as copper[0] or a copper[I] compound such as copper[I]oxide, copper[I]bromide or copper[I]iodide in the presence of a suitable base (such as a metal carbonate, for example K$_2$CO$_3$) to neutralize the acid generated in the reaction. This reaction is reviewed in Houben-Weyl "Methoden der Organischen Chemie", Band 11/1, page 32-33, 1958, in Organic Reactions, 14, page 19-24, 1965 and by J. Lindley (1984) in Tetrahedron, 40, page 1433-1456. The amount of catalyst is typically in the range of 1 to 20 mole percent. The reaction is carried out in an inert, aprotic solvent such as an ether (for example dimethoxyethane or dioxane) or an amide (for example dimethylformamide or N-methylpyrrolidone), under an inert atmosphere in the temperature range of 60-180° C.

An alternative amination process involves using a Group VIII element, where the metal core of the catalyst should be a zero-valent transition metal, such as palladium or nickel, which has the ability to undergo oxidative addition to the aryl-halogen bond. The zero valent state of the metal may be generated in situ from the M[II] state. The catalyst complexes may include chelating ligands, such as alkyl, aryl or heteroaryl derivatives of phosphines or biphosphines, imines or arsines. Preferred catalysts contain palladium or nickel. Examples of such catalysts include palladium[II]chloride, palladium[II]acetate, tetrakis(triphenyl-phosphine)palladium[0] and nickel[II]acetylacetonate. The metal catalyst is typically in the range of 0.1 to 10 mole percent. The chelating ligands may be either monodentate, as in the case for example of trialkyphosphines, such as tributylphosphine, triarylphosphines, such as tri-(ortho-tolyl)phosphine, and triheteroaryl phosphines, such as tri-2-furylphosphine; or they may be bidentate such as in the case of 2,2'-bis(diphenylphosphino)-1,1'binaphthyl, 1,2-bis(diphenylphosphino)ethane, 1,1'-bis(diphenylphosphino)ferrocene and 1-(N,N-dimethylamino)-1'-(dicyclohexylphosphino)biphenyl. The supporting ligand may be complexed to the metal center in the form of a metal complex prior to being added to the reaction mixture or may be added to the reaction mixture as a separate compound. The supporting ligand is typically present in the range 0.01 to 20 mole percent. It is often necessary to add a suitable base to the reaction mixture, such as a trialkylamine (for example DIEA or 1,5-diazabicyclo[5,4,0]undec-5-ene), a Group I alkali metal alkoxide (for example potassium tert-butoxide) or carbonate (for example cesium carbonate) or potassium phosphate. The reaction is typically carried out in an inert aprotic solvent such as an ether (for example dimethoxyethane or dioxane) or an amide (for example, DMF or N-methylpyrrolidone), under an inert atmosphere in the temperature range of 60-180° C.

The amination is preferably carried out in an inert, aprotic, preferably anhydrous, solvent or solvent mixture, for example in a carboxylic acid amide, for example DMF or dimethylacetamide, a cyclic ether, for example THF or dioxane, or a nitrile, for example CH$_3$CN, or in a mixture thereof, at an appropriate temperature, for example in a temperature range of from about 40° C. to about 180° C., and if necessary under an inert gas atmosphere, for example a nitrogen or argon atmosphere.

Scheme 6

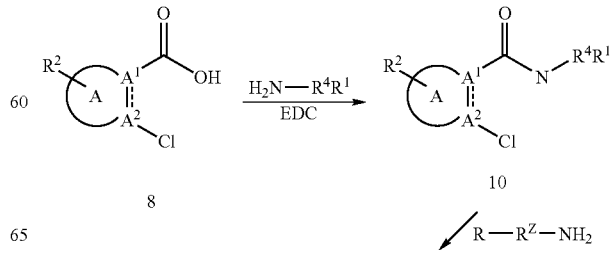

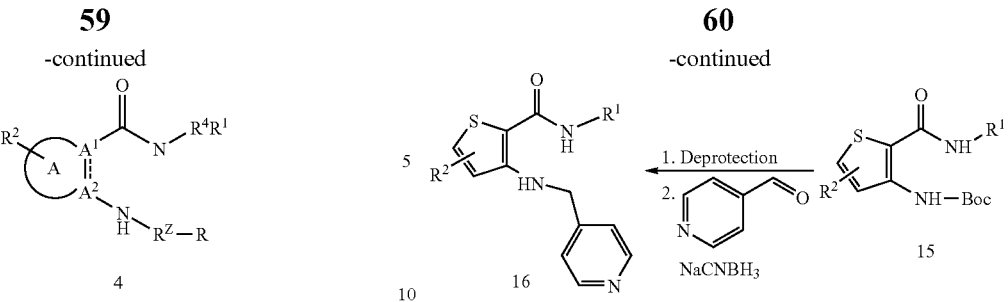

Substituted carboxamides 4 can be prepared from the corresponding halo analogs 8 by the process outlined in Scheme 6. The chloro acid 8 is coupled with an amine, preferably in the presence of a coupling agent such as EDC, to form the corresponding chloro amide 10. Substituted amino-amides 4 are prepared from the corresponding chloro compounds 10 such as by reacting with an amine at a suitable temperature, such as about 80° C. The amination reaction can be run in the presence of an appropriate catalyst such as a palladium catalyst, in the presence of an aprotic base such as sodium t-butoxide or cesium carbonate, or a nickel catalyst, or a copper catalyst.

Substituted thiophenes 16 can be prepared by the method of Scheme 8. The free amino group of a 3-amino-2-thiophenecarboxylic acid ester 13 can be protected such as by the addition of $Boc_2O$ in a suitable solvent such as $CH_2Cl_2$ and DMAP. The ester is removed such as with base to form the free acid 14. The thiophene amide 15 is formed from the acid 14 such as by coupling with a substituted amine in the presence of DIEA, EDC and HOBt. The 2-protected-aminothiophene amide 15 is deprotected, such as with 25% TFA/$CH_2Cl_2$. The free amine is alkylated such as with a substituted carboxaldehyde or similar active carbonyl compound, in the presence of a reducing agent $NaCNBH_3$ and the like, to form compounds 16.

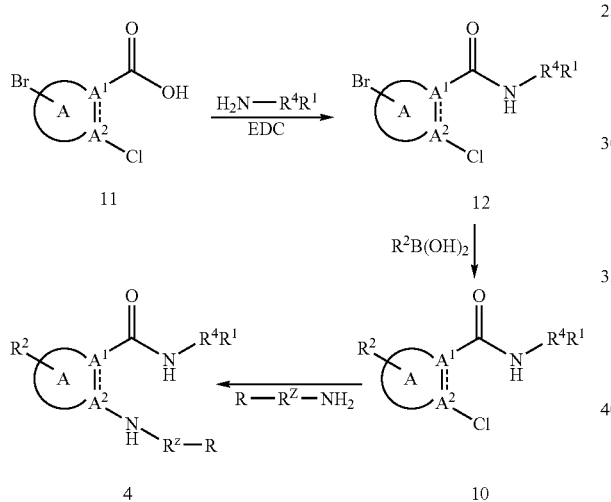

Substituted carboxamides 4 can be prepared from the corresponding bromo/chloro analogs 11 by the process outlined in Scheme 7. The bromo/chloro acid 11 is coupled with an amine, preferably in the presence of a coupling agent such as EDC, to form the corresponding bromo substituted amide 12. Suzuki coupling with the bromo amide 12 and suitable boronic acids provides the substituted amide 10. Substituted amino-amides 4 are prepared from the corresponding chloro compounds 10 as described in Scheme 6.

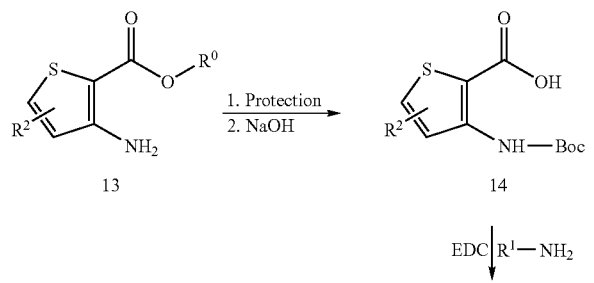

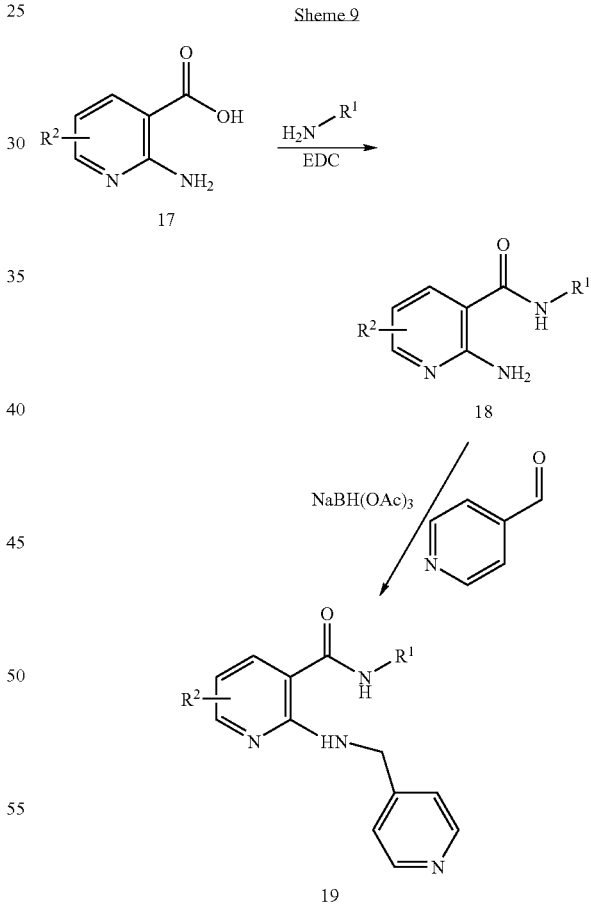

Substituted pyridines can be prepared such as by the method found in Scheme 9. 2-Aminonicotinic acid 17 is coupled with a substituted amine at a suitable temperature, nonprotic solvent such as $CH_2Cl_2$, such as with EDC and HOBt, to form the nicotinamide 18. The nicotinamide 18 is reductively alkylated such as with 4-pyridinecarboxaldehyde and $NaBH(OAc)_3$, to yield the 2-substituted amino-pyridyl carboxamides 19.

Scheme 10

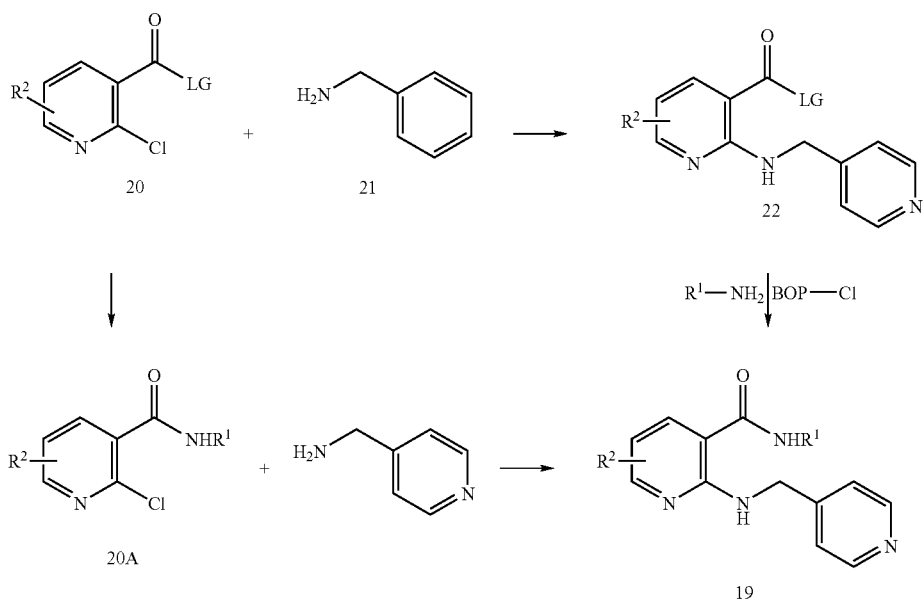

Substituted pyridines may be prepared by the method found in Scheme 10. 2-Chloro-nicotinic acid 20 is coupled with an amine 21 at a suitable temperature, such as a temperature over about 100° C. to give the 2-substituted amino-nicotinic acid 22. The 2-substituted amino-nicotinic acid 22 is reacted with a substituted amine in the presence of a coupling reagent, such as BOP—Cl and base, such as TEA to form the 2-substituted amino-nicotinamide 19.

Alternatively, 2-chloro-nicotinoyl chloride (LG is Cl) is coupled first with $R^1$—$NH_2$ such as in the presence of base, e.g., $NaHCO_3$, in a suitable solvent, such as $CH_2Cl_2$, to form the amide 20A, then coupling with a pyridylmethylamine to yield the 2-substituted amino-nicotinamide 19.

Scheme 11

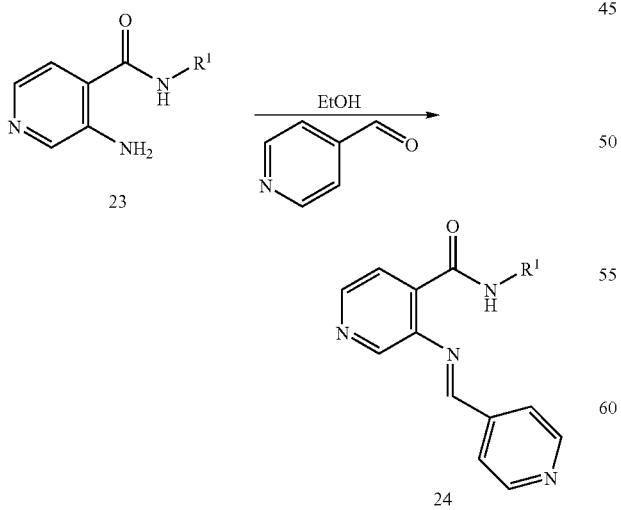

Imino-substituted pyridines may be prepared by the method found in Scheme 11. (2-Amino-(4-pyridyl))-carboxamide 23 is reacted with 4-pyridine-carboxaldehyde, such as in the presence of p-toluenesulfonic acid monohydrate to yield the imino compound 24.

Scheme 12

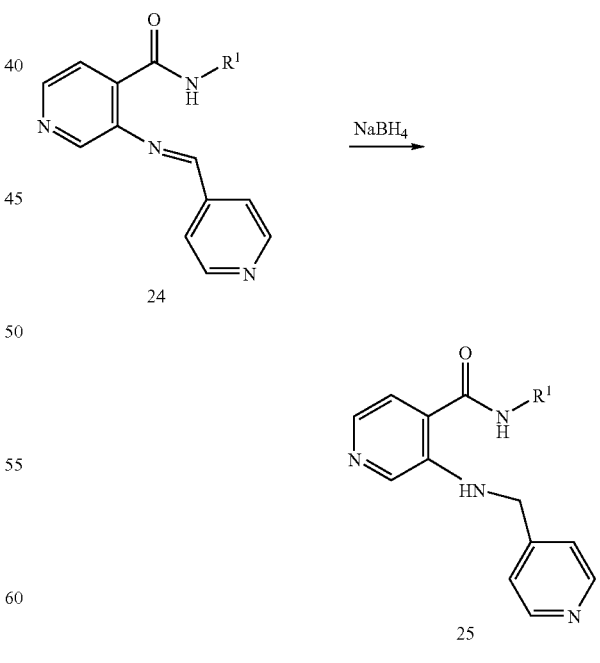

Substituted pyridines alternatively may be prepared by the method found in Scheme 12. The imino compound 24 is reduced, such as with $NaBH_4$, to form the substituted amine 25.

Scheme 13

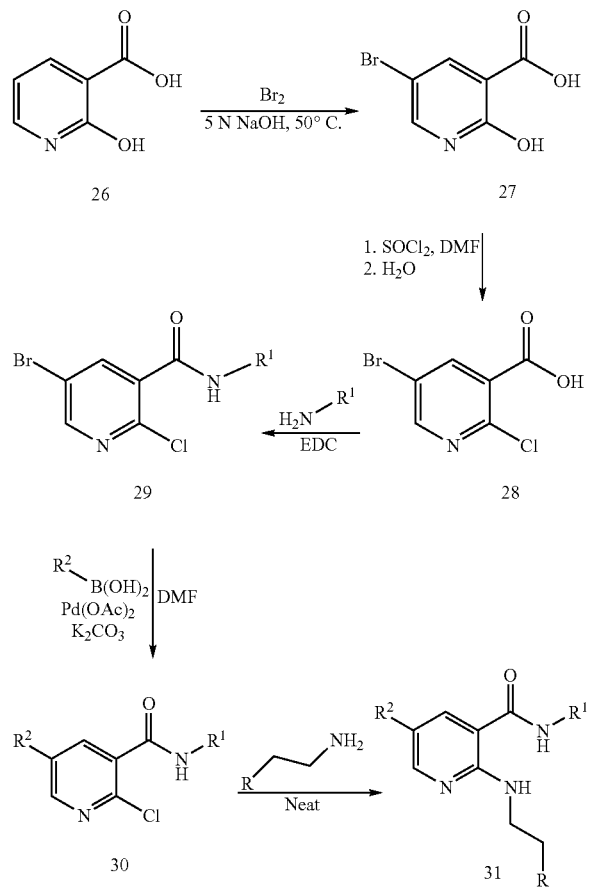

Substituted pyridines can be prepared by the process outlined in Scheme 13. A solution of sodium hypobromide is freshly prepared and added to 2-hydroxynicotinic acid 26 and heated, preferably at a temperature at about 50° C. Additional sodium hypobromide may be needed to form the bromo compound 27. The 5-bromo-2-hydroxynicotinic acid 27 is reacted with thionyl chloride, preferably at a temperature >RT, more preferably at about 80° C. to form the 2-chloro-nicotinic acid analog 28. The acid is coupled with an amine, preferably in the presence of EDC, HOBT, and DIEA to form the corresponding substituted amide 29. Suzuki coupling with the bromo amide and suitable boronic acids, provides the substituted nicotinamide 30. 2-Amino-nicotinamides 31 are prepared from the corresponding chloro compounds 30 such as by reacting with substituted amines at a suitable temperature, such as about 80° C.

Scheme 14

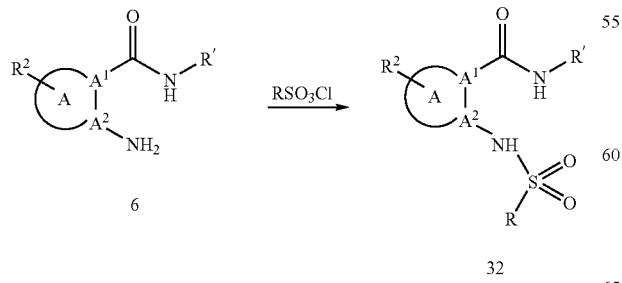

Sulfonamides 32 can be prepared from amines 6 as shown in Scheme 14. Substituted sulfonyl compounds, such as sulfonyl halides, preferably chloro or bromo, sulfonic acids, an activated ester or reactive anhydride, or in the form of a cyclic amide, and the like, are added to the amine 6 to give the sulfonamide compounds 32.

The reaction is carried out in a suitable solvent, such as $CH_2Cl_2$, at a temperature between about RT to about the reflux temperature of the solvent, in the presence of a suitable base, such as DIEA or DMAP.

The amino group of compounds 6 is preferably in free form, especially when the sulfonyl group reacting therewith is present in reactive form. The amino group may, however, itself be a derivative, for example by reaction with a phosphite, such as diethylchlorophosphite, 1,2-phenylene chlorophosphite, ethyldichlorophosphite, ethylene chlorophosphite or tetraethylpyrophosphite. A derivative of such a compound having an amino group also can be a carbamic acid halide or an isocyanate.

The condensation of activated sulfonic esters, reactive anhydrides or reactive cyclic amides with the corresponding amines is customarily carried out in the presence of an inorganic base, such as an alkaline metal hydrogen carbonate of carbonate, or especially an organic base, for example simple lower $(alkyl)_3$-amines, for example TEA or tributylamine, or one of the above-mentioned organic bases. If desired, a condensation agent is additionally used, for example as described for free carboxylic acids.

The condensation is preferably carried out in an inert, aprotic, preferably anhydrous, solvent or solvent mixture, for example in a carboxylic acid amide, for example formamide or DMF, a halogenated hydrocarbon, for example $CH_2Cl_2$, $CCl_4$ or chlorobenzene, a ketone, for example acetone, a cyclic ether, for example THF or dioxane, an ester, for example EtOAc, or a nitrile, for example $CH_3CN$, or in a mixture thereof, as appropriate at reduced or elevated temperature, for example in a temperature range of from about −40° C. to about +100° C., preferably from about −10° C. to about 70° C., and when arylsulfonyl esters are used, also at temperatures of from about 10-30° C., and if necessary under an inert gas atmosphere, for example a nitrogen or argon atmosphere.

Alcoholic solvents, for example EtOH, or aromatic solvents, for example benzene or toluene, may also be used. When alkali metal hydroxides are present as bases, acetone may also be added where appropriate.

Scheme 15

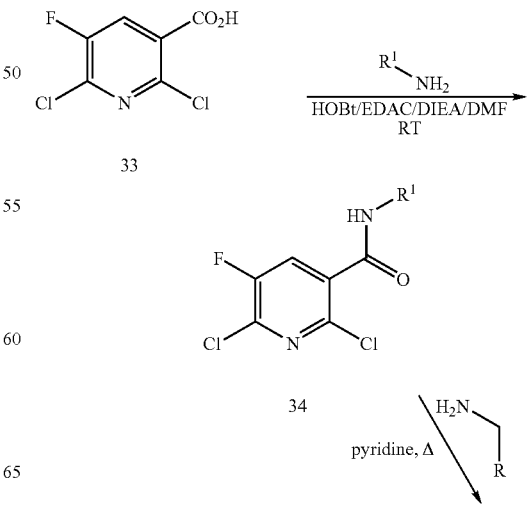

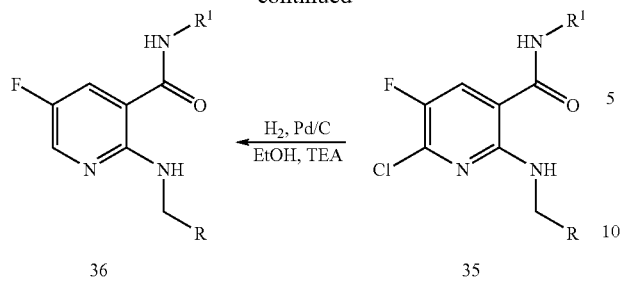

Substituted pyridines can be prepared by the process outlined in Scheme 15. 2-Chloronicotinic acid 33 and substituted amine are coupled under conditions similar to that described in the previous schemes to give the amide 34. 6-Chloro-2-aminopyridines 35 are prepared from the amide 34, such as by reacting with substituted amines at a suitable temperature, such as above about 80° C., preferably above about 100° C., more preferably at about 130° C., neat. 6-Chloro-2-aminopyridines 35 are de-chlorinated such as by hydrogenation, for example by treatment with $H_2$ in the presence of Pd/C, to yield other compounds of the present invention 36.

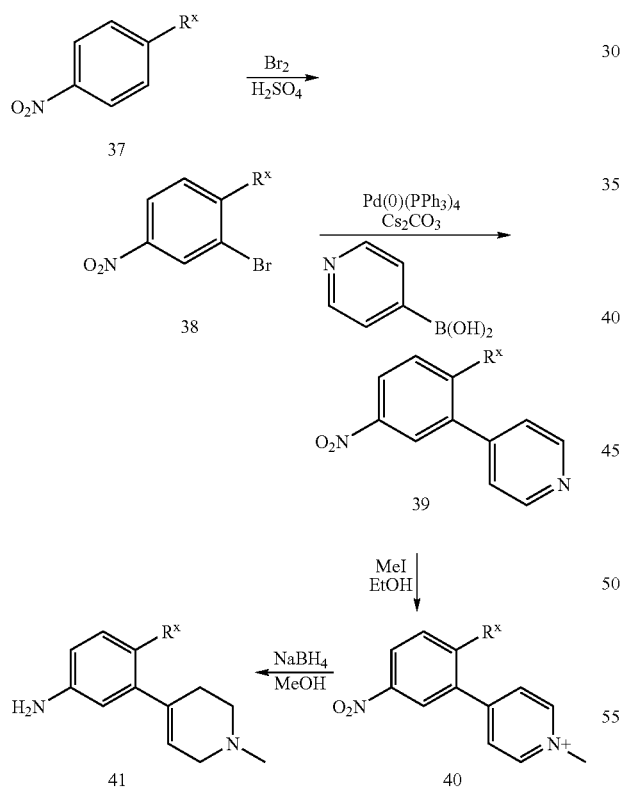

1,2,3,6-Tetrahydro-pyridyl substituted anilines are prepared such as by the procedure described in Scheme 16 (where $R^x$ is a substituent selected from those available for substituted $R^1$). Nitrobenzenes 37 are brominated, such as with bromine in the presence of acid, $H_2SO_4$ for example, or with NBS to yield the 3-bromo derivative 38. Suzuki coupling of the bromo-derivative 38 and a substituted pyridylboronic acid, in an appropriate solvent such as toluene, such as at a temperature above RT, preferably above about 50° C., and more preferably at about 80° C., yields the pyridyl derivative 39. Alkylation of the nitrophenyl-pyridine 39, such as by treatment with iodomethane, preferably above about 50° C., and more preferably at about 80° C., yields the pyridinium compound 40, which upon reduction, such as by $NaBH_4$, yields the tetrahydropyridine 41.

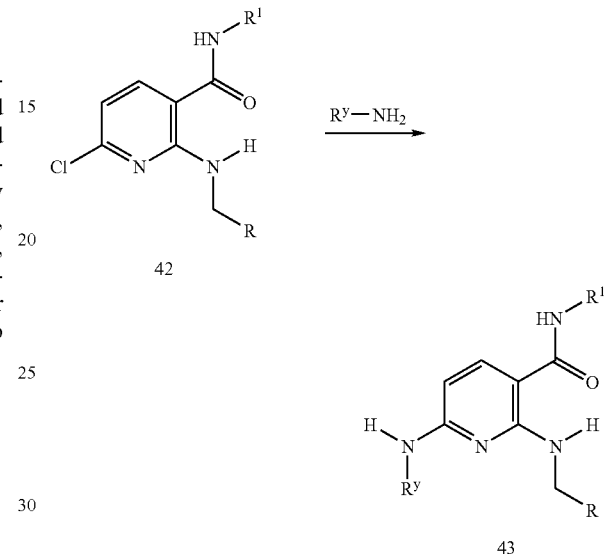

6-Amino substituted pyridines are prepared such as by the procedure described in Scheme 17. Similar to the method of Scheme 13, chloropyridine 42 and is reacted with an amine, preferably above about 50° C., and more preferably at about 80° C., to yield the 6-aminopyridines 43.

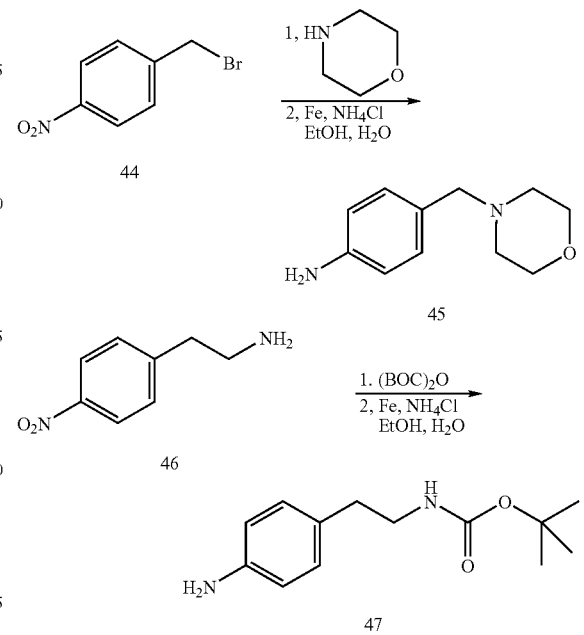

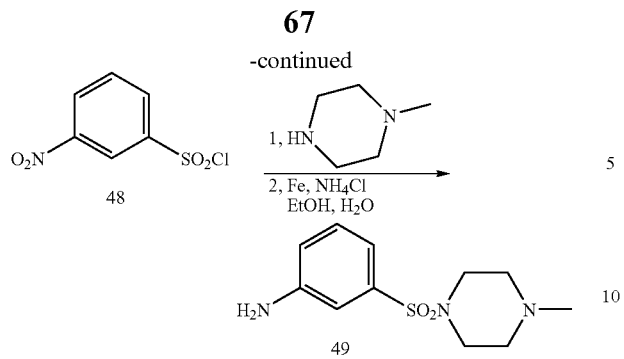

A series of substituted anilines are prepared such as by the procedure described in Scheme 18. A nitrobenzyl bromide 44 is coupled with morpholine, such as at a temperature at about RT, to yield the heterocyclylmethyl nitrobenzene derivative. Reduction of the nitro compound, such as with iron powder, preferably above about 50° C., and more preferably at about 80° C., yields the heterocyclylmethyl substituted aniline 45.

Protected alkylamine substituted anilines can be prepared from the nitro free amines 46, such as with standard protecting agents and chemistry known in the art, such as BOC chemistry. Reduction of the protected nitro compound, such as with iron powder, preferably above about 50° C., and more preferably at about 80° C., yields the aniline 47.

Sulfonamide substituted anilines can be prepared from nitrobezenesulfonyl chlorides 48. Coupling of nitrobezenesulfonyl chlorides 48 with reactive heterocyclic compounds, such as substituted piperazines, piperidines, and the like, in a protic solvent such as EtOH, such as at a temperature about RT, yields the nitrobezenesulfonamides 48. Reduction of the nitro benzenesulfonamide, such as with iron powder, preferably above about 50° C., and more preferably at about 80° C., yields the aniline 49.

Scheme 19

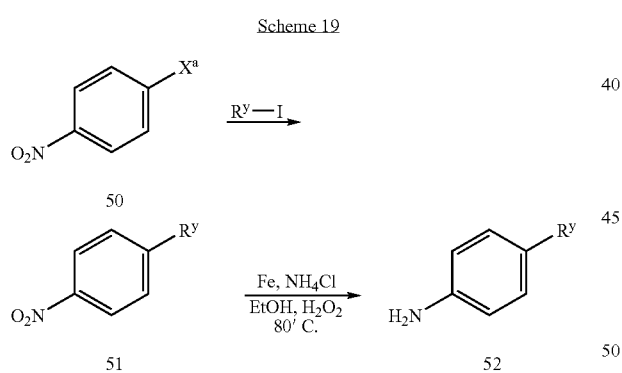

A series of perhaloalkyl-substituted anilines 52, where $R^y$ represents perhaloalkyl radicals, are prepared such as by the procedure described in Scheme 19. 1-Nitro-4-(perfluoroethyl)benzene can be synthesized by the method described in the reference [John N. Freskos, Synthetic Communications, 18(9), 965-972 (1988)]. Alternatively, 1-Nitro-4-(perfluoroalkyl)benzene can be synthesized from the nitro compound, where $X^a$ is a leaving group, such as iodo, by the method described by W. A. Gregory, et al. [J. Med. Chem., 1990, 33, 2569-2578].

Reduction of the nitrobenzenes 51, such as with iron powder, at a temperature above about 50° C., and preferably at about 80° C., yields the aniline 52. Hydrogenation, such as with $H_2$ in the presence of catalyst, such as Pd/C, is also possible.

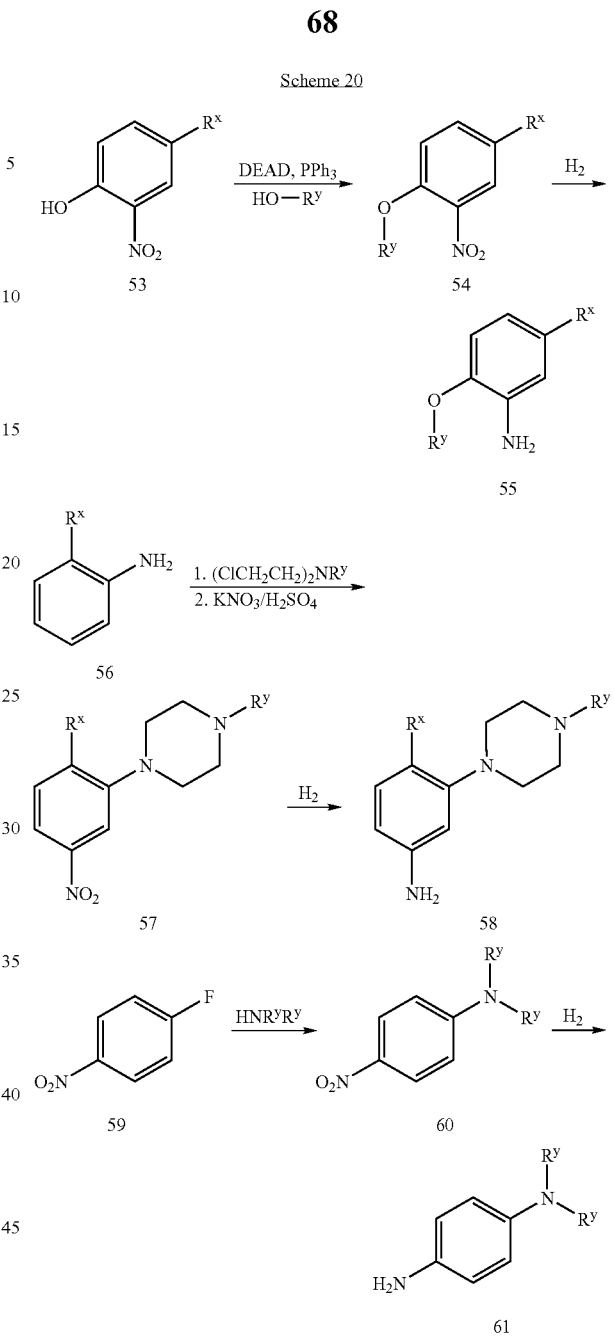

Additional series of substituted anilines are prepared such as by the procedures described in Scheme 20 (where $R^x$ is a substituent selected from those available for substituted $R^1$). 2-Alkoxy substituted anilines 55 are prepared from the corresponding phenol compounds 53 such as by the Mitsunobu reaction, including treatment with a N,N-dialkylethanolamine and $PPh_3$ and DEAD to give the corresponding nitro compound 54, followed by hydrogenation, such as with $H_2$ to give the aniline 55.

Alternatively, piperazinyl substituted anilines 58 can be prepared by the treatment of an aniline 56 with an N-substituted-bis(2-chloroethyl)amine, base, such as $K_2CO_3$ and NaI, at a temperature above about 50° C., preferably above about 100° C., and more preferably at about 170° C., to give the piperazinylbenzene compound 57. Nitration, such as with $H_2SO_4$ and $HNO_3$, at a temperature above 0° C., and preferably at about RT, followed by hydrogenation, such as with H$_2$ atmosphere gives the substituted aniline 58.

Alternatively, piperazinyl substituted anilines 61 can be prepared by the treatment of a fluoro-nitro-substituted aryl compounds 59. The fluoro-nitro-substituted aryl compounds 59 and 1-substituted piperazines are heated, preferably neat, at a temperature above about 50° C., and preferably at about 90° C., to yield the piperazinyl-nitroaryl compounds 60. Hydrogenation, such as with H$_2$ atmosphere in the presence of a catalyst, such as 10% Pd/C, gives the substituted aniline 61.

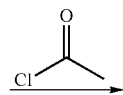

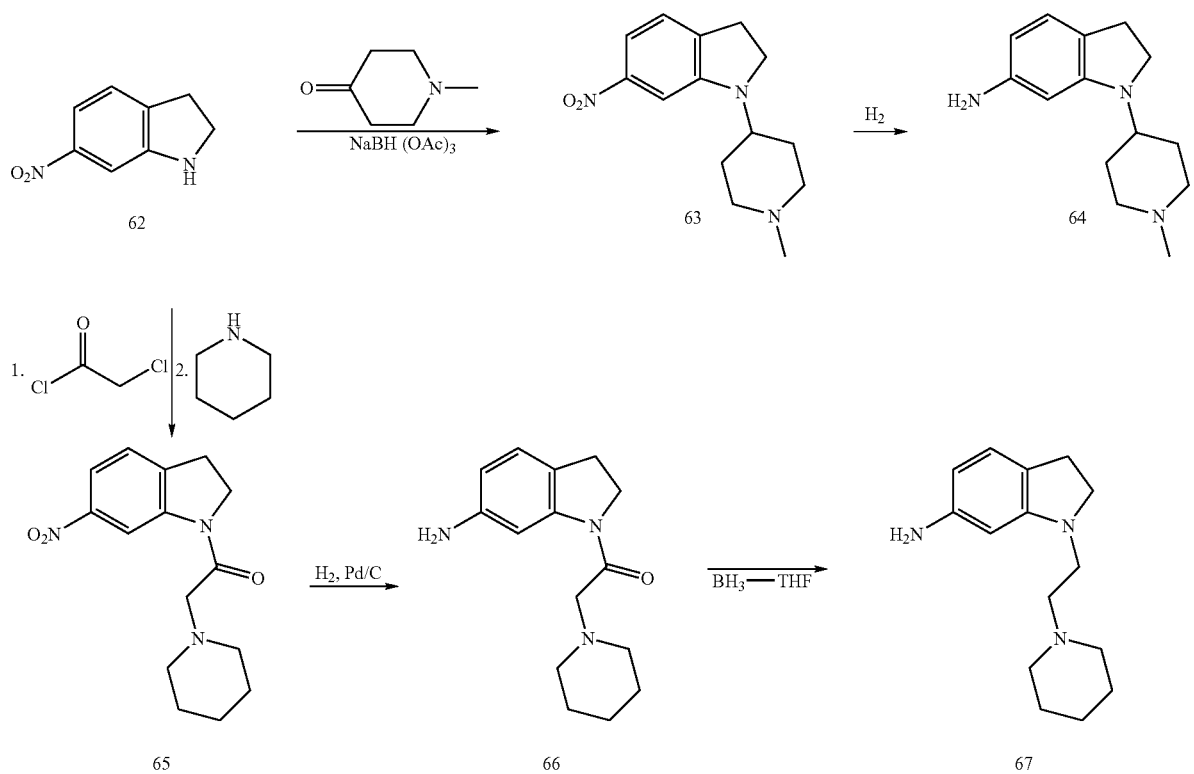

Substituted indolines are prepared such as by the procedures described in Scheme 21. Substituted amino-indolines 64 are prepared from the nitroindoline 62 and a ketone in the presence of NaHB(OAc)$_3$ to form the 1-substituted indoline 63. The nitroindoline 63 is hydrogenated, such as with H$_2$ in the presence of a catalyst, such as Pd/C, to yield the amino-indoline 64.

Alternatively, substituted amino-indolines 67 are prepared from the nitroindoline 62. Nitroindoline 62, is reacted with an acid chloride to form an amide. Further treatment with a primary or secondary amine, preferably a secondary amine, such as in the presence of NaI, at a temperature above about 50° C., and preferably at about 70° C. yields the nitroindoline 65. The nitro compound 65 is hydrogenated, such as with H$_2$ in the presence of a catalyst, such as Pd/C, to yield the amino-indoline 66. The carbonyl is reduced, such as with BH$_3$-THF yields 1-aminoalkyl-indolines 67.

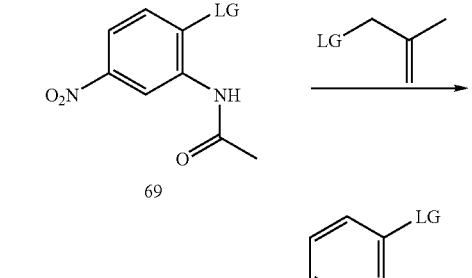

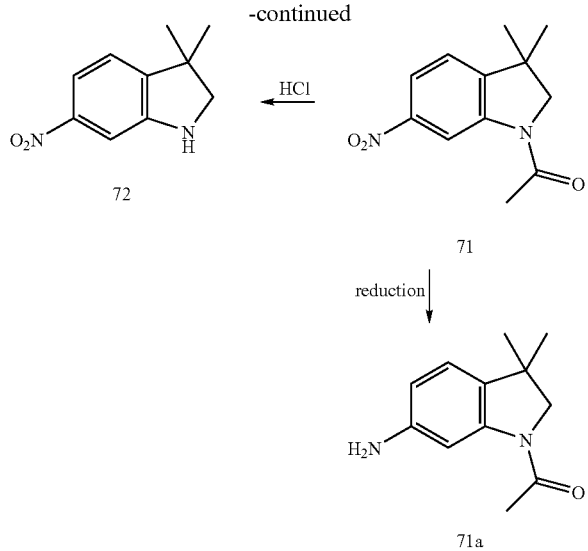

Substituted indolines are prepared such as by the procedures described in Scheme 22. Substituted acetamides 69 are prepared from the acylation of halo-5-nitroanilines 68 (where LG is bromo or chloro, preferably chloro) with an acylating agent, such as acetyl chloride or acetic anhydride, under standard coupling chemistry, such as with DIEA, and DMAP, at a temperature of about RT, in a suitable solvent, such as $CH_2Cl_2$, DMF and/or DMAC. The N-(2-methylprop-2-enyl) acetamide 70 is prepared from the acetamide 69, such as by the treatment of base, such as NaH in anhydrous DMF and a 3-halo-2-methylpropene such as 3-bromo-2-methylpropene or 3-chloro-2-methylpropene, at a temperature between about 0° C. and RT, and preferably at about RT; or with $CsCO_3$ at a temperature above RT, preferably above about 50° C. and more preferably above about 60° C. Cyclization of the N-(2-methylprop-2-enyl)acetamide 70, such as by the Heck-type reaction (treatment with $Pd(OAc)_2$ in the presence of base, for example tetraethyl-ammonium chloride, sodium formate, and NaOAc) at a temperature above about 50° C., and preferably at about 80° C., yields the protected (3,3-dimethyl-2,3-dihydro-indol-1-yl)ethanone 71. Deprotection, such as with strong acid such as AcOH on HCl at a temperature above about 50° C., and preferably at about 70-80° C., yields the 3,3-dimethyl-6-nitro-2,3-dihydro-indol-1-yl 72. Alternatively, the protected dihydro-6-nitro indoline 71 can be reduced, such as with Fe, or with 10% Pd/C in the presence of an excess of $NH_4CO_2H$, or with $H_2$ in the presence of a catalyst to form the protected dihydro-6-amino indoline 71a.

Scheme 23

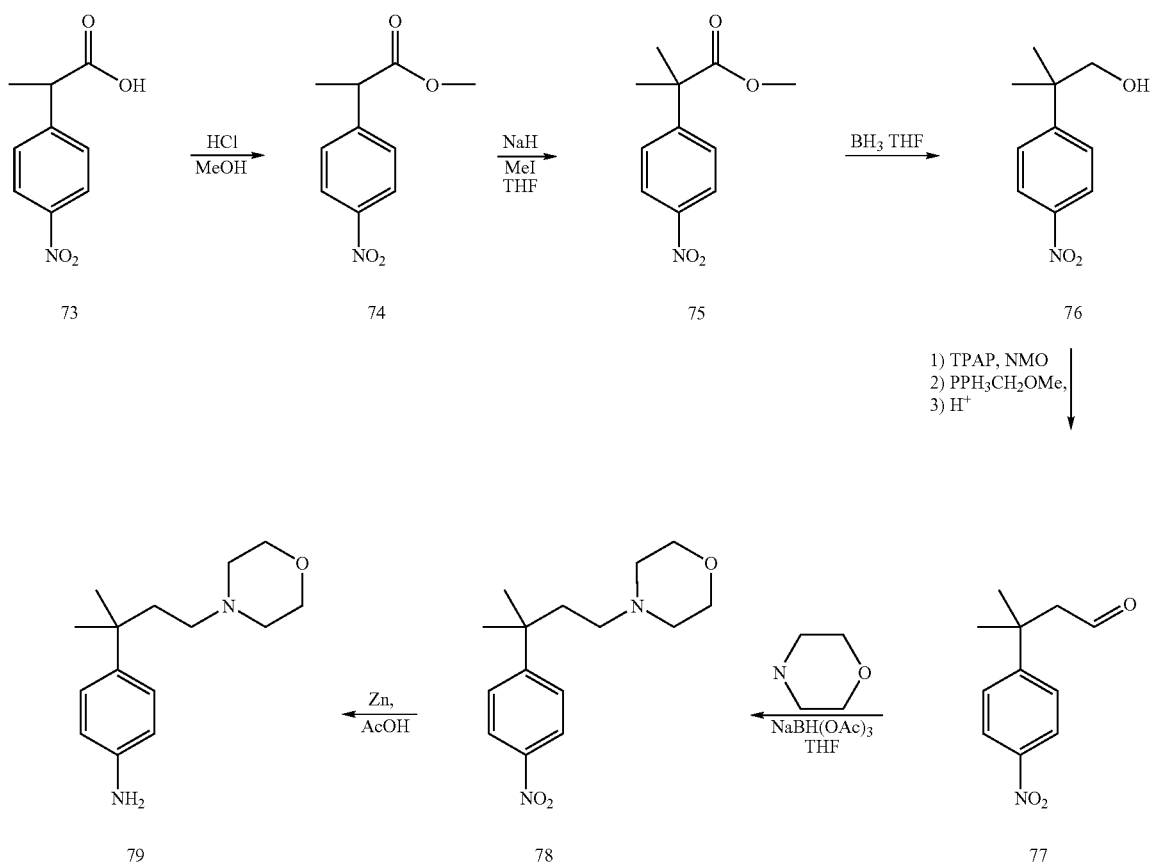

Substituted anilines are prepared such as by the procedures described in Scheme 23. Nitrophenyl esters 74 are formed from the acid 73, such as by treatment with MeOH and acid. Alkylation of the ester 74, such as by treatment with base, followed by alkyl halide, yields the branched alkyl compounds 75. Reduction of the ester 75, such as with $BH_3$, yields the alcohol 76. The aldehyde 77 is prepared from the alcohol 76, such as by treatment with TPAP in the presence of N-methylmorpholine-N-oxide. Subsequent treatment with methoxymethyltriphenylphosphonium chloride and KHMDS yields 77. Coupling of the aldehyde 77 with morpholine, such as with $NaBH(OAc)_3$ yields the tertiary amine 78. Reduction of the nitro compound, such as with acid, for example AcOH, and zinc yields the aniline 79.

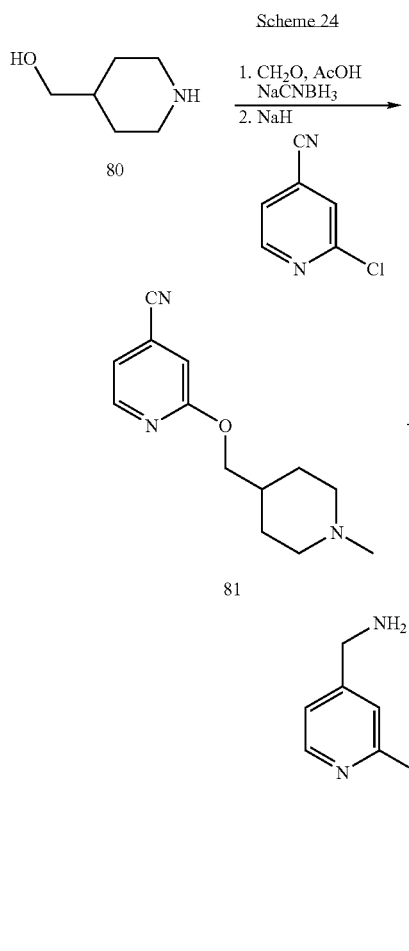

Substituted aminomethyl compounds are prepared such as by the procedure described in Scheme 24. A piperidinemethanol 80 is reacted with formaldehyde and $NaCNBH_3$. Subsequently, base, such as sodium hydride, and a halo substituted cyclic nitrile gives the ether 81. Hydrogenation of 81 under conditions described above, furnishes the aminomethyl compound 82.

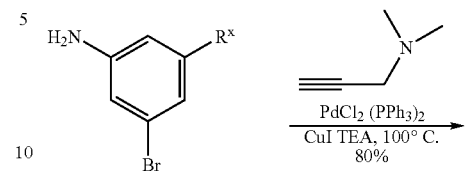

Substituted aniline compounds are prepared such as by the procedure described in Scheme 25 (where $R^x$ is a substituent selected from those available for substituted $R^1$, preferably haloalkyl or alkyl). Alkynyl-aniline 84, prepared similar to that described in Scheme 46, is hydrogenated such as with $H_2$ in the presence of a catalyst, such as $Pd(OH)_2$, to yield the substituted alkyl 85.

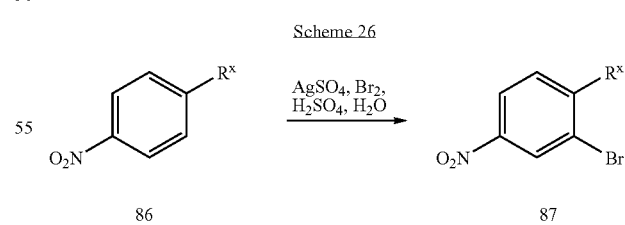

Substituted bromophenyl compounds are prepared such as by the procedure described in Scheme 26. Bromine is added to a optionally substituted nitrobenzene 86, silver(II)sulfate and acid, such as $H_2SO_4$, to provide the bromo derivative 87.

Scheme 27

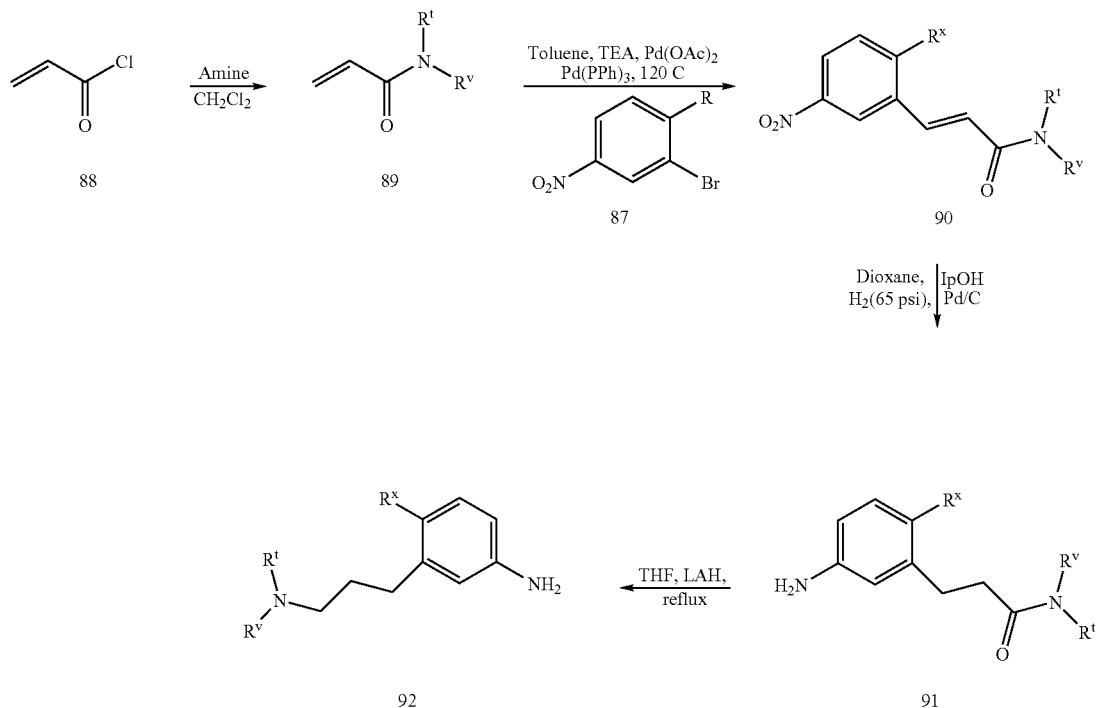

Substituted anilines are prepared such as by the procedure described in Scheme 27 (where $R^t$ and $R^v$ are alkyl, or together with the nitrogen atom form a 4-6 membered heterocyclic ring). Acryloyl chloride 88 is reacted with an amine, preferably a secondary amine, such as at a temperature between about 0° C. and about RT, to form the amide 89. A bromo-nitrobenzene 87 is reacted with the amide 89, such as in the presence of base, for example TEA, together with $Pd(OAc)_2$ and $Pd(PPh_3)_4$, at a temperature above about 50° C., and preferably at about 120° C., such as in a sealed container, to form the substituted alkene 90. Hydrogenation of the alkene 90, such as with $H_2$-in the presence of a catalyst, for example Pd/C catalyst yields the substituted aniline 91. Reduction of the amide 91, such as with $LiAlH_4$, at a temperature above about 50° C., and preferably at about 80° C. yields the aniline 92.

Scheme 28

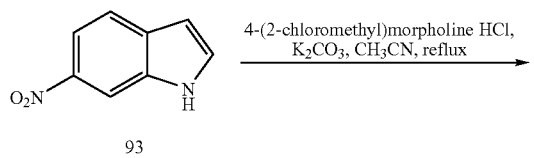

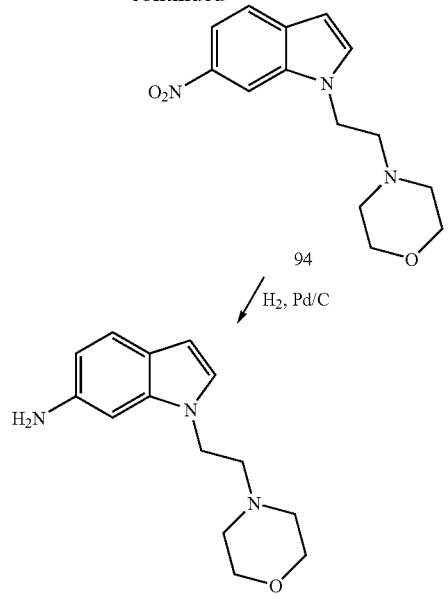

Substituted indoles are prepared such as by the procedure described in Scheme 28. A nitroindole 93 is coupled with a halo compound, in the presence of base, for example $K_2CO_3$. Heating at a temperature above about 50° C., and preferably at about reflux yields the substituted-nitro-1H-indole 94. Hydrogenation similar to conditions described above yield the amino derivative 95.

Scheme 29

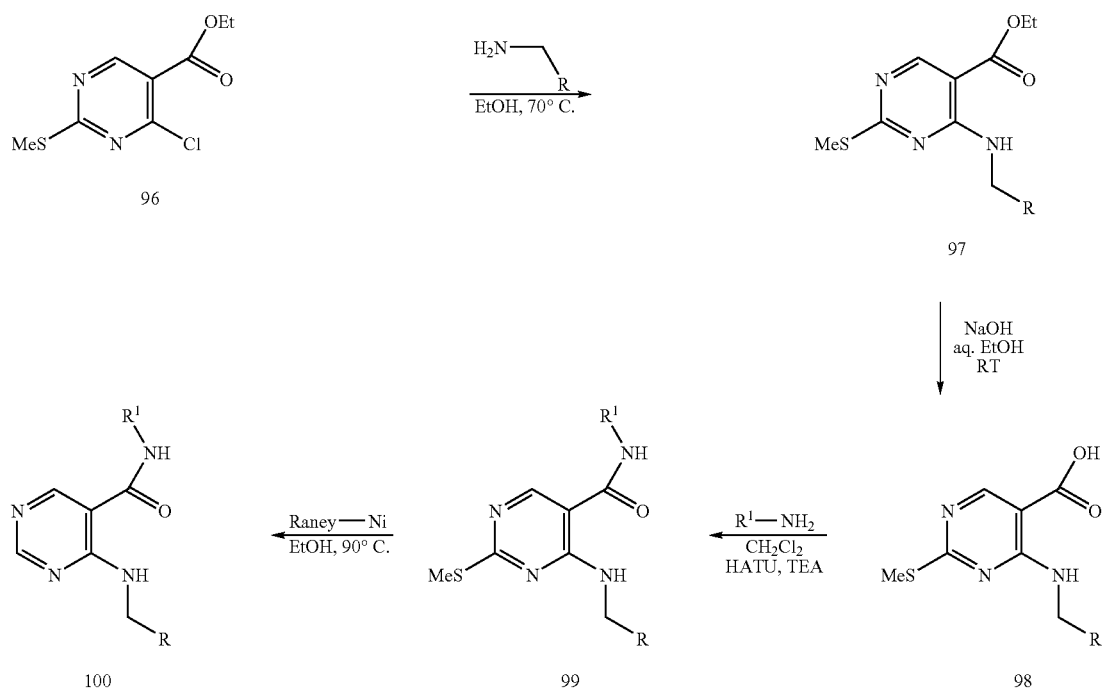

Substituted pyrimidines are prepared such as by the procedure described in Scheme 29. 2-Methylthio-5-pyrimidyl acids 98 are prepared from the corresponding esters 96 similar to procedures described above. The amides 99 are formed from the acids 98 by coupling with the amine such as in the presence of HATU and base, TEA for example. The methylthio group can be removed, such as with Raney-Ni and heat, preferably at about reflux temperature, to form the pyrimidine 100.

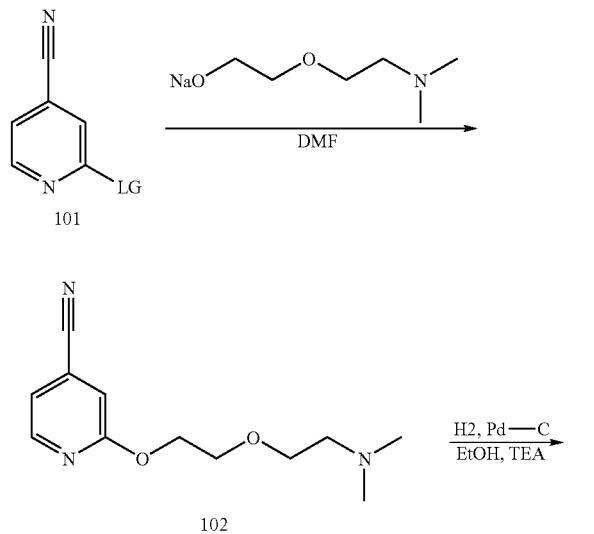

-continued

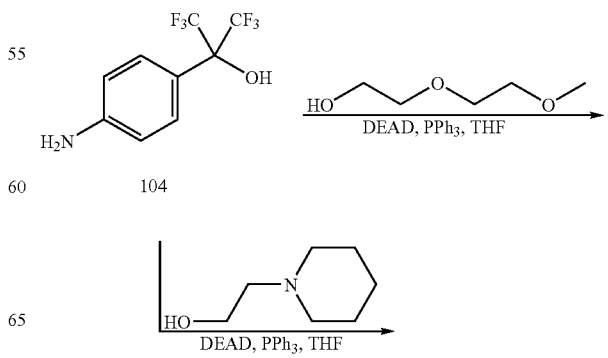

Substituted aminomethyl compounds are prepared such as by the procedure described in Scheme 30 (where LG is a leaving group, such as Cl). Strong base, such as NaH is added to an alcohol and heated at about 50° C. to form the sodium alkoxide, which is added to a halo compound, such as 2-chloro-4-cyanopyridine and heated at a temperature above about 50° C., and preferably at about 70° C. to form the ether 102. Hydrogenation yields the aminomethyl derivative 103.

Scheme 32

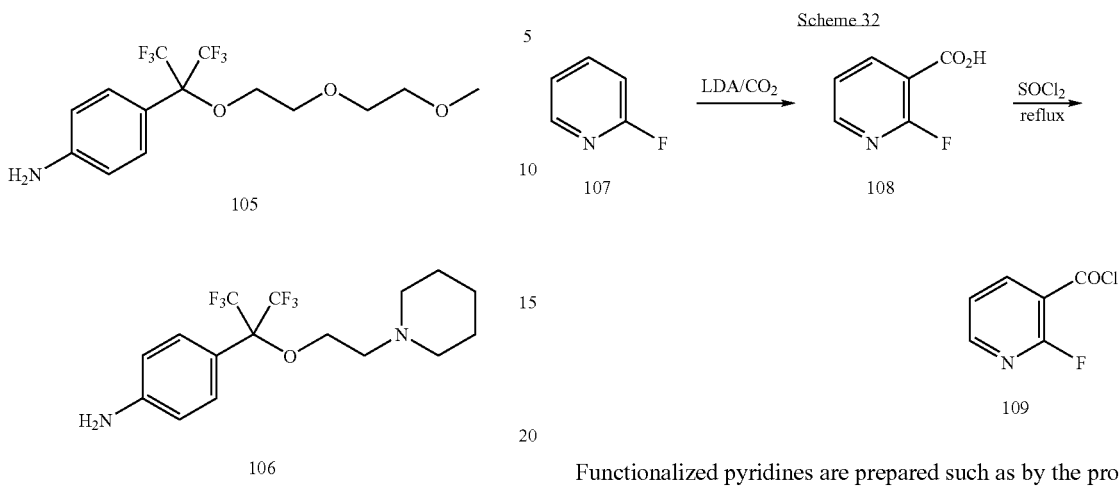

Functionalized pyridines are prepared such as by the procedure described in Scheme 32. 2-Fluoropyridine 107 is treated with base, such as LDA at a temperature below about 0° C., and preferably at about −78° C., and quenched with a stream of dry $CO_2$ to form the nicotinic acid 108. Alternatively, solid $CO_2$ (dry ice) can be used, preferably dried with $N_2$ prior to use. The acid 108 is converted to the acid halide 109, such as by treatment with thionyl chloride and heating at a temperature above about 50° C., and preferably at about reflux.

Substituted anilines are prepared such as by the procedure described in Scheme 31. Treatment with the haloalkyl alcohol 104 with an alcohol, such as in the presence of DEAD and $PPh_3$ yields the ether 105 or 106.

Scheme 33

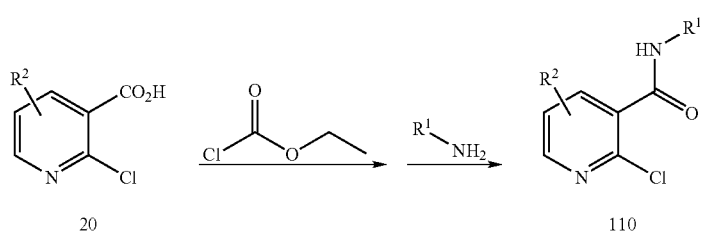

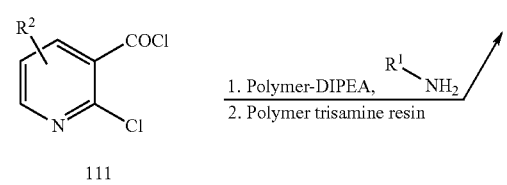

Chloro-substituted pyridines 110 are prepared such as by the procedure described in Scheme 33. 2-Chloronicotinic acid is activated with ethyl chloroformate, in the presence of base, such as TEA, at a temperature of about RT. Reaction with an amine produces amide 110. Alternatively, the amine can be coupled with the acid chloride 111, such as with polymer-supported DIPEA, to form amide 110. Excess acid chloride is removed by treating the reaction mixture with polymer-supported trisamine resin.

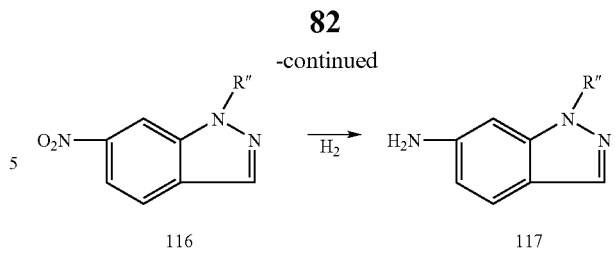

Alkylated indazoles can be prepared by the process outlined in Scheme 35. To a solution of 6-nitroindazole 115 in a solvent such as THF is added strong base, such as NaH at a temperature below RT, preferably at about 0° C. Alkylhalides, such as where R" is methyl, are added and reacted at a temperature about RT to give 1-alkyl-6-nitro-1H-indazole 116. The nitro indazole 116 is hydrogenated, such as with an $H_2$ atmosphere in the presence of a catalyst, such as Pd/C to give the 1-substituted-6-amino-1H-indazole 117.

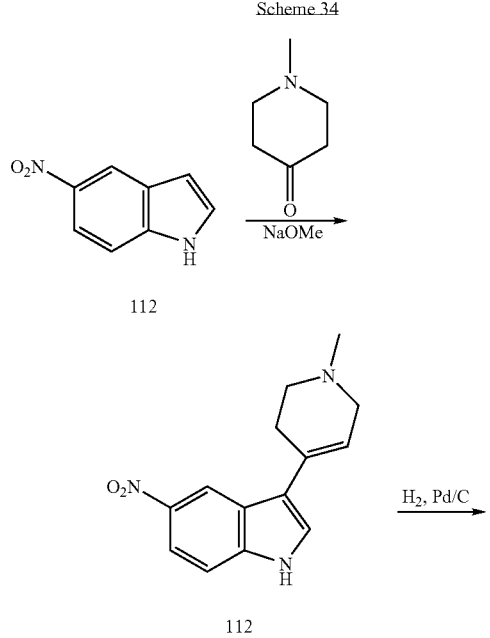

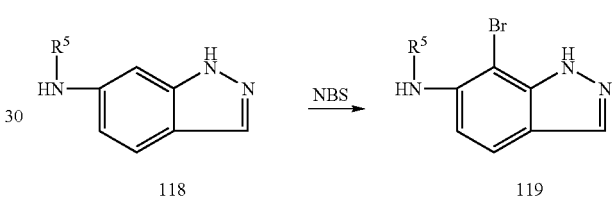

Brominated indazoles can be prepared by the process outlined in Scheme 36. NBS is slowly added to an acidic solution, such as a mixture of TFA:$H_2SO_4$ (5:1) and tert-butyl-4-nitrobenzene 118 at a temperature of about RT to yield the brominated compound 119.

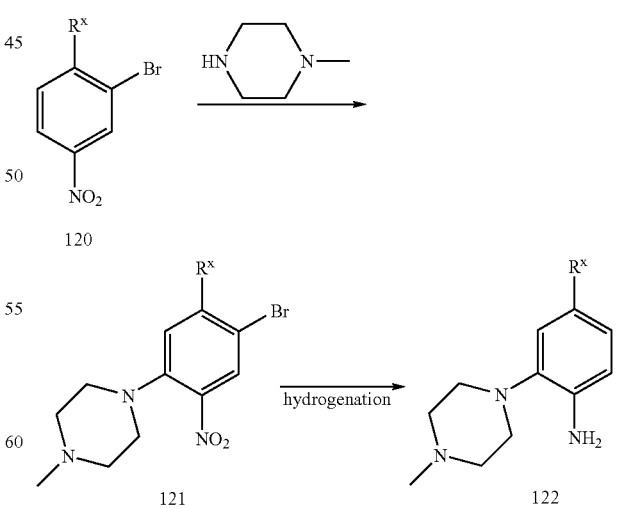

Amino-substituted indoles 110 are prepared such as by the procedure described in Scheme 34. Nitroindoline 112 is reacted with N-methyl-4-piperidone in the presence of NaOMe at a temperature above about 50° C., and preferably at about reflux, to form the 3-substituted indole 113. Hydrogenation as previously discussed yields the amino indole 114.

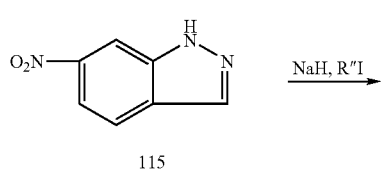

Substituted anilines can be prepared by the process outlined in Scheme 38. A mixture of 1-(substituted)-2-bromo-4-nitrobenzene 120 (where $R^x$ is a substituent selected from those available for substituted R[1]) and N-methylpiperazine is heated, such as with or without solvent, preferably without solvent, at a temperature above RT, preferably at a temperature above about 100° C., and more preferably at a temperature at about 130° C. to give the 1-[5-(substituted)-2-nitrophenyl]-4-methylpiperazine 121. The nitro compound 121 is hydrogenated, such as with an $H_2$ atmosphere in the presence of a catalyst, such as Pd/C to furnish 4-(substituted)-2-(4-methylpiperazinyl)phenylamine 122.

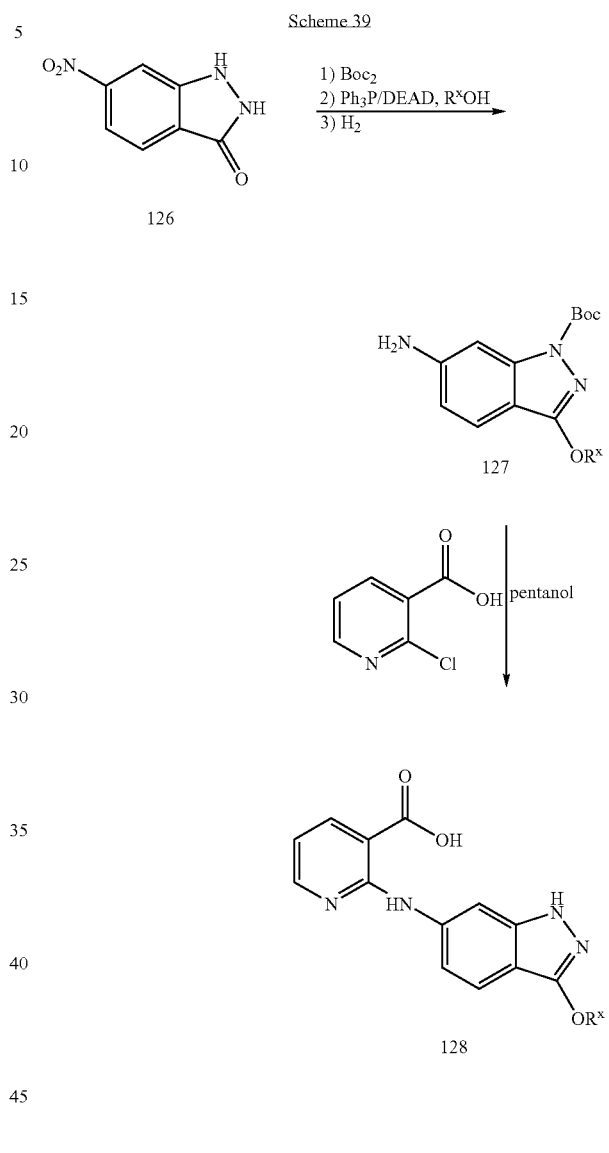

Tricyclic heterocycles can be prepared by the process outlined in Scheme 38. 7-Nitro-2,3,4-trihydroisoquinolin-1-one 123 is heated in $POCl_3$ at a temperature above RT, preferably at a temperature sufficient for reflux, to form the 1-chloro-7-nitro-3,4-dihydroisoquinoline 124. The 1-chloro-7-nitro-3,4-dihydroisoquinoline 124 is dissolved in a solvent, such as THF, and $H_2NNH_2$ is added. The reaction is evaporated to a residue, then heated with $HC(OEt)_3$ at a temperature above RT, preferably at a temperature above about 75° C., and more preferably at a temperature at about 115° C. to give the nitro-substituted tricyclic. Hydrogenation, such as with an $H_2$ atmosphere in the presence of a catalyst, such as Pd/C, gives 2-amino-5,6,7-trihydro-1,2,4-triazolo[3,4-a]isoquinoline 125.

Indazolyl ethers can be prepared by the process outlined in Scheme 39. 6-Nitro-1H-2-hydroindazol-3-one 126 is protected such as with $Boc_2O$ and DMAP in $CH_2Cl_2$ at a temperature of about RT, to give the protected 6-nitro-2-hydroindazol-3-one. The protected 6-nitro-2-hydroindazol-3-one is reacted with an alcohol (where $R^x$ is an appropriate substituent selected from the possible substituents on R) and $Ph_3P$ in a solvent, such as THF, and DEAD, at a temperature of about RT, to give the protected 6-nitro(indazol-3-yl) ether. The nitro intermediate is hydrogenated, such as with an $H_2$ atmosphere in the presence of a catalyst, such as Pd/C, to give the protected 6-amino(indazol-3-yl) ether 127. The amine 127 is coupled and 2-chloronicotinic acid in a solvent, such as an alcohol, preferably pentanol, at a temperature above RT, preferably at a temperature above about 75° C., and more preferably at a temperature at about 130° C. to give the coupled and deprotected compound 128.

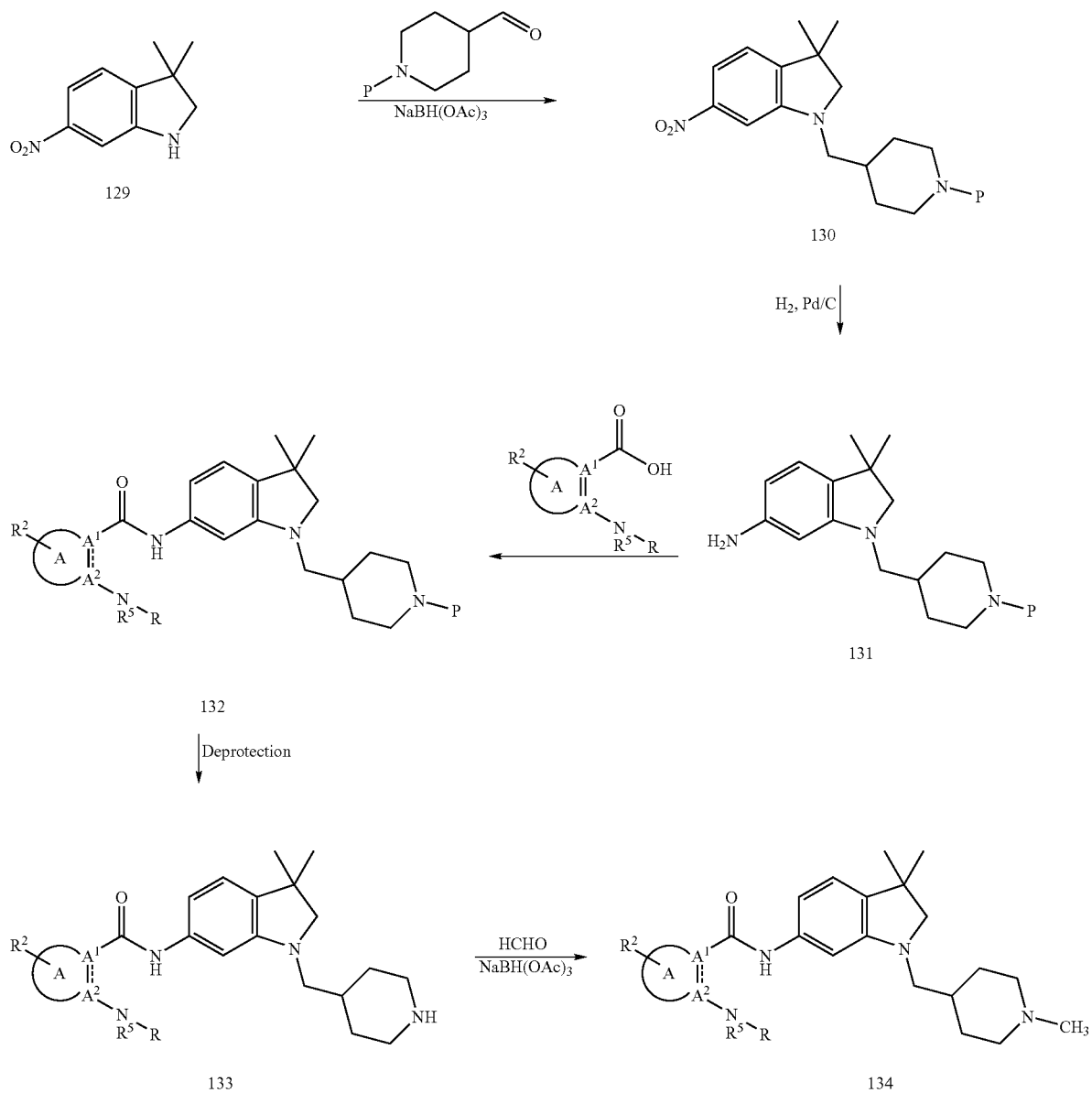

Indolinyl substituted carboxamides can be prepared from the corresponding nitro indoline 129 by the process outlined in Scheme 40. For example, 3,3-dimethyl-6-nitroindoline 129 is alkylated, such as with N-protected-4-formylpiperidine in the presence of NaHB(OAc)$_3$ and acid, such as glacial AcOH, and solvent, such as dichloromethane, at a temperature of about RT, to afford the alkylated indane 130. Hydrogenation of the alkylated indane 130, such as with an H$_2$ atmosphere in the presence of a catalyst, such as Pd/C, in the presence of a solvent, such as an alcohol, preferably MeOH, to give the amino intermediate 131. Alternatively, other hydrogenation methods can be used, such as Fe powder with NH$_4$Cl. Coupling of the amine 131, such as with 2-chloronicotinic acid and DIEA, HOBt and EDC, in a solvent such as CH$_2$Cl$_2$ at a temperature of about RT provides the protected carboxamide 132, which upon deprotection and alkylation yields other compounds of the invention, 133 and 134, respectively. Alternatively, amine 131 is reacted with 2-fluoronicotinoyl chloride to form a 2-fluoronicotinamide, which can be alkylated, such as in Scheme 10.

Scheme 41

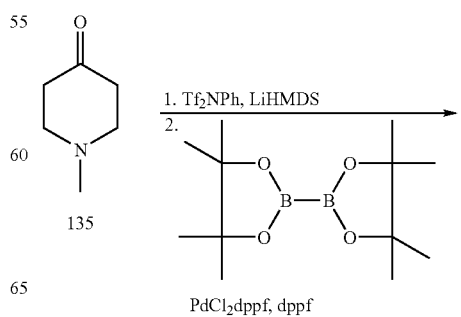

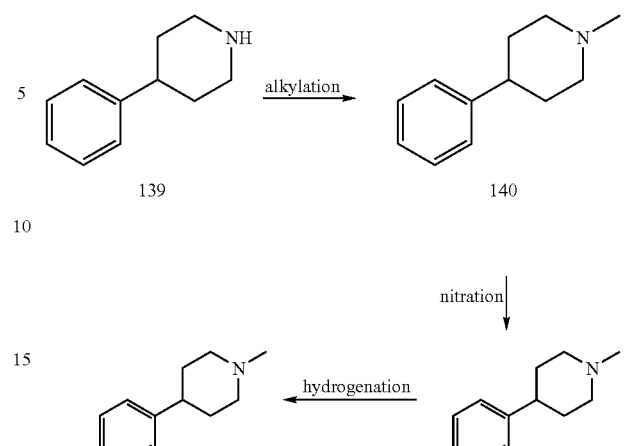

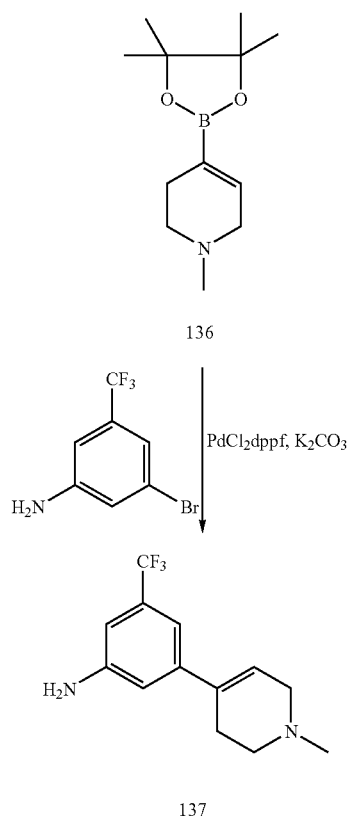

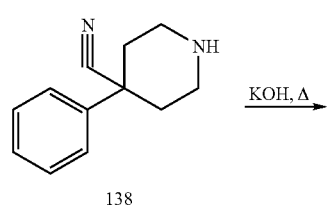

Substituted anilines can be prepared by the process outlined in Scheme 41. 1-Methyl-4-piperidinone 135 is added to a solution of strong base such as LIHMDS, in a solvent such as THF, at a temperature below RT, preferably lower than about −50° C., more preferably at about −78° C. Tf₂NPh is reacted with the enolate at a temperature of about RT, to give 1-methyl-4-(1,2,5,6-tetrahydro)pyridyl-(trifluoromethyl) sulfonate. A mixture of the triflate intermediate, bis(pinacolato)diboron, potassium acetate, PdCl₂dppf, and dppf in a solvent such as dioxane is heated at a temperature above RT, preferably at a temperature above about 50° C., and more preferably at a temperature at about 80° C. to give 4,4,5,5-tetramethyl-2-(1-methyl(4-1,2,5,6-tetrahydropyridyl))-1,3,2-dioxaborolane 136. The substituted aniline 137 is formed from the 1,3,2-dioxaborolane 136 such as with treatment with an amine in the presence of 1,1'-bis(diphenyphosphino)ferrocene-palladium dichloride and base, such as K₂CO₃, in a solvent such as DMF at a temperature above RT, preferably at a temperature above about 50° C., and more preferably at a temperature at about 80° C.

Substituted anilines can be prepared by the process outlined in Scheme 42. 4-Cyano-4-phenylpiperidine hydrochloride 138 is treated with base, such as KOH, at a temperature above RT, preferably at a temperature above about 100° C., and more preferably at a temperature at about 160° C., to provide the phenyl piperidine 139. Alkylation of the phenyl piperidine 139, such as with formaldehyde and NaCNBH₃ in a solvent such as CH₃CN, with sufficient acid to maintain the reaction pH near 7, to provide the alkylated piperidine 140. Nitration of the phenylpiperidine 140, such as with H₂SO₄ and fuming HNO₃ at a temperature below RT, and preferably at about 0° C., gives the nitro intermediate 141. Hydrogenation of the nitro intermediate 141, such as with an H₂ atmosphere in the presence of a catalyst, such as Pd/C, in the presence of a solvent, such as an alcohol, preferably MeOH, to give the amino intermediate 142.

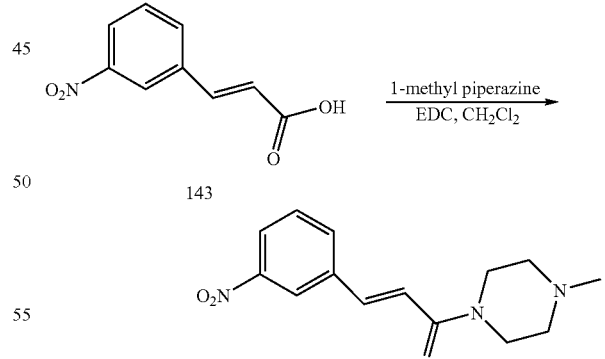

Substituted amides can be prepared by the process outlined in Scheme 43. 3-Nitrocinnamic acid 143 is coupled with 1-methylpiperazine in the presence of EDC and a solvent such as CH₂Cl₂, at a temperature of about RT gives the carboxamide 144.

Scheme 44

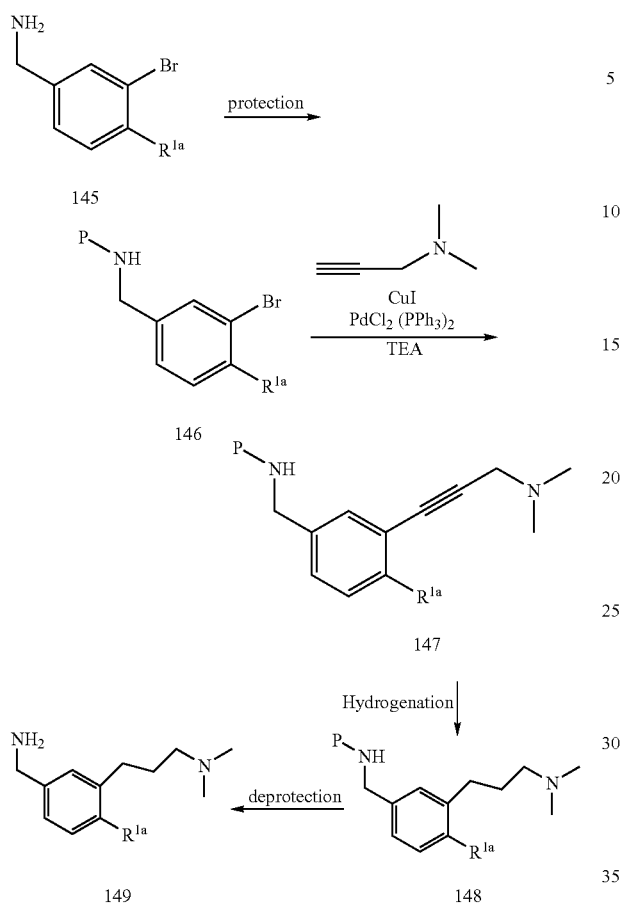

Substituted benzylamines can be prepared by the process outlined in Scheme 44. A substituted bromobenzylamine 145 where $R^{1a}$ is a substituent described for $R^1$ is protected such as with $Boc_2O$ in the presence of base, such as TEA in an appropriate solvent such as $CH_2Cl_2$. The protected bromobenzylamine 146 is alkylated, such as with 1-dimethylamino-2-propyne in the presence of catalyst, such as $PdCl_2(PPh_3)_2$, and CuI, in the presence of base, such as TEA, at a temperature above RT, preferably at a temperature above about 50° C., and more preferably at a temperature at about 100° C., such as in a sealed tube, to form the propynylbenzylamine 147. The propynylbenzylamine is hydrogenated such as with $H_2$ in the presence of $Pd(OH)_2$ and MeOH to provide the propylbenzylamine 148. Deprotection, such as with strong acid, such as TFA, for removal of a Boc protecting group, yields the propylbenzylamine 149.

Scheme 45

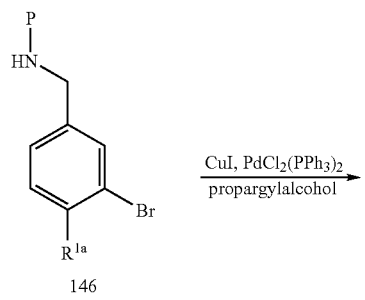

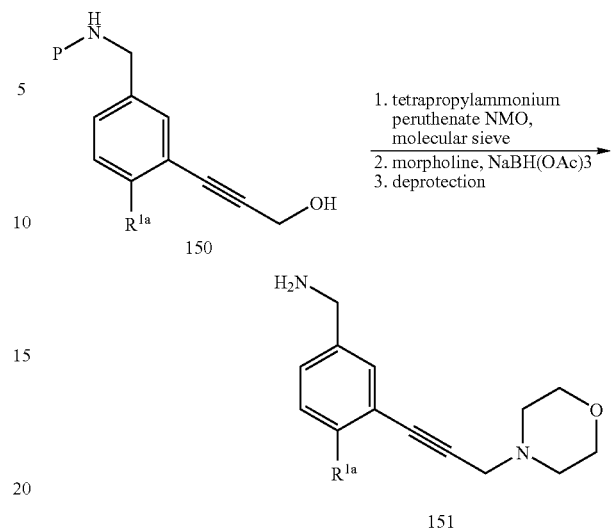

Substituted benzylamines can be prepared by the process outlined in Scheme 45. The protected bromobenzylamine 146 is alkylated, such as with propargyl alcohol in the presence of catalyst, such as $PdCl_2(PPh_3)$, and CuI, in the presence of base, such as TEA, at a temperature above RT, preferably at a temperature above about 50° C., and more preferably at a temperature at about 100° C., such as in a sealed tube, to form the protected hydroxypropynylbenzylamine 150. The protected hydroxypropynylbenzylamine is treated with N-methylmorpholine oxide in the presence of a catalyst, such as tetrapropylammonium perruthenate, to form the aldehyde intermediate. Reductive amination, such as with the addition of morpholine and $NaBH(OAc)_3$ provides the morpholinyl derivative. Deprotection, such as with strong acid, such as TFA, for removal of a Boc protecting group, yields the propylbenzylamine 151.

Scheme 46

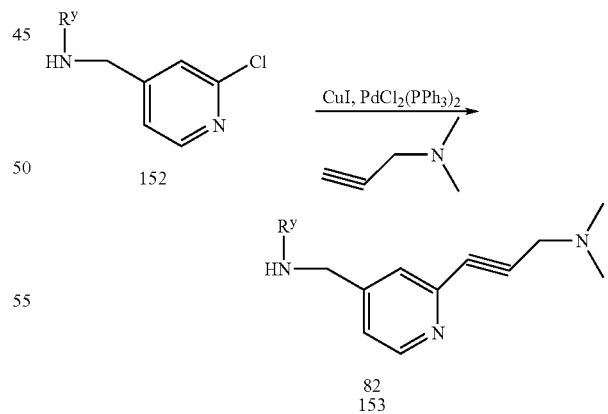

Substituted aminomethyl compounds are prepared such as by the procedure described in Scheme 46. A halo compound 152, is reacted with an alkyne in the presence of $PdCl_2(PPh_3)_2$ and CuI, with base is heated at a temperature above about 50° C., and preferably at about 100° C., such as in a sealed container, to provide the substituted alkyne 153.

Scheme 47

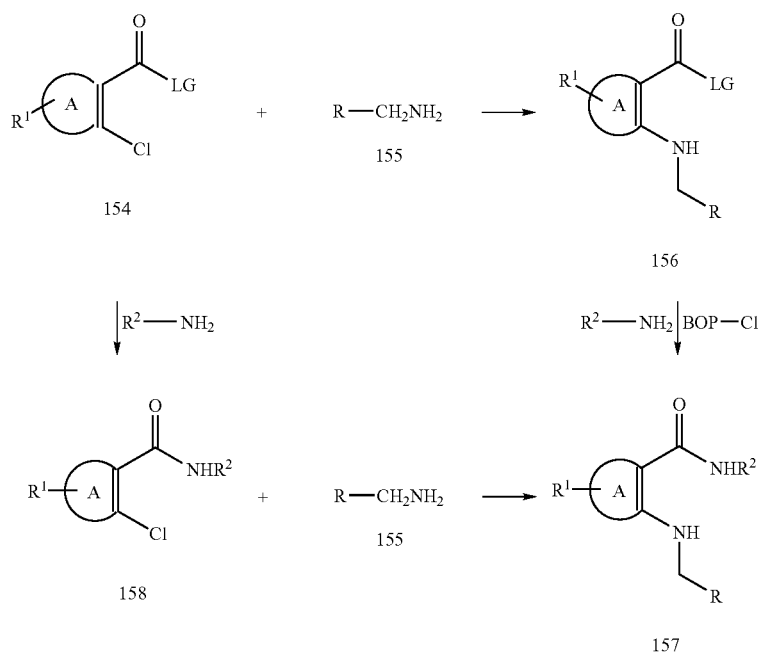

Substituted heterocycles may be prepared by the method found in Scheme 47. Chloro-heterocycles 154 (where LG is OH) is coupled with an amine 155 at a suitable temperature, such as a temperature over about 100° C. to give the 2-substituted amino-nicotinic acid 156. The 2-substituted amino-nicotinic acid 156 is reacted with a substituted amine in the presence of a coupling reagent, such as BOP—Cl and base, such as TEA to form the 2-substituted amino-nicotinamide 157.

Alternatively, 2-chloro-nicotinoyl chloride 154 (where LG is Cl) is coupled first with $R^2$—$NH_2$, such as in the presence of base, e.g., $NaHCO_3$, in a suitable solvent, such as IpOH or $CH_2Cl_2$, to form the amide 158, then coupled with an amine 155 to yield the 2-substituted amino-nicotinamide 157. Where A is a pi-electron rich heterocycle, the addition of KF, such as 40% KF on alumina in IpOH, at a temperature over about 100° C., preferably about 160° C., can be used in the formation of 157 from 158.

Scheme 48

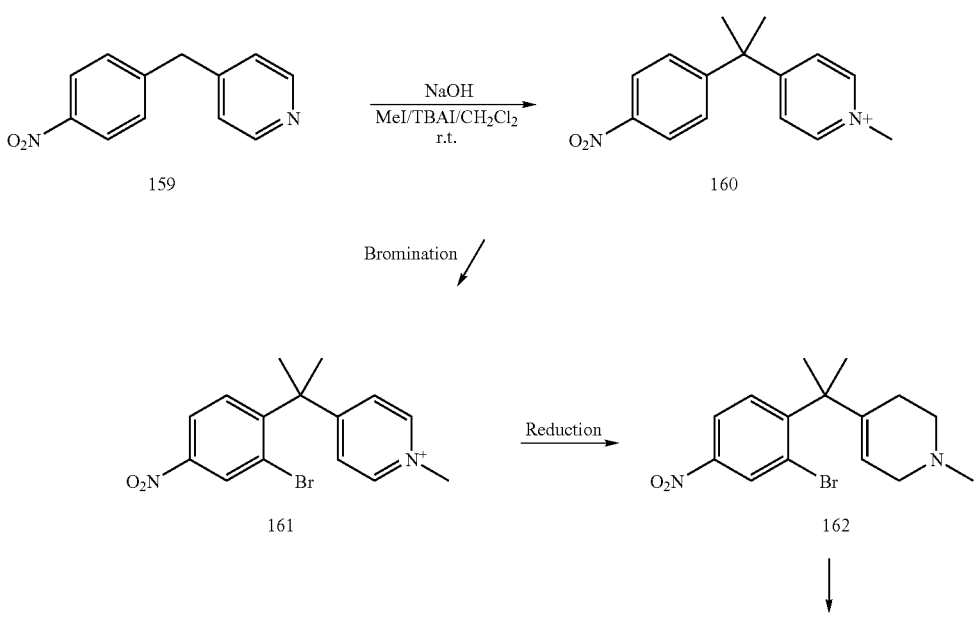

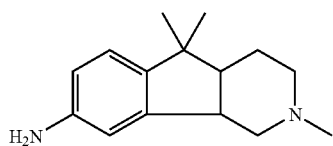 164

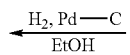
H₂, Pd—C
EtOH

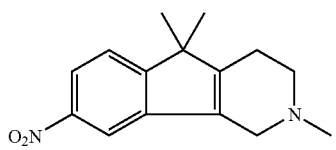 163

2,3,4,4a,9,9a-hexahydro-1H-3-aza-fluoren-6-ylamine may be prepared by the method found in Scheme 48. Nitrobenzylpyridines 159 are alkylated, such as with MeI, in the presence of TBAI and base to form the pyridinium compound 160. The pyridinium compounds 160 are halogenated, such as brominated with NBS, to form the brominated pyridinium compounds 161 which are reduced such as with NaBH₄ to form the tetrahydro-pyridines 162. Palladium catalyzed intramolecular Heck coupling followed by hydrogenation forms the hexahydro-fluorenes 164.

The starting compounds defined in Schemes 1-48 may also be present with functional groups in protected form if necessary and/or in the form of salts, provided a salt-forming group is present and the reaction in salt form is possible. If so desired, one compound of formulas I-XII can be converted into another compound of formulas I-XII or a N-oxide thereof; a compound of formulas I-XII can be converted into a salt; a salt of a compound of formulas I-XII can be converted into the free compound or another salt; and/or a mixture of isomeric compounds of formulas I-XII can be separated into the individual isomers.

N-Oxides can be obtained in a known matter by reacting a compound of formulas I-XII with hydrogen peroxide or a peracid, e.g. 3-chloroperoxy-benzoic acid, in an inert solvent, e.g. dichloromethane, at a temperature between about −10-35° C., such as about 0° C.-RT.

If one or more other functional groups, for example carboxy, hydroxy, amino, or mercapto, are or need to be protected in a compound of formulas I-XII or in the synthesis of a compound of formulas I-XII, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formulas I-XII with a salt-forming group may be prepared in a manner known per se. Acid addition salts of compounds of formulas I-XII may thus be obtained by treatment with an acid or with a suitable anion exchange reagent. A salt with two acid molecules (for example a dihalogenide of a compound of formulas I-XII) may also be converted into a salt with one acid molecule per compound (for example a monohalogenide); this may be done by heating to a melt, or for example by heating as a solid under a high vacuum at elevated temperature, for example from about 130° C. to about 170° C., one molecule of the acid being expelled per molecule of a compound of formulas I-XII.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

A compound of formulas I-XII, wherein Z is oxygen, can be converted into the respective compound wherein Z is sulfur, for example, by using an appropriate sulfur compound, e.g. using reaction with Lawesson's reagent (2,4-bis-(4-methoxyphenyl)-1,3-dithia-2,4-diphosphetane-2,4-disulfide) in a halogenated hydrocarbon, such as CH₂Cl₂, or an aprotic solvent, such as toluene or xylene, at temperatures from about 30° C. to reflux.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., ethyl acetate, ethers, typically aliphatic ethers, e.g., diethylether, or cyclic ethers, e.g., THF, liquid aromatic hydrocarbons, typically benzene or toluene, alcohols, typically MeOH, EtOH or 1-propanol, IPOH, nitriles, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formulas I-XII, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

For example, amine 1 can be prepared by reduction of the corresponding nitro. The reduction preferably takes place in the presence of a suitable reducing agent, such as tin(II) chloride or hydrogen in the presence of an appropriate catalyst, such as Raney nickel (then preferably the hydrogen is used under pressure, e.g. between 2 and 20 bar) or $PtO_2$, in an appropriate solvent, e.g. an alcohol, such as MeOH. The reaction temperature is preferably between about 0° C. and about 80° C., especially about 15° C. to about 30° C.

It would also be possible to reduce the nitro compound after forming the amide compound under reaction conditions analogous to those for the reduction of nitro compounds described above. This would eliminate the need to protect the free amino group as described in Scheme 1.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

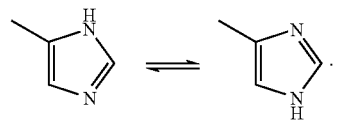

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necesssary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); A. Katritzky and A. Pozharski, Handbook of Heterocyclic Chemistry, $2^{nd}$ Ed. (2001); M. Bodanszky, A. Bodanszky: *The practice of Peptide Synthesis* Springer-Verlag, Berlin Heidelberg 1984; J. Seyden-Penne: Reductions by the Alumino- and Borohydrides in *Organic Synthesis*, $2^{nd}$ Ed., Wiley-VCH, 1997; and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formulas I-XII. These detailed descriptions fall within the scope, and serve to exemplify, the above described General Synthetic Procedures which form part of the invention. These detailed descriptions are presented for illustrative purposes only and are not intended as a restriction on the scope of the invention.

Unless otherwise noted, all materials were obtained from commercial suppliers and used without further purification. Anhydrous solvents such as DMF, THF, $CH_2Cl_2$ and toluene were obtained from the Aldrich Chemical Company. All reactions involving air- or moisture-sensitive compounds were performed under a nitrogen atmosphere. Flash chromatography was performed using Aldrich Chemical Company silica gel (200-400 mesh, 60A) or Biotage pre-packed column. Thin-layer chromatography (TLC) was performed with Analtech gel TLC plates (250μ). Preparative TLC was performed with Analtech silica gel plates (1000-2000μ). Preparative HPLC was conducted on Beckman or Waters HPLC system with 0.1% TFA/$H_2O$ and 0.1% TFA/$CH_3CN$ as mobile phase. The flow rate was at 20 ml/min. and gradient method was used. $^1$H NMR spectra were determined with super conducting FT NMR spectrometers operating at 400 MHz or a Varian 300 MHz instrument. Chemical shifts are expressed in ppm downfield from internal standard tetramethylsilane. All compounds showed NMR spectra consistent with their assigned structures. Mass spectra (MS) were determined on a Perkin Elmer—SCIEX API 165 electrospray mass spectrometer (positive and, or negative) or an HP 1100 MSD LC-MS with eletrospray ionization and quadrupole detection. All parts are by weight and temperatures are in Degrees centigrade unless otherwise indicated.

The following abbreviations are used:
AIBN—2,2'-azobisisobutyronitrile
Ar—argon
$AgSO_4$—silver sulfate
ATP—adenosine triphosphate
$BH_3$—borane
Boc—tert-butyloxycarbonyl
$Boc_2O$—Boc anhydride
BOP—Cl—bis(2-oxo-3-oxazolidinyl)phosphinic chloride
$Br_2$—bromine
BSA—bovine serum albumin
t-BuOH—tert-butanol
CAN—ammonium cerium(IV) nitrate
$CH_3CN$, ACCN—acetonitrile
$CH_2Cl_2$—dichloromethane
$CH_3I$, MeI—iodomethane, methyl iodide
$CCl_4$—carbon tetrachloride
$CCl_3$—chloroform
$CO_2$—carbon dioxide
$Cs_2CO_3$—cesium carbonate
DIEA—diisopropylethylamine
CuI—copper iodide
DCE—1,2-dichloroethane
DEAD—diethyl azodicarboxylate
DIEA—diisopropylethylamine
dppf—1,1-diphenylphosphinoferrocene
DMAP—4-(dimethylamino)pyridine
DMAC—N,N-dimethylacetamide
DMF—dimethylformamide
DMSO—dimethylsulfoxide
DTT—dithiothreitol
EDC, EDAC-1-(3-dimethylaminopropyl)-3ethylcarbodiimide hydrochloride
EGTA—ethylene glycol-bis(β-aminoethyl ether)-N,N,N',N'-tetraacetic acid
EtOAc—ethyl acetate
EtOH—ethanol
$Et_2O$—diethyl ether
Fe—iron
g—gram
h—hour
HATU—O-(7-azabenzotriazol-1-yl)-N,N,N',N'-tetramethyluronium hexafluorophosphate
$H_2$—hydrogen
$H_2O$—water
HCl—hydrochloric acid
$H_2SO_4$—sulfuric acid
$H_2NNH_2$—hydrazine
$HC(OEt)_3$—triethylorthoformate
HCHO, $H_2CO$—formaldehyde
$HCO_2Na$—sodium formate
HOAc, AcOH—acetic acid
HOAt—1-hydroxy-7-azabenzotriazole
HOBt—hydroxybenzotriazole
IpOH—isopropanol
$K_2CO_3$—potassium carbonate
KHMDS—potassium hexamethylsilazane
$KNO_3$—potassium nitrate KOAc—potassium acetate
KOH—potassium hydroxide
LAH, LiAlH$_4$—lithium aluminum hydride
LDA—lithium diisopropylamide
LiCl—lithium chloride
LiHMDS—lithium hexamethyldisilazide
MeOH—methanol
MgCl$_2$—magnesium chloride
MgSO$_4$—magnesium sulfate
mg—milligram
ml—milliliter
MnCl$_2$—manganese chloride
NBS—N-bromosuccinimide
NMO—4-methylmorpholine, N-oxide
NMP—N-methylpyrrolidone
Na$_2$SO$_4$—sodium sulfate
Na$_2$S$_2$O$_5$—sodium metabisulfite
NaHCO$_3$—sodium bicarbonate
Na$_2$CO$_3$—sodium carbonate
NaCl—sodium chloride
NaH—sodium hydride
NaI—sodium iodide
NaOH—sodium hydroxide
NaOMe—sodium methoxide
NaCNBH$_3$—sodium cyanoborohydride
NaBH$_4$—sodium borohydride
NaNO$_2$—sodium nitrate
NaBH(OAc)$_3$—sodium triacetoxyborohydride
NH$_4$Cl—ammonium chloride
N$_2$—nitrogen
Pd/C—palladium on carbon
PdCl$_2$(PPh$_3$)$_2$—palladium chloride bis(triphenylphosphine)
PdCl$_2$(dppf)-1,1-bis(diphenylphosphino)ferrocene palladium chloride
Pd(PPh$_3$)$_4$—palladium tetrakis triphenylphosphine
Pd(OH)$_2$—palladium hydroxide
Pd(OAc)$_2$—palladium acetate
PMB—para methoxybenzyl
POCl$_3$—phosphorus oxychloride
PPh$_3$—triphenylphosphine
PtO$_2$—platinum oxide
RT—room temperature
SiO$_2$—silica
SOCl$_2$—thionyl chloride
TBAI—tetrabutylammonium iodide
TEA—triethylamine
Tf$_2$NPh—N-phenyltrifluoromethanesulfonimide
TFA—trifluoroacetic acid
THF—tetrahydrofuran
TPAP—tetrapropylammoniumperruthenate
Tris-HCl—Tris(hydroxymethyl)aminomethane hydrochloride salt
Zn—zinc Preparation I—3-nitro-5-trifluoromethyl-phenol 1-Methoxy-3-nitro-5-trifluoromethyl-benzene (10 g, Aldrich) and pyridine-HCl (41.8 g, Aldrich) were mixed together and heated neat at 210° C. in an open flask. After 2.5 h the mixture was cooled to RT and partitioned between 1N HCl and EtOAc. The EtOAc fraction was washed with 1N HCl (4×), brine (1×), dried with Na$_2$SO$_4$, filtered and concentrated in vacuo to form 3-nitro-5-trifluoromethyl-phenol as an off-white solid.

Preparation II—1-Boc-4-(3-nitro-5-trifluoromethyl-phenoxy)-piperidine

3-Nitro-5-trifluoromethyl-phenol (8.81 g) was dissolved in THF (76 ml). 1-Boc-4-hydroxy-piperidine (8.81 g, Aldrich) and Ph$_3$P (11.15 g) were added and the solution was cooled to −20° C. A solution of DEAD (6.8 ml, Aldrich) in THF (36 ml) was added dropwise, maintaining the temperature between −20 and −10° C. The reaction was warmed to RT and stirred overnight. The reaction was concentrated in vacuo and triturated with hexane. The yellow solid was removed by filtration and washed with Et$_2$O (25 ml), and hexane. The white filtrate was washed with 1N NaOH (2×), brine (1×) and the hexane layer was dried over Na$_2$SO$_4$, filtered and concentrated in vacuo. The crude material was purified with flash chromatography (SiO$_2$, 5-10% EtOAc/hexane) to obtain 1-Boc-4-(3-nitro-5-trifluoromethyl-phenoxy)-piperidine.

The following compounds were prepared similarly to the procedure outlined above:
a) (S)-1-Boc-[2-(5-nitro-2-trifluoromethylphenoxymethyl]-pyrrolidine
b) (R)-1-Boc-[2-(5-nitro-2-trifluoromethylphenoxymethyl]-pyrrolidine.
c) (R) 1-Boc-2-(3-Nitro-5-trifluoromethyl-phenoxymethyl)-pyrrolidine
d) 4-(2-tert-Butyl-5-nitro-phenoxymethyl)-1-methyl-piperidine.
e) (S) 1-Boc-2-(3-Nitro-5-trifluoromethyl-phenoxymethyl)-pyrrolidine
f) 1-Boc-3-(5-nitro-2-pentafluoroethyl-phenoxymethyl)-azetidine.
g) N-Boc-[2-(5-nitro-2-pentafluoroethyl-phenoxy)-ethyl]amine.
h) (R) 3-(2-tert-Butyl-5-nitro-phenoxymethyl)-1-Boc-pyrrolidine.
i) 3-(2-tert-Butyl-5-nitro-phenoxymethyl)-1-Boc-azetidine.
j) (S)-1-Boc-[2-(5-nitro-2-tert-butylphenoxymethyl]-pyrrolidine
k) (S) 3-(2-tert-Butyl-5-nitro-phenoxymethyl)-1-Boc-pyrrolidine.
l) (R)-1-Boc-[2-(5-nitro-2-tert-butylphenoxymethyl]-pyrrolidine Preparation III—1-Boc-4-(3-amino-5-trifluoromethyl-phenoxy)-piperidine 1-Boc-4-(3-nitro-5-trifluoromethyl-phenoxy)-piperidine (470 mg) was dissolved in MeOH (12 ml) and Pd/C (10 mg) was added. After sparging briefly with H$_2$, the mixture was stirred under H$_2$ for 6H. The catalyst was removed by filtration and the MeOH solution was concentrated in vacuo to yield 1-Boc-4-(3-amino-5-trifluoromethyl-phenoxy)-piperidine as an off-white foam.

The following compounds were prepared similarly to the procedure outlined above:
a) 1-Boc-2-(3-Amino-5-trifluoromethyl-phenoxymethyl)-pyrrolidine.
b) 2-(3-Amino-5-trifluoromethyl-phenoxymethyl)-1-methyl-pyrrolidine.
c) [2-(1-Methylpiperidin-4-yloxy)-pyridin-4-yl]methylamine. ESI (M+H)=222.
d) [2-(2-Morpholin-4-yl-ethoxy)-pyridin-4-yl]methylamine.
e) [2-(2-Morpholin-4-yl-propoxy)-pyridin-4-yl]methylamine.
f) [2-(1-Methyl-pyrrolidin-2-ylmethoxy)-pyridin-4-yl]methylamine. ESI MS: (M+H)=222.
g) (4-Aminomethyl-pyridin-2-yl)-(3-morpholin-4-yl-propyl)-amine. ESI MS: (M+H)=251.
h) 4-tert-Butyl-3-(1-methyl-piperidin-4-ylmethoxy)-phenylamine.
i) 4-tert-Butyl-3-(2-piperidin-1-yl-ethoxy)-phenylamine.

j) 3-(1-Methyl-piperidin-4-ylmethoxy)-4-pentafluoroethyl-phenylamine.
k) 3-(1-Isopropyl-piperidin-4-ylmethoxy)-4-pentafluoroethyl-phenylamine.
l) (S) 3-Oxiranylmethoxy-4-pentafluoroethyl-phenylamine.
m) 3-(2-Pyrrolidin-1-yl-ethoxy)-4-trifluoromethyl-phenylamine.
n) 3-(2-Piperidin-1-yl-ethoxy)-4-trifluoromethyl-phenylamine.
o) (S) 3-(1-Boc-pyrrolidin-2-ylmethoxy)-4-pentafluoroethyl-phenylamine.
p) (R) 3-(1-Boc-pyrrolidin-2-ylmethoxy)-4-pentafluoroethyl-phenylamine.
q) (R) 3-(1-Methyl-pyrrolidin-2-ylmethoxy)-5-trifluoromethyl-phenylamine.
r) (S) 3-(1-Methyl-pyrrolidin-2-ylmethoxy)-5-trifluoromethyl-phenylamine
s) (R) 3-Oxiranylmethoxy-4-pentafluoroethyl-phenylamine.
t) (R) 2-(5-Amino-2-pentafluoroethyl-phenoxy)-1-pyrrolidin-1-yl-ethanol.
u) 3-(1-Boc-azetidin-3-ylmethoxy)-4-pentafluoroethyl-phenylamine.
v) 3-(2-(Boc-amino)ethoxy)-4-pentafluoroethyl-phenylamine.
w) 6-Amino-2,2-dimethyl-4H-benzo[1,4]oxazin-3-one. M+H 193.2. Calc'd 192.1.
x) 2,2,4-Trimethyl-3,4-dihydro-2H-benzo[1,4]oxazin-6-ylamine.
y) 1-(6-Amino-2,2-dimethyl-2,3-dihydro-benzo[1,4]oxazin-4-yl)-ethanone. M+H 221.4. Calc'd 220.3.
z) [2-(1-Benzhydryl-azetidin-3-yloxy)-pyridin-4-yl]-methylamine.
aa) [2-(1-Methyl-piperidin-4-ylmethoxy)-pyridin-4-yl]-methylamine. M+H 236.3. Calc'd 235.2.
ab) 3-(4-Boc-piperazin-1-ylmethyl)-5-trifluoromethyl-phenylamine. M+H 360.3.
ac) 2-Boc-4,4-dimethyl-1,2,3,4-tetrahydro-isoquinolin-7-ylamine.
ad) 3-Morpholin-4-ylmethyl-4-pentafluoroethyl-phenylamine.
ae) 3-(4-Methyl-piperazin-1-ylmethyl)-4-pentafluoroethyl-phenylamine. M+H 410.3. Calc'd 409.4.
af) 7-Amino-2-(4-methoxy-benzyl)-4,4-dimethyl-3,4-dihydro-2H-isoquinolin-1-one. M+H 311.1.
ag) 7-Amino-4,4-dimethyl-3,4-dihydro-2H-isoquinolin-1-one.
ah) (3-Amino-5-trifluoromethyl-phenyl)-(4-Boc-piperazin-1-yl)-methanone. M+H 374.3; Calc'd 373.
ai) 3-(4-Boc-piperazin-1-ylmethyl)-5-trifluoromethyl-phenylamine.
aj) 1-(7-Amino-4,4-dimethyl-3,4-dihydro-1H-isoquinolin-2-yl)-ethanone. M+H 219.2.
ak) {2-[2-(1-Methylpiperidin-4-yl)ethoxy]-pyridin-4-yl}-methylamine.
al) {2-[2-(1-Pyrrolidinyl)ethoxy]-pyridin-4-yl}-methylamine.
am) {2-[2-(1-Methylpyrrolin-2-yl)ethoxy]-pyridin-4-yl}-methylamine.
an) (2-Chloro-pyrimidin-4-yl)-methylamine.
ao) 3-(1-Boc-azetidin-3-ylmethoxy)-5-trifluoromethyl-phenylamine.
ap) 4-tert-Butyl-3-(1-Boc-pyrrolidin-3-ylmethoxy)-phenylamine. M+H 385.
aq) 4-tert-Butyl-3-(1-Boc-azetidin-3-ylmethoxy)-phenylamine. M+Na 357.
ar) (S) 4-tert-Butyl-3-(1-Boc-pyrrolidin-2-ylmethoxy)-phenylamine. M+Na 371.
as) 3-tert-Butyl-4-(4-Boc-piperazin-1-yl)-phenylamine
at) 3-(1-Methyl-piperidin-4-yl)-5-trifluoromethyl-phenylamine.
au) 3,3-Dimethyl-2,3-dihydro-benzofuran-6-ylamine.
av) 3,9,9-Trimethyl-2,3,4,4a,9,9a-hexahydro-1H-3-azafluoren-6-ylamine.
aw) 4-[1-Methyl-1-(1-methyl-piperidin-4-yl)-ethyl]-phenylamine was prepared using EtOH as the solvent.
ax) 4-tert-Butyl-3-(4-pyrrolidin-1-yl-but-1-enyl)-phenylamine.
ay) (R) 3-(1-Boc-pyrrolidin-2-ylmethoxy)-5-trifluoromethyl-phenylamine.
az) (S) 3-(1-Boc-pyrrolidin-2-ylmethoxy)-5-trifluoromethyl-phenylamine.

Preparation IV—1-Boc-4-{3-[(2-fluoro-pyridine-3-carbonyl)-amino]-5-trifluoromethyl-phenoxy}-piperidine 1-Boc-4-(3-amino-5-trifluoromethyl-phenoxy)-piperidine (4.37 g) was dissolved in $CH_2Cl_2$ (100 ml) and $NaHCO_3$ (2.4 g, Baker) was added. 2-Fluoropyridine-3-carbonyl chloride (2.12 g) was added an the reaction was stirred at RT for 2.5 h. The reaction was filtered and concentrated in vacuo to yield a yellow foam. (30%) EtOAc/Hexane was added and 1-Boc-4-{3-[(2-fluoro-pyridine-3-carbonyl)-amino]-5-trifluoromethyl-phenoxy}-piperidine precipitated as an off white solid.
The following compounds were prepared similarly to the procedure outlined above:
a) 2-Fluoro-N-[3-(3-piperidin-1-yl-propyl)-5-trifluoromethyl-phenyl]-nicotinamide.
b) N-[4-tert-Butyl-3-(2-piperidin-1-yl-ethoxy)-phenyl]-2-fluoro-nicotinamide.
c) N-[3,3-Dimethyl-1-(1-methyl-piperidin-4-ylmethyl)-2,3-dihydro-1H-indol-6-yl]-2-fluoro-nicotinamide.
d) N-[1-(2-Dimethylamino-acetyl)-3,3-dimethyl-2,3-dihydro-1H-indol-6-yl]-2-fluoro-nicotinamide
e) N-[3,3-Dimethyl-1-(2-(Boc-amino)acetyl)-2,3-dihydro-1H-indol-6-yl]-2-fluoro-nicotinamide.
f) N-(4-Acetyl-2,2-dimethyl-3,4-dihydro-2H-benzo[1,4]oxazin-6-yl)-2-fluoro-nicotinamide. M+H 344.5. Calc'd 343.4.
g) 2-Fluoro-N-(2,2,4-trimethyl-3,4-dihydro-2H-benzo[1,4]oxazin-6-yl)-nicotinamide. M+H 316.2. Calc'd 315.1.
h) N-(2,2-Dimethyl-3-oxo-3,4-dihydro-2H-benzo[1,4]oxazin-6-yl)-2-fluoro-nicotinamide. M+H 316.1. Calc'd 315.10.
i) 2-Fluoro-N-[3-(4-methyl-piperazin-1-ylmethyl)-5-trifluoromethyl-phenyl]-nicotinamide. M+H 481. Calc'd 480.
j) 2-Fluoro-N-(2-Boc-4,4-dimethyl-1,2,3,4-tetrahydro-isoquinolin-7-yl)-nicotinamide. M+H 400.
k) 2-Fluoro-N-[3-(4-methyl-piperazin-1-ylmethyl)-4-pentafluoroethyl-phenyl]-nicotinamide. M+H 447.0. Calc'd 446.
l) 2-Fluoro-N-(3-morpholin-4-ylmethyl-4-pentafluoroethyl-phenyl)-nicotinamide.
m) 2-Fluoro-N-[4-iodophenyl]-nicotinamide.
n) 2-Fluoro-N-(4,4-dimethyl-1-oxo-1,2,3,4-tetrahydro-isoquinolin-7-yl)-nicotinamide. M+H 314.0, Calc'd 311.
o) 2-Fluoro-N-[3-(4-Boc-piperazine-1-carbonyl)-5-trifluoromethyl-phenyl]-nicotinamide. M+H 495.
p) 2-Fluoro-N-[3-(4-Boc-piperazin-1-ylmethyl)-5-trifluoromethyl-phenyl]-nicotinamide. M+H 483.3; Calc'd 482.
q) N-(2-Acetyl-4,4-dimethyl-1,2,3,4-tetrahydro-isoquinolin-7-yl)-2-fluoro-nicotinamide. M+H 430.0.

r) N-[3,3-Dimethyl-1-(1-methyl-piperidin-4-yl)-2,3-dihydro-1H-indol-6-yl]-2-fluoro-nicotinamide. M+H 383.2; Calc'd 382.5.
s) N-(4-tert-Butylphenyl)-2-fluoronicotinamide.
t) N-(4-Trifluoromethylphenyl)-2-fluoronicotinamide.
u) 2-Fluoro-N-[3-(1-Boc-azetidin-3-ylmethoxy)-5-trifluoromethyl-phenyl]-nicotinamide. M-H 468.2; Calc'd 469.16.
v) 2-Fluoro-N-[3-(1-Boc-azetidin-3-ylmethoxy)-4-tert-butyl-phenyl]-nicotinamide.
w) (S)N-[4-tert-Butyl-3-(1-Boc-pyrrolidin-2-ylmethoxy)-phenyl]-2-fluoro-nicotinamide. M+Na 494.
x) N-[3-(1-Methyl-piperidin-4-yl)-5-trifluoromethyl-phenyl]-2-fluoro-nicotinamide was prepared with $K_2CO_3$. instead of $NaHCO_3$.
y) N-(3-Bromo-5-trifluoromethyl-phenyl)-2-fluoro-nicotinamide.
z) 2-Fluoro-N-(3,9,9-trimethyl-2,3,4,4a,9,9a-hexahydro-1H-3-aza-fluoren-6-yl)-nicotinamide.
aa) 2-Fluoro-N-{4-[1-methyl-1-(1-methyl-piperidin-4-yl)-ethyl]-phenyl}-nicotinamide
ab) N-[3,3-Dimethyl-1-(1-Boc-piperidin-4-ylmethyl)-2,3-dihydro-1H-indol-6-yl]-2-fluoro-nicotinamide.

Preparation V—1-Boc-4-{3-[(2-chloro-pyridine-3-carbonyl)-amino]-5-trifluoromethyl-phenoxy}-piperidine 1-Boc-4-{3-[(2-chloro-pyridine-3-carbonyl)-amino]-5-trifluoromethyl-phenoxy}-piperidine was prepared from 1-Boc-4-(3-amino-5-trifluoromethyl-phenoxy)-piperidine and 2-chloropyridine-3-carbonyl chloride by a procedure similar to that described in the preparation of 1-Boc-4-{3-[(2-fluoro-pyridine-3-carbonyl)-amino]-5-trifluoromethyl-phenoxy}-piperidine.

The following compounds were prepared similarly to the procedure outlined above:
a) N-(4-tert-Butyl-3-nitro-phenyl)-2-chloro-nicotinamide.
b) 2-Chloro-N-[3-(3-piperidin-1-yl-propyl)-5-trifluoromethyl-phenyl]-nicotinamide.
c) 2-Chloro-N-[3-(3-morpholin-4-yl-propyl)-5-trifluoromethyl-phenyl]-nicotinamide.
d) 2-Chloro-N-[3-(1-methylpiperidin-4-yl)-5-trifluoromethyl-phenyl]-nicotinamide.
e) 2-Chloro-N-[3-(1-methyl-piperidin-4-ylmethoxy)-4-pentafluoroethyl-phenyl]-nicotinamide.
f) 2-Chloro-N-[3-(1-isopropyl-piperidin-4-ylmethoxy)-4-pentafluoroethyl-phenyl]-nicotinamide.
g) (S) 2-Chloro-N-[4-(oxiranylmethoxy)-3-pentafluoroethyl-phenyl]-nicotinamide.
h) 2-Chloro-N-[3-(2-pyrrolidin-1-yl-ethoxy)-4-trifluoromethyl-phenyl]-nicotinamide.
i) 2-Chloro-N-[3-(2-piperidin-1-yl-ethoxy)-4-pentafluoroethyl-phenyl]-nicotinamide.
j) (R) 2-Chloro-N-[3-(1-Boc-pyrrolidin-2-ylmethoxy)-4-pentafluoroethyl-phenyl]-nicotinamide.
k) (S) 2-Chloro-N-[3-(1-Boc-pyrrolidin-2-ylmethoxy)-4-pentafluoroethyl-phenyl]-nicotinamide.
l) (R) 2-Chloro-N-[3-(1-methyl-pyrrolidin-2-ylmethoxy)-5-trifluoromethyl-phenyl]-nicotinamide.
m) (S) 2-Chloro-N-[3-(1-methyl-pyrrolidin-2-ylmethoxy)-5-trifluoromethyl-phenyl]-nicotinamide.
n) (R) 2-Chloro-N-[4-(oxiranylmethoxy)-3-pentafluoroethyl-phenyl]-nicotinamide.
o) (R) Acetic acid 2-{5-[(2-chloro-pyridine-3-carbonyl)-amino]-2-pentafluoroethyl-phenoxy}-1-pyrrolidin-1-yl-ethyl ester.
p) 2-Chloro-N-[3-(4-methyl-piperazin-1-ylmethyl)-5-trifluoromethyl-phenyl]-nicotinamide.
q) 2-Chloro-N-[2-(4-methoxy-benzyl)-4,4-dimethyl-1-oxo-1,2,3,4-tetrahydro-isoquinolin-7-yl]-nicotinamide. M+H 450.2. Calc'd 449.
r) 2-Chloro-N-(4,4-dimethyl-1-oxo-1,2,3,4-tetrahydro-isoquinolin-7-yl)-nicotinamide. M+H 330.1, Calc'd 329.
s) 2-Chloro-N-[3-(4-Boc-piperazin-1-ylmethyl)-5-trifluoromethyl-phenyl]-nicotinamide.
t) 2-{3-[(2-Chloro-pyridine-3-carbonyl)-amino]-phenyl}-2-methyl-propionic acid methyl ester. M+H 405
u) N-{4-tert-Butyl-3-[2-(1-Boc-piperidin-4-yl)-ethyl]-phenyl}-2-chloro-nicotinamide. M+Na 524. Calc'd 501.1.
v) N-[3,3-Dimethyl-1,1-dioxo-2,3-dihydro-1H-benzo[d]isothiazol-6-yl]-2-chloro-nicotinamide.
w) N-[1,1,4,4-Tetramethyl-1,2,3,4-tetrahydro-naphth-6-yl]-2-chloro-nicotinamide.
x) 2-Chloro-N-[3,3-dimethyl-2,3-dihydro-benzofuran-6-yl]-2-chloro-nicotinamide.
y) 2-Chloro-N-[3-(1-Boc-piperidin-4-yloxy)-5-trifluoromethyl-phenyl]-nicotinamide.
z) 2-Chloro-N-[3-(1-methyl-piperidin-4-ylmethyl)-5-trifluoromethyl-phenyl]-nicotinamide.
aa) 2-Chloro-N-[3-(3-piperidin-1-yl-propyl)-5-trifluoromethyl-phenyl]-nicotinamide.
ab) N-[4-tert-Butyl-3-(4-pyrrolidin-1-yl-but-1-enyl)-phenyl]-2-chloro-nicotinamide.
ac) (R) 2-Chloro-N-[3-(1-Boc-pyrrolidin-2-ylmethoxy)-5-trifluoromethyl-phenyl]-nicotinamide.
ad) (S) 2-Chloro-N-[3-(1-Boc-pyrrolidin-2-ylmethoxy)-5-trifluoromethyl-phenyl]-nicotinamide.

Preparation VI—1-Boc-2-{3-[(2-fluoro-pyridine-3-carbonyl)-amino]-5-trifluoromethyl-phenoxymethyl}-pyrrolidine 1-Boc-2-{3-[(2-Fluoro-pyridine-3-carbonyl)-amino]-5-trifluoromethyl-phenoxymethyl}-pyrrolidine was prepared from 1-Boc-2-(3-amino-5-trifluoromethyl-phenoxymethyl)-pyrrolidine by a procedure similar to that described in the preparation of 1-Boc-4-{3-[(2-fluoro-pyridine-3-carbonyl)-amino]-5-trifluoromethyl-phenoxy}-piperidine.

Preparation VII—2-(3-nitro-5-trifluoromethyl-phenoxymethyl)-pyrrolidine

1-Boc-2-(3-nitro-5-trifluoromethyl-phenoxymethyl)-pyrrolidine (2.35 g) was dissolved in $CH_2Cl_2$ (60 ml) and TFA (20 ml) was added. After stirring for 1 h at RT, the mixture was concentrated in vacuo to yield 2-(3-nitro-5-trifluoromethyl-phenoxymethyl)-pyrrolidine as an oil that solidified upon standing. The material was used as is without further purification.

The following compounds were prepared similarly to the procedure outlined above:
a) (4-Aminomethyl-pyrimidin-2-yl)-(3-morpholin-4-yl-propyl)-amine.
b) (4-Aminomethyl-pyrimidin-2-yl)-[2-(1-methyl-pyrrolidin-2-yl)-ethyl]-amine.

Preparation VIII—1-methyl-2-(3-nitro-5-trifluoromethyl-phenoxymethyl)-pyrrolidine 2-(3-Nitro-5-trifluoromethyl-phenoxymethyl)-pyrrolidine (6 mmol) was dissolved in $CH_3CN$ (20 ml) and formaldehyde (2.4 ml, 37% aqueous) was added. $NaBH_3CN$ (607 mg) was added, an exotherm was observed. The pH is monitored every 15 min and adjusted to ~7 with AcOH. After 45 min, the mixture was concentrated in vacuo and the residue is dissolved in EtOAc, washed with 6N NaOH, 1N NaOH, and 2N HCl (3×). The acid washings were combined, adjusted to ~pH 10 with solid $Na_2CO_3$ and extracted with EtOAc (2×). The EtOAc fractions were combined, dried with $Na_2SO_4$, and purified with flash chromatography ($SiO_2$, 95:5:0.5 $CH_2Cl_2$:MeOH:$NH_4OH$) to afford 1-methyl-2-(3-nitro-5-trifluoromethyl-phenoxymethyl)-pyrrolidine.

The following compounds were prepared similarly to the procedure outlined above:
a) 2-(1-Methylpiperidin-4-yl)-ethanol.
b) 2-{3-[(2-Fluoro-pyridine-3-carbonyl)-amino]-5-trifluoromethyl-phenoxymethyl}-1-methylpyrrolidine.

Preparation IX—4-tert-butyl-3-nitro-phenylamine

A mixture of 1,3-dinitro-4-tert-butylbenzene (10.0 g) in $H_2O$ (56 ml) was heated to reflux. A mixture of $Na_2S$ (21.42 g) and sulfur (2.85 g) in $H_2O$ (34 ml) was added over 1 h via an addition funnel. The reaction maintained at reflux for 1.5 h then cooled to RT and extracted with EtOAc. The organic extracts were combined and washed with $H_2O$, brine, dried over $MgSO_4$ and concentrated in vacuo to afford 4-tert-butyl-3-nitro-phenylamine which was used as is without further purification.

Preparation X—N-(3-bromo-5-trifluoromethyl-phenyl)-acetamide

3-Bromo-5-(trifluoromethyl)phenylamine (5 g, Alfa-Aesar) was dissolved in AcOH (140 ml) and $Ac_2O$ (5.9 ml, Aldrich) was added. The reaction was stirred at RT overnight. The mixture was added slowly to $H_2O$ (~700 ml) forming a white precipitate. The solid was isolated by filtration, washed with $H_2O$ and dried under vacuum to yield N-(3-bromo-5-trifluoromethyl-phenyl)-acetamide.

Preparation XI—N-[3-(3-piperidin-1-yl-propyl)-5-trifluoromethyl-phenyl]-acetamide Allylpiperidine (1.96 g, Lancaster) was degassed under vacuum, dissolved in 0.5 M 9-BBN in THF (31.2 ml, Aldrich), and heated to reflux for 1 h, then cooled to RT. PD(dppf)$Cl_2/CH_2Cl_2$ was added to a degassed mixture of N-(3-bromo-5-trifluoromethyl-phenyl)-acetamide, $K_2CO_3$ (9.8 g) DMF (32.1 ml and $H_2O$ (3 ml). The allyl piperidine solution was added heated to 60° C. for 3 h. After cooling to RT and reheating at 60° C. for 6 h, the mixture was cooled to RT and poured into $H_2O$. The mixture was extracted with EtOAc (2×), and the EtOAc portion was washed with 2 N HCl (2×) and brine. The aqueous phases were combined and the pH was adjusted to ~11 with NaOH (15%) forming a cloudy suspension. The cloudy suspension was extracted with EtOAc (2×) and the EtOAc portion was dried with $Na_2SO_4$, filtered and concentrated in vacuo. The crude material was purified by flash chromatography ($SiO_2$, 95:5:0.5 $CH_2Cl_2$:MeOH:$NH_4OH$) to afford N-[3-(3-piperidin-1-yl-propyl)-5-trifluoromethyl-phenyl]-acetamide as a brown oil that solidified under vacuum.

The following compounds were prepared similarly to the procedure outlined above:
a) N-(3-Morpholin-4-ylpropyl-5-trifluoromethyl-phenyl)-acetamide from 4-allyl-morpholine.
b) N-(3-(1-methylpiperdin-4-ylmethyl-5-trifluoromethyl-phenyl)-acetamide from 1-Methyl-4-methylene-piperidine.

Preparation XII—3-(3-piperidin-1-yl-propyl)-5-trifluoromethyl-phenylamine

N-[3-(3-Piperidin-1-yl-propyl)-5-trifluoromethyl-phenyl]-acetamide (1.33 g) was dissolved in EtOH (40 ml) and 12 N HCl (40 ml) was added. After stirring overnight at 70° C. and RT, the mixture was concentrated in vacuo, affording 3-(3-piperidin-1-yl-propyl)-5-trifluoromethyl-phenylamine as a brown oil.

The following compounds were prepared similarly to the procedure outlined above:
a) 3,3-Dimethyl-6-nitro-2,3-dihydro-1H-indole. M+H 193.1; Calc'd 192.2.
b) 3-(1-Methyl-piperidin-4-ylmethyl)-5-trifluoromethyl-phenylamine.
c) 3-Morpholin-4-ylmethyl-5-trifluoromethyl-phenylamine.

Preparation XIII—3,3-Dimethyl-6-nitro-1-piperidin-4-ylmethyl-2,3-dihydro-1H-indole 3,3-Dimethyl-1-(1-Boc-piperidin-4-ylmethyl)-6-nitro-2,3-dihydro-1H-indole was dissolved in HCl/EtOAc and stirred for 2 h. The mixture was concentrated in vacuo and partitioned between 1,2-dichloroethane and 1N NaOH. The organic layer was removed, washed with brine, dried ($Na_2SO_4$) and filtered. The material was used without further purification.

Preparation XIV—N-[3-(3-morpholin-4-yl-propyl)-5-trifluoromethyl-phenyl]-acetamide N-[3-(3-Morpholin-4-yl-propyl)-5-trifluoromethyl-phenyl]-acetamide was prepared from allyl morpholine and N-(3-bromo-5-trifluoromethyl-phenyl)-acetamide similar to that described in the preparation of N-[3-(3-piperidin-1-yl-propyl)-5-trifluoromethyl-phenyl]-acetamide.

Preparation XV—3-(3-morpholin-4-yl-propyl)-5-trifluoromethyl-phenylamine 3-(3-Morpholin-4-yl-propyl)-5-trifluoromethyl-phenylamine was prepared from N-[3-(3-morpholin-4-yl-propyl)-5-trifluoromethyl-phenyl]-acetamide similar to that described in the preparation of 3-(3-piperidin-1-yl-propyl)-5-trifluoromethyl-phenylamine.

Preparation XVI—1-methyl-4-methylene-piperidine $Ph_3PCH_3I$ (50 g, Aldrich) was suspended in $Et_2O$ (20 ml) and butyllithium (77.3 ml, 1.6 M in hexanes, Aldrich) was added dropwise. The reaction was stirred for 2 h at RT then 1-methylpiperidone (12.3 ml, Aldrich) was added slowly. The mixture was stirred at RT overnight. The solid was removed by filtration, the volume was reduced to ~400 ml and additional solid was removed by filtration. The $Et_2O$ was washed with $H_2O$ (2×) and 2N HCl (4×). The pH of the acid washings was adjusted to ~11 with 6 N NaOH, then they were extracted with $CH_2Cl_2$ (4×). The $CH_2Cl_2$ washings were dried over $Na_2SO_4$ and concentrated cold in vacuo to provide 1-methyl-4-methylene-piperidine which was used as is.

Preparation XVII—N-[3-(1-methylpiperidin-4-yl)-5-trifluoromethyl-phenyl]-acetamide N-[3-(1-Methylpiperidin-4-yl)-5-trifluoromethyl-phenyl]-acetamide was prepared from 1-methyl-4-methylene-piperidine and N-(3-bromo-5-trifluoromethyl-phenyl)-acetamide similar to that described in the preparation of N-[3-(3-piperidin-1-yl-propyl)-5-trifluoromethyl-phenyl]-acetamide.

Preparation XVIII—3-(1-methylpiperidin-4-yl)-5-trifluoromethyl-phenylamine 3-(1-Methylpiperidin-4-yl)-5-trifluoromethyl-phenylamine was prepared from N-[3-(1-methylpiperidin-4-yl)-5-trifluoromethyl-phenyl]-acetamide similar to the procedure described in the preparation of 3-(3-piperidin-1-yl-propyl)-5-trifluoromethyl-phenylamine.

Preparation XIX—2-(1-methylpiperidin-4-yloxy)-4-pyridylcarbonitrile

4-Hydroxy-1-methylpiperidine (25.4 g) was dissolved in THF (50 ml) in a 100 mL r.b. flask. NaH/mineral oil mixture (9.58 g) was slowly added to the flask and stirred for 20 min. 2-Chloro-4-cyanopyridine was added to the mixture and stirred at RT until completion. Diluted mixture with EtOAc and added H$_2$O to quench mixture, then transferred contents to a sep. funnel. The organic phase was collected while the aqueous phase was washed two times with EtOAc. The combined organics were dried over Na$_2$SO$_4$, filtered, then concentrated in vacuo. Then redissolved mixture in CH$_2$Cl$_2$, 10% HCl (300 ml) was added and the mixture was transferred to sep. funnel. The org. was extracted, while EtOAc along with 300 mL 5N NaOH was added to the sep. funnel. The organic phases were collected, dried over Na$_2$SO$_4$, filtered and concentrated in vacuo affording 2-(1-methylpiperidin-4-yloxy)-4-pyridylcarbonitrile as a brown solid. ESI (M+H)=218.

The following compounds were prepared similarly to the procedure outlined above:
a) 2-(1-methylpiperidin-4-ylmethoxy)-4-pyridylcarbonitrile. M+H 232.1. Calc'd 231.1.
b) 2-(1-Benzhydryl-azetidin-3-yloxy)-4-pyridylcarbonitrile. M+H 342.2. Calc'd 341.2.
c) 2-(1-methylpiperidin-4-ylethoxy)-4-pyridylcarbonitrile.
d) 2-(1-pyrrolidinylethoxy)-4-pyridylcarbonitrile.
e) 2-(1-methylpyrrolin-2-ylethoxy)-4-pyridylcarbonitrile.
f) 2-[2-(1-Boc-azetidin-3-yl)-ethoxy]-4-pyridylcarbonitrile.

Preparation XX—[2-(1-methylpiperidin-4-yloxy)-pyridin-4-yl]methylamine bis hydrochloride

[2-(1-Methylpiperidin-4-yloxy)-pyridin-4-yl]methylamine was diluted with Et$_2$O (50 ml) and 1M HCl/Et$_2$O (47 ml) was added. The vessel was swirled until precipitate formed.

Preparation XXI—2-(2-morpholin-4-yl-ethoxy)-4-pyridylcarbonitrile 2-(2-Morpholin-4-yl-ethoxy)-4-pyridylcarbonitrile was prepared from 2-chloro-4-cyanopyridine and 2-morpholin-4-yl-ethanol by a procedure similar to that described in the preparation of 2-(1-methylpiperidin-4-yloxy)-4-pyridylcarbonitrile. The hydrochloride salt was prepared similar to that described for [2-(1-methylpiperidin-4-yloxy)-pyridin-4-yl] methylamine bis hydrochloride.

Preparation XXII—2-morpholin-4-yl-propanol

LAH powder (1.6 g) was added to a flask while under N$_2$ atmosphere, immediately followed by THF (50 ml). The mixture was chilled to 0° C., methyl 2-morpholin-4-yl-propionate (5 g) was added dropwise to the reaction mixture and stirred at 0° C. After 1 h, the mixture was worked up by adding H$_2$O (44 mL), 2N NaOH (44 mL), then H$_2$O (44 mL, 3×). After 30 min of stirring, the mixture was filtered through Celite® and the organic portion was concentrated in vacuo providing 2-morpholin-4-yl-propanol as a colorless oil.

The following compounds were prepared similarly to the procedure outlined above:
a) (1-Methyl-piperidin-4-yl)-methanol. M+H 130.2. Calc'd 129.1.

Preparation XXIII—2-(2-morpholin-4-yl-propoxy)-4-pyridylcarbonitrile 2-(2-Morpholin-4-yl-propoxy)-4-pyridylcarbonitrile was prepared from 2-chloro-4-cyanopyridine and 2-morpholin-4-yl-propanol by a procedure similar to that described in the preparation of 2-(1-methylpiperidin-4-yloxy)-4-pyridylcarbonitrile.

Preparation XXIV—2-(1-Methyl-pyrrolidin-2-yl-methoxy)-4-pyridylcarbonitrile 2-(1-Methyl-pyrrolidin-2-ylmethoxy)-4-pyridylcarbonitrile was prepared from 2-chloro-4-cyanopyridine and 1-methyl-pyrrolidin-2-ylmethanol by a procedure similar to that described in the preparation of 2-(1-methylpiperidin-4-yloxy)-4-pyridylcarbonitrile. ESI MS: (M+H)=218.

Preparation XXV—2-(3-morpholin-4-yl-propylamino)-4-pyridylcarbonitrile

To a flask charged with 2-chloro-4-cyanopyridine (2.0 g), was added the aminopropyl morpholine (2.11 ml). The mixture was heated to 79° C. for 5 h and stirred. After 5 h the reaction was incomplete. The mixture was then heated at 60° C. overnight. The crude compound was purified on silica gel (1-5% MeOH/CH$_2$Cl$_2$ gradient). ESI MS: (M+H)=247, (M−H)=245.

Preparation XXVI—5-Nitro-2-pentafluoroethylphenol

Combined 2-methoxy-4-nitro-1-pentafluoroethylbenzene (9.35 g) and pyridine hydrochloride in a round bottom flask and heated at 210° C. for 1 h then cooled to RT. The mixture was diluted with EtOAc and 2N HCl (>500 ml) until all residue dissolved. The organic layer was removed, washed with 2N HCl (2×) and concentrated in vacuo. The residue was dissolved in hexanes and Et$_2$O, washed with 2N HCl, then brine. Dried organic layer over Na$_2$SO$_4$, filtered, concentrated in vacuo and dried under high vacuum to provide 5-nitro-2-pentafluoromethylphenol.

Preparation XXVII—2-tert-Butyl-5-nitro-aniline

To H$_2$SO$_4$ (98%, 389 mL) in a 500 mL 3-neck flask was added 2-tert-butyl aniline (40.6 mL). The reaction was cooled to −10° C. and KNO$_3$ in 3.89 g aliquots was added every 6 min for a total of 10 aliquots. Tried to maintain temperature at −5° C. to −10° C. After final addition of KNO$_3$, stirred the reaction for five min then it was poured onto ice (50 g). The black mix was diluted with H$_2$O and extracted with EtOAc. The aqueous layer was basified with solid NaOH slowly then extracted with EtOAc (2×). The combined organic layers were washed with 6N NaOH and then with a mix of 6N NaOH and brine, dried over Na$_2$SO$_4$, filtered and concentrated in vacuo to obtain crude 2-tert-butyl-5-nitro-aniline as a dark red-black oil which solidified when standing at RT. The crude material was triturated with about 130 mL hexanes. After decanting the hexanes, the material was dried to obtain a dark-red black solid.

Preparation XXVIII—2-tert-Butyl-5-nitrophenol

In a 250 ml round bottom flask, 20 mL concentrated $H_2SO4$ was added to 2-tert-butyl-5-nitro-aniline (7.15 g) by adding 5 mL aliquots of acid and sonicating with occasional heating until all of the starting aniline went into solution. $H_2O$ (84 ml) was added with stirring, then the reaction was cooled to 0° C. forming a yellow-orange suspension. A solution of $NaNO_2$ (2.792 g) in $H_2O$ (11.2 mL) was added dropwise to the suspension and stirred for 5 min. Excess $NaNO_2$ was neutralized with urea, then the cloudy solution was transferred to 500 ml 3-necked round bottom flask then added 17 mL of $1:2H_2SO_4:H_2O$ solution, and heated at reflux. Two additional 5 mL aliquots of $1:2H_2SO_4:H_2O$ solution, a 7 mL aliquot of $1:2H_2SO_4:H_2O$ solution and another 10 mL of $1:2H_2SO_4: H_2O$ were added while heating at reflux. The mixture was cooled to RT forming a black layer floating on top of the aqueous layer. The black layer was diluted with EtOAc (300 mL) and separated. The organic layer was washed with $H_2O$ then brine, dried over $Na_2SO_4$ and concentrated in vacuo. Crude oil was purified on silica gel column with 8% EtOAc/Hexanes. Upon drying under vacuum, the 2-tert-butyl-5-nitrophenol was isolated as a brown solid.

Preparation XXIX—1-methylpiperidine-4-carboxylic acid ethyl ester

Piperidine-4-carboxylic acid ethyl ester (78 g) was dissolved in MeOH (1.2 L) at RT then formaldehyde (37%, 90 ml) and acetic acid (42 ml) were added and stirred for 2 h. The mixture was cooled to 0° C., $NaCNBH_3$ (70 g) was added, and the mix was stirred for 20 min at 0° C., then overnight at RT. The mixture was cooled to 0° C. then quenched with 6N NaOH. The mixture was concentrated in vacuo to an aqueous layer, which was extracted with EtOAc (4×), brine-washed, dried over $Na_2SO_4$, and concentrated in vacuo to provide 1-methylpiperidine-4-carboxylic acid ethyl ester.

The following compounds were prepared similarly to the procedure outlined above:
a) (1-Methyl-piperidin-4-yl)-methanol. M+H 130.2. Calc'd 129.1.

Preparation XXX—N-[4-tert-Butyl-3-(1-methyl-piperidin-4-ylmethoxy)-phenyl]-2-chloro-nicotinamide N-[4-tert-Butyl-3-(1-methyl-piperidin-4-ylmethoxy)-phenyl]-2-chloro-nicotinamide was prepared from 4-tert-butyl-3-(1-methyl-piperidin-4-ylmethoxy)-phenylamine by a procedure similar to that described in the preparation of 1-Boc-4-{3-[(2-chloro-pyridine-3-carbonyl)-amino]-5-trifluoromethyl-phenoxy}-piperidine.

Preparation XXXI—1-[2-(2-tert-Butyl-5-nitro-phenoxy)-ethyl]-piperidine

To 2-tert-butyl-5-nitrophenol (1.01 g) and $K_2CO_3$ (1.72 g) was added acetone (35 ml) and $H_2O$ (10.5 mL), then 1-(2-chloroethyl)piperidine HCl (1.909 g) and TBAI (153 mg). The mixture was stirred at reflux overnight. Additional $K_2CO_3$ (850 mg) and 1-(2-chloroethyl)-piperidine HCl (950 mg) were added and the mixture was heated at reflux for 6 h. The mixture was concentrated in vacuo to an aqueous layer which was acidified with 2N HCl and extracted with EtOAc. The aqueous layer was basified with 6N NaOH and washed with $CH_2Cl_2$ (3×). The combined organic layers were washed with brine/1N NaOH and dried over $Na_2SO_4$. Washed the EtOAc layer with 2N NaOH/brine and dried over $Na_2SO_4$. The crude material was purified by silica gel column chromatography with 15% EtOAc/Hexanes to yield 1-[2-(2-tert-butyl-5-nitro-phenoxy)-ethyl]-piperidine as a light tan solid. (M+1)=307.3.

Preparation XXXII—1-Boc-Piperidine-4-carboxylic acid ethyl ester

To a stirred solution of piperidine-4-carboxylic acid ethyl ester (23.5 g) in EtOAc (118 ml) at 0° C. was added dropwise $Boc_2O$ in EtOAc (60 ml). The reaction was warmed to RT and stirred overnight. Washed reaction with $H_2O$, 0.1N HCl, $H_2O$, $NaHCO_3$ and brine. The organic layer was dried over $Na_2SO_4$, filtered and concentrated in vacuo. The liquid was dried under vacuum to provide 1-Boc-piperidine-4-carboxylic acid ethyl ester.

The following compounds were prepared similarly to the procedure outlined above:
a) N-Boc-(2-chloropyrimidin-4-yl)-methylamine.
b) 1-(2-tert-Butyl-4-nitrophenyl)-4-Boc-piperazine.
c) 1-Boc-azetidine-3-carboxylic acid
d) 1-Boc-4-Hydroxymethyl-piperidine using TEA.

Preparation XXXIII—1-Boc-4-hydroxymethyl-piperidine

1-Boc-4-Hydroxymethyl-piperidine was prepared from 1-Boc-piperidine-4-carboxylic acid ethyl ester by a procedure similar to that described in the preparation of 2-morpholin-4-yl-propanol.

Preparation XXXIV—1-Boc-4-Methylsulfonyloxymethyl-piperidine

Dissolved 1-Boc-4-hydroxymethyl-piperidine in anhydrous $CH_2Cl_2$ (50 ml) and TEA (4.5 ml) and cooled to 0° C. Mesyl chloride (840 µl) was added and the mixture was stirred for 15 min then at RT for 45 min. The mixture was washed with brine/1N HCl and then brine, dried over $Na_2SO_4$, concentrated in vacuo and dried under high vacuum to provide 1-Boc-4-methylsulfonyloxymethyl-piperidine as a yellow orange thick oil.

The following compounds were prepared similarly to the procedure outlined above:
a) 1-Boc-3-methylsulfonyloxymethyl-azetidine.

Preparation XXXV—1-Boc-4-(3-nitro-6-pentafluoroethyl-phenoxymethyl)-piperidine

To a slurry of 60% NaH suspension in DMF (30 mL) at RT added a solution of 5-nitro-2-pentafluoroethyl-phenol (3.6 g) in 5 mL DMF. The dark red mixture was stirred at RT for 10 min then added a solution of 1-Boc-4-methylsulfonyloxymethyl-piperidine (3.1 g) in 5 mL DMF. The reaction was stirred at 60° C. and 95° C. After 1 h, added 2.94 g $K_2CO_3$ and stirred overnight at 105° C. After cooling to RT, the reaction was diluted with hexanes and 1N NaOH. Separated layers, and washed organic layer with 1N NaOH and with brine, dried over $Na_2SO_4$, filtered and concentrated in vacuo. Purification with silica gel column chromatography with 8% EtOAc/Hexanes yielded 1-Boc-4-(3-nitro-6-pentafluoroethyl-phenoxymethyl)-piperidine as a light yellow thick oil.

Preparation XXXVI—4-(3-nitro-6-pentafluoroethyl-phenoxymethyl)-piperidine 4-(3-Nitro-6-pentafluoroethyl-phenoxymethyl)-piperidine was prepared from 1-Boc-4-(3-nitro-6-pentafluoroethyl-phenoxymethyl)-piperidine by a procedure similar to that described in the preparation of 2-(3-nitro-5-trifluoromethyl-phenoxymethyl)-pyrrolidine.

Preparation XXXVII—1-methyl-4-(3-nitro-6-pentafluoroethyl-phenoxymethyl)-piperidine 4-(3-Nitro-6-pentafluoroethyl-phenoxymethyl)-piperidine (316.5 mg) was dissolved in 2.7 mL acetonitrile, then added 37% formaldehyde/$H_2O$ (360 ul) and then $NaBH_3CN$ (90 mg). Upon addition of $NaCNBH_3$ the reaction exothermed slightly. The reaction was stirred at RT and pH was maintained at ~7 by addition of drops of glacial acetic acid. After about 1 h, the mixture was concentrated in vacuo, treated with 8 mL 2N KOH and extracted two times with 10 mL $Et_2O$. The organic layers were washed with 0.5N KOH and then the combined organic layers were extracted two times with 1N HCl. The aqueous layer was basified with solid KOH and extracted two times with $Et_2O$. This organic layer was then washed with brine/1N NaOH, dried over $Na_2SO_4$, filtered, concentrated in vacuo and dried under high vacuum to give pure compound.

Preparation XXXVIII—1-Isopropyl-4-(5-nitro-2-pentafluoroethyl-phenoxymethyl)-piperidine Dissolved 4-(5-nitro-2-pentafluoroethyl-phenoxymethyl)-piperidine (646 mg) in 1,2-dichloroethane (6.4 ml), then added acetone (136 ul), $NaBH(OAc)_3$ (541 mg) and finally acetic acid (105 ul). Stirred the cloudy yellow solution under $N_2$ at RT overnight. Added another 130 uL acetone and stirred at RT over weekend. Quenched the reaction with 30 mL N $NaOH/H_2O$ and stirred 10 min. Extracted with $Et_2O$ and the organic layer was brine-washed, dried over $Na_2SO_4$, filtered and concentrated in vacuo. Dried under high vacuum for several h to obtain 1-isopropyl-4-(5-nitro-2-pentafluoroethyl-phenoxymethyl)-piperidine as a yellow orange solid.

The following compounds were prepared similarly to the procedure outlined above:
a) 3,3-Dimethyl-1-(1-methyl-piperidin-4-yl)-6-nitro-2,3-dihydro-1H-indole was prepared using 1-methyl-piperidin-4-one. M+H 290; Calc'd 289.4.
b) 3,3-Dimethyl-1-(1-Boc-piperidin-4-ylmethyl)-6-nitro-2,3-dihydro-1H-indole using 1-Boc-4-formyl-piperidine.

Preparation XXXIX—3,3-Dimethyl-1-(1-methyl-piperidin-4-ylmethyl)-6-nitro-2,3-dihydro-1H-indole 3,3-Dimethyl-1-piperidin-4-ylmethyl-6-nitro-2,3-dihydro-1H-indole was treated with an excess of formaldehyde and $NaBH(OAc)_3$ and stirred overnight at RT. The reaction was quenched with MeOH and concentrated in vacuo. The residue was partitioned between EtOAc and 1N NaOH. The organic layer was removed, washed with brine, dried ($Na_2SO_4$), filtered and concentrated to provide the compound.

Preparation XL—(S) 2-(5-Nitro-2-pentafluoroethyl-phenoxymethyl)-oxirane

Combined 5-nitro-2-pentafluoromethylphenol (2.69 g), DMF (25 ml) $K_2CO_3$ (3.03 g) and (S) toluene-4-sulfonic acid oxiranyl-methyl ester (2.27 g) and stirred the mixture at 90° C. After about 4 hours, the mix was cooled, diluted with EtOAc, washed with $H_2O$, 1N NaOH (2×), 1N HCl and then with brine. Dried over $Na_2SO_4$, filtered and concentrated in vacuo. Purified the crude on silica gel column with 5% EtOAc/hexane and drying under high vacuum provided the (S)-2-(5-nitro-2-pentafluoroethyl-phenoxymethyl)-oxirane.

The following compounds were prepared similarly to the procedure outlined above:
a) (R)-2-(5-Nitro-2-pentafluoroethyl-phenoxymethyl)-oxirane.

Preparation XLI—(S) 2-Chloro-N-[3-(2-hydroxy-3-pyrrolidin-1-yl-propoxy)-4-pentafluoroethyl-phenyl]-nicotinamide (S) 2-Chloro-N-[4-(2-oxiranylmethoxy-)-3-pentafluoroethyl-phenyl]-nicotinamide (1.11 g) in a sealed tube and added pyrrolidine (285 µl). Stirred after sealing tube at 60° C. After 12 h, the mix was concentrated in vacuo and purified on a silica gel column (5:95:0.5 MeOH:$CH_2Cl_2$:$NH_4OH$—8:92:1, MeOH:$CH_2Cl_2$:$NH_4OH$). Concentrated in vacuo and dried under high vacuum to obtain pure compound.

The following compounds were prepared similarly to the procedure outlined above:
a) (R) 1-(5-Nitro-2-pentafluoroethyl-phenoxy)-3-pyrrolidin-1-yl-propan-2-ol.

Preparation XLII—5-nitro-2-trifluoromethylanisole

Cooled 140 mL pyridine in a large sealable vessel to −40° C. Bubbled in trifluoromethyl iodide from a gas cylinder which had been kept in freezer overnight. After adding $ICF_3$ for 20 min, added 2-iodo-5-nitroanisole (24.63 g) and copper powder (67.25 g). Sealed vessel and stirred vigorously for 22 h at 140° C. After cooling to −50° C., carefully unsealed reaction vessel and poured onto ice and $Et_2O$. Repeatedly washed with $Et_2O$ and $H_2O$. Allowed the ice—$Et_2O$ mixture to warm to RT. Separated layers, washed organic layer with 1N HCl (3×), then brine, dried over $Na_2SO_4$, filtered and concentrated in vacuo. Eluted material through silica gel plug (4.5:1 Hex:$CH_2Cl_2$) to provide 5-nitro-2-trifluoromethylanisole.

Preparation XLIII—1-[2-(5-nitro-2-trifluoromethylphenoxy)ethyl]pyrrolidine

1-[2-(5-Nitro-2-trifluoromethylphenoxy)ethyl]-pyrrolidine was prepared from 5-nitro-2-trifluoromethyl-phenol and 1-(2-chloroethyl)pyrrolidine by a procedure similar to that described for 1-[2-(2-tert-butyl-5-nitro-phenoxy)-ethyl]-piperidine.

Preparation XLIV—1-[2-(5-Nitro-2-pentafluoroethyl-phenoxy)-ethyl]-piperidine 1-[2-(5-Nitro-2-pentafluoroethyl-phenoxy)-ethyl]-piperidine was prepared from 5-nitro-2-pentafluoroethylphenol and 1-(2-chloroethyl)piperidine by a procedure similar to that described in the preparation of 1-[2-(2-tert-butyl-5-nitro-phenoxy)-ethyl]-piperidine.

Preparation XLV—3-(1-Boc-pyrrolidin-2-yl-methoxy)-4-pentafluoroethyl-phenylamine 3-(2-Pyrrolidin-1-yl-methoxy)-4-trifluoromethyl-phenylamine was prepared from 1-[2-(5-nitro-2-trifluoromethylphenoxy)methyl]-pyrrolidine by a procedure similar to that described in the preparation of 1-Boc-4-(3-amino-5-trifluoromethyl-phenoxy)-piperidine.

Preparation XLVI—2-Chloro-N-[3-(2-pyrrolidin-1-yl-ethoxy)-4-trifluoromethyl-phenyl]-nicotinamide 2-Chloro-N-[3-(2-pyrrolidin-1-yl-ethoxy)-4-trifluoromethyl-phenyl]-nicotinamide was prepared from 3-(2-pyrrolidin-1-yl-ethoxy)-4-trifluoromethyl-phenylamine and 2-chloropyridine-3-carbonyl chloride by a procedure similar to that described in the preparation of 1-Boc-4-{3-[(2-chloro-pyridine-3-carbonyl)-amino]-5-trifluoromethyl-phenoxy}-piperidine.

Preparation XLVII—(R) Acetic acid 2-(5-nitro-2-pentafluoroethyl-phenoxy)-1-pyrrolidin-1-ylmethyl-ethyl ester Dissolved 1-(5-nitro-2-pentafluoroethyl-phenoxy)-3-pyrrolidin-1-yl-propan-2-ol (3.5 g) in $CH_2Cl_2$ (15 ml) added TEA (2.55 ml) and cooled to 0° C. Acetyl chloride (781.3 µl) was added dropwise, forming a suspension. The mixture was warmed to RT and stirred for 1.5 h. Additional acetyl chloride (200 µl) was added and the mix was stirred for another h. The mixture was diluted with $CH_2Cl_2$ and washed with sat. $NaHCO_3$. The organic layer was removed, washed with brine and back extracted with $CH_2Cl_2$. Dried the combined organic layers over $Na_2SO_4$, filtered and concentrated in vacuo. The residue was purified over silica gel column (5:94.5:0.5 MeOH: $CH_2Cl_2$:$NH_4OH$) to provide acetic acid 2-(5-nitro-2-pentafluoroethyl-phenoxy)-1-pyrrolidin-1-ylmethyl-ethyl ester as a yellow brown oil.

The following compounds were prepared similarly to the procedure outlined above:
a) (R) Acetic acid 2-(5-amino-2-pentafluoroethyl-phenoxy)-1-pyrrolidin-1-yl-methyl-ethyl ester.
b) 1-(2,2-Dimethyl-6-nitro-2,3-dihydro-benzo[1,4]oxazin-4-yl)-ethanone. M-$NO_2$ 206.4; Calc'd 250.1.

Preparation XLVIII—(R) 2-Chloro-N-[3-(2-hydroxy-2-pyrrolidin-1-yl-propoxy)-4-pentafluoroethyl-phenyl]-nicotinamide (R) Acetic acid 2-{5-[(2-chloro-pyridine-3-carbonyl)-amino]-2-pentafluoroethyl-phenoxy}-1-pyrrolidin-1-yl-ethyl ester (408 mg) was dissolved in MeOH (15 ml) and $NH_4OH$ (6 ml) was added and the mixture was stirred at RT for 6 h. The reaction was concentrated in vacuo and dried under high vacuum. The residue was purified over silica gel column (8:92:0.6 MeOH: $CH_2Cl_2$:$NH_4OH$). The purified fractions were concentrated in vacuo and dried again to provide (R)-2-chloro-N-[3-(2-hydroxy-2-pyrrolidin-1-yl-ethoxy)-4-pentafluoroethyl-phenyl]-nicotinamide as a white foam.

Preparation XLIX—2-Dimethylamino-1-(3,3-dimethyl-6-nitro-2,3-dihydro-indol-1-yl)-ethanone 3,3-Dimethyl-6-nitro-2,3-dihydro-1H-indole (5 g) was dissolved in DMF (100 ml) and HOAt (3.89 g) dimethylamino-acetic acid (5.83 g) and EDC (3.89 g) were added. The reaction was stirred overnight. The mixture was diluted with $CH_2Cl_2$ (1 L) and washed with sat'd $NaHCO_3$ (3×200 ml). The organic layer was washed with brine, dried over $Na_2SO_4$, filtered and concentrated in vacuo. The residue was purified by flash chromatography ($SiO_2$, EtOAc to 5% MeOH/EtOAc) to afford the title compound.

The following compounds were prepared similarly to the procedure outlined above:
a) 1-(3,3-Dimethyl-6-nitro-2,3-dihydro-indol-1-yl)-2-(N-Boc-amino)-ethanone.

Preparation L—1-(6-Amino-3,3-dimethyl-2,3-dihydro-indol-1-yl)-2-(N-Boc-amino)-ethanone 1-(3,3-Dimethyl-6-nitro-2,3-dihydro-indol-1-yl)-2-(N-Boc-amino)-ethanone (3.9 g) was dissolved in EtOH (30 ml) and Fe powder (3.1 g) $NH_4Cl$ (299 mg) and $H_2O$ (5 ml) were added. The reaction was stirred at 80° C. overnight. The reaction was filtered through Celite® and evaporated off the MeOH. The residue was partitioned between $CH_2Cl_2$ and sat'd $NaHCO_3$. The organic layer was removed, washed with brine, dried over $Na_2SO_4$, filtered and concentrated in vacuo. The residue was purified by flash chromatography ($SiO_2$, 25% EtOAc/hexane). The purified fractions were concentrated in vacuo to afford the compound as a white powder.

The following compounds were prepared similarly to the procedure outlined above:
a) 1-(6-Amino-3,3-dimethyl-2,3-dihydro-indol-1-yl)-2-dimethylamino-ethanone.
b) 3,3-Dimethyl-1-(1-methyl-piperidin-4-ylmethyl)-2,3-dihydro-1H-indol-6-ylamine.
c) 3-(4-Methyl-piperazin-1-ylmethyl)-4-pentafluoroethyl-phenylamine. M+H 324.2. Calc'd 323.
d) 3,3-Dimethyl-1-(1-methyl-piperidin-4-yl)-2,3-dihydro-1H-indol-6-ylamine. M+H 259.6; Calc'd 259.3.
e) 3,3-Dimethyl-1,1-dioxo-2,3-dihydro-1H-1λ6-benzo[d]isothiazol-6-ylamine
f) 1,1,4,4-Tetramethyl-1,2,3,4-tetrahydro-naphth-6-ylamine.
g) 3,3-Dimethyl-1-(1-Boc-piperidin-4-ylmethyl)-2,3-dihydro-1H-indol-6-ylamine.

Preparation LI—2-Boc-4,4-dimethyl-7-nitro-1,2,3,4-tetrahydro-isoquinoline 4,4-Dimethyl-7-nitro-1,2,3,4-tetrahydro-isoquinoline (150 mg) was dissolved with $CH_2Cl_2$ (3 ml) DIEA (100 ul) DMAP (208 mg and $Boc_2O$ (204 mg) and the mixture was stirred for 6 h at RT. The reaction was diluted with $CH_2Cl_2$, washed with sat'd $NaHCO_3$ and dried over $MgSO_4$, filtered and concentrated to provide the compound which was used without further purification.

The following compounds were prepared similarly to the procedure outlined above substituting $Ac_2O$:
a) 1-(4,4-Dimethyl-7-nitro-3,4-dihydro-1H-isoquinolin-2-yl)-ethanone. M+H 249.3.

Preparation LII—2-Bromo-N-(4-methoxy-benzyl)-5-nitro-benzamide

PMB-amine (5.35 ml) in $CH_2Cl_2$ (130 ml) was slowly added to 2-bromo-5-nitro-benzoyl chloride (10.55 g) and $NaHCO_3$ (9.6 g) and the mixture was stirred at RT for 1 h. The mixture was diluted with $CH_2Cl_2$ (1 L), filtered, washed with dilute HCl, dried, filtered again, concentrated and dried under vacuum to provide the compound as a white solid. M+H 367. Calc'd 366.

Preparation LIII—2-Bromo-N-(4-methoxy-benzyl)-N-(2-methyl-allyl)-5-nitro-benzamide To a suspension of NaH (1.22 g) in DMF (130 ml) was added 2-bromo-N-(4-methoxy-benzyl)-5-nitro-benzamide (6.2 g) in DMF (60 ml) at −78 C. The mixture was warmed to 0° C., 3-bromo-2-methyl-propene (4.57 g) was added and the mixture was stirred for 2 h at 0° C. The reaction was poured into ice water, extracted with EtOAc (2×400 ml), dried over MgSO$_4$, filtered and concentrated to a DMF solution which was used without further purification.

Preparation LIV—of 2-(4-Methoxy-benzyl)-4,4-dimethyl-7-nitro-3,4-dihydro-2H-isoquinolin-1-one 2-Bromo-N-(4-methoxy-benzyl)-N-(2-methyl-allyl)-5-nitro-benzamide (23.4 mmol) was dissolved in DMF (150 ml) and Et$_4$NCl (4.25 g), HCO$_2$Na (1.75 g) and NaOAc (4.99 g) were added. N$_2$ was bubbled through the solution for 10 min, then Pd(OAc)$_2$ (490 mg) was added and the mixture was stirred overnight at 70° C. The mixture was extracted with EtOAc, washed with sat'd NH$_4$Cl, dried over MgSO$_4$, filtered and concentrated until the compound precipitated as a white solid.

The following compounds were prepared similarly to the procedure outlined above:
a) 3,3-Dimethyl-6-nitro-2,3-dihydro-benzofuran was prepared from 1-bromo-2-(2-methyl-allyloxy)-4-nitro-benzene.
b) 3,9,9-Trimethyl-6-nitro-4,9-dihydro-3H-3-aza-fluorene was prepared from 4-[1-(2-bromo-4-nitro-phenyl)-1-methyl-ethyl]-1-methyl-1,2,3,6-tetrahydro-pyridine.

Preparation LV—4,4-Dimethyl-7-nitro-3,4-dihydro-2H-isoquinolin-1-one 2-(4-Methoxy-benzyl)-4,4-dimethyl-7-nitro-3,4-dihydro-2H-isoquinolin-1-one (2.0 g) was dissolved in CH$_3$CN (100 ml) and H$_2$O (50 ml) and cooled to 0° C. CAN (9.64 g) was added and the reaction was stirred at 0° C. for 30 min, then warmed to RT and stirred for 6 h. The mixture was extracted with CH$_2$Cl$_2$ (2×300 ml) washed with sat'd NH$_4$Cl, dried over MgSO$_4$, filtered and concentrated. The crude material was recrystallized in CH$_2$Cl$_2$/EtOAc (1:1) to give 4,4-dimethyl-7-nitro-3,4-dihydro-2H-isoquinolin-1-one as a white solid.

Preparation LVI—4,4-Dimethyl-7-nitro-1,2,3,4-tetrahydro-isoquinoline 4,4-Dimethyl-7-nitro-3,4-dihydro-2H-isoquinolin-1-one (230 mg) was dissolved in THF (10 ml) and BH$_3$Me$_2$S (400 ul) was added and the reaction was stirred overnight at RT. The reaction was quenched with MeOH (10 ml) and NaOH (200 mg) and heating at reflux for 20 min. The mixture was extracted with EtOAc, washed with sat'd NH$_4$Cl, extracted with 10% HCl (20 ml). The acidic solution was treated with 5N NaOH (15 ml), extracted with EtOAc (30 ml) dried, filtered and evaporated to give the compound as a yellow solid. M+H 207.2, Calc'd 206.

The following compounds were prepared similarly to the procedure outlined above:
a) 4-Boc-2,2-dimethyl-6-nitro-3,4-dihydro-2H-benzo[1,4]oxazine.

Preparation LVII—2-Bromomethyl-4-nitro-1-pentafluoroethyl-benzene

2-Methyl-4-nitro-1-pentafluoroethyl-benzene (2.55 g) was dissolved in CCl$_4$ (30 ml) and AIBN (164 mg) and NBS (1.96 g) were added. The reaction was heated to reflux and stirred for 24 h. The mix was diluted with CH$_2$Cl$_2$, washed with sat'd NaHCO$_3$, dried over MgSO$_4$ and concentrated to give the compound as an oil which was used without further purification.

Preparation LVIII—1-Methyl-4-(5-nitro-2-pentafluoroethyl-benzyl)-piperazine

2-Bromomethyl-4-nitro-1-pentafluoroethyl-benzene (2.6 g) was added to N-methylpiperazine (5 ml) and stirred at RT for 3 h. The mixture was filtered and the filtrate was treated with 1-chlorobutane, extracted with 2N HCl (100 ml). The acidic solution was treated with 5N NaOH (6 ml) then extracted with EtOAc. The organic layer was removed, dried over MgSO$_4$ and concentrated to give the compound as an oil.

The following compounds were prepared similarly to the procedure outlined above:
a) 4-(5-Nitro-2-pentafluoroethyl-benzyl)-morpholine.

Preparation LIX—1-Boc-4-(5-nitro-2-pentafluoroethyl-benzyl)-piperazine

2-Bromomethyl-4-nitro-1-pentafluoroethyl-benzene (2.5 g) was dissolved in CH$_2$Cl$_2$ and added to N-Boc-piperazine (2.5 g) and NaHCO$_3$ (1 g) and stirred at RT overnight. The mixture was diluted with CH$_2$Cl$_2$ (100 ml), washed with sat'd NH$_4$Cl, dried over MgSO$_4$, filtered and concentrated. The residue was purified by silica gel chromatography (hexane, CH$_2$Cl$_2$:hexane 2:8) to give the compound as an yellow solid.

Preparation LX—(4-Boc-piperazin-1-yl)-(3-nitro-5-trifluoromethyl-phenyl)-methanone A mixture of 3-nitro-5-trifluoromethyl-benzoic acid (4.13 g), 4-Boc-piperazine (2.97 g), EDC (3.88 g), HOBt (2.74 g), DIEA (3.33 ml) in CH$_2$Cl$_2$ (120 ml) was stirred at RT for 3 h. The mixture was diluted with CH$_2$Cl$_2$ (100 ml), washed with sat'd NH$_4$Cl, dried over MgSO$_4$, filtered and concentrated. The residue was purified by silica gel chromatography (hexane, CH$_2$Cl$_2$:hexane 1:2) to give the compound as a white solid.

Preparation LXI—1-Boc-4-(3-nitro-5-trifluoromethyl-benzyl)-piperazine (4-Boc-piperazin-1-yl)-(3-nitro-5-trifluoromethyl-phenyl)-methanone (403 mg) was dissolved in THF (6 ml) and BH$_3$Me$_2$S (300 µl) was added and the reaction was stirred for 3 h at 60° C. and 2 h at RT. The reaction was quenched with MeOH (5 ml) and NaOH (100 mg) and stirred at RT for 1 h. The mixture was concentrated and dissolved in CH$_2$Cl$_2$, washed with sat'd NH$_4$Cl/NaHCO$_3$, dried (MgSO$_4$), filtered and evaporated to give the compound as an oil. M+H 390.3.

Preparation LXII—2-Ethyl-4-aminomethylpyridine

To a solution of 2-ethyl-4-thiopyridylamide (10 g) in MeOH (250 ml) was added Raney 2800 Nickel (5 g, Aldrich) in one portion. The mixture was stirred at RT for 2 days then at 60° C. for 16 h. The mixture was filtered, concentrated to provide the desired compound.

Preparation LXIII—N-Boc-[2-(4-morpholin-4-yl-butyl)-pyrimidin-4-ylmethyl]-amine

N-Boc-(2-chloropyrimidine)-methylamine (663 mg) and 4-(aminopropyl)morpholine (786 mg) were dissolved in MeOH and concentrated in vacuo. The residue was heated at 100° C. for 15 min, forming a solid which was dissolved in $CH_2Cl_2$/MeOH then concentrated again and heated 15 min more. Concentrated in vacuo and dried under high vacuum. Triturated with a small amount of IpOH and allowed to settle over a weekend. Filtered, rinsing with a small amount of IpOH to provide the compound as a white solid.

The following compounds were prepared similarly to the procedure outlined above:
a) (4-Bocaminomethyl-pyrimidin-2-yl)-[2-(1-methyl-pyrrolidin-2-yl)-ethyl]-amine. M+H 336.5; Calc'd 335.45.

Preparation LXIV—2-fluoronicotinic acid

In a flame dried 3-necked round bottom flask equipped with a dropping funnel and thermometer, under $N_2$, THF (250 ml) was added via cannula. LDA (2M in cyclohexane, 54 ml) was added via cannula as the flask was cooled to −78° C. At −78° C., 2-fluoropyridine (8.87 ml) was added dropwise over 10 min. The reaction was stirred for 3 h. Condensation was blown off (with $N_2$) a few cubes of solid $CO_2$ and they were added to the mixture. The mixture was warmed to RT once the solution turned yellow, and it was stirred overnight. The reaction was cooled to 0° C. and the pH was adjusted to ~2.5 with 5N HCl. The mixture was concentrated in vacuo and extracted with EtOAc. The EtOAc layer was washed with brine, dried over $MgSO_4$, filtered and concentrated to dryness. The resulting solid was slurried in EtOAc (100 ml), filtered, washed with cold EtOAc and dried at 50° C. for 1 h to afford 2-fluoronictinic acid. M+H 142.1; Calc'd 141.0.

Preparation LXV—4-cyano-2-methoxypyridine

Under a stream of $N_2$ and with cooling, Na metal (2.7 g) was added to MeOH (36 ml) with a considerable exotherm. After the Na is dissolved, a solution of 2-chloro-4-cyanopyridine (15 g) in dioxane:MeOH (1:1, 110 ml) was added via dropping funnel over a 10 min period. The reaction was heated to reflux for 3.5 h then cooled at ~10° C. overnight. Solid was filtered off and the solid was washed with MeOH. The filtrate was concentrated to ~60 ml and $H_2O$ (60 ml) was added to redissolve a precipitate. Upon further concentration, a precipitate formed which was washed with $H_2O$. Further concentration produced additional solids. The solids were combined and dried in vacuo overnight at 35° C. to provide 4-cyano-2-methoxypyridine which was used as is.

Preparation LXVI—(2-methoxypyridin-4-yl)methylamine

4-Cyano-2-methoxypyridine (1.7 g) was dissolved in MeOH (50 ml) and conc. HCl (4.96 ml) was added. Pd/C (10%) was added and $H_2$ was added and let stand overnight. The solids were filtered through Celite® and the cake was washed with MeOH (~250 ml). Concentration in vacuo produced an oil which was dissolved in MeOH (~20 ml). $Et_2O$ (200 ml) was added and stirred for 1 h. The resulting precipitate was filtered and washed with $Et_2O$ to afford (2-methoxypyridin-4-yl)methylamine (hydrochloride salt) as an off-white solid.

Preparation LXVII—2-(4-Amino-phenyl)-2-methyl-propionic acid methyl ester

2-Methyl-2-(4-nitro-phenyl)-propionic acid methyl ester (2.1 g) was dissolved in THF (70 ml) and acetic acid (5 ml) and Zn (10 g) were added. The mixture was stirred for 1 h and filtered through Celite®. The filtrate was rinsed with EtOAc and the organics were evaporated to a residue which was purified on silica gel chromatography (40% EtOAc/hexanes) to provide the desired compound as a yellow oil. M+H 194.

Preparation LXVIII—1-(2-tert-Butyl-phenyl)-4-methyl-piperazine 2-tert-Butyl-phenylamine and bis-(2-chloro-ethyl)-methylamine were mixed together with $K_2CO_3$ (25 g), NaI (10 g) and diglyme (250 mL) and heated at 170° C. for 8 h. Cooled and filtered solid and evaporated solvent. Diluted with EtOAc, washed with $NaHCO_3$ solution, extracted twice more with EtOAc, washed with brine, dried over $Na_2SO_4$ and evaporated to give the compound as a dark solid.

The following compounds were prepared similarly to the procedure outlined above:
a) 1-Bromo-2-(2-methyl-allyloxy)-4-nitro-benzene was prepared from methallyl bromide.

Preparation LXIX 3-(1-Methyl-1,2,3,6-tetrahydro-pyridin-4-yl)-5-trifluoromethyl-phenylamine 3-(5,5-Dimethyl-[1,3,2]dioxaborinan-2-yl)-5-trifluoromethyl-phenylamine (8.8 g, 0.032 mol) was added to trifluoromethanesulfonic acid 1-methyl-1,2,3,6-tetrahydro-pyridin-4-yl ester (7.91 g, 0.032 mol) and 2N $Na_2CO_3$ aqueous solution (25 mL) was bubbled through $N_2$ for 5 min. $Pd(PPh_3)_4$ (3.7 g, 3.2 mmol) was added and the reaction was heated to 80° C. for 16 h. The reaction was cooled to RT and diluted with $Et_2O$ (100 mL). The mixture was filtered through Celite® and the filtrate was washed with $NaHCO_3$ aqueous solution (25 ml) followed by brine (25 mL). The organic phase was dried over $Na_2SO_4$ and concentrated in vacuo. The desired product was isolated by passing through silica gel column chromatography (EtOAc, then (2M $NH_3$) in MeOH/EtOAc) to provide a yellow oil.

Preparation LXX—3,3-Dimethyl-6-nitro-2,3-dihydro-benzo[d]isothiazole 1,1-dioxide 3,3-Dimethyl-2,3-dihydro-benzo[d]isothiazole 1,1-dioxide was added to $KNO_3$ in $H_2SO_4$ cooled to 0° C. and stirred for 15 min. The reaction was warmed to RT and stirred overnight. The mix was poured into ice and extracted with EtOAc (3×), washed with $H_2O$ and brine, dried and evaporated to give the product which was used without further purification.

The following compounds were prepared similarly to the procedure outlined above:
a) 1,1,4,4-Tetramethyl-6-nitro-1,2,3,4-tetrahydro-naphthalene Preparation LXXI—3-(1-Methyl-1,2,3,4-tetrahydro-pyridin-4-yl)-5-trifluoromethyl-phenylamine 3-(5,5-Dimethyl-[1,3,2]dioxaborinan-2-yl)-5-trifluoromethyl-phenylamine (1.2 g) was added to trifluoro-methanesulfonic acid 1-methyl-1,2,3,6-tetrahydro-pyridin-4-yl ester (1.0 g), LiCl (500 mg, Aldrich), $PPh_3$ (300 mg, Aldrich) and 2M $Na_2CO_3$ aqueous solution (6 ml) and was bubbled with $N_2$ for 5 min. $Pd(PPH_3)_4$ (300 mg, Aldrich) was added and the reaction was heated to 80° C. for 16 h. The reaction was cooled to RT and diluted with $Et_2O$ (100 mL). The mixture was filtered through Celite® and the filtrate was washed with $NaHCO_3$ aqueous solution (25 ml) followed by brine (25 mL). The organic phase was dried over $Na_2SO_4$ and concentrated in vacuo. The desired compound was isolated by silica gel column chromatography (EtOAc 10% (2M $NH_3$) in MeOH/EtOAc) to provide yellow oil. M+H 257.2; Calc'd 256.1.

Preparation LXXII—Trifluoromethylsulfonic acid 1-methyl-1,2,3,6-tetrahydro-pyridin-4-yl ester In a three-necked round bottom flask equipped with a thermometer and an additional funnel was placed anhydrous THF (200 mL) and 2M LDA (82.8 mL). The solution was cooled to −78° C. and a solution of 1-methyl-piperidin-4-one (20 mL) in anhydrous THF (70 mL) was added drop-wise. The reaction was warmed to −10° C. over 30 min and cooled down again to −78° C. $Tf_2NPh$ (54.32 g) in 200 mL of anhydrous THF was added through the additional funnel over 30 min and anhydrous THF (30 mL) was added to rinse the funnel. The reaction was warmed to RT and the reaction solution was concentrated in vacuo. The residue was dissolved in $Et_2O$ purified on neutral $Al_2O_3$ column chromatography ($Et_2O$ as elutant). The product was obtained as orange oil. (20 g)

Preparation LXXIII—3-(5,5-Dimethyl-[1,3,2]diox-aborinan-2-yl)-5-trifluoromethyl-phenylamine $N_2$ was bubbled through a solution of 3-bromo-5-trifluoromethyl-phenylamine (2.38 g), 5,5,5',5'-tetramethyl-[2,2']bi[[1,3,2]dioxaborinanyl] (2.24 g, Frontier Scientific) and KOAc (2.92 g), dppf (165 mg, Aldrich) in anhydrous dioxane (50 ml) for 2 min. $PdCl_2$ (dppf) (243 mg, Aldrich) was added and the reaction was heated to 80° C. for 4 h. After cooling to RT, the mix was diluted with 50 mL of $Et_2O$, filtered through Celite®, and the filtrate was concentrated in vacuo. The residue was dissolved in $Et_2O$ (100 mL), washed with sat. $NaHCO_3$ aqueous solution (50 mL) followed by brine (50 mL). The organic phase was dried over $Na_2SO_4$ and concentrated in vacuo. The residue was dissolved in 3:2 $Et_2O$/Hex (100 mL), filtered through Celite® and the filtrate was concentrated in vacuo to afford a dark brown semi-solid.

Preparation LXXIV—1-Boc-3-Hydroxymethyl-azetidine

A solution of 1-Boc-azetidine-3-carboxylic acid (1.6 g) and $Et_3N$ (2 ml) in anhydrous THF (60 ml) was cooled to 0° C. Isopropyl chloroformate (1.3 g) was added via a syringe slowly; forming a white precipitate almost immediately. The reaction was stirred for 1 h at 0° C. and the precipitate was filtered out. The filtrate was cooled to 0° C. again and aqueous $NaBH_4$ solution (900 mg, 5 ml) was added via pipette and stirred for 1 h. The reaction was quenched with $NaHCO_3$ solution (50 mL) and the product was extracted with EtOAc (200 mL). The organic phase was washed with brine (50 mL), dried over $Na_2SO_4$ and concentrated in vacuo. The residue was dissolved in EtOAc and passed through a short silica gel pad. Concentrating the filtrate in vacuo provided the compound as a light yellow oil.

Preparation LXXV—1-Boc-3-(3-nitro-5-trifluoromethyl-phenoxymethyl)-azetidine A mixture of 1-Boc-3-methylsulfonyloxymethyl-azetidine (1.47 g), 3-nitro-5-trifluoromethyl-phenol (1.15 g) and $K_2CO_3$ (1.15 g) in DMF(20 ml) at 80° C. was stirred overnight. The reaction was cooled to RT and diluted with 25 mL of sat. $NaHCO_3$ and 50 mL of EtOAc. The organic phase was separated and washed with brine (25 mL), dried over $Na_2SO_4$ and concentrated in vacuo. The crude compound was purified by column chromatography (50% EtOAc/hex).

Preparation LXXVI—2,2-Dimethyl-6-nitro-3,4-dihydro-2H-benzo[1,4]oxazine 2,2-Dimethyl-6-nitro-4H-benzo[1,4]oxazin-3-one was added to $BH_3$-THF complex (Aldrich) in THF with ice cooling. The mixture was heated to reflux for 2 h then carefully diluted with 12 mL of MeOH and heated to reflux for an additional 1 h. Concentrated HCl (12 mL) was added and heated to reflux for 1 h. The mixture was concentrated and the resulting solid was suspended in a dilute aqueous solution of NaOH (1 M) and extracted with EtOAc (100 mL×4). The organic layers were washed with $H_2O$ and dried over $MgSO_4$. Evaporation of solvent gave a yellow solid.

Preparation LXXVII—2,2,4-Trimethyl-6-nitro-4H-benzo[1,4]oxazin-3-one 2,2-Dimethyl-6-nitro-4H-benzo[1,4]oxazin-3-one (1.1 g) was mixed with MeI (850 mg, Aldrich), $K_2CO_3$ (1.38 g, Aldrich) and DMF (30 ml, Aldrich) at 40° C. for 48 h. The DMF was removed in vacuo and the residue was diluted with EtOAc (80 ml). The organic phase was washed with $H_2O$ (50 ml), aqueous $Na_2SO_3$ (50 ml) and brine (50 ml). The resulting solution was dried ($MgSO_4$) and concentrated to provide the compound which was used as is.

Preparation LXXVIII—2-Bromo-N-(2-hydroxy-5-nitro-phenyl)-2-methyl-propionamide 2-Amino-4-nitro-phenol (3.08 g, Aldrich) was stirred with THF (30 ml, Aldrich) in an ice bath. 2-Bromo-2-methyl-propionyl bromide (2.47 ml, Aldrich) and $Et_3N$ (2.0 g, Aldrich) was slowly added via syringe. The mixture was stirred for 45 min then poured into ice. The aqueous phase was extracted by EtOAc (50 mL×4). The organic layer was dried and concentrated. The desired product was crystallized from EtOAc. (*Chem. Pharm. Bull* 1996, 44(1) 103-114).

Preparation LXXIX—2,2-Dimethyl-6-nitro-4H-benzo[1,4]oxazin-3-one

2-Bromo-N-(2-hydroxy-5-nitro-phenyl)-2-methyl-propionamide was mixed with $K_2CO_3$ in 20 mL of DMF and stirred overnight at 50° C. The reaction mixture was poured into ice water. The precipitate was collected by filtration and washed with $H_2O$. The crude compound was recrystallized from EtOH.

Preparation LXXX—4-[1-(2-Bromo-4-nitro-phenyl)-1-methyl-ethyl]-1-methyl-pyridinium iodide 1-Methyl-4-[1-methyl-1-(4-nitro-phenyl)-ethyl]-pyridinium (8 g) was dissolved in glacial HOAc (10 ml) then diluted with $H_2SO_4$ (50 ml), then NBS (3.8 g) was added. After 1 h, additional NBS (1.2 g) was added, 30 min later another 0.5 g of NBS, then 15 min later 200 mg more NBS. After 1 h, the mixture was neutralized with $NH_4OH$ (conc.) with ice bath cooling. The neutralized mixture was then concentrated and used as is.

Preparation LXXXI—4-[1-(2-Bromo-4-nitro-phenyl)-1-methyl-ethyl]-1-methyl-1,2,3,6-tetrahydropyridine 4-[1-(2-Bromo-4-nitro-phenyl)-1-methyl-ethyl]-1-methyl-pyridiniumiodide was mixed with MeOH (400 ml) and $CH_2Cl_2$ (200 ml), then treated with $NaBH_4$ (2.5 g) in portions. After stirring at RT for 2 h, the mixture was extracted with $CH_2Cl_2$ (300 mL×3). The $CH_2Cl_2$ layer was washed with brine, dried over $Na_2SO_4$ and concentrated in vacuo, to provide the desired product.

Preparation LXXXII—1-Methyl-4-[1-methyl-1-(4-nitro-phenyl)-ethyl]-pyridinium iodide 4-(4-Nitro-benzyl)-pyridine (4.3 g) was mixed with MeI (4 ml, 9.12 g)/NaOH (5N, 30 ml), $Bu_4NI$ (150 mg) and $CH_2Cl_2$ (50 ml) and stirred at RT overnight. Additional MeI (2 mL) was added along with 50 mL of NaOH (5N). 6 h later, more MeI (2 mL) was added. The mixture was stirred at RT over the weekend. The mixture was cooled on ice bath and the base was neutralized by conc. HCl (aq) addition dropwise to pH 7. The compound was used as is.

Preparation LXXXIII—1-Methyl-4-(4-nitro-benzyl)-1,2,3,6-tetrahydro-pyridine 4-(4-Nitrobenzyl)pyridine (64 g) and TBAI (6 g) were dissolved in $CH_2Cl_2$ (500 mL) and the solution was suspended with NaOH (aq. 5N, 450 mL) in a 3 L 3-necked round bottom flask. With vigorous stirring, iodomethane (213 g) was added and stirred vigorously at RT for 60 h (or until blue color disappears). The reaction was quenched with dimethylamine (100 mL) and MeOH (300 mL) and stirred for 2 h. $NaBH_4$ (19 g) was added to the mixture in small portions. The reaction mixture was stirred for 30 min at RT, then partitioned between $CH_2Cl_2/H_2O$ (500 mL/500 mL). The organic layer was collected and the aqueous layer was washed with $CH_2Cl_2$ (300 mL×3). The combined organic layers was washed with brine then concentrated in vacuo. The residue was purified on a silica wash-column (7% TEA in EtOAc). The desired fractions were combined and concentrated under vacuum to give the desired compound as a dark gray solid. (MS: M+1=261).

Preparation LXXXIV—1-Boc-4-formylpiperidine

4A Molecular sieves were heated to 100° C. and a vacuum was applied. They were cooled to RT and purged with N2. $CH_2Cl_2$ (420 ml) and $CH_3CN$ (40 ml), NMO (40 g) and 1-Boc-4-hydroxymethylpiperidine (50 g) were added and the mix was stirred for 5 min then cooled to 15° C. TPAP (4.1 g) is added and an exotherm was observed. The reaction was maintained at RT with external cooling. The reaction was stirred at RT for 3 h, filtered, concentrated, diluted with 50% EtOAc/hexanes and purified on a silica gel plug (50% EtOAc/hexanes). The eluant fractions were concentrated to afford a yellow oil.

Preparation LXXXV 2-Chloro-4-cyanopyridine

2-Chloro-4-cyanopyridine was prepared similar to the method described by Daves et al., J. Het. Chem., 1, 130-32 (1964).

Preparation LXXXVI 4-(2-tert-Butyl-5-nitro-phenyl)-but-3-en-1-ol

A mix of 1-(tert-butyl)-2-bromo-4-nitrobenzene (3.652 g), TEA (5.92 ml), 3-buten-1-ol (5.48 ml), $Pd(OAc)_2$ (32 mg), $Pd(PPh_3)_4$ (327 mg) and toluene (40 ml) was degassed with nitrogen and heated in a sealed vessel for 16 h at 120° C. The next day, the reaction mixture was cooled to RT, filtered, and concentrated in vacuo. The crude was eluted on a silica gel column with 15% to 22% EtOAc/hexanes gradient system to yield a yellow-brown oil.

Preparation LXXXVII 4-(2-tert-Butyl-5-nitro-phenyl)-but-3-enal 4-(2-tert-Butyl-5-nitro-phenyl)-but-3-en-1-ol (1.024 g) was dissolved in 10 ml of $CH_2Cl_2$ and added dropwise over 5 min to a −78 C mix of oxalyl chloride (0.645 ml), DMSO (0.583 ml), and 10 ml $CH_2Cl_2$. The reaction was stirred at −78 C for 1 h, then treated with a solution of TEA (1.52 ml) in 7 ml $CH_2Cl_2$ and stirred at −78 C for an additional 25 min, then warmed to −30° C. for 35 min. The reaction was treated with 50 ml of saturated aqueous $NH_4Cl$, diluted with $H_2O$ and extracted with EtOAc. The organic layer was brine-washed, dried over $Na_2SO_4$, filtered, and concentrated in vacuo to yield a yellow oil which was used as is in Preparation LXXXVIII.

Preparation LXXXVIII 1-[4-(2-tert-Butyl-5-nitro-phenyl)-but-3-enyl]-pyrrolidine 4-(2-tert-Butyl-5-nitro-phenyl)-but-3-enal (895 mg) was dissolved in 40 ml THF, and to the solution was added pyrrolidine (0.317 ml). To the deep orange solution was added $NaBH(OAc)_3$ (1.151 g) and glacial AcOH (0.207 ml). The reaction was stirred at RT overnight, then treated with saturated aqueous $NaHCO_3$ and diluted with $Et_2O$ and some 1N NaOH. The layers were separated, and the organic layer was extracted with aqueous 2N HCl. The acidic aqueous layer was basified to pH>12 with 6 N NaOH, extracted with $Et_2O$, brine-washed, dried over $Na_2SO_4$, filtered, and concentrated in vacuo to provide 1-[4-(2-tert-butyl-5-nitro-phenyl)-but-3-enyl]-pyrrolidine as a orange-brown oil.

Preparation LXXXVIV N-Boc-(2-chloropyrimidin-4-yl)-methylamine

To 2-chloropyrimidine-4-carbonitrile [2.5 g, prepared by the procedure of Daves et. al. [J. Het. Chem. 1964, 1, 130-132)] in EtOH (250 ml) under $N_2$ was added $Boc_2O$ (7.3 g). After the mixture was briefly placed under high vacuum and flushed with $N_2$, 10% Pd/C (219 mg) was added. $H_2$ was bubbled though the mixture (using balloon pressure with a needle outlet) as it stirred 4.2 h at RT. After filtration through Celite®, addition of 1.0 g additional $Boc_2O$, and concentration, the residue was purified by silica gel chromatography (5:1→4:1 hexanes/EtOAc) to obtain N-Boc-(2-chloropyrimidin-4-yl)-methylamine.

EXAMPLE 1

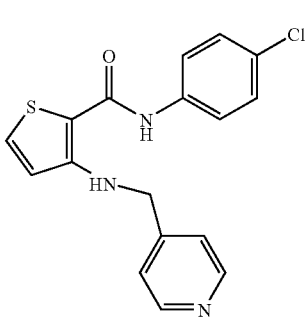

N-(4-Chlorophenyl){3-[(4-pyridylmethyl)amino](2-thienyl)}carboxamide

Step A—Preparation of 3-[(tert-butoxy)carbonylamino]thiophene-2-carboxylic acid To a mixture of methyl 3-amino-2-thiophenecarboxylate (8 g, 51 mmol) and $BOC_2O$ (11 g, 50 mmol) in $CH_2Cl_2$ (400 ml) was added 4-(dimethylamino)pyridine (1 g, 8.1 mmol). The reaction was stirred at RT overnight and washed with 1N HCl (100 ml), followed by water and brine. The organic layer was dried over $Na_2SO_4$ and evaporated under reduced pressure and used for the next step without further purification. To the residue (2 g, ~7 mmol) in EtOH (50 ml) was added 1N NaOH (25 ml), the reaction was stirred at RT for 1 h and the solvent was evaporated under reduced pressure. Water (5 ml) was added and the solution was acidified with HOAc. The precipitate was filtered and used in the next step without further purification. MS (ES-): 242 (M-H)⁻.

Step B—Preparation of {3-[(tert-butoxy)carbonylamino](2-thienyl)}-N-(4-chlorophenyl)carboxamide To a mixture of the thienyl carboxylic acid from Step A (300 mg, 1.23 mmol) and 4-chloroaniline (160 mg, 1.25 mmol) and DIEA (300 µl, 1.6 mmol) was added EDC (300 mg, 1.6 mmol) and HOBt (170 mg, 1.25 mmol) in $CH_2Cl_2$, the reaction was stirred at RT overnight. The solution was washed with 1N HCl and saturated $NaHCO_3$, followed by $H_2O$ and brine. The organic layer was dried over $Na_2SO_4$ and evaporated under reduced pressure and purified with preparative TLC to give the amide. MS (ES+): 353 (M+H)⁺; (ES-): 351 (M-H)⁻.

Step C—Preparation of N-(4-chlorophenyl){3-[(4-pyridylmethyl)amino](2-thienyl)}carboxamide The amide from Step B was mixed with 25% TFA/$CH_2Cl_2$ and stirred at RT for 1 h (monitored by HPLC). The solvent was evaporated under reduced pressure and the residue was mixed with 4-pyridine carboxaldehyde (260 mg, 2.5 mmol) and $NaCNBH_3$ (160 mg, 2.5 mmol) in MeOH (40 ml). The reaction was stirred at RT overnight and evaporated under reduced pressure. The final product was purified by prep-HPLC as TFA salt. MS (ES+): 344 (M+H)⁺; (ES-): 342 (M-H)⁻. Calc'd. for $C_{17}H_{14}ClN_3OS$–343.84.

EXAMPLE 2

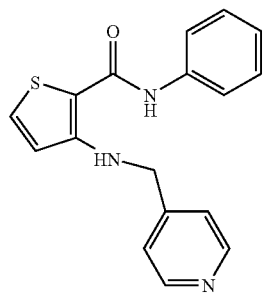

N-Phenyl{3-[(4-pyridylmethyl)amino](2-thienyl)}carboxamide

The title compound was analogously synthesized by method described in Example 1. The final product was purified by preparative HPLC as TFA salt. MS (ES+): 310 (M+H)⁺; (ES-): 308 (M-H)⁻. Calc'd. for $C_{17}H_{15}N_3OS$–309.4.

EXAMPLE 3

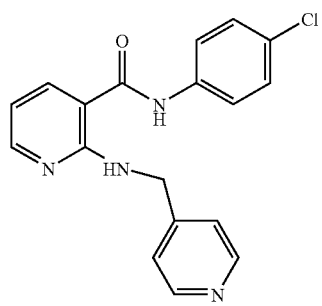

N-(4-Chlorophenyl){2-[(4-pyridylmethyl)amino](3-pyridyl)}carboxamide

Step A—Preparation of (2-amino(3-pyridyl))-N-(4-chlorophenyl)carboxamide

To a mixture of 2-aminonicotinic acid (5.3 g, 38 mmol) and 4-chloroaniline (4.9 g, 38 mmol) and DIEA (9 ml, 48 mmol) at 0° C. in $CH_2Cl_2$ was added EDC (9.5 g, 48 mmol) and HOBt (5.1 g, 38 mmol), the reaction was warmed to RT and stirred overnight. The solvent was evaporated under reduced pressure and quenched with 2N NaOH solution (60 ml) and stirred for 20 min. The precipitate was filtered to give the titled compound. MS (ES+): 248 (M+H)⁺; (ES-): 246 (M-H)⁻.

Step B—Preparation of N-(4-chlorophenyl){2-[(4-pyridylmethyl)amino](3-pyridyl)}carboxamide To a mixture of the pyridyl carboxamide (400 mg, 1.6 mmol) from Step A and 4-pyridinecarboxaldehyde (200 µl, 2 mmol) and HOAc (200 µl) in $CH_2Cl_2$ was added NaBH(OAc)₃ (600 mg, 2.8 mmol), the reaction was stirred at RT overnight. The reaction mixture was washed with $H_2O$ and brine and dried over $Na_2SO_4$. The solution was evaporated and purified by prep-TLC to give the title compound. MS (ES+): 339 (M+H)⁺; (ES-): 337 (M-H)⁻. Calc'd for $C_{18}H_{15}ClN_4O$–338.796.

EXAMPLE 4

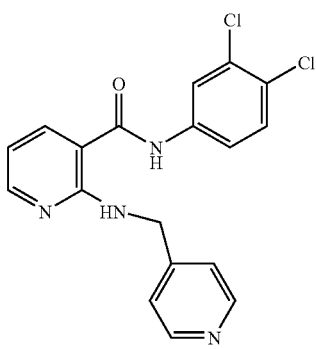

N-(3,4-Dichlorophenyl){2-[(4-pyridylmethyl)amino](3-pyridyl)}-carboxamide

The title compound was analogously synthesized by the method described in Example 3. MS (ES+): 373 (M+H)$^+$; (ES−) 370.9 (M−H)$^−$. Calc'd for $C_{18}H_{14}Cl_2N_4O$−373.24.

EXAMPLE 5

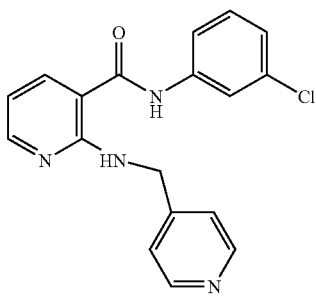

N-(3-Chlorophenyl){2-[(4-pyridylmethyl)amino](3-pyridyl)}carboxamide

The title compound was analogously synthesized by the method described in Example 3. MS (ES+): 339 (M+H)$^+$; (ES−): 337 (M−H)$^−$. Calc'd. for $C_{18}H_{15}ClN_4O$−338.1.

EXAMPLE 6

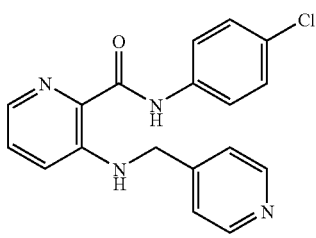

N-(4-Chlorophenyl){3-[(4-pyridylmethyl)amino](2-pyridyl)}carboxamide

The title compound was analogously synthesized by method described in Example 3. MS (ES+): 339 (M+H)$^+$; (ES−): 337 (M−H)$^−$. Calc'd. for $C_{18}H_{15}ClN_4O$−338.8

EXAMPLE 7

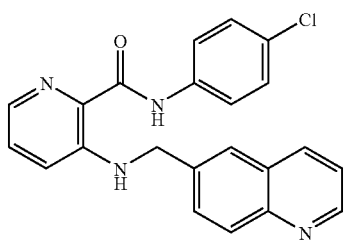

N-(4-Chlorophenyl){3-[(6-quinolylmethyl)amino](2-pyridyl)}carboxamide

The title compound was analogously synthesized by the method described in Example 3. MS (ES+): 389 (M+H)$^+$; (ES−): 387 (M−H)$^−$. Calc'd. for $C_{22}H_{17}ClN_4O$−388.86.

EXAMPLE 8

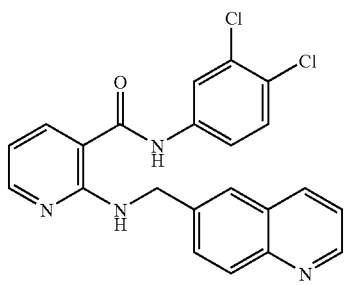

N-(3,4-Dichlorophenyl){2-[(6-quinolylmethyl)amino](3-pyridyl)}-carboxamide

The title compound was analogously synthesized by the method described in Example 3. MS (ES+): 423 (M+H)$^+$; (ES−) 421 (M−H)$^−$. Calc'd. for $C_{22}H_{16}Cl_2N_4O$−423.30.

EXAMPLE 9

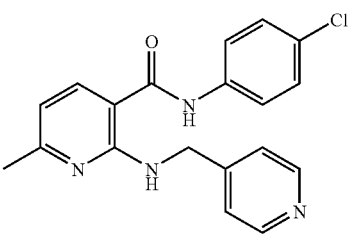

N-(4-Chlorophenyl){6-methyl-2-[(4-pyridylmethyl)amino](3-pyridyl)}carboxamide

Step A—Preparation of 6-methyl-2-[(4-pyridylmethyl)amino]pyridine-3-carboxylic acid The mixture of 2-chloro-6-methyl-nicotinic acid (1.0 eq.) and 4-aminomethyl-pyridine (2.0 eq.) was stirred in a sealed tube at 130° C. overnight. The resulted mixture was cooled to RT, diluted with $CH_2Cl_2$, filtered to collected the brown solid. The brown solid was recrystallized in ethanol to give the substituted amine as light brown solid. MS (ES+): 244 (M+H)+.

Step B—Preparation of N-(4-chlorophenyl){6-methyl-2-[(4-pyridylmethyl)amino](3-pyridyl)}-carboxamide To the mixture of the substituted amine from Step A (1.0 eq.) and 4-chloroaniline (2.0 eq) in $CH_2Cl_2$ was added bis(2-oxo-3-oxazolidinyl)phosphinic chloride (1.1 eq.) and TEA (1.1 eq.). The mixture was stirred overnight, diluted with $CH_2Cl_2$, washed with saturated $NH_4Cl$ solution, dried over $Na_2SO_4$, filtered and concentrated, purified by flash chromatography (4% MeOH/$CH_2Cl_2$) to give the title compound as an white solid. MS (ES+): 353 (M+H); (ES-): 351 (M-H). Calc'd. for $C_{19}H_{17}ClN_4O$–352.82.

EXAMPLE 10

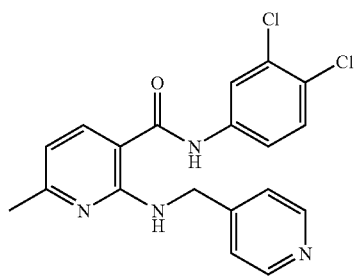

N-(3,4-Dichlorophenyl){6-methyl-2-[(4-pyridylmethyl)amino](3-pyridyl)}carboxamide The title compound was analogously synthesized by the method described in Example 9. MS (ES+): 387 (M+H); (ES-): 385 (M-H). Calc'd. for $C_{19}H_{16}Cl_2N_4O$–387.27.

EXAMPLE 11

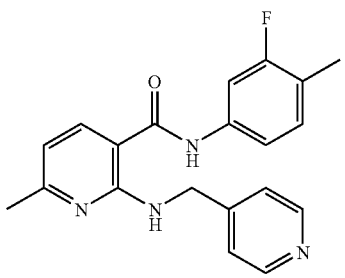

N-(3-Fluoro-4-methylphenyl){6-methyl-2-[(4-pyridylmethyl)amino](3-pyridyl)}carboxamide The title compound was analogously synthesized by the method described in Example 9. MS (ES+): 351 (M+H); (ES-): 349 (M-H). Calc'd. for $C_{20}H_{19}FN_4O$–350.39.

EXAMPLE 12

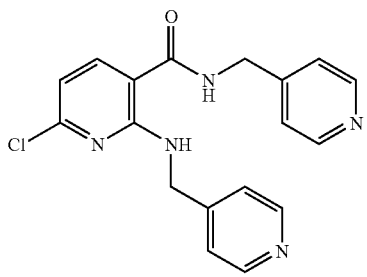

{6-Chloro-2-[(4-pyridylmethyl)amino](3-pyridyl)}-N-(4-pyridylmethyl)carboxamide

The title compound was analogously synthesized by the method described in Example 9. MS (ES+): 354 (M+H); (ES-): 352 (M-H). Calc'd. for $C_{18}H_{16}ClN_5O$–353.81.

EXAMPLE 13

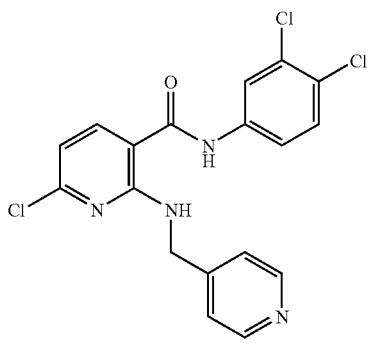

N-(3,4-Dichlorophenyl){6-chloro-2-[(4-pyridylmethyl)amino](3-pyridyl)}carboxamide The title compound was analogously synthesized by the method described in Example 9. MS (ES+): 409 (M+H). Calc'd. for $C_{18}H_{19}Cl_3N_4O$–407.7.

EXAMPLE 14

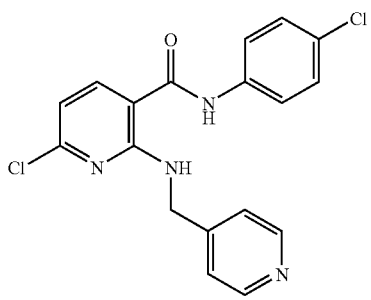

N-(4-Chlorophenyl){6-chloro-2-[(4-pyridylmethyl)amino](3-pyridyl)}carboxamide

The title compound was analogously synthesized by method described in Example 9. MS (ES+): 374 (M+H); (ES−): 372 (M−H). Calc'd. for $C_{18}H_{14}Cl_2N_4O$−373.24.

EXAMPLE 15

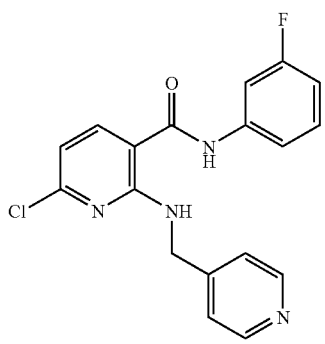

{6-Chloro-2-[(4-pyridylmethyl)amino](3-pyridyl)}-N-(3-fluorophenyl)carboxamide

The title compound was analogously synthesized by the method described in Example 9. MS (ES+): 357 (M+H); (ES−): 355 (M−H). Calc'd. for $C_{18}H_{19}FN_4OCl$−356.5.

EXAMPLE 16

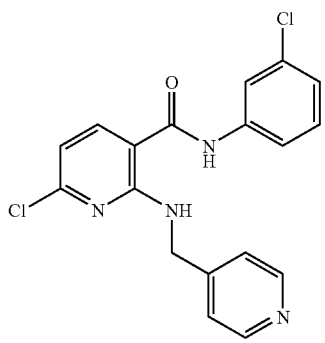

N-(3-Chlorophenyl){6-chloro-2-[(4-pyridylmethyl)amino](3-pyridyl)}carboxamide

The title compound was analogously synthesized by the method described in Example 9. MS (ES+): 374 (M+H); (ES−): 372 (M−H). Calc'd. for $C_{18}H_{14}Cl_2N_4O$−373.24.

EXAMPLE 17

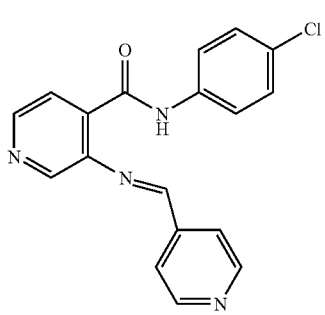

N-(4-Chlorophenyl){3-[(4-pyridylmethylene)amino](4-pyridinecarboxamide

A mixture of (2-amino(4-pyridyl))-N-(4-chlorophenyl)carboxamide (350 mg, 1.4 mmol) (similar procedure to Example 3, Step A) and 4-pyridine carboxaldehyde (200 μl, 2 mmol) and 4-toluenesulfonic acid monohydrate (50 mg) in EtOH (50 ml) was heated to reflux overnight. The solvent was evaporated and the residue was purified by prep-TLC. MS (ES+): 337 (M+H)$^+$; (ES−): 335 (M−H)$^-$. Calc'd. for $C_{18}H_{13}ClN_4O$−336.8.

EXAMPLE 18

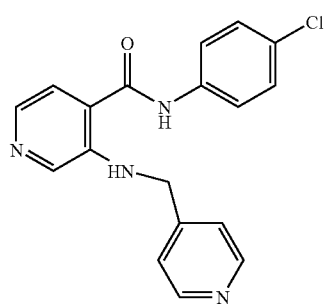

N-(4-Chlorophenyl){3-[(4-pyridylmethyl)amino](4-pyridyl)}carboxamide

The compound from Example 17 was mixed with NaBH$_4$ (100 mg) in EtOH (20 ml) and heated to reflux for 5 min. The solvent was evaporated under reduced pressure and the residue was purified by prep-TLC to give the titled compound. MS (ES+): 339 (M+H)$^+$; (ES−): 337 (M−H)$^-$. Calc'd. for $C_{18}H_{15}ClN_4O$−338.8.

EXAMPLE 19

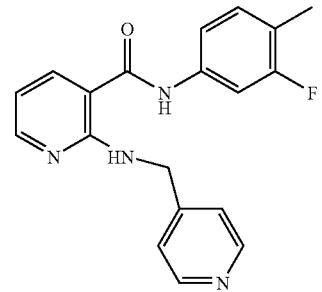

N-(3-Fluoro-4-methylphenyl){2-[(4-pyridylmethyl)amino](3-pyridyl)}carboxamide

The title compound was analogously synthesized by the method in Examples 17-18. MS (ES−): 337 (M−H)$^-$. Calc'd. for $C_{19}H_{17}FN_4O$−336.37.

EXAMPLE 20

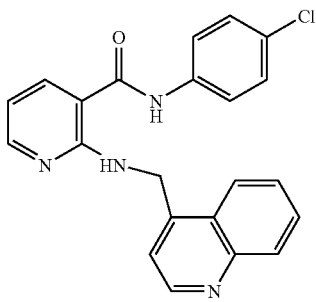

N-(4-Chlorophenyl){2-[(4-quinolylmethyl)amino](3-pyridyl)}carboxamide

The title compound was analogously synthesized by the method described in Examples 17-18. MS (ES+): 389 (M+H)+; (ES−): 387 (M−H)−. Calc'd. for $C_{22}H_{17}ClN_4O$− 388.86.

EXAMPLE 21

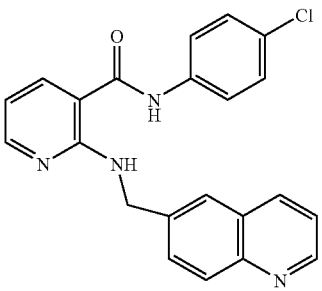

N-(4-Chlorophenyl){2-[(6-quinolylmethyl)amino](3-pyridyl)}carboxamide

The title compound was analogously synthesized by the method described in Examples 17-18. MS (ES+): 389 (M+H)+; (ES−): 387 (M−H)−. Calc'd. for $C_{22}H_{17}ClN_4O$− 388.86.

EXAMPLE 22

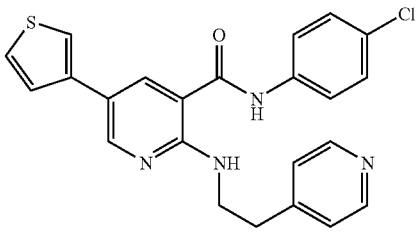

N-(4-Chlorophenyl){2-[(4-pyridylethyl)amino]-5-(3-thienyl)-(3-pyridyl)}carboxamide

Step A—Preparation of 5-bromo-2-hydroxynicotinic acid

A solution of sodium hypobromide was made by adding Br$_2$ (1.01 ml, 39.5 mmol, 1.1 eq) slowly over a period of 5 min to NaOH (5N, 40 ml) that was previously cooled to 0° C. in an ice bath. The solution was stirred for 10 min before adding 2-hydroxynicotinic acid (5.0 g, 35.9 mmol) and placed in a 50° C. oil bath and stirred. Concurrently, a second pot of sodium hypobromide solution was made by slowly adding Br$_2$ (1.01 ml, 39.5 mmol, 1.1 eq) to a NaOH solution (5N, 40 ml) in an ice bath. The second pot of sodium hypobromide was added to the solution of 2-hydroxynicotinic acid after 24 h of heating then was stirred for an additional 24 h. The solution was cooled to RT, placed in an ice bath and acidified with concentrated HCl while stirring. The precipitate which formed was filtered, washed and dried to afford the desired compound as an off-white solid.

Step B—Preparation of 5-bromo-2-chloronicotinic acid

A solution of 5-bromo-2-hydroxynicotinic acid, from Step A (8.3 g, 38.1 mmol) and SOCl$_2$ (40 ml) in a 150 ml round bottom flask was placed in an 80° C. oil bath and stirred while adding 10 ml of DMF. The solution was heated at reflux for 4 h at 80° C. before cooling to RT. Excess SOCl$_2$ was stripped off under reduced pressure forming a yellow-brown residue. The yellow-brown residue was placed in an ice bath and cooled to 0° C. Residual SOCl$_2$ was neutralized and the chloro compound was precipitated by the dropwise addition of water. Precipitate was filtered, washed and dried to afford the desired chloro compound as a light yellow solid.

Step C—Preparation of 5-bromo-2-chloro-N-(4-chlorophenyl)nicotinamide

To a mixture of 4-chloroanaline (594 mg, 4.7 mmol, 1. eq.), EDC (1.62 g, 8.5 mmol, 2 eq.), HOBT (572 mg, 4.2 mmol, 1 eq.), and DIEA (1.1 ml, 6.3 mmol, 1.5 eq.) in CH$_2$Cl$_2$ (50 ml) was added 5-bromo-2-chloronicotinic acid from Step B (1.0 g, 4.2 mmol). The reaction was stirred at RT overnight. The solution was quenched with water and the organic layer was purified by chromatography (50% EtOAc in hexane) to afford a light-yellow compound. MS (ES+): 347.0, 349.0 (M+H)+; (ES−): 345.0, 347.0 (M−H)−.

Step D—Preparation of 5-(3-thiophene)-2-chloro-N-(4-chlorophenyl)nicotinamide 3-Thiophene boronic acid (204 mg, 1.6 mmol, 1.1 eq), Pd(OAc)$_2$ (33 mg, 0.2 mmol, 0.2 eq.), and K$_2$CO$_3$ (505 mg, 4.3 mmol, 3 eq.) were added to a solution of 5-bromo-2-chloro-N-(4-chlorophenyl)nicotinamide from Step C (500 mg, 1.4 mmol) in DMF (20 ml). The reaction was placed in a 50° C. oil bath and stirred overnight. The reaction was filtered and purified by medium pressure chromatography (30% EtOAc in hexane) to afford the desired thienyl compound as an off white solid.

Step E—Preparation of N-(4-chlorophenyl){2-[(4-pyridylethyl)amino]-5-(3-thienyl)-(3-pyridyl)}carboxamide 4-(Aminoethyl)pyridine (10 ml) was added to a 25 ml round-bottom flask containing 5-(3-thiophene)-2-chloro-N-(4-chlorophenyl)nicotinamide from Step D (200 mg, 0.6 mmol). The solution was placed in an 80° C. oil bath and stirred overnight. The reaction was cooled to RT, and after an aqueous work-up, was purified by medium-pressure chromatography (80% EtOAc in hexane) to afford the title compound as a light yellow solid. MS: (ES+) 435.1 (M+H); (ES−) 432.8 (M−H). Calc'd. for $C_{23}H_{19}ClN_4OS-434.95$.

EXAMPLE 23

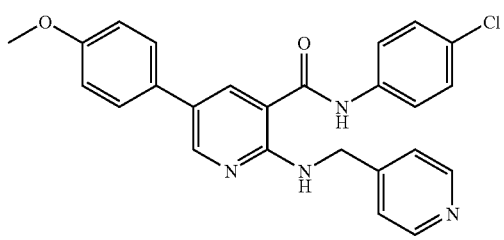

N-(4-Chlorophenyl){5-(4-methoxyphenyl)-2-[(4-pyridylmethyl)amino]-(3-pyridyl)}carboxamide The title compound was prepared analogously to Example 22. MS: (ES+) 445.1 (M+H). Calc'd. for $C_{25}H_{21}ClN_4O-444.92$.

EXAMPLE 24

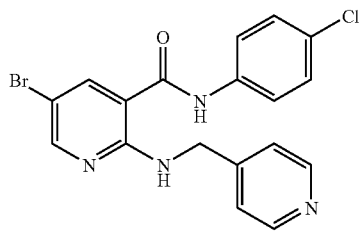

N-(4-Chlorophenyl){5-bromo-2-[(4-pyridylmethyl)amino]-(3-pyridyl)}carboxamide

The title compound was prepared analogously to Example 22, Steps A, B, C and E. MS: (ES+) 419 (M+H) (ES−) 417 (M−H). Calc'd. for $C_{18}H_{14}BrClN_4O-417.69$.

EXAMPLE 25

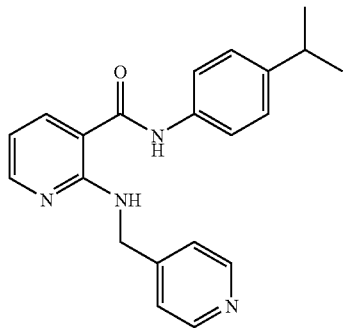

N-(4-Isopropylphenyl) {2-[(4-pyridylmethyl)amino](3-pyridyl)}carboxamide

Step A: Preparation of (2-chloro-3-pyridyl)-N-(4-isopropylphenyl)carboxamide

To a mixture of 2-chloronicotinic acid (6.3 g) and 4-isopropylaniline (5.26 ml) and DIEA (10 ml) in $CH_2Cl_2$ (200 ml) was added EDC (10 g) and HOBt (5.4 g). The reaction was stirred at RT overnight and washed with 2 N NaOH (100 ml), $H_2O$ (250 ml) and brine (100 ml). The organic layer was dried over $Na_2SO_4$ and evaporated to give (2-chloro-3-pyridyl)-N-(4-isopropylphenyl)-carboxamide.

Step B: Preparation of N-[4-(isopropyl)phenyl]{2-[(4-pyridylmethyl)amino](3-pyridyl)}carboxamide hydrochloride A mixture of (2-chloro(3-pyridyl))-N-(4-isopropylphenyl) carboxamide (1.5 g, from Step A) and 4-aminomethylpyridine (0.71 ml) was heated at 130° C. neat for 3 h. The reaction was cooled and diluted with $CH_2Cl_2$ and washed with $H_2O$ twice followed by brine. The organic layer was dried with $Na_2SO_4$ and evaporated under reduced pressure. The residue was purified by column chromatography with EtOAc and further mixed with MeOH and 1 N $HCl/Et_2O$ (2 ml). The solution was evaporated to furnish the titled compound. MS (ES+): 347 (M+H)$^+$; (ES−): 345 (M−H). Calc'd. for $C_{21}H_{22}N_4O-346.18$.

The following compounds (Examples 26-81) were synthesized by the method described in Example 25 unless specifically described. Detailed intermediate preparations are included.

TABLE 1
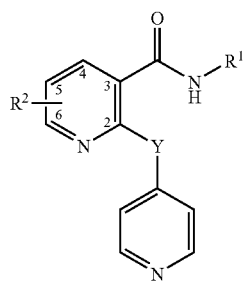
| # | Y | R¹ | R² | M + H | calc'd |
|---|---|---|---|---|---|
| 26 | —NH—CH₂— | 3-isopropylphenyl | H | 347 | 346.2 |
| 27 | NH—CH₂— | isoquinolin-3-yl | H | 356 | 355.1 |
| 28 | NH—CH₂— | 4-(1,1,1,3,3,3-hexafluoro-2-hydroxypropan-2-yl)phenyl | H | 471 | 470.1 |
| 29 | NH—CH₂— | 5-tert-butyl-3-methylisoxazol-? | H | 352 | 351.4 |
| 30 | NH—CH₂— | 5-tert-butyl-1,3-dimethylpyrazol-? | H | 365 | 364.2 |
| 31 | NH—CH₂— | 4-tert-butyl-2-methylthiazol-? | H | 368 | 367.5 |
| 32 | NH—CH₂— | 5-tert-butyl-2-methyl-1,3,4-thiadiazol-? | H | 369 | 368.5 |
| 33 | NH—CH₂— | 4-(4-hydroxybutyl)phenyl | H | 377 | 376.2 |
| 34 | NH—CH₂— | 4-chloro-phenylpropyl | H | 366.8 | 366.8 |

TABLE 1-continued
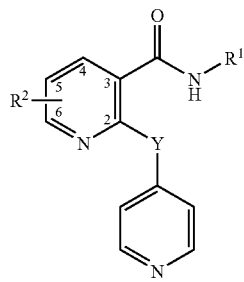
| # | Y | R¹ | R² | M + H | calc'd |
|---|---|---|---|---|---|
| 35 | NH—CH$_2$— | 4-Cl-phenylpropyl | 5-Br | 447.0 | 445.7 |
| 36 | NH—CH$_2$— | 4-phenoxyphenylpropyl | H | 425.0 | 424.5 |
| 37 | NH—CH$_2$— | 4-methoxyphenylpropyl | H | 363.2 | 362.4 |
| 38 | NH—CH$_2$— | 3,4-dimethoxyphenylpropyl | H | 393.2 | 392.4 |
| 39 | NH—CH$_2$— | 3-ethoxy-4-hydroxyphenylpropyl | H | 393.2 | 392.4 |
| 40 | NH—CH$_2$— | 4-fluorophenylpropyl | H | 350.8 | 350.4 |
| 41 | NH—CH$_2$— | 4-tert-butylphenylpropyl | H | 389.2 | 388.5 |
| 42 | NH—CH$_2$— | 3-fluorophenylpropyl | H | 351.0 | 350.4 |
| 43 | NH—CH$_2$— | 3-chlorophenylpropyl | H | 367.1 | 366.8 |
| 44 | NH—CH$_2$— | 3-trifluoromethylphenylpropyl | H | 401.3 | 400.4 |

TABLE 1-continued
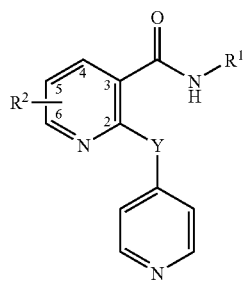
| # | Y | R¹ | R² | M + H | calc'd |
|---|---|---|---|---|---|
| 45 | NH—CH₂— | 3-ethoxyphenyl-propyl | H | 377.2 | 376.5 |
| 46 | NH—CH₂— | 2,4-dimethylphenyl-propyl | H | 361.4 | 360.4 |
| 47 | NH—CH₂— | benzo[1,3]dioxol-5-yl-propyl | H | 377.1 | 376.4 |
| 48 | NH—CH₂— | 4-methylphenyl-propyl | H | 347.1 | 346.4 |
| 49 | NH—CH₂— | 4-hydroxyphenyl-propyl | H | 349.1 | 348.4 |
| 50 | NH—CH₂— | 3,4-dimethoxyphenyl-propyl | H | 393.2 | 392.4 |
| 51 | NH—CH₂— | 4-bromophenyl-propyl | H | 411.2 | 411.3 |
| 52 | NH—CH₂— | 3,4-dichlorophenyl-propyl | H | 403.1 | 401.3 |
| 53 | NH—CH₂— | 4-fluorosulfonylphenyl-propyl | H | 415.2 | 414.4 |
| 54 | NH—CH₂— | 3,5-dimethoxyphenyl-propyl | H | 393.2 | 392.4 |

TABLE 1-continued
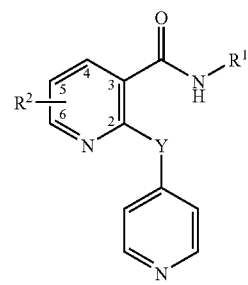
| # | Y | R¹ | R² | M + H | calc'd |
|---|---|---|---|---|---|
| 55 | NH—CH₂— | 2,4-dichlorophenyl-propyl | H | 403.2 | 401.3 |
| 56 | NH—CH₂— | 2-fluorophenyl-propyl | H | 351.0 | 350.4 |
| 57 | NH—CH₂— | 2-chlorophenyl-propyl | H | 369.1 | 366.8 |
| 58 | NH—CH₂— | 4-sulfamoylphenyl-propyl | H | 412.3 | 411.5 |
| 59 | NH—CH₂— | 2-thienyl-propyl | H | 338.8 | 338.4 |
| 60 | NH—CH₂— | 2-pyridyl-propyl | H | 334.1 | 333.4 |
| 61 | NH—CH₂— | 3-pyridyl-propyl | H | 333.6 | 333.4 |
| 62 | NH—CH₂— | 4-pyridyl-propyl | H | 333.6 | 333.4 |
| 63 | NH—CH₂— | phenyl-pentyl | H | 361.1 | 360.4 |

TABLE 1-continued

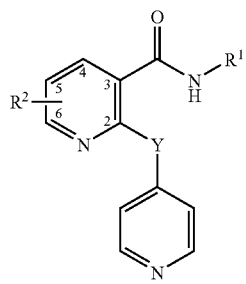

| # | Y | R¹ | R² | M + H | calc'd |
|---|---|---|---|---|---|
| 64 | NH—CH₂— | (HO, butyl, phenoxy group) | H | 379.0 | 378.4 |
| 65 | NH—CH₂— | (4-isopropylphenyl group) | H | 399 | 398.9 |
| 66 | NH—CH₂— | (4,4,7-trimethyl-2-(4-methoxybenzyl)-1-oxo-tetrahydroisoquinoline group) | H | 522.3 | 521 |

EXAMPLE 67

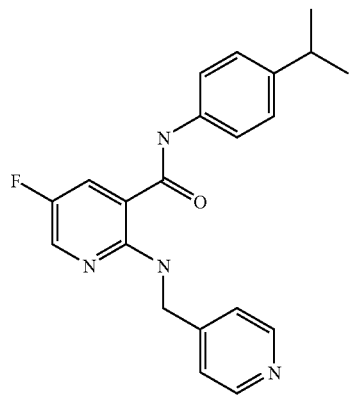

{5-Fluoro-2-[(4-pyridylmethyl)amino](3-pyridyl)}-
N-[4-(isopropyl)phenyl]carboxamide {6-Chloro-5-fluoro-2-[(4-pyridylmethyl)amino](3-pyridyl)}-N-[4-(methylethyl)phenyl]carboxamide (50 mg, 0.125 mmol, from Example 66) dissolved in EtOH (10 mL) with TEA (0.5 mL) and suspended with Pd/C (10%, 5 mg). The mixture was stirred at RT under a H₂ balloon for 45 min. The mixture was filtered through a layer of Celite® and the filtrate was concentrated in vacuo. The residue was partitioned between CH₂Cl₂ and aq. NaHCO₃ (sat.). The organic solution was dried over Na₂SO₄ and concentrated in vacuo to give the title compound. MS: 365 (M+1). Calc'd. for $C_{21}H_{21}FN_4O$–364.42.

EXAMPLE 68

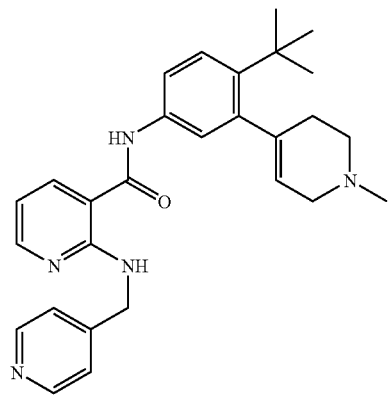

2-[(Pyridin-4-ylmethyl)amino]-N-[4-tert-butyl-3-(1,
2,3,6-tetrahydropyridin-4-yl)phenyl](3-pyridyl)car-
boxamide Step A Preparation of
2-bromo-1-tert-butyl-4-nitrobenzene NBS (125.0 g, 697.5 mmol) was slowly added to a solution of TFA:$H_2SO_4$ (5:1, 750 mL) and tert-butyl-4-nitrobenzene (100.0 g, 558.0 mmol) at RT. The solution was stirred for 24 h then poured over 5 kg of ice. The resulting suspension was filtered and washed with a 1:1 MeOH:$H_2O$ solution (200 mL) and dried in a vacuum oven. MS (ES+): 258.1, 260.1 (M+H)$^+$. Calc'd for $C_{10}H_{12}BrNO_2$: 257.01.

Step B Preparation of
4-(2-tert-butyl-5-nitrophenyl)pyridine

To a solution of 2-bromo-1-tert-butyl-4-nitrobenzene (8.6 g, 33.3 mmol) and toluene (70 mL) in a 150 mL round bottom flask, 4-pyridylboronic acid (4.5 g, 36.6 mmol), Pd(PPh$_3$)$_4$ (3.8 g, 3.3 mmol) and $K_2CO_3$ (13.8 g, 99.9 mmol) were added. The solution was stirred for 24 h at 80° C. before cooling to RT. The solution was filtered through a pad of Celite® and purified by silica flash chromatography (30% EtOAc/Hexanes). This afforded the desired compound as a yellow solid. MS (ES+): 257.2 (M+H)$^+$; (ES−): 255.2 (M−H)$^−$. Calc'd for $C_{15}H_{16}N_2O_2$: 256.12.

Step C Preparation of
4-(2-tert-butyl-5-nitrophenyl)-1-methylpyridinium 4-(2-tert-Butyl-5-nitrophenyl)pyridine (2.0 g, 7.8 mmol, Step B) was added to a round-bottom flask and dissolved in EtOH (10 mL). MeI (30 mL) was added and the flask was placed in an 80° C. sand bath and heated to reflux. After 6 h the solution was cooled to RT and the excess MeI and EtOH was concentrated in vacuo resulting in the desired compound as a light brown solid. MS (ES+): 271.2 (M+H)$^+$; (ES−): 269.2 (M−H)$^−$. Calc'd for $C_{16}H_{19}N_2O_2{}^+$: 271.14.

Step D Preparation of 4-tert-butyl-3-(1-methyl-1,2,3,
6-tetrahydropyridin-4-yl)aniline 4-(2-tert-Butyl-5-nitrophenyl)-1-methylpyridinium (2.1 g, 7.8 mmol, Step C) was added to a 100 mL round-bottom flask and dissolved in a 10% $H_2O$/EtOH mixture. To the flask iron dust (1.31 g, 23.4 mmol) and NH$_4$Cl (460 mg, 8.6 mmol) were added. The flask was placed in a 100° C. sand bath and heated to reflux. After 2 h the solution was cooled to RT and filtered through a pad of Celite®. The resulting solution was concentrated in vacuo to a yellow solid and re-dissolved in MeOH (20 mL, anhydrous). The solution was cooled to 0° C. by placing it in an ice bath and slowly adding NaBH$_4$ (450 mg, 11.7 mmol). After addition of the NaBH$_4$, the solution was cooled to RT and stirred for 30 min. The solvent was concentrated in vacuo and the solid was re-dissolved in $CH_2Cl_2$ and filtered. The solution was again concentrated in vacuo to afford an amorphous clear yellow solid. MS (ES+): 245.2 (M+H)$^+$. Calc'd for $C_{16}H_{24}N_2$: 244.19.

Step E Preparation of 2-[(pyridin-4-ylmethyl)
amino]-N-[4-tert-butyl-3-(1,2,3,6-tetrahydropyridin-
4-yl)phenyl](3-pyridyl)carboxamide The titled compound was prepared from 4-tert-butyl-3-(1-methyl-1,2,3,6-tetrahydropyridin-4-yl)aniline (Step D) by the method described in Example 25. MS: (ES+) 456.3 (M+H); (ES−) 454.4 (M−H). Calc'd for $C_{28}H_{33}N_5O$−455.59.

EXAMPLE 69

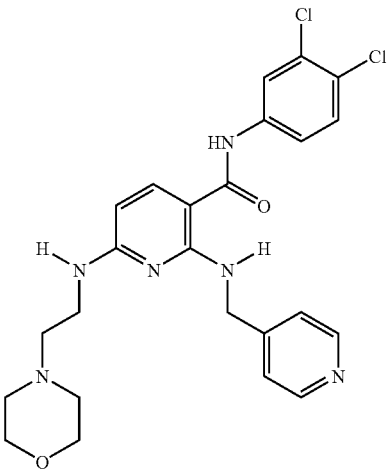

N-(3,4-Dichlorophenyl){6-[(2-morpholin-4-ylethyl)
amino]-2-[(4-pyridylmethyl)amino](3-pyridyl)}car-
boxamide A mixture of N-(3,4-dichlorophenyl){6-chloro-2-[(4-pyridylmethyl)amino](3-pyridyl)}carboxamide (18 mg, 0.044 mmol, made from 2,6-dichloronicotinic acid) and 2-morpholin-4-ylethylamine (300 μL) was stirred at 80° C. for 20 h. The reaction mixture was purified on silica gel chromatography to yield N-(3,4-dichlorophenyl){6-[(2-morpholin-4-ylethyl)amino]-2-[(4-pyridylmethyl)amino](3-pyridyl)}carboxamide. MS (ES+): 501 (M+H)$^+$; (ES−): 499 (M−H)$^−$. Calc'd for $C_{24}H_{26}Cl_2N_6O_2$−500.15.

EXAMPLE 70

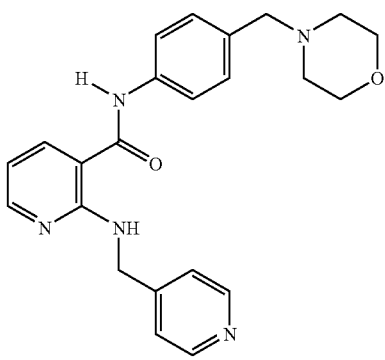

N-[4-(Morpholin-4-ylmethyl)phenyl]{2-[(4-pyridyl-
methyl)amino](3-pyridyl)}carboxamide Step A Preparation of
4-[(4-nitrophenyl)methyl]morpholine A mixture of nitrobenzyl bromide (648 mg, 3.0 mmol) and morpholine (522 mg, 6.0 mmol) in $CH_2Cl_2$ was stirred for 5 h at RT. Filtration to remove the white solid, and the filtrate was concentrated to give 4-[(4-nitrophenyl)-methyl]morpholine as a solid, which was used in next step without further purification.

Step B Preparation of 4-(morpholin-4-ylmethyl)phenylamine

A mixture of 4-[(4-nitrophenyl)methyl]morpholine (220 mg, 1.0 mmol, Step A), iron powder (279 mg, 5.0 mmol) and NH₄Cl (39 mg, 0.7 mmol) in EtOH (3 mL) and H₂O (3 mL) was stirred for 4 h at 80° C. Filtration and concentration gave the crude 4-(morpholin-4-ylmethyl)-phenylamine, which was used in next step without further purification.

Step C Preparation of N-[4-(morpholin-4-ylmethyl)phenyl]{2-[(4-pyridylmethyl)amino](3-pyridyl)}carboxamide The titled compound was prepared from 4-(morpholin-4-ylmethyl)phenylamine (Step B) by the method described in Example 25. MS (ES+): 404 (M+H); (ES−): 402 (M−H). Calc'd. for $C_{22}H_{24}N_4O_2$–403.20.

EXAMPLE 71

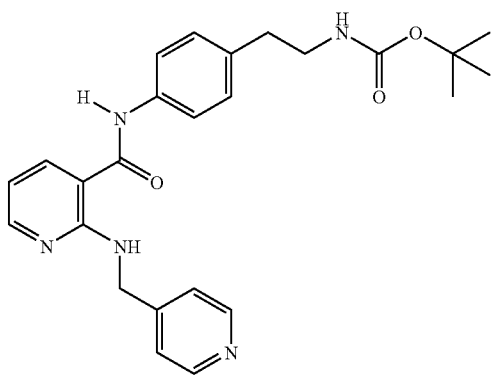

N-(4-{2-[(tert-Butoxy)carbonylamino]ethyl}phenyl){2-[(4-pyridylmethyl)amino](3-pyridyl)}carboxamide

Step A Preparation of (tert-butoxy)-N-[2-(4-nitrophenyl)ethyl]carboxamide

A mixture of 2-(4-nitrophenyl)ethylamine (1.01 g, 5.0 mmol), and di-tert-butyl dicarbonate (1.09 g, 5.0 mmol) in CH₂Cl₂ (20 mL) and 1N NaOH (20 mL) was stirred for 20 h at RT. The mixture was extracted with CH₂Cl₂, washed with brine, and dried with MgSO₄. Filtration and concentration yielded (tert-butoxy)-N-[2-(4-nitrophenyl)ethyl]carboxamide, which was used in next step without further purification.

Step B Preparation of N-[2-(4-aminophenyl)ethyl](tert-butoxy)carboxamide

A mixture of (tert-butoxy)-N-[2-(4-nitrophenyl)ethyl]-carboxamide (570 mg, 2.15 mmol, Step A), iron powder (602 mg, 10.75 mmol) and NH₄Cl (82 mg, 1.5 mmol) in EtOH (6 mL) and H₂O (6 ml) was stirred for 4 h at 80° C. Filtration and concentration gave the crude compound, which was used in next step without further purification.

Step C Preparation of N-[4-(morpholin-4-ylmethyl)phenyl]{2-[(4-pyridylmethyl)amino](3-pyridyl)}carboxamide The titled compound was prepared from N-[2-(4-aminophenyl)ethyl](tert-butoxy)carboxamide (Step B) by the method described in Example 25. MS (ES+): 448 (M+H); (ES−): 446 (M−H). Calc'd. for $C_{25}H_{29}N_5O_3$–447.23.

EXAMPLE 72

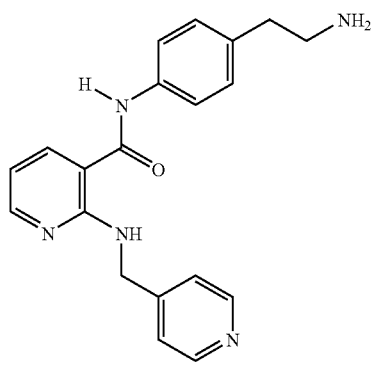

N-[4-(2-Aminoethyl)phenyl]{2-[(4-pyridylmethyl)amino](3-pyridyl)}carboxamide

To the solution of N-(4-{2-[(tert-butoxy)carbonylamino]ethyl}phenyl){2-[(4-pyridylmethyl)amino](3-pyridyl)}carboxamide (96 mg, 0.22 mmol, Example 71) in CH₂Cl₂ (3 mL) was added TFA (3 mL). The mixture was stirred for 3 h at RT. The reaction mixture was concentrated and dried in vacuo to yield N-[4-(2-aminoethyl)phenyl]{2-[(4-pyridylmethyl)-amino](3-pyridyl)}carboxamide. MS (ES+): 348 (M+H); (ES−): 346 (M−H). Calc'd. for $C_{20}H_{21}N_5O$–347.17.

The following compounds (Example a-m) were synthesized by the method described above, unless specifically described.

a) N-[3-(azetidin-3-ylmethoxy)-5-trifluoromethyl-phenyl]-2-[(pyridin-4-ylmethyl)-amino]-nicotinamide.

b) 2-[(2,3-Dihydro-benzofuran-5-ylmethyl)-amino]-N-[3,3-dimethyl-1-(piperidin-4-ylmethyl)-2,3-dihydro-1H-indol-6-yl]-nicotinamide. M+H 512.3; Calc'd 511.7.

c) N-[3-(piperazine-1-carbonyl)-5-trifluoromethyl-phenyl]-2-[(pyridin-4-ylmethyl)-amino]-nicotinamide. M+H 485.3.

d) N-[3-(piperazine-1-methyl)-4-pentafluoroethyl-phenyl]-2-[(pyridin-4-ylmethyl)-amino]-nicotinamide. M+H 521.4.

e) N-[3-(piperazine-1-methyl)-5-trifluoromethyl-phenyl]-2-[(pyridin-4-ylmethyl)-amino]-nicotinamide. M+H 471.2; Calc'd 470.

d) N-[1-(2-Amino-acetyl)-3,3-dimethyl-2,3-dihydro-1H-indol-6-yl]-2-[(2-methoxy-pyridin-4-ylmethyl)-amino] nicotinamide. M+H 461.1.

e) N-[1-(2-Amino-acetyl)-3,3-dimethyl-2,3-dihydro-1H-indol-6-yl]-2-[(pyridin-4-ylmethyl)-amino]nicotinamide. M+H 431.4.

f) (S)N-[3-(pyrrolidin-2-yl-methoxy)-4-pentafluoroethyl-phenyl]-2-[(pyridin-4-ylmethyl)-amino]-nicotinamide. M+H 522.6; Calc'd 521.5.

g) (R)N-[3-(pyrrolidin-2-yl-methoxy)-4-trifluoromethyl-phenyl]-2-[(pyridin-4-ylmethyl)-amino]-nicotinamide. M+H 472.6; Calc'd 471.5.

h) (R)N-[3-(pyrrolidin-2-yl-methoxy)-4-pentafluoroethyl-phenyl]-2-[(pyridin-4-ylmethyl)-amino]-nicotinamide. M+H 522.3; Calc'd 521.5.

i) (S)N-[3-(pyrrolidin-2-yl-methoxy)-5-trifluoromethyl-phenyl]-2-[(pyridin-4-yl-methyl)-amino]-nicotinamide. M+H 472; Calc'd 471.5.

j) (S)N-[3-(4-piperdinyloxy)-5-trifluoromethyl-phenyl]-2-[(pyridin-4-ylmethyl)-amino]-nicotinamide. M+H 472; Calc'd 471.5.

k) 2-[(2-Methoxy-pyridin-4-yl-methyl)-amino]-N-[3-(piperidin-4-yloxy)-5-trifluoromethyl-phenyl]-nicotinamide.

l) N-{4-tert-Butyl-3-[2-(piperidin-4-yl)-methoxy]-phenyl}-2-[(pyridin-4-ylmethyl)-amino]-nicotinamide. M+H 474.

m) N-[4-tert-Butyl-3-(pyrrolidin-2-ylmethoxy)-phenyl]-2-[(pyridin-4-ylmethyl)-amino]-nicotinamide. M+H 460.

n) 2-[(2-Methoxy-pyridin-4-ylmethyl)-amino]-N-[3-(pyrrolidin-2-ylmethoxy)-5-trifluoromethyl-phenyl]-nicotinamide.

o) N-(3,3-Dimethyl-1-pyrrolidin-2-ylmethyl-2,3-dihydro-1H-indol-6-yl)-2-[(pyridin-4-ylmethyl)-amino]-nicotinamide.

EXAMPLE 73

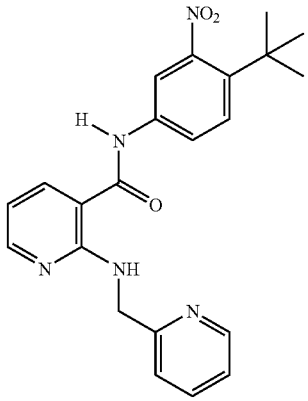

N-[4-(tert-Butyl)-3-nitrophenyl]{2-[(2-pyridylmethyl)amino](3-pyridyl)}carboxamide MS (ES+): 406 (M+H); (ES−): 405 (M−H). Calc'd. for C$_{22}$H$_{23}$N$_5$O$_3$–405.18.

EXAMPLE 74

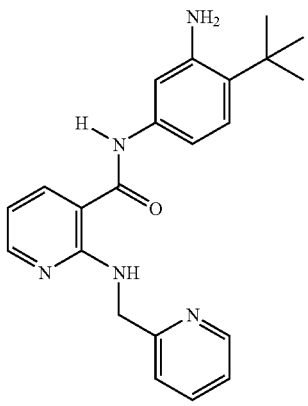

N-[3-Amino-4-(tert-butyl)phenyl]{2-[(2-pyridylmethyl)amino](3-pyridyl)}carboxamide A mixture of N-[4-(tert-butyl)-3-nitrophenyl]{2-[(2-pyridylmethyl)amino](3-pyridyl)}carboxamide (100 mg, 0.25 mmol, Example 73), iron powder (69 mg, 1.25 mmol) and NH$_4$Cl (10 mg, 0.17 mmol) in EtOH (0.5 mL) and H$_2$O (0.5 ml) was stirred for 4 h at 80° C. The reaction mixture was filtered, concentrated, and purified through column chromatography to give the product. MS (ES+):376 M+H); (ES−): 374(M−H). Calc'd. for C$_{22}$H$_{25}$N$_5$O–375.21.

EXAMPLE 75

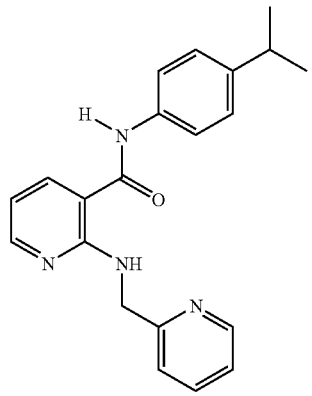

N-[4-(Isopropyl)phenyl]{2-[(2-pyridylmethyl)amino](3-pyridyl)}carboxamide

MS (ES+): 347 (M+H); (ES−): 345 (M−H). Calc'd. for C$_{21}$H$_{22}$N$_4$O–346.18.

EXAMPLE 76

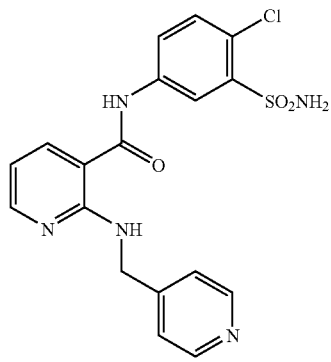

N-(3-Aminosulfonyl-4-chlorophenyl){2-[(4-pyridylmethyl)amino](3-pyridyl)}carboxamide MS (ES+): 418 (M+H); (ES−): 416 (M−H). Calc'd. for C$_{18}$H$_{16}$N$_5$O$_3$S–417.07.

EXAMPLE 77

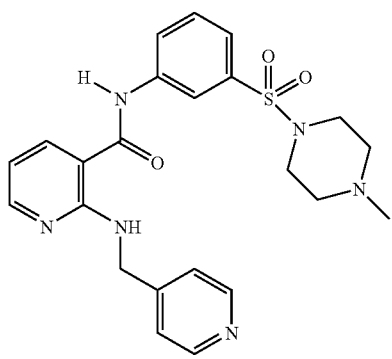

N-{3-[(4-Methylpiperazinyl)sulfonyl]phenyl}{2-[(4-pyridylmethyl)amino](3-pyridyl)}carboxamide

Step A Preparation of 3-[(4-methylpiperazinyl)sulfonyl]-1-nitrobenzene

A mixture of 3-nitrobezenesulfonyl chloride (664 mg, 3.0 mmol) and methylpiperazine (600 mg, 6.0 mmol) in EtOH was stirred for 2 h at RT. The reaction was concentrated and triturated in $Et_2O$ to yield a yellowish solid, 3-[(4-methylpiperazinyl) sulfonyl]-1-nitrobenzene, and was used in next step without further purification.

Step B Preparation of 3-[(4-methylpiperazinyl)sulfonyl]phenylamine

3-[(4-Methylpiperazinyl)sulfonyl]phenylamine was analogously synthesized from 3-[(4-methylpiperazinyl) sulfonyl]-1-nitrobenzene (Step A) by the method described in Example 74, which was used in next step without further purification. MS (ES+): 256 (M+H). Calc'd. for $C_{11}H_{17}N_3O_2S$–255.10.

Step C Preparation of N-[4-(morpholin-4-ylmethyl)phenyl]{2-[(4-pyridylmethyl)amino](3-pyridyl)}carboxamide The titled compound was prepared from 3-[(4-methylpiperazinyl)sulfonyl]phenylamine (Step B) by the method described in Example 25. MS (ES+): 467 (M+H); (ES−): 465 (M−H). Calc'd. for $C_{23}H_{26}N_6O_3S$–466.18.

EXAMPLE 78

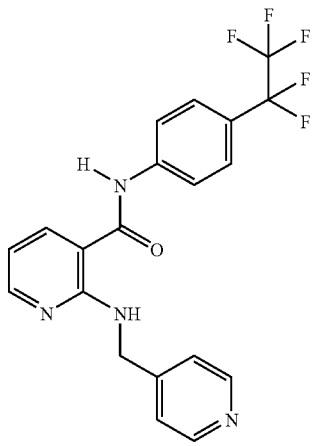

N-[4-(1,1,2,2,2-Pentafluoroethyl)phenyl]{2-[(4-pyridylmethyl)amino](3-pyridyl)}carboxamide

Step A Preparation of 4-(1,1,2,2,2-pentafluoroethyl)phenylamine

1-Nitro-4-(1,1,2,2,2-pentafluoroethyl)benzene was synthesized by the method described in the reference [John N. Freskos, Synthetic Communications, 18(9), 965-972 (1988)]. It was reduced with Fe similar to that described in Example 74. It was used in next step without further purification.

Step B Preparation of N-[4-(1,1,2,2,2-Pentafluoroethyl)phenyl]{2-[(4-pyridylmethyl)amino](3-pyridyl)}carboxamide The titled compound was prepared from 4-(1,1,2,2,2-pentafluoroethyl)phenylamine (Step A) by the method described in Example 25. MS (ES+): 423 (M+H); (ES−): 421 (M−H). Calc'd. for $C_{20}H_{15}FN_4O$–422.12.

EXAMPLE 79

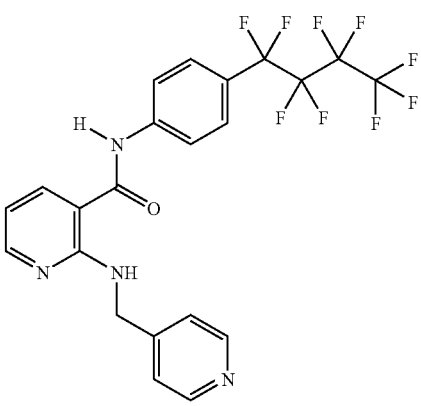

N-[4-(1,1,2,2,3,3,4,4,4-Nonafluorobutyl)phenyl]{2-[(4-pyridylmethyl)amino](3-pyridyl)}carboxamide Step A Preparation of 4-(1,1,2,2,3,3,4,4,4-nonafluorobutyl)phenylamine The title intermediate was analogously synthesized by the method described of W. A. Gregory, et al. [J. Med. Chem., 1990, 33, 2569-2578]. 1-nitro-4-(1,1,2,2,3,3,4,4,4-monofluorobutyl) benzene was reduced with Fe described in Example 68, Step D, and used in next step without further purification.

Step B Preparation of N-[4-(1,1,2,2,3,3,4,4,4-nonafluorobutyl)phenyl]{2-[(4-pyridylmethyl)amino](3-pyridyl)}carboxamide The titled compound was prepared from 4-(1,1,2,2,3,3,4,4,4-nonafluorobutyl)phenylamine (Step A) by the method described in Example 25. MS (ES+): 523 (M+H); (ES−): 521 (M−H). Calc'd. for $C_{22}H_{15}F_9N_4O$−522.37.

EXAMPLE 80

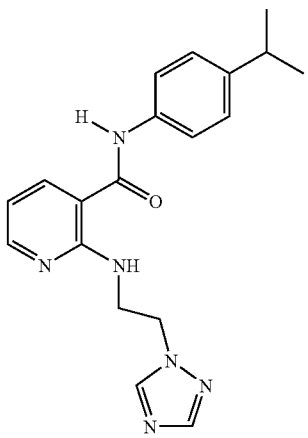

N-[4-(Isopropyl)phenyl]{2-[(2-(1,2,4-triazolyl)ethyl)amino](3-pyridyl)}carboxamide Step A Preparation of 2-(1,2,4-triazolyl)ethylamine A mixture of (tert-butoxy)-N-(2-chloroethyl)-carboxamide (900 mg, 5 mmol), 1,2,4-triazole (690 mg, 10 mmol) and $Na_2CO_3$ (1.06 g, 10 mmol) in DMF (3 mL) was stirred overnight at 100° C. The mixture was filtered and concentrated to give an oil. The oil was treated with TFA (10 mL) and stirred for 3 h. The reaction was concentrated to give the titled intermediate, which was used in next step without further purification.

Step B Preparation of N-[4-(methylethyl)phenyl]{2-[(2-(1,2,4-triazolyl)ethyl)amino](3-pyridyl)}carboxamide The titled compound was prepared from 2-(1,2,4-triazolyl)ethylamine (Step A) by the method described in Example 25. MS (ES+): 351 (M+H); (ES−): 349 (M−H). Calc'd. for $C_{19}H_{22}N_6O$−350.19.

EXAMPLE 81

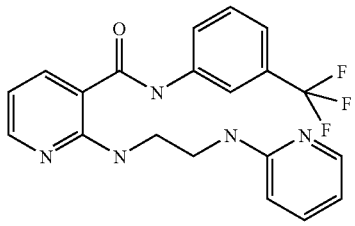

(2-{[2-(2-Pyridylamino)ethyl]amino}(3-pyridyl))-N-[3-(trifluoromethyl)phenyl]carboxamide Step A Preparation of 2-(2-pyridylamino)ethylamine Ethylenediamine (6 g, 0.1 mol) and 2-fluoropyridine (10 g, 0.1 mol) were heated neat at 120° C. overnight. The reaction was cooled and the residue was used in next step without further purification.

Step B Preparation of (2-{[2-(2-pyridylamino)ethyl]amino}-(3-pyridyl))-N-[3-(trifluoromethyl)phenyl]carboxamide The titled compound was prepared from 2-(2-pyridylamino)ethylamine (Step A) by the method described in Example 25. MS (ES+): 402 (M+H); (ES−): 400 (M−H). Calc'd. for $C_{20}H_{18}F_3N_5O$−401.15.

EXAMPLE 82

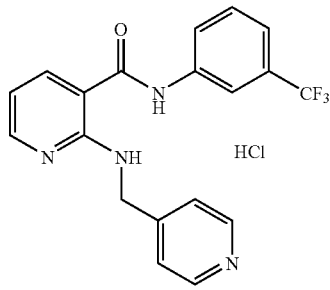

2-[(Pyridin-4-ylmethyl)-amino]-N-(3-trifluoromethyl-phenyl)-nicotinamide

Step A: Preparation of (2-chloro(3-pyridyl))-N-(3-trifluoromethylphenyl)carboxamide 2-Chloropyridine-3-carbonyl chloride (18.02 g, 0.102 mol) in $CH_2Cl_2$ (100 ml) was added dropwise (via an addition funnel) to a stirred solution of 3-(trifluoromethyl)-aniline (15.00 g, 0.093 mol) and DIEA (24.39 ml, 0.14 mol) in $CH_2Cl_2$ (500 ml) at 0° C. The mixture gradually was warmed to RT. The reaction continued for 18 h before washing several times with saturated $NaHCO_3$ aqueous solution and brine, respectively. The organic layer was dried over $Na_2SO_4$ and evaporated. The resulting oil was purified over silica gel with EtOAc/hexane (2:1) as eluant to leave the amide as a white solid (26.08 g). MS: (ES+) 301 (M+1)$^+$; (ES-): 299 (M-1)$^-$. Calc'd for $C_{13}H_8ClF_3N_2O$: 300.03.

Step B: Preparation of N-[3-trifluoromethylphenyl phenyl]{2-[(4-pyridylmethyl)amino](3-pyridyl)}carboxamide hydrochloride The amide (10.0 g 0.033 mol, Step A) and 4-aminomethylpyridine (10.81 g, 0.10 mol) were combined and heated at 120° C. for 4 h. After cooling to RT, the residue was dissolved in EtOAc and washed several times with saturated $NaHCO_3$ aqueous solution and brine, respectively. The organic layer was dried over $Na_2SO_4$ and evaporated. The crude yellow oil was purified over silica gel with EtOAc as eluant to leave an amber oil (10.9 g). The free base was dissolved in MeOH (20 ml) and treated with a HCl ethereal solution (1.0 eq.). The solvent was evaporated to leave the salt as a white solid. The HCl salt was dried in vacuo at 30° C. for 24 h. MS: (ES+) 373 (M+1)$^+$; (ES-): 371 (M-1)$^-$. Calc'd. for $C_{19}H_{15}F_3N_4O$-372.12.

The following compounds (Examples 83-138) were analogously synthesized by the method described in Example 82 unless specifically described. Detailed intermediate preparations are included.

TABLE 2

| # | Y | R$^1$ | R$^2$ | M + H | calc'd |
|---|---|---|---|---|---|
| 83 | —NH—CH$_2$— | 8-methylquinolin-2-yl | H | 356 | 355.14 |
| 84 | —NH—CH$_2$— | 4-(4-chlorophenoxy)-3-methylphenyl | H | 431 | 430.12 |
| 85 | —NH—CH$_2$— | 2,3,6-trifluoro-4-methylphenyl | H | 359 | 358.1 |
| 86 | —NH—CH$_2$— | 3-methylnaphthalen-2-yl | H | 355 | 354.15 |
| 87 | —NH—CH$_2$— | 8-methyl-5,6,7,8-tetrahydronaphthalen-1-yl | H | 359 | 358.18 |
| 88 | —NH—CH$_2$— | 6-methylbenzo[d][1,3]dioxol-5-yl | H | 349 | 348.128 |

TABLE 2-continued
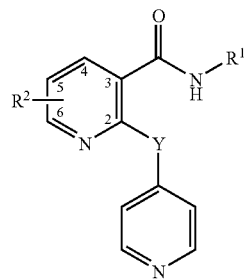
| # | Y | R¹ | R² | M + H | calc'd |
|---|---|---|---|---|---|
| 89 | —NH—CH₂— | 1-methylnaphthalenyl | H | 355 | 354.15 |
| 90 | —NH—CH₂— | 3-benzylphenyl | H | 395 | 394.18 |
| 91 | —NH—CH₂— | (S)-1-cyclohexylethyl (H₃C, methyl wedge) | H | 339 | 338.12 |
| 92 | —NH—CH₂— | (R)-1-cyclohexylethyl (H₃C, methyl dash) | H | 339 | 338.12 |
| 93 | —NH—CH₂— | 2-indanyl | H | 345 | 344.16 |
| 94 | —NH—CH₂— | 4-tert-butylphenyl | H | 361 | 360.20 |
| 95 | —NH—CH₂— | 4-sec-butylphenyl | H | 361 | 360.20 |
| 96 | —NH—CH₂— | 4-methylphenyl (CH₃) | H | 319 | 318.5 |

TABLE 2-continued
| # | Y | R¹ | R² | M + H | calc'd |
|---|---|---|---|---|---|
| 97 | —NH—CH₂— | 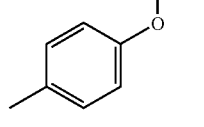 | H | 389 | 388.11 |
| 98 | —NH—CH₂— | 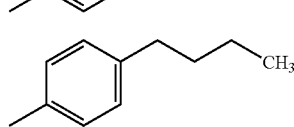 | H | 333 | 332.16 |
| 99 | —NH—CH₂— | 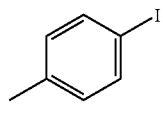 | H | 361 | 360.2 |
| 100 | —NH—CH₂— | 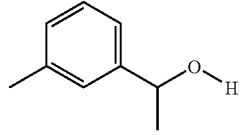 | H | 431 | 430 |
| 101 | —NH—CH₂— | 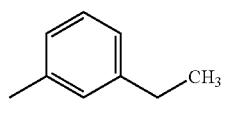 | H | 349 | 348.16 |
| 102 | —NH—CH₂— | 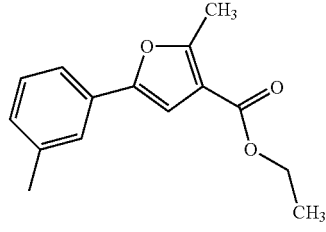 | H | 333 | 332.16 |
| 103 | —NH—CH₂— | 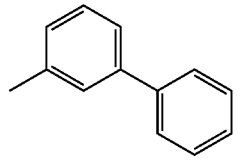 | H | 457 | 456.18 |
| 104 | —NH—CH₂— | 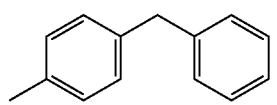 | H | 381 | 380.16 |
| 105 | —NH—CH₂— |  | H | 395 | 394.18 |

TABLE 2-continued
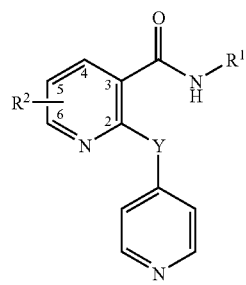
| # | Y | R¹ | R² | M + H | calc'd |
|---|---|---|---|---|---|
| 106 | —NH—CH₂— | 2-methyl-6-ethylpyridin-4-yl | H | 334 | 333.16 |
| 107 | —NH—CH₂— | 2-methyl-6-propylpyridin-4-yl | H | 348 | 347.17 |
| 108 | —NH—CH₂— | 2-methyl-4-tert-butylpyridin-4-yl | H | 362 | 361.19 |
| 109 | —NH—CH₂— | 3-hydroxy-methylphenyl | H | 321 | 320.13 |
| 110 | —NH—CH₂— | 2-methyl-4-isopropylpyridin-4-yl | H | 348 | 347.17 |
| 111 | —NH—CH₂— | 3,5-bis(trifluoromethyl)phenyl | H | 441 | 440.11 |
| 112 | —NH—CH₂— | 2-chloro-3-trifluoromethylphenyl | H | 407 | 406.08 |
| 113 | —NH—CH₂— | 3-chlorophenyl | H | 353 | 352.11 |

TABLE 2-continued
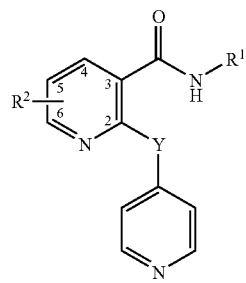
| # | Y | R¹ | R² | M + H | calc'd |
|---|---|---|---|---|---|
| 114 | —NH—CH₂— | 4-(methylsulfonyl)phenyl | H | 383 | 382.11 |
| 115 | —NH—CH₂— | 1-acetyl-6-methylindolin-5-yl | H | 388 | 387.43 |
| 116 | —NH—CH₂— | 6-methylindolin-5-yl | H | 346 | 345.00 |
| 117 | —NH—CH₂— | 6-methyl-1H-indol-5-yl | H | 344 | 343.38 |
| 118 | —NH—CH₂— | 5-methyl-1H-indol-6-yl | H | 344 | 343.38 |
| 119 | —NH—CH₂— | 7-methyl-1H-indol-6-yl | H | 344 | 343.38 |
| 120 | —NH—CH₂— | 3-tert-butyl-5-methyl-1H-pyrazol-4-yl | H | 351 | 350.43 |
| 121 | —NH—CH₂— | 5-methyl-3-phenyl-1H-pyrazol-4-yl | H | 371 | 370.43 |

EXAMPLE 122

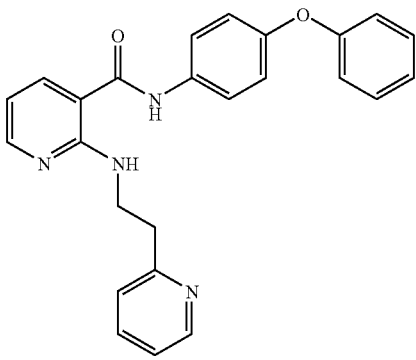

N-(4-Phenoxyphenyl){2-[(2-(2-pyridyl)ethyl)amino](3-pyridyl)}carboxamide

MS: 411 (M+1); 409 (M−1). Calc'd. for $C_{25}H_{22}N_4O_2$−410.17.

EXAMPLE 123

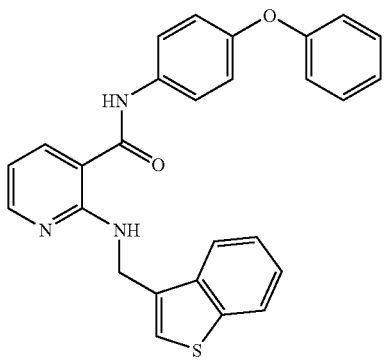

2-[(Benzo[b]thiophen-3-ylmethyl)amino](3-pyridyl)}-N-(4-phenoxyphenyl)carboxamide MS: (ES+) 452 (M+1)$^+$; (ES−): 450 (M−1)$^−$. Calc'd. for $C_{27}H_{21}N_3O_2S$−451.14.

EXAMPLE 124

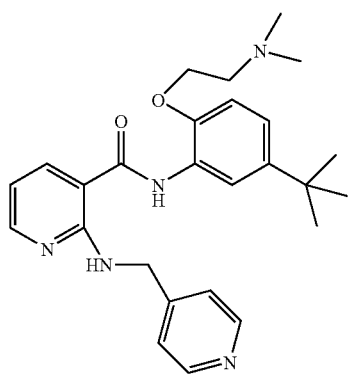

N-{2-[2-(Dimethylamino)ethoxy]-5-(tert-butyl)phenyl}{2-[(4-pyridylmethyl)amino](3-pyridyl)}carboxamide Step A—Preparation of {2-[4-(tert-butyl)-2-nitrophenoxy]-ethyl}dimethylamine To a mixture of 2-nitro-4-tert-butylphenol (2 g) and N,N-dimethylethanolamine (1.3 g) and PPh$_3$ (4 g) in THF (50 ml) was added DEAD (2.6 ml). The reaction was stirred at RT for 1 h, diluted with EtOAc (50 ml) and washed with 1 N HCl twice. The aqueous layer was basified with NaHCO$_3$, extracted with EtOAc twice and washed with H$_2$O and brine. The organic layer was dried over Na$_2$SO$_4$ and evaporated to give {2-[4-(tert-butyl)-2-nitrophenoxy]-ethyl}dimethylamine, was used in next step without further purification.

Step B—Preparation of {2-[4-(tert-butyl)-2-aminophenoxy]-ethyl}dimethylamine

{2-[4-(tert-Butyl)-2-nitrophenoxy]-ethyl}dimethylamine (Step A) was hydrogenated under H$_2$ atmosphere to give {2-[4-(tert-butyl)-2-aminophenoxy]-ethyl}dimethylamine, and used in next step without further purification.

Step C—Preparation of N-{2-[2-(dimethylamino)ethoxy]-5-(tert-butyl)phenyl}{2-[(4-pyridylmethyl)amino](3-pyridyl)}carboxamide The titled compound was prepared from {2-[4-(tert-butyl)-2-aminophenoxy]-ethyl}dimethylamine (Step B) by the method described in Example 82. MS (ES+): 448 (M+H); (ES−): 446 (M−H). Calc'd. for $C_{26}H_{33}N_5O_2$−447.26.

EXAMPLE 125

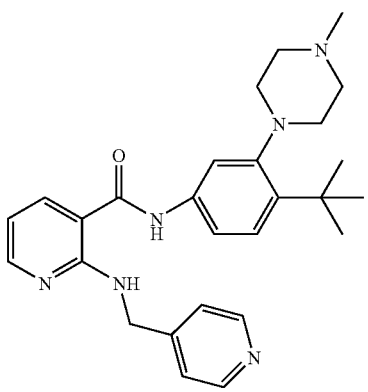

N-[4-(tert-Butyl)-3-(4-methylpiperazinyl)phenyl]{2-[(4-pyridylmethyl)amino](3-pyridyl)}carboxamide Step A—Preparation of 1-[2-(tert-butylphenyl]-4-methylpiperazine A mixture of 2-tert-butylaniline (5.4 g) and N-methylbis(2-chloroethyl)amine hydrochloride (7 g) and K$_2$CO$_3$ (5 g) in NaI (2 g) in diglyme (150 ml) was heated at 170° C. for 8 h. The reaction was filtered and the filtrate was evaporated under high vacuum. The residue was mixed with EtOAc (200 ml) and H$_2$O (200 ml) and extracted with EtOAc twice. The combined organic layer was washed with brine, dried over $Na_2SO_4$ and evaporated to give crude 1-[2-(tert-butylphenyl]-4-methyl-piperazine, which was used in next step without further purification.

Step B—Preparation of 1-[2-(tert-butyl)-5-aminophenyl]-4-methylpiperazine

The crude 1-[2-(tert-butylphenyl]-4-methylpiperazine (260 mg, Step A) was stirred with $H_2SO_4$ (3 ml) at 0° C. and $HNO_3$ (1.2 ml) was slowly added to the reaction. The reaction was warmed to RT, stirred for 30 min. and poured on ice and basified with $K_2CO_3$ slowly. The solution was extracted with EtOAc three times, washed with $H_2O$, followed by brine, dried over $Na_2SO_4$, and evaporated under reduced pressure. The residue was purified by column chromatography to give 1-[2-(tert-butyl)-5-nitrophenyl]-4-methylpiperazine (260 mg), which was hydrogenated under $H_2$ atmosphere to give 1-[2-(tert-butyl)-5-aminophenyl]-4-methylpiperazine.

Step C—Preparation of N-[4-(tert-Butyl)-3-(4-methylpiperazinyl)phenyl]{2-[(4-pyridylmethyl)amino](3-pyridyl)}carboxamide The titled compound was prepared from 1-[2-(tert-butyl)-5-aminophenyl]-4-methylpiperazine (Step B) by the method described in Example 82. MS (ES+): 459 (M+H); (ES−): 457 (M−H). Calc'd. for $C_{27}H_{34}N_6O$–458.28.

EXAMPLE 126

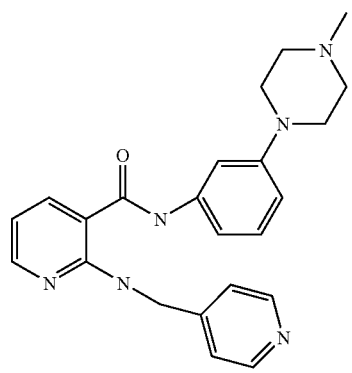

N-[3-(4-Methylpiperazinyl)phenyl]{2-[(4-pyridylmethyl)amino](3-pyridyl)}carboxamide

Step A—Preparation of 3-(4-methylpiperazinyl)phenylamine

The intermediate was analogously synthesized from 3-nitroaniline by the method described in Example 130.

Step B—Preparation of N-[3-(4-methylpiperazinyl)phenyl]{2-[(4-pyridylmethyl)amino](3-pyridyl)}carboxamide The titled compound was prepared from 3-(4-methylpiperazinyl)phenylamine (Step A) by the method described in Example 82. MS (ES+): 403 (M+H); (ES−): 401 (M−H). Calc'd. for $C_{23}H_{26}N_6O$–402.22.

EXAMPLE 127

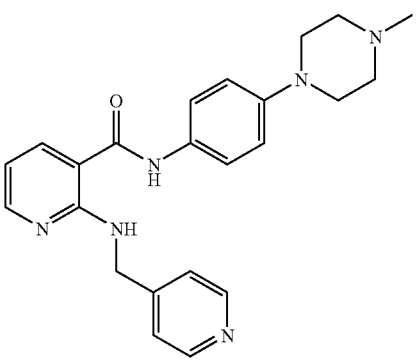

N-[4-(4-Methylpiperazinyl)phenyl]{2-[(4-pyridylmethyl)amino](3-pyridyl)}formamide

Step A—Preparation of 4-methyl-1-(4-nitrophenyl)piperazine

1-Fluoro-4-nitrobenzene (3.0 g, 0.021 mol) and 1-methylpiperazine (6.98 ml, 0.63 mol) were combined and heated neat at 90° C. for 48 h. Upon cooling to RT, the resulting brown oil solidified. The crude material was purified by recrystallization from EtOAc/Hexane mixtures to leave the title compound as an orange solid (3.59 g). MS: (ES+) 222 (M+1)$^+$; (ES−): 220 (M−1)$^−$. Calc'd for $C_{11}H_{15}N_3O_2$: 221.12.

Step B—Preparation of 4-methyl-1-(4-aminophenyl)piperazine

4-Methyl-1-(4-nitrophenyl)piperazine (2.0 g, 9 mmol, Step A) and 10% Pd/C (200 mg) were added to EtOH/MeOH (1:1) (50 ml) at RT. The reaction stirred under a $H_2$ atmosphere (via balloon) overnight. The mixture was filtered through a plug of Celite® and the filtrate was concentrated under reduced pressure to leave the desired material as a light yellow oil. The material was used in subsequent reaction without purification. MS: (ES+) 192 (M+1)$^+$; (ES−): 190 (M−1)$^−$. Calc'd for $C_{11}H_{17}N_3$: 191.14.

Step C Preparation of N-[4-(4-methylpiperazinyl)phenyl]{2-[(4-pyridylmethyl)amino](3-pyridyl)}formamide The titled compound was prepared from 4-methyl-1-(4-aminophenyl)piperazine (Step B) by the method described in Example 82. MS (ES+): 403 (M+H); (ES−): 401 (M−H). Calc'd. for $C_{23}H_{26}N_6O$–402.22.

EXAMPLE 128

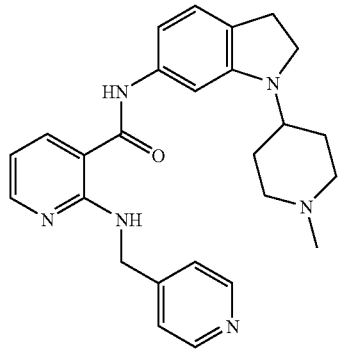

N-[1-(1-Methyl-(4-piperidyl))indolin-6-yl]{2-[(4-pyridylmethyl)amino](3-pyridyl)}carboxamide

Step A—Preparation of 1-(1-methyl(4-piperidyl))-6-nitroindoline

6-Nitroindoline (5 g) was dissolved in 200 mL of dichloroethane, N-methyl-4-piperidone (5 g) was added to the mixture, followed by 12 g NaBH(OAc)$_3$ and 1 mL of glacial ACOH. The mixture was stirred at RT overnight. Saturated NaHCO$_3$ solution (200 mL) was added to the reaction mixture and stirred for 1 h. The resulting mixture was separated by separation funnel, the organic layer was extracted once with saturated NaHCO$_3$ solution and once with brine. The resulting organic layer was dried over MgSO$_4$, filtered and concentrated in vacuo. The crude material was purified by flash chromatography on silica gel with 2:1 EtOAc:MeOH to afford an orange oil. MS: 262 (M+1). Calc'd. for $C_{14}H_{19}N_3O_2$—261.32.

Step B—Preparation of 1-(1-methyl-4-piperidyl)indoline-6-ylamine 1-(1-Methyl(4-piperidyl))-6-nitroindoline (3 g, Step A) was dissolved in 100 mL MeOH, and the mixture was bubbled with N$_2$ for 10 min. 10% Pd/C (200 mg) was added and the mixture was stirred under H$_2$ overnight. The mixture was filtered through Celite® and concentrated in vacuo to afford a light yellow oil. MS: 232 (M+1). Calc'd. for $C_{14}H_{21}N_3$—231.34.

Step C—Preparation of N-[1-(1-methyl(4-piperidyl)) indolin-6-yl]{2-[(4-pyridylmethyl)amino](3-pyridyl)}carboxamide The titled compound was prepared from 1-(1-methyl-4-piperidyl)indoline-6-ylamine (Step B) by the method described in Example 82. MS: 443 (M+1). Calc'd. for $C_{26}H_{30}N_6O$—442.56.

EXAMPLE 129

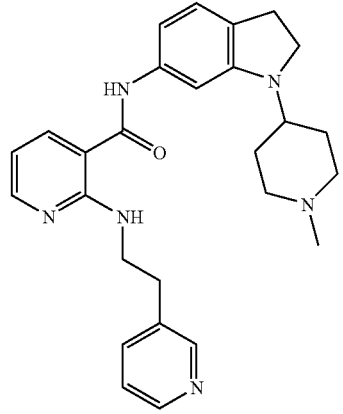

N-[1-(1-Methyl-(4-piperidyl))indolin-6-yl]{2-[(2-(3-pyridyl)ethyl)amino](3-pyridyl)}carboxamide MS: 457 (M+1). Calc'd. for $C_{27}H_{32}N_6O$—456.58.

EXAMPLE 130

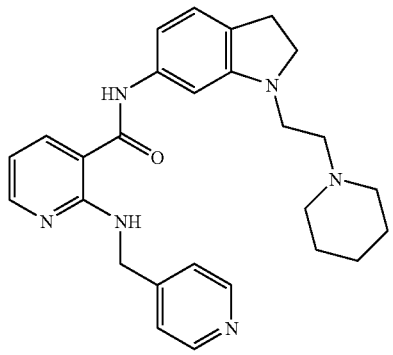

N-[1-(2-Piperidylethyl)indolin-6-yl]{2-[(4-pyridylmethyl)amino](3-pyridyl)}carboxamide

Step A—Preparation of 1-(6-nitroindolinyl)-2-piperidylethan-1-one

6-Nitroindoline (2.5 g) was dissolved in 200 mL of CH$_2$Cl$_2$, followed by DIEA (2.5 g). The mixture was cooled down to 0° C. in ice bath. Chloroacetyl chloride (1.7 g) in 20 mL CH$_2$Cl$_2$ was added dropwise to the mixture over 10 min and the mixture was stirred at RT overnight. The mixture was extracted once with saturated NaHCO$_3$ solution and once with brine, the resulting organic layer was dried over MgSO$_4$, filtered and concentrated in vacuo. The crude material was purified by flash chromatography on silica gel with 3:2 Hexane:EtOAc to afford a yellow oil (1.4 g) which was added to piperidine (5 mL), followed by NaI (100 mg). The mixture was heated at 70° C. overnight then concentrated in vacuo and extracted between EtOAc and saturated NaHCO$_3$ solution, the organic layer was washed with brine, the resulting organic layer was dried over MgSO$_4$, filtered and concentrated in vacuo. The crude material was purified by flash chromatography on silica gel with 9:1 EtOAc:MeOH to afford a yellow oil. MS: 290 (M+1). Calc'd. for $C_{15}H_{19}N_3O_3$–289.33.

Step B—Preparation of 1-(2-piperidylethyl)indoline-6-ylamine 1-(6-Nitroindolinyl)-2-piperidylethan-1-one (1.6 g, Step A) was dissolved in 100 mL MeOH, the mixture was bubbled with $N_2$ for 10 min. 10% Pd/C (200 mg) was added and the mixture was stirred under $H_2$ overnight. The mixture was filtered through Celite® and concentrated in vacuo to afford a yellow solid. 400 mg was dissolved in 20 mL anhydrous THF, 5 mL borane-THF (1 M) solution was added dropwise and the mixture was stirred at RT overnight. The mixture was quenched with MeOH, 100 mg NaOH added and heated at 70° C. for 30 min. The resulting mixture was concentrated in vacuo and extracted between EtOAc and saturated $NaHCO_3$ solution, the organic layer was washed with brine, the resulting organic layer was dried over $MgSO_4$, filtered and concentrated in vacuo to afford a yellow oil. MS: 246 (M+1). Calc'd. for $C_{15}H_{23}N_3$–246.36.

Step C—Preparation of N-[1-(2-piperidylethyl)indolin-6-yl]{2-[(4-pyridylmethyl)amino](3-pyridyl)}carboxamide The titled compound was prepared from 1-(2-piperidylethyl)indoline-6-ylamine (Step B) by the method described in Example 82. MS: 457 (M+1). Calc'd. for $C_{27}H_{32}N_6O$–456.58.

EXAMPLE 131

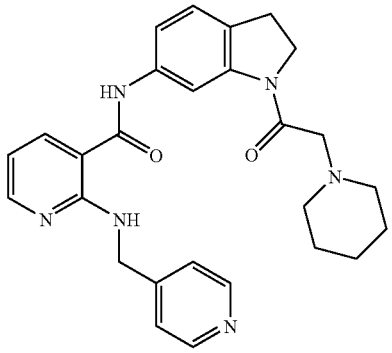

N-[1-(2-Piperidylacetyl)indolin-6-yl]{2-[(4-pyridylmethyl)amino](3-pyridyl)}carboxamide MS: 471 (M+1). Calc'd. for $C_{27}H_{30}N_6O_2$–470.57.

EXAMPLE 132

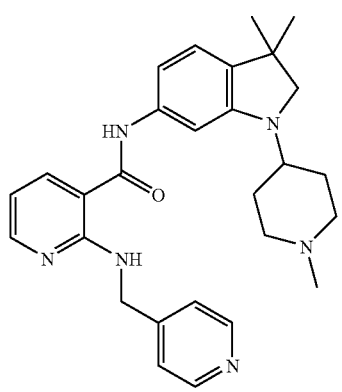

N-[3,3-Dimethyl-1-(1-methyl(piperid-4-yl)indolin-6-yl]{2-[(4-pyridylmethyl)amino](3-pyridyl)}carboxamide

Step A—Preparation of N-(2-bromo-5-nitrophenyl)acetamide

2-Bromo-5-nitroaniline (10 g) was dissolved in 500 mL of $CH_2Cl_2$, DIEA (6.6 g) was added to the mixture, followed by DMAP (100 mg). The mixture was cooled to 0° C. in ice bath. Acetyl chloride (4 g in 50 mL $CH_2Cl_2$) was added dropwise to the reaction mixture. After the mixture was stirred at RT over 3 h, extracted once with saturated $NaHCO_3$ solution and once with brine, the resulting organic layer was dried over $MgSO_4$, filtered and concentrated in vacuo. The crude material was purified by flash chromatography on silica gel with 1:1 EtOAc:Hexane to 100% EtOAc to afford N-(2-bromo-5-nitrophenyl)acetamide as a white solid. MS: 258 (M-1). Calc'd. for $C_8H_7BrN_2O_3$–259.06.

Step B—Preparation of N-(2-bromo-5-nitrophenyl)-N-(2-methylprop-2-enyl)acetamide A suspension of 2 g NaH (95% powder) in anhydrous DMF (100 mL) was cooled to –78° C., N-(2-bromo-5-nitrophenyl)acetamide (7 g, Step A) in dry DMF (50 mL) was added to the mixture under $N_2$ atmosphere. After the mixture was warmed to 0° C., 3-bromo-2-methylpropene (7.3 g in 20 dry DMF) was added to the mixture. The mixture was stirred at RT overnight. Next morning, the mixture was poured into a container of ice and extracted between saturated $NaHCO_3$ solution and EtOAc. The resulting organic layer was dried over $MgSO_4$, filtered and concentrated in vacuo. The crude material was purified by flash chromatography on silica gel with 7:2 hexane:EtOAc to afford the title compound as a yellow gum. MS: 314 (M+1). Calc'd. for $C_{12}H_{13}BrN_2O_3$–313.15.

Step C—Preparation of 1-(3,3-dimethyl-6-nitro-2,3-dihydro-indol-1-yl)ethanone N-(2-Bromo-5-nitrophenyl)-N-(2-methylprop-2-enyl)acetamide (4.5 g, Step B) was dissolved in anhydrous DMF (50 mL), tetraethyl-ammonium chloride (2.5 g), sodium formate (1.2 g), NaOAc (3 g) were added, and the resulting mixture was bubbled with $N_2$ gas for 10 min. $Pd(OAc)_2$ (350 mg) was added and the mixture was heated at 80° C. under $N_2$ atmosphere overnight. After the mixture was concentrated in vacuo, it was partitioned between saturated $NaHCO_3$ solution and EtOAc, the resulting organic layer was dried over $MgSO_4$, filtered and concentrated in vacuo. The crude material was purified by flash chromatography on silica gel with 2:1 Hexane:EtOAc to afford the title compound as a yellow gum. MS: 235 (M+1). Calc'd. for $C_{12}H_{14}N_2O_3$–234.25.

Step D—Preparation of 3,3-dimethyl-6-nitroindoline 1-(3,3-Dimethyl-6-nitro-2,3-dihydro-indol-1-yl)ethanone (1.8 g, Step C) was dissolved in EtOH (50 mL), 12N HCl (50 mL) was added and the resulting mixture was heated at 70° C. overnight. After the mixture was concentrated in vacuo, it was partitioned between saturated $NaHCO_3$ solution and EtOAc, the resulting organic layer was dried over $MgSO_4$, filtered and concentrated in vacuo to afford a yellow solid. MS: 193 (M+1). Calc'd. for $C_{10}H_{12}N_2O_2$–192.21.

Step E—Preparation of 3,3-dimethyl-1-(1-methylpiperidin-4-yl)-6-nitro-2,3-dihydro-1H-indole 3,3-Dimethyl-6-nitroindoline (0.8 g) was dissolved in $CH_2Cl_2$ (50 mL), N-methyl-4-piperidone (1 g) was added to the mixture, followed by 2.5 g NaBH(OAc)₃ and glacial AcOH (1 mL). The mixture was stirred at RT overnight. Saturated NaHCO₃ solution (50 ml) was added to the reaction mixture and stirred for 1 h. The resulting mixture was separated by separation funnel, the organic layer was extracted once with saturated NaHCO₃ solution and once with brine, the resulting organic layer was dried over MgSO₄, filtered and concentrated in vacuo. The crude material was purified by flash chromatography on silica gel with 9:1 EtOAc:MeOH to afford the title compound as an orange oil. MS: 290 (M+1). Calc'd. for $C_{16}H_{23}N_3O_2$–289.37.

Step F—Preparation of 3,3-dimethyl-1-(1-methyl(4-piperidyl))indoline-6-ylamine 3,3-Dimethyl-1-(1-methyl-piperidin-4-yl)-6-nitro-2,3-dihydro-1H-indole (600 mg, Step E) was dissolved in MeOH (20 mL), the mixture was bubbled with H₂ for 10 min. 10% Pd/C (100 mg) was added and the mixture was stirred under H₂ overnight. The mixture was filtered through Celite® and concentrated in vacuo to afford the title compound as an oil. MS: 260 (M+1). Calc'd. for $C_{16}H_{25}N_3$–259.39.

Step G—Preparation of N-[3,3-dimethyl-1-(1-methyl(4-piperidyl))indolin-6-yl]{2-[(4-pyridylmethyl)amino](3-pyridyl)}carboxamide The titled compound was prepared from 3,3-dimethyl-1-(1-methyl(4-piperidyl))indoline-6-ylamine (Step E) by the method described in Example 82. MS: 471 (M+1). Calc'd. for $C_{28}H_{34}N_6O$–470.61.

EXAMPLE 133

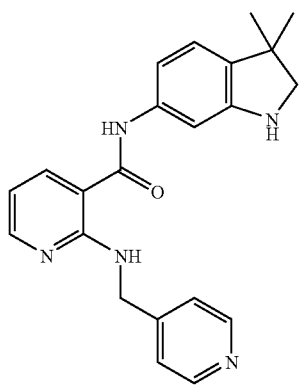

N-(3,3-Dimethylindolin-6-yl){2-[(4-pyridylmethyl)amino](3-pyridyl)}carboxamide

Step A—Preparation of 1-acetyl-6-amino-3,3-dimethylindoline

1-Acetyl-3,3-dimethyl-6-nitroindoline (250 mg) was dissolved in MeOH (20 mL), the mixture was bubbled with H₂ for 10 min. 10% Pd/C (50 mg) was added and the mixture was stirred under H₂ overnight. The mixture was filtered through Celite® and concentrated in vacuo. The crude material was purified by flash chromatography on silica gel with 1:1 EtOAc:CH₂Cl₂ to afford the title compound as a white crystalline material. MS: 205 (M+1). Calc'd. for $C_{12}H_{16}N_2O$–204.27.

Step B—Preparation of N-(1-acetyl-3,3-dimethylindolin-6-yl){2-[(4-pyridylmethyl)amino](3-pyridyl)}carboxamide The titled compound was prepared from 1-acetyl-6-amino-3,3-dimethylindoline (Step A) by the method described in Example 82.

Step C—Preparation of N-(3,3-dimethylindolin-6-yl){2-[(4-pyridylmethyl)amino](3-pyridyl)}carboxamide The titled compound was prepared from N-(1-acetyl-3,3-dimethylindolin-6-yl){2-[(4-pyridylmethyl)amino](3-pyridyl)}carboxamide (Step B) by the deacylation method described in Example 993. MS: 374 (M+1). Calc'd. for $C_{22}H_{23}N_5O$–373.45.

EXAMPLE 134

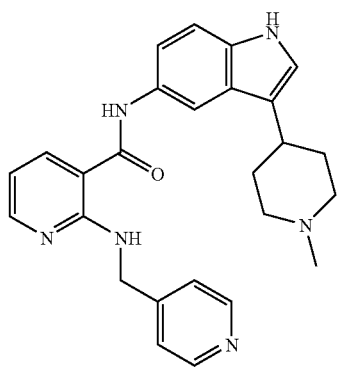

N-[3-(1-Methyl-(4-piperidyl))indol-5-yl]{2-[(4-pyridylmethyl)amino](3-pyridyl)}carboxamide Step A—Preparation of 3-(1-methyl-1,2,3,6-tetrahydro-pyridin-4-yl)-5-nitro-1H-indole 5-Nitroindole (2.6 g) was dissolved in anhydrous MeOH (100 ml), followed by N-methyl-4-piperidone (5 g) and NaOMe powder (5 g). The mixture was heated to reflux under N₂ overnight. The mixture was concentrated in vacuo. The crude was partitioned between saturated NaHCO₃ solution and EtOAc, the resulting organic layer was dried over MgSO₄, filtered and concentrated in vacuo to afford a yellow solid. This solid was washed with EtOAc (5 mL) and MeOH (2 ml) to afford the title compound as a bright yellow solid. MS: 258 (M+1). Calc'd. for $C_{14}H_{15}N_3O_2$–257.29.

Step B—Preparation of 3-(1-methyl-4-piperidyl)indole-5-ylamine 3-(1-Methyl-1,2,3,6-tetrahydro-pyridin-4-yl)-5-nitro-1H-indole (2.7 g, Step A) was dissolved in MeOH (50 mL), the mixture was bubbled with H₂ for 10 min. 10% Pd/C (150 mg) was added and the mixture was stirred under H₂ overnight. The mixture was filtered through Celite® and concentrated in vacuo to afford 3-(1-methyl-4-piperidyl)indole-5-ylamine as a yellow oil. MS: 230 (M+1). Calc'd. for $C_{14}H_{19}N_3$–229.32.

Step C—Preparation of N-[3-(1-methyl-(4-piperidyl))indol-5-yl]{2-[(4-pyridylmethyl)amino](3-pyridyl)}carboxamide The titled compound was prepared from 3-(1-methyl-4-piperidyl)indole-5-ylamine (Step B) by the method described in Example 82. MS: 441 (M+1). Calc'd. for $C_{26}H_{28}N_6O$–440.54.

EXAMPLE 135

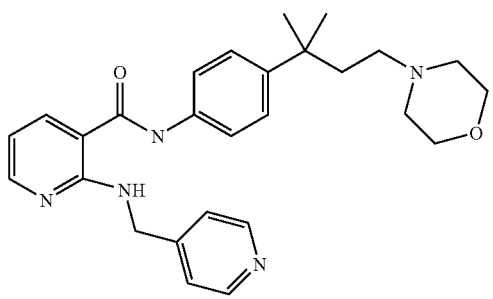

N-[4-(1,1-Dimethyl-3-morpholin-4-ylpropyl)phenyl]{2-[(4-pyridylmethyl)amino](3-pyridyl)}carboxamide Step A—Preparation of methyl 2-methyl-2-(4-nitrophenyl)propionate To a stirred solution of 2-(4-nitrophenyl)-propionic acid (9 g, 46 mmol) in MeOH (300 mL) was added HCl (4M in dioxane, 11.5 mL, 46 mmol). The mixture was stirred at RT overnight and quenched with aqueous $NaHCO_3$. The mixture was extracted with EtOAc. The organic layer was dried over $MgSO_4$, evaporated under reduced pressure and to the partial residue at 0° C. in THF (100 mL) was added NaH (1.66 g, 41.5 mmol). The mixture was stirred at RT for 1 h and MeI (2.58 g, 41.5 mmol) was added. The reaction was stirred at RT overnight and was quenched with $H_2O$. The mixture was extracted with EtOAc, the organic layer was dried over $MgSO_4$, evaporated under reduced pressure to give the title compound which was used in the next step without further purification. Calc'd for $C_{11}H_{13}NO_4$: 223.08.

Step B—Preparation of 2-methyl-2-(4-nitro-phenyl)-propan-1-ol

To a stirred solution of methyl 2-methyl-2-(4-nitrophenyl) propionate (5.32 g, 23.8 mmol, Step A) in THF (200 mL) at 0° C. was added a solution of $BH_3$ 1M in THF (25.8 mL, 45.8 mmol). The reaction was stirred at RT overnight and quenched with MeOH. THF was evaporated under reduced pressure and the residue was diluted in EtOAc and aqueous 1M HCl was added. The mixture was extracted with EtOAc, the organic layer was dried over $MgSO_4$ and evaporated under reduced pressure. The product was purified by flash chromatography using 40% EtOAc-hexane to give the title compound as a yellow solid.

Step C—Preparation of 2-methyl-2-(4-nitro-phenyl)-propionaldehyde

To a stirred solution of the alcohol (2.08 g, 10.8 mmol, Step B) at 0° C. in $CH_2Cl_2$ was added NMO (1.9 g, 16.1 mmol), molecular sieves 4 Å and TPAP (76 mg, 0.2 mmol). The reaction was stirred for 1 h and was filtered on silica pad. Solvent was evaporated under reduced pressure. Crude aldehyde was used without further purification in the next step.

Step D—Preparation of 3-methyl-3-(4-nitrophenyl)butan-1-aldehyde

To a suspension of methoxymethyltriphenyl-phosphonium chloride (6.4 g, 18.6 mmol) in THF (150 mL) was added a solution of KHMDS 0.5 M in toluene (37 mL, 18.5 mmol). The mixture was stirred for 30 min and crude aldehyde (Step C) was added. The reaction was stirred at RT for 1 h and quenched with $H_2O$. Mixture was extracted with EtOAc, dried and evaporated under reduced pressure. $Et_2O$ was added and the formed precipitate was filtered on silica pad (rinsed with 40% EtOAc-hexane). The solvent was removed and crude product was dissolved in $CH_2Cl_2$. A solution of TFA-$H_2O$ (1:1, 10 mL) was added and the reaction was stirred for 2 h at RT. Aqueous $NaHCO_3$ was added until pH 7 and residue was extracted with $CH_2Cl_2$. Organic layer was dried, filtered and evaporated. Crude compound was purified by flash chromatography (40% EtOAc-hexane) to give the title compound as a yellow oil. Calc'd for $C_{11}H_{13}NO_3$: 207.09.

Step E—Preparation of 4-[3-methyl-3-(4-nitro-phenyl)-butyl]-morpholine

To a stirred solution of 3-methyl-3-(4-nitrophenyl)butan-1-aldehyde (509 mg, 2.4 mmol, Step D) and morpholine (0.21 mL, 2.4 mmol) in THF (30 mL) was added $NaBH(OAc)_3$ (0.73 g, 3.4 mmol). The mixture was stirred at RT overnight and was washed with 1M HCl. $CH_2Cl_2$ was added and the layers were separated. The aqueous layer was basified to pH 9 using 1M NaOH and extracted with $CH_2Cl_2$. This organic layer was dried and evaporated yielding the morpholino compound. Calc'd for $C_{15}H_{22}N_2O_3$: 278.16.

Step F Preparation of 4-(1,1-dimethyl-3-morpholin-4-ylpropyl)phenylamine

To a solution of 4-[3-methyl-3-(4-nitro-phenyl)-butyl]-morpholine (0.50 g, 1.8 mmol, Step E) in THF (40 mL) was added AcOH (1.97 mmol, 34.5 mmol) followed by zinc (9.1 g, 137 mmol). The mixture was stirred for 1 h and filtered on Celite®. The mixture was diluted with $H_2O$, and aqueous $NaHCO_3$ and the THF was evaporated. The residue was extracted with EtOAc, dried and evaporated to give the title intermediate. Calc'd for $C_{15}H_{24}N_2O$: 248.19.

Step G—Preparation of N-[4-(1,1-dimethyl-3-morpholin-4-ylpropyl)phenyl]{2-[(4-pyridylmethyl)amino](3-pyridyl)}carboxamide The titled compound was prepared from 4-(1,1-dimethyl-3-morpholin-4-ylpropyl)phenylamine (Step F) by the method described in Example 82. MS: 460.0 (M+1). Calc'd. for $C_{27}H_{33}N_5O_2$ –459.60.

EXAMPLE 136

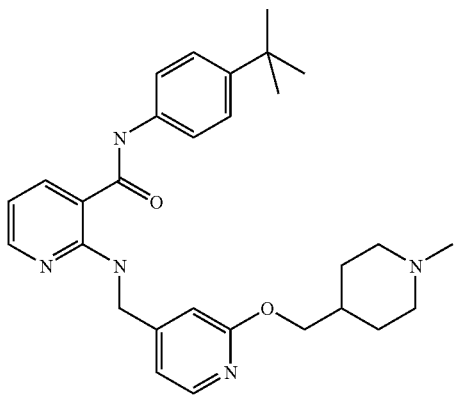

N-[4-(tert-Butyl)phenyl]{2-[({2-[(1-methyl(4-piperidyl))-methoxy](4-pyridyl)}methyl)amino](3-pyridyl)}carboxamide

Step A—Preparation of 4-hydroxymethyl-1-methylpiperidine

To a solution of 4-piperidylmethanol (1.0 g, 8.7 mmol) and HCHO (2 mL, 25 mmol, 37% in $H_2O$) in $CH_3CN$ was added $NaCNBH_3$ (0.5 g, 12.5 mmol). The resulting mixture was stirred for 1 h and filtered. The filtrate was concentrated and the residue was distilled (105° C., 40 torr) to give the title intermediate.

Step B—Preparation of {2-[(1-methyl-4-piperidyl)methoxy]-4-pyridyl}methylamine To a suspension of NaH (0.44 g, 12.7 mmol, 60% in mineral oil) in DMF (25 mL) was added a solution of alcohol (1.1 g, 8.5 mmol, Step A) in 3 mL of DMF. After 20 min, a solution of 2-chloro-4-cyanopyridine (1.2 g, 8.5 mmol) in 2 mL of DMF was added. The resulting mixture was stirred for 2 h, diluted with $CH_2Cl_2$, and washed with $H_2O$ twice. The organic layer was dried over $Na_2SO_4$ and concentrated to give 2-[(1-methyl-4-piperidyl)methoxy]pyridine-4-carbonitrile, which was hydrogenated under regular conditions to furnish the title intermediate. MS (ES+): 236 (M+H)$^+$. Calc'd $C_{13}H_{21}N_3O$–235.33.

Step C—Preparation of N-[4-(tert-butyl)phenyl]{2-[({2-[(1-methyl(4-piperidyl))-methoxy](4-pyridyl)}methyl)amino](3-pyridyl)}carboxamide The title compound was prepared from {2-[(1-methyl-4-piperidyl)methoxy]-4-pyridyl}methylamine (Step B) by the method described in Example 82. MS (ES+): 488 (M+H)$^+$; (ES–): 486 (M–H)$^-$. Calc'd $C_{29}H_{37}N_5O_2$–487.64.

EXAMPLE 137

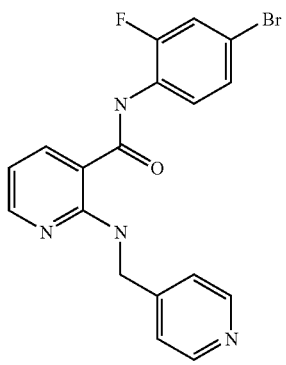

N-(4-Bromo-2-fluorophenyl){2-[(4-pyridylmethyl)amino](3-pyridyl)}carboxamide

MS (ES+): 402 (M+H)$^+$; (ES–): 400. Calc'd $C_{18}H_{14}BrFN_4O$–401.238.

EXAMPLE 138

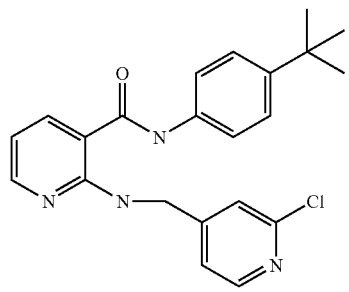

N-[4-(tert-Butyl)phenyl]{2-([(2-chloro(4-pyridyl))methyl]amino}(3-pyridyl))carboxamide MS (ES+): 395 (M+H)$^+$; (ES–): 393(M–H)$^-$. Calc'd $C_{22}H_{23}ClN_4O$–394.90.

EXAMPLE 139

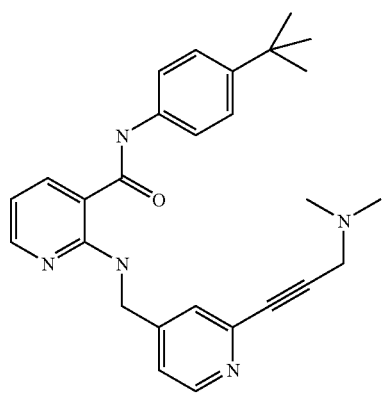

{2-[({2-[3-(Dimethylamino)prop-1-ynyl](4-pyridyl)}methyl)amino](3-pyridyl)}-N-[4-(tert-butyl)phenyl]carboxamide A mixture of N-[4-(tert-butyl)phenyl](2-{[(2-chloro(4-pyridyl))methyl]amino}(3-pyridyl))carboxamide (0.15 g, 0.38 mmol, Example 139), 1-dimethylamino-2-propyne (62 mg, 0.76 mmol), $PdCl_2(PPh_3)_2$ (13 mg, 0.0019 mmol) and CuI (7 mg, 0.019 mmol) in 1 mL of TEA was heated at 100° C. in a sealed tube for 3 h. The resulting mixture was filtered over Celite®. The filtrate was concentrated, and the residue was purified by prep-HPLC (reverse phase) to give the title compound. MS (ES+): 442 (M+H)$^+$; (ES−): 440(M−H)$^−$. Calc'd $C_{27}H_{31}N_5O$−441.58.

EXAMPLE 140

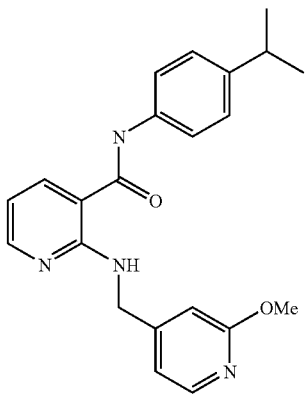

(2-{[(2-Methoxy(4-pyridyl))methyl]amino}(3-pyridyl))-N-[4-(methylethyl)phenyl]carboxamide Step A—Preparation of (2-methoxy-4-pyridyl)methylamine A solution of 2-methoxyisonicotinylcarboxamide (1.0 g, 6.5 mmol) and $BH_3$-THF complex (35 mmol) in 35 mL of THF was stirred at RT for 16 h. The reaction was quenched by addition of MeOH, and the resulting mixture was concentrated. The residue was diluted with 1N aq. NaOH and $CH_2Cl_2$. The organic layer was separated, dried over $Na_2SO_4$, and concentrated.

Step B—Preparation of (2-{([(2-methoxy(4-pyridyl))methyl]-amino}(3-pyridyl))-N-[4-(methylethyl)phenyl]carboxamide The title compound was prepared from (2-methoxy-4-pyridyl)methylamine (Step A) by the method described in Example 82. MS (ES+): 377 (M+H)$^+$; (ES−): 375 (M−H)$^−$. Calc'd $C_{22}H_{24}N_4O_2$−376.46.

EXAMPLE 141

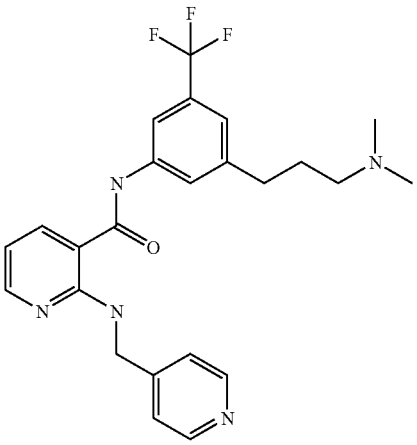

N-{3-[3-(Dimethylamino)propyl]-5-(trifluoromethyl)phenyl}-{2-[(4-pyridylmethyl)amino](3-pyridyl)}carboxamide Step A—Preparation of {3-[3-amino-5-(trifluoromethyl)phenyl]propyn-2-yl}dimethylamine A mixture of 3-bromo-5-trifluoromethylaniline (1.4 g, 5.9 mmol), 1-dimethylamino-2-propyne (1.3 mL, 0.76 mmol), $PdCl_2(PPh_3)_2$ (0.26 g, 0.29 mmol) and CuI (114 mg, 0.60 mmol) in 10 mL of TEA was heated at 100° C. in a sealed tube for 3 h. The resulting mixture was filtered over Celite®. The filtrate was concentrated, and the residue was purified by prep-HPLC (reverse phase) to give the titled compound. MS (ES+): 243. (M+H)$^+$; (ES−): 241 (M−H)$^−$. Calc'd $C_{12}H_{13}F_3N_2$−242.24.

Step B—Preparation of {3-[3-amino-5-(trifluoromethyl)phenyl]propyl}dimethylamine A mixture of the propynyl-aniline (7 g, 29 mmol, Step A) and $Pd(OH)_2$ (0.5 g) in MeOH (250 mL) was stirred under 50 psi $H_2$. After 2 h, the resulting mixture was filtered over Celite®. The filtrate was concentrated, and the residue was diluted with aq. 1N HCl. The aq. layer was washed with $Et_2O$, made basic with aq. 5N NaOH, and extracted with $CH_2Cl_2$. The organic solution was dried over $NaSO_4$ and concentrated to give the titled compound. MS (ES+): 386 (M+H)$^+$; (ES−): 384 (M−H)$^−$. Calc'd $C_{18}H_{19}ClF_3N_3O$−385.81.

Step C—Preparation of N-{3-[3-(dimethylamino)propyl]-5-(trifluoromethyl)phenyl}-{2-[(4-pyridylmethyl)amino](3-pyridyl)}carboxamide The title compound was prepared by the method described in Example 82. MS (ES+): 458 (M+H)$^+$; (ES−): 456 (M−H)$^−$. Calc'd $C_{24}H_{26}F_3N_5O$−457.497.

EXAMPLE 142

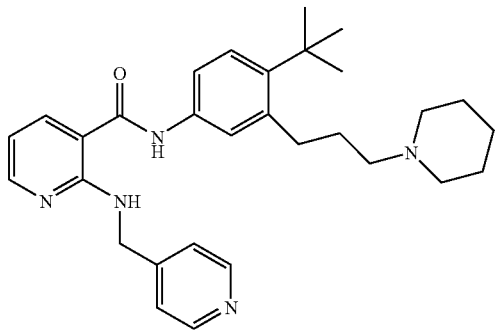

N-[4-(tert-Butyl)-3-(3-piperidylpropyl)phenyl]{2-[(4-pyridylmethyl)amino](3-pyridyl)}carboxamide

Step A—Preparation of 1-piperidylprop-2-en-1-one

To a 0° C. solution of acryloyl chloride (4.576 g, 50.558 mmol) in 50 ml of $CH_2Cl_2$ was added dropwise and very carefully piperidine (4.305 g, 50.558 mmol). The reaction flask was vented during the exothermic addition. After the addition was completed, the white slurry was stirred at 0° C. for 40 min and at RT for 1 h. The reaction was diluted with 70 ml $CH_2Cl_2$ and washed first with about 60 ml 2N HCl and then with about 60 ml of a mix of 2N NaOH and brine. The organic layer was dried over $Na_2SO_4$. The solution was evaporated by heating in a $H_2O$ bath at 60° C. without vacuum. Once most solvent had been evaporated off, it was furthered dried to a clear oil under high vacuum at RT for 30 min.

Step B—Preparation of 1-bromo-2-(tert-butyl)-5-nitrophenyl $Br_2$ (17.4 ml) was added dropwise over 40 min to a stirred mixture of 4-tert-butylnitrobenzene (59.5 g, 332 mmol), $AgSO_4$ (56.5 g, 181 mmol), $H_2SO_4$ (300 ml), and $H_2O$ (33 ml) at RT. The mixture was stirred for 3 h, then poured into 0.1 M $Na_2S_2O/H_2O$ (1 L). The solid was filtered, washed with $H_2O$, $Et_2O$, and $CH_2Cl_2$. The filtrate layers were separated. The aqueous fraction was extracted with $Et_2O$. The combined organic layers were combined, dried over $Na_2SO_4$, and concentrated in vacuo. The yellow solid was triturated with hexanes to give a pale yellow crystalline solid.

Step C—Preparation of (2E)-3-[2-(tert-butyl)-5-nitrophenyl]-1-piperidylprop-2-en-1-one 1-(tert-Butyl)-2-bromo-4-nitrobenzene (6.885 g, 26.674 mmol, Step B), 1-piperidylprop-2-en-1-one (4.827 g, 34.677 mmol, Step A), and TEA (7.44 ml, 53.35 mmol) were dissolved into toluene (70 ml). To this solution was added $Pd(OAc)_2$ (60 mg, 0.267 mmol) and $Pd(PPh_3)_4$ (617 mg, 0.5335 mmol). The mix was degassed with $N_2$ and heated in a sealed vessel at 120° C. for 15 h. The reaction mixture was cooled to RT, filtered, and concentrated in vacuo. The dark crude oil was eluted through a silica gel column with 15% to 22% EtOAc/hexanes gradient system to yield a thick amber oil as the title intermediate.

Step D—Preparation of (2E)-3-[2-(tert-butyl)-5-aminophenyl]-1-piperidylprop-2-en-1-one (2E)-3-[2-(tert-Butyl)-5-nitrophenyl]-1-piperidylprop-2-en-1-one (3.22 g, 10.177 mmol, step C) was dissolved in dioxane (20 ml) and IpOH (40 ml). To the $N_2$-degassed solution was added 10% by weight Pd/C catalyst (2 g). The mix was placed into a Parr hydrogenator and stirred for 18 h under 60 psi $H_2$. The reaction was not complete the next day, so the reaction was continued for an additional 20 h with fresh catalyst. The mix was filtered through Celite® and concentrated in vacuo to give a foamy oil.

Step E—Preparation of 4-(tert-butyl)-3-(3-piperidylpropyl)phenylamine (2E)-3-[2-(tert-Butyl)-5-aminophenyl]-1-piperidylprop-2-en-1-one (2.312 g, 7.619 mmol, step D) was dissolved in THF (100 ml) at RT. To this solution was added $LiAlH_4$ (434 mg, 11.43 mmol). After the reaction mixture stopped exotherming, it was heated at reflux at about 80° C. for 4 h. The reaction was cooled to 0° C. and treated by dropwise addition of 0.458 ml $H_2O$, 0.730 ml 10% aqueous NaOH, and 1.19 ml $H_2O$, respectively. The mix was stirred at RT for 40 min. $Na_2SO_4$ (3 g) was added and the mix was stirred for 20 min. The mix was filtered through Celite® and concentrated in vacuo. The crude was eluted through silica gel column with a gradient system of 95:5 to 90:10 $CH_2Cl_2$:MeOH, to yield an amber thick oil as the title compound.

Step F—Preparation of N-[4-(tert-butyl)-3-(3-piperidylpropyl)phenyl]{2-[(4-pyridylmethyl)amino](3-pyridyl)}carboxamide The title compound was prepared from 4-(tert-butyl)-3-(3-piperidylpropyl)phenylamine (Step E) similar to the method described in Example 82. MS: 486.2 (M+1). Calc'd. for $C_{30}H_{39}N_5O$–485.68.

EXAMPLE 143

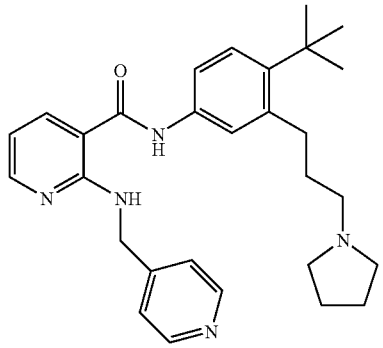

N-[4-(tert-Butyl)-3-(3-pyrrolidinylpropyl)phenyl]{2-[(4-pyridylmethyl)amino](3-pyridyl)}carboxamide MS: 472.5 (M+1). Calc'd. for $C_{29}H_{37}N_5O$–471.65.

EXAMPLE 144

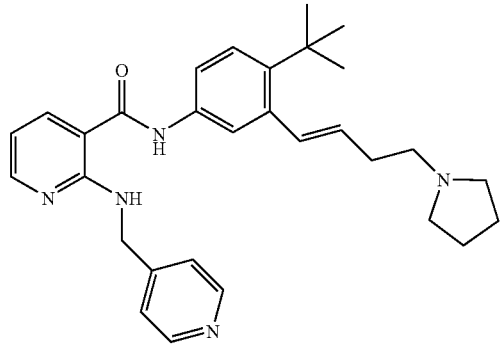

N-[3-((1E)-4-Pyrrolidinylbut-1-enyl)-4-(tert-butyl)phenyl]{2-[(4-pyridylmethyl)amino](3-pyridyl)}carboxamide MS: 484.0 (M+1). Calc'd. for $C_{30}H_{37}N_5O$–483.66.

EXAMPLE 145

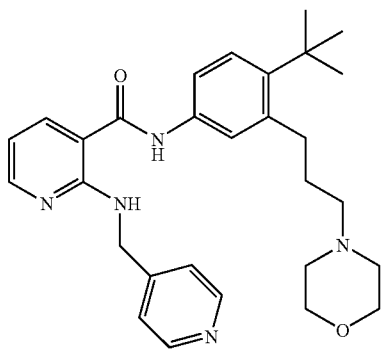

N-[4-(tert-Butyl)-3-(3-morpholin-4-ylpropyl)phenyl]{2-[(4-pyridylmethyl)amino](3-pyridyl)}carboxamide MS: 488.4 (M+1). Calc'd. for $C_{29}H_{37}N_5O_2$–487.65.

EXAMPLE 146

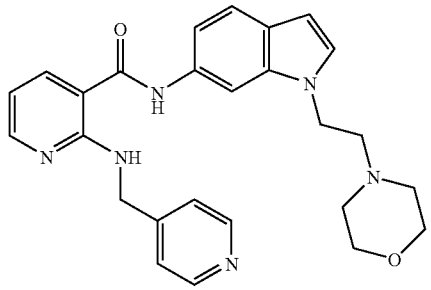

N-[1-(2-Morpholin-4-ylethyl)indol-6-yl]{2-[(4-pyridylmethyl)amino](3-pyridyl)}carboxamide Step A—Preparation of 1-(2-morpholin-4-ylethyl)indole-6-ylamine $K_2CO_3$ (5.08 g, 36.726 mmol) was added to a slurry of 6-nitroindole (1.985 g, 12.242 mmol), 4-(2-chloroethyl)morpholine hydrochloride (2.278 g, 12.242 mmol), and $CH_3CN$ (100 ml). The mix was heated at reflux for 18 h, then cooled to RT, filtered, and concentrated in vacuo. The crude was eluted through a silica gel column with a gradient of 3:97 to 5:95 and finally 8:92 MeOH:$CH_2Cl_2$, to yield upon drying 1-(2-morpholin-4-yl-ethyl)-6-nitro-1H-indole which was hydrogenated at regular condition described early to yield the title compound.

Step B—Preparation of N-[1-(2-morpholin-4-ylethyl)indol-6-yl]{2-[(4-pyridylmethyl)amino](3-pyridyl)}carboxamide The title compound was prepared from 1-(2-morpholin-4-ylethyl)indole-6-ylamine (Step A) similar to the method described in Example 82. MS: 457.3 (M+1). Calc'd. for $C_{26}H_{28}N_6O_2$–456.55.

EXAMPLE 147

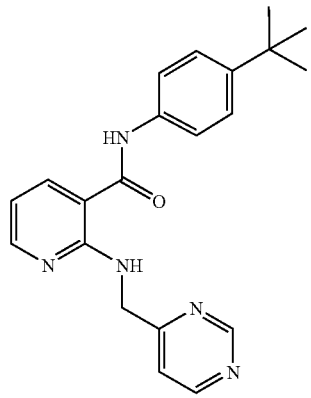

N-[4-(tert-Butyl)phenyl]{2-[(pyrimidin-4-ylmethyl)amino](3-pyridyl)}carboxamide

Step A—Preparation of pyrimidine-4-yl formaldehyde

Pyrimidine-4-yl formaldehyde was prepared from 4-methylpyrimidine through a reference described in M.C. Liu et al., J Med. Chem., 1995, 38 (21), 4234-4243.

Step B—Preparation of N-[4-(tert-butyl)phenyl]{2-[(pyrimidin-4-ylmethyl)amino](3-pyridyl)}carboxamide The title compound was prepared from pyrimidine-4-yl formaldehyde (Step A) similar to the method described in Example 82. MS (ES+): 362 (M+H); (ES−): 360(M−H). Calc'd. for $C_{21}H_{23}N_5O$–361.19.

EXAMPLE 148

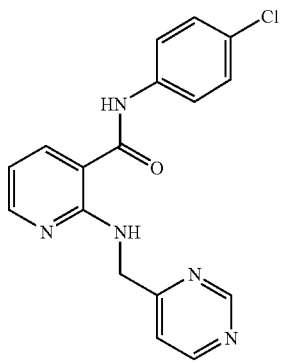

N-(4-Chlorophenyl){2-[(pyrimidin-4-ylmethyl)amino](3-pyridyl)}carboxamide

MS (ES+): 340 (M+H); (ES−): 338 (M−H). Calc'd for $C_{17}H_{14}ClN_5O$–339.09.

EXAMPLE 149

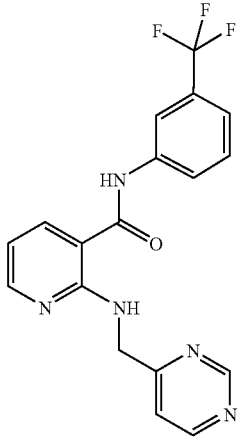

{2-[(Pyrimidin-4-ylmethyl)amino](3-pyridyl)}-N-[3-(trifluoromethyl)phenyl]carboxamide MS (ES+): 374 (M+H); (ES−): 372 (M−H). Calc'd for $C_{18}H_{14}F_3N_5O$–373.12.

EXAMPLE 150

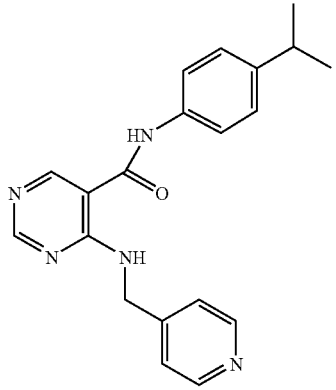

N-[4-(Isopropyl)phenyl](4-[(4-pyridylmethyl)amino]pyrimidin-5-yl)carboxamide

Step A—Preparation of ethyl 2-methylthio-4-[benzylamino]pyrimidine-5-carboxylate A solution of ethyl 4-chloro-2-methylthio-pyrimidine-5-carboxylate (2.8 g, 12.2 mmol) and 4-aminomethylpyridine (1.24 mL, 12.2 mmol) in EtOH (20 mL) was heated at 70° C. for 2 h. The resulting suspension was concentrated, and the residue was purified by $SiO_2$ chromatography to give ethyl 2-methylthio-4-[benzylamino]pyrimidine-5-carboxylate. MS (ES+): 305 (M+H)$^+$; (ES−): 303 (M−H)$^-$. Calc'd $C_{15}H_{17}N_3O_2S$: 303.38.

Step B—Preparation of N-[4-(isopropyl)phenyl]{2-methylthio-4-[(4-pyridylmethyl)amino]pyrimidin-5-yl}carboxamide To a solution of ethyl 2-methylthio-4-[benzylamino]-pyrimidine-5-carboxylate (0.1 g, 0.3 mmol, Step A) in EtOH (3 mL) was added 1 mL of aq. 1N NaOH solution. The resulting mixture was stirred at 45° C. for 2 h. The resulting mixture was neutralized with aq. 1N HCl and concentrated. To the residue in 3 mL of $CH_2Cl_2$ was added 4-isopropylaniline (90 mg, 0.66 mmol), HATU (0.18 g, 0.45 mmol), and 0.5 mL of TEA (0.36 g, 3.5 mmol). The resulting mixture was stirred at RT for 4 h and diluted with $CH_2Cl_2$. The organic solution was washed with $H_2O$, dried over $Na_2SO_4$ and concentrated. The residue was purified by $SiO_2$ chromatography to give N-[4-(isopropyl)phenyl]{2-methylthio-4-[(4-pyridylmethyl)amino]pyrimidin-5-yl}carboxamide. MS (ES+): 394 (M+H)$^+$; (ES−): 392 (M−H)$^-$. Calc'd $C_{21}H_{23}N_5OS$–393.51.

Step C—Preparation of N-[4-(isopropyl)phenyl](4-[{4-pyridylmethyl)amino]pyrimidin-5-yl}carboxamide A mixture of N-[4-(isopropyl)phenyl]{2-methylthio-4-[(4-pyridylmethyl)amino]pyrimidin-5-yl}carboxamide (50 mg, 0.13 mmol, Step B) and Raney-Ni in EtOH (10 mL) was heated at reflux for 2 h. The resulting mixture was filtered, and the filtrate was concentrated to give the titled compound. MS (ES+): 348 (M+H)$^+$; (ES−): 346 (M−H)$^-$. Calc'd $C_{20}H_{21}N_5O$–347.42.

EXAMPLE 151

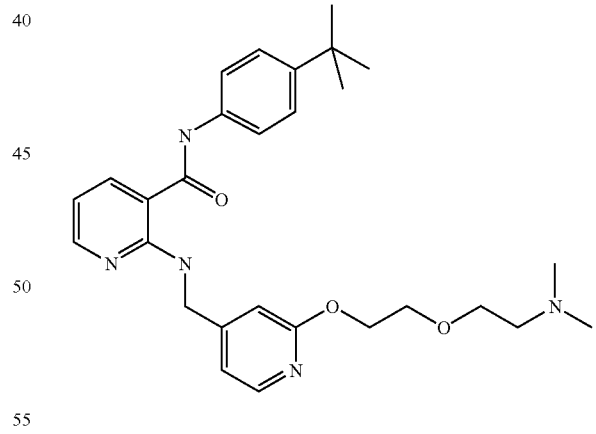

(2-{[(2-(2-[2-(Dimethylamino)ethoxy]ethoxy)(4-pyridyl))methyl]amino}(3-pyridyl))-N-[4-(tert-butyl)phenyl]carboxamide Step A—Preparation of 2-{2-[2-(dimethylamino)ethoxy]ethoxy}pyridine-4-carbonitrile To a DMF (30 mL) solution of 2-[2-(dimethylamino)ethoxy]ethan-1-ol (3.33 g, 25 mmol) was added NaH (60% in mineral oil, 900 mg, 22.5 mmol, hexane washed) and heated at 50° C. for 2 h. The warm sodium alkoxide solution was added to 2-chloro-4-cyanopyridine (3.12 g, 22.5 mmol) in DMF (10 mL). After the addition, the reaction mixture was heated to 70° C. for 2 h, then DMF was removed in vacuo. The residue was partitioned between $CH_2Cl_2/H_2O$. The organic layer was washed with brine, dried over $Na_2SO_4$, and concentrated in vacuo to give a light yellow oil (5.6 g). MS: 236 (M+1). Calc'd. for $C_{12}H_{17}N_3O_2$–235.29.

Step B—Preparation of (2-{2-[4-(aminomethyl)(2-pyridyloxy)]ethoxy}ethoxy)dimethylamine 2-{2-[2-(Dimethylamino)ethoxy]ethoxy}pyridine-4-carbonitrile (330 mg 1.4 mmol, Step A) was dissolved in EtOH (10 mL) along with TEA (2 mL) and suspended with Pd/C (10%, 40 mg). The reaction mixture was stirred overnight at RT under balloon filled with $H_2$. After removing the balloon, the reaction suspension was filtered through a layer of Celite®. The Celite® layer was rinsed with MeOH. The combined filtrate was concentrated in vacuo to give a light yellow oil. MS: 240 (M+1). Calc'd. for $C_{12}H_{21}N_3O_2$–239.32.

Step C—Synthesis of 2-fluoropyridine-3-carboxylic acid

To a solution of 2-fluoropyridine (10 g, 100 mmol) in THF (150 mL) under –78° C. was dropwise added an LDA solution (2M in heptane/THF/ethylbenzene, 60 mL). The mixture was stirred at –78° C. for 3 h after the addition of LDA then quenched with $N_2$ dried solid $CO_2$. After warming to RT, the reaction was partitioned between EtOAc (100 mL) and $H_2O$ (200 mL). The aqueous layer was acidified to pH between 3-4 and extracted with EtOAc. The organic solution was collected and washed with brine and dried over $Na_2SO_4$. After removing solvent in vacuum, a brown oil was received as the desired compound. MS: 140 (M–H). Calc'd. for $C_6H_4FNO_2$–141.10.

Step D—Synthesis of 2-fluoropyridine-3-carbonyl chloride

2-Fluoropyridine-3-carboxylic acid (7 g, Step C) was suspended in $SOCl_2$ (100 mL). After heating under reflux for 2 h, the mixture became homogeneous. Excess $SOCl_2$ was removed in vacuo to afford a brown solid as desired product.

Step E—Synthesis of N-[4-(tert-butyl)phenyl]2-fluoropyridine-3-carboxamide

To a suspension of 2-fluoropyridine-3-carbonyl chloride (3.2 g, 20 mmol, Step D) and $NaHCO_3$ (4 g, 48 mmol) in $CH_2Cl_2$ added in dropwise a solution of 4-tert butylaniline (3.0 g, 20 mmol). After the addition, the suspension was stirred at RT for 5 h. Solid inorganic salts were removed via filtration. The filtrate was concentrated to afford a brown solid as desired compound. MS: 273 (M+H). Calc'd. for $C_{16}H_{17}FN_2O$–272.33.

Step F—Synthesis of {2-[({2-[2-(2-N,N-dimethylaminoethoxy)ethoxy]-4-pyridyl}methyl)amino](3-pyridyl)}-N-(4-tert-butylphenyl)carboxamide N-[4-(tert-Butyl)phenyl]2-fluoropyridine-3-carboxamide (544 mg, 2 mmol, Step E) was dissolved in pyridine (5 mL) along with (2-{2-[4-(aminomethyl)(2-pyridyloxy)]ethoxy}ethoxy)dimethylamine (570 mg, 2.38 mmol, Step A). The reaction was heated to 85° C. for 48 h. After removal of pyridine in vacuo, the residue was dissolved in $CH_2Cl_2$ and washed with $NaHCO_3$ (Sat. aq), then brine. After drying over $Na_2SO_4$, the $CH_2Cl_2$ solution was concentrated in vacuo and purified via prep. HPLC ($H_2O/CH_3CN$: 5%-95% gradient) to give the title product. MS: 492 (M+1). Calc'd. for $C_{28}H_{37}N_5O_3$–491.63

The following compounds (Examples 152-157) were analogously synthesized by the method described in Example 151 unless specifically described. Detailed intermediate preparations are included.

EXAMPLE 152

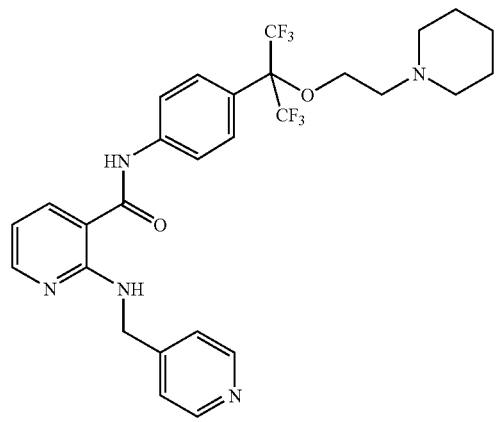

{2-[(4-Pyridylmethyl)amino](3-pyridyl)}-N-{4-[2,2,2-trifluoro-1-(2-piperidylethoxy)-1-(trifluoromethyl)ethyl]phenyl}carboxamide Step A—Preparation of 4-[2,2,2-trifluoro-1-(2-piperidin-1-yl-ethoxy)-1-trifluoromethyl-ethyl]-phenylamine DEAD (366 mg, 2.1 mmol) was added drop-wise to the solution of 2-(4-aminophenyl)-1,1,1,3,3,3-hexafluoropropan-2-ol (520 mg, 2 mmol), 2-piperidylethan-1-ol (260 mg, 2 mmol) and $PPh_3$ (550 mg, 2.1 mmol) in THF (10 mL). The mixture was stirred for 2 h. The reaction was partitioned between EtOAc and aqueous $NaHCO_3$ solution and the organic phase was washed with brine. After concentrated in vacuo, the organic residue was purified by flash chromatography on silica to give the title intermediate.

Step B—Preparation of {2-[(4-pyridylmethyl)amino](3-pyridyl)}-N-{4-[2,2,2-trifluoro-1-(2-piperidylethoxy)-1-(trifluoromethyl)ethyl]phenyl}carboxamide The title compound was synthesized by the method described in Example 151. MS: 582 (M+1). Calc'd. for $C_{28}H_{29}F_6N_5O_2$–581.56.

EXAMPLE 153

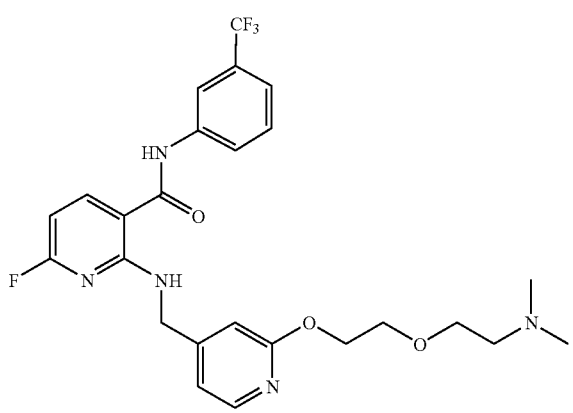

(2-{[(2-(2-[2-(Dimethylamino)ethoxy]ethoxy}(4-pyridyl))methyl]amino)-6-fluoro(3-pyridyl))-N-[3-(trifluoromethyl)phenyl]carboxamide

Step A Preparation of 2,6-difluoropyridine-3-carbonyl chloride

The title compound was prepared similar to that described in Example 151, Step D.

Step B—Preparation of (2-{[(2-{2-[2-(dimethylamino)-ethoxy]ethoxy}(4-pyridyl))methyl]amino}-6-fluoro(3-pyridyl))-N-[3-(trifluoromethyl)phenyl]carboxamide The title compound was synthesized by the method described in Example 151. MS: 522 (M+1). Calc'd. for $C_{25}H_{27}F_4N_5O_3$–521.51.

EXAMPLE 154

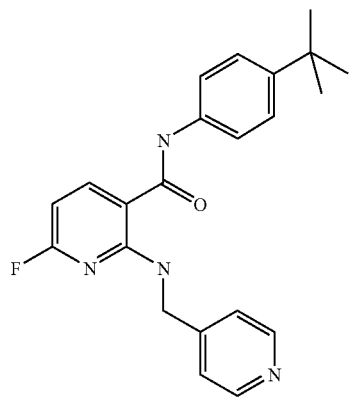

N-[4-(tert-Butyl)phenyl]{6-fluoro-2-[(4-pyridylmethyl)amino](3-pyridyl)}carboxamide

Step A—Preparation of N-(4-tert-butyl-phenyl)-2,6-difluoro-nicotinamide

A solution of 2,6-difluoropyridine-3-carboxylic acid (3.2 g, 20 mmol), t-butylaniline (3.0 g, 20 mmol), HOBt (2.6 g, 20 mmol), EDAC (8 g, 40 mmol), and DIEA (8 mL) in $CH_2Cl_2$ (80 mL) was stirred at RT for 1 h. The mixture was washed with aq. $NaHCO_3$ and brine. The organic solution was dried over $Na_2SO_4$ and concentrated in vacuo. The residue was purified via flash chromatography on silica (Hex:EtOAc=4:1) to give a light yellow flaky crystal as desired product.

Step B—Preparation of N-[4-(tert-butyl)phenyl]{6-fluoro-2-[(4-pyridylmethyl)amino](3-pyridyl)}carboxamide The title compound was synthesized similar to that described in Example 151 except that it was synthesized at RT. MS: 379 (M+1). Calc'd. for $C_{22}H_{23}FN_4O$–378.45.

The following compounds were analogously synthesized by the method described in Example 154. Detailed intermediate preparations are described.

EXAMPLE 155

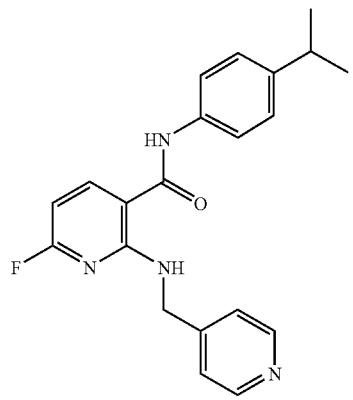

{6-Fluoro-2-[(4-pyridylmethyl)amino](3-pyridyl)}-N-[4-(isopropyl)phenyl]carboxmide MS: 365 (M+1). Calc'd. for $C_{21}H_{21}FN_4O$–364.42.

EXAMPLE 156

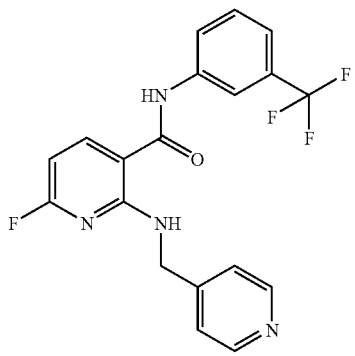

{6-Fluoro-2-[(4-pyridylmethyl)amino](3-pyridyl)}-N-[3-(trifluoromethyl)phenyl]carboxamide MS: 391 (M+1). Calc'd. for $C_{19}H_{14}F_4N_4O$–390.34.

EXAMPLE 157

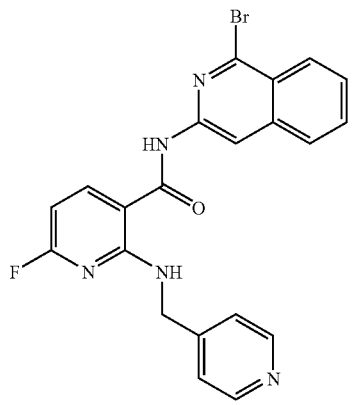

N-(1-Bromo(3-isoquinolyl)){6-fluoro-2-[(4-pyridyl-methyl)amino](3-pyridyl)}-carboxamide MS: 452/454 (M+1). Calc'd. for $C_{21}H_{15}BrFN_5O$–452.29.

EXAMPLE 158

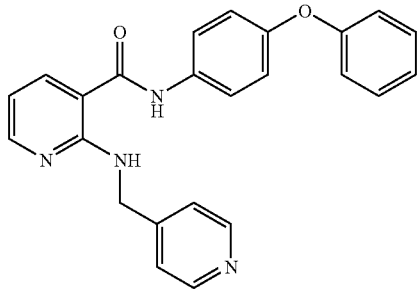

N-(4-Phenoxyphenyl){2-[(4-pyridylmethyl)amino](3-pyridyl)}carboxamide

Step A—Preparation of (2-chloro(3-pyridyl))-N-(4-phenoxy-phenyl)carboxamide

2-Chloronicotinic acid (0.78 g, 5.0 mmol) and TEA (1.6 ml, 10.0 mmol) were added to anhydrous THF (50 ml) under a $N_2$ atmosphere at 0° C. After stirring for 5 min, ethyl chloroformate (0.54 g, 5.0 mmol) was added dropwise and the mixture gradually came to RT over a period of 1 h. 4-Phenoxyaniline (0.83 g, 5.0 mmol) was added and the mixture was stirred for 14 h. The mixture was partitioned between $H_2O$ and EtOAc. The aqueous layer was extracted two additional times with EtOAc (50 ml). The combined organic layers were then washed with brine, dried over $Na_2SO_4$, and evaporated. The resulting brown oil was used directly in the subsequent reaction without further purification. MS m/z: 325 (M+1). Calc'd for $C_{18}H_{13}ClN_2O_2$: 324.07.

Step B—Preparation of N-(4-phenoxyphenyl){2-[(4-pyridylmethyl)amino](3-pyridyl)}carboxamide hydrochloride The amide (0.500 g, 1.5 mmol, Step A) and 4-aminomethylpyridine (0.486 g, 4.5 mmol) were combined and heated neat at 90° C. for 48 h. After cooling to RT, the mixture was poured into a saturated $NaHCO_3$ solution and extracted with EtOAc. The combined organic layers were washed with brine, dried over $Na_2SO_4$, and evaporated. The resulting brown oil was purified by column chromatography with EtOAc/hexanes (2:1) as eluant to leave N-(4-phenoxyphenyl){2-[(4-pyridylmethyl)amino](3-pyridyl)}formamide as a clear oil. This material was converted directly into the HCl salt by dissolution in MeOH (5 ml), treatment with 3 equivalents of an HCl ethereal solution, and evaporation of solvent to leave the titled product as a light yellow solid. MS (ES+): 397 (M+H)$^+$; (ES–): 395 (M–H). Calc'd. for $C_{24}H_{20}N_4O_2$–396.16.

The following compounds (Examples 159-161) were prepared similar to the method described in Example 158.

EXAMPLE 159

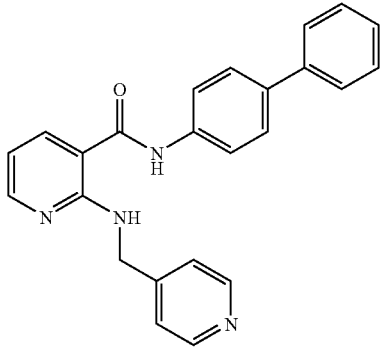

N-(4-Biphenyl){2-[(4-pyridylmethyl)amino](3-pyridyl)}carboxamide

MS: 381 (M+1); 379 (M–1). Calc'd. for $C_{24}H_{20}N_4O$–380.16.

EXAMPLE 160

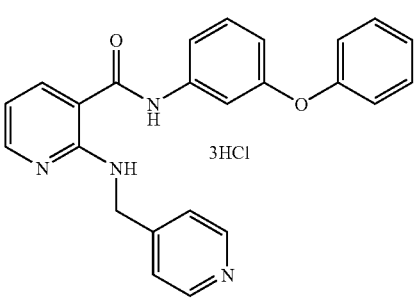

N-(3-Phenoxyphenyl){2-[(4-pyridylmethyl)amino](3-pyridyl)}carboxamide hydrochloride MS: 397 (M+1); 395 (M−1). Calc'd. for $C_{24}H_{20}N_4O_2$–396.16.

EXAMPLE 161

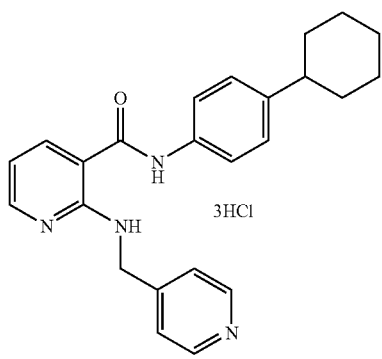

N-(4-Cyclohexylphenyl){2-[(4-pyridylmethyl)amino](3-pyridyl)}carboxamide

MS: 387 (M+1); 385 (M−1). Calc'd. for $C_{24}H_{26}N_4O$–386.21.

EXAMPLE 162

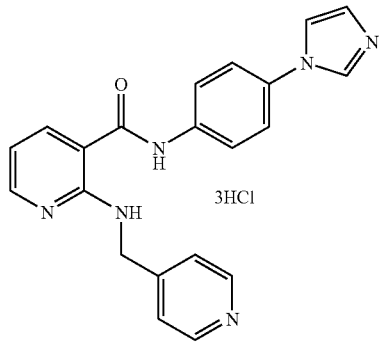

N-(4-Imidazol-1-ylphenyl){2-[(4-pyridylmethyl)amino](3-pyridyl)}carboxamide

Step A—Preparation of (2-Chloro(3-pyridyl))-N-(4-imidazolylphenyl)carboxamide

A slurry of 4-imidazolylphenylamine (15.9 mg, 0.100 mmol), polymer-supported DIPEA (0.100 g, 0.362 mmol, 3.62 mmol/g loading) in $CH_2Cl_2$ (2 ml) was treated with a 2-chloropyridine-3-carbonyl chloride solution (0.10 M, 0.200 mmol, 2.0 ml, 2.0 eq) in $CH_2Cl_2$. The mixture was vortexed at RT for 14 h. Afterwards, the excess acid chloride was removed by treating the reaction mixture with polymer-supported trisamine resin (0.100 g, 0.375 mmol, 3.75 mmol/g loading). The slurry was shaken at RT for an additional 18 h. The reaction mixture was filtered, rinsed with $CH_2Cl_2$ (1 ml), and the filtrate was concentrated under reduced pressure. The resulting brown oil was used directly in the subsequent reaction.

Step B—Synthesis of N-(4-imidazolylphenyl){2-[(4-pyridylmethyl)amino](3-pyridyl)}carboxamide hydrochloride (2-Chloro-(3-pyridyl))-N-(4-imidazolylphenyl)-carboxamide was treated with 4-aminomethylpyridine (0.100 g, 0.93 mmol) and heated neat at 120° C. for 18 h. After cooling to RT, the material was purified by preparative HPLC. The final product was converted into an HCl salt by dissolution in a minimum of MeOH, treatment with an HCl ethereal solution, and evaporation of solvent. MS: (ES+) 371 (M+1)$^+$; (ES−): 369 (M−1)$^−$. Calc'd. for $C_{21}H_{18}N_6O$–370.15.

The following compounds (Examples 163-166) were analogously synthesized by the method described in Example 162.

EXAMPLE 163

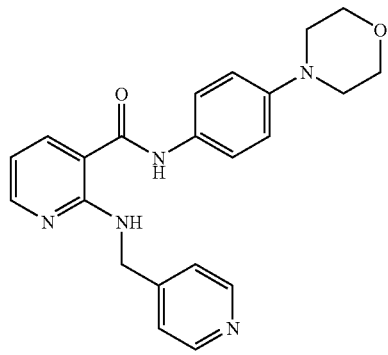

N-(4-Morpholin-4-ylphenyl){2-[(4-pyridylmethyl)amino](3-pyridyl)}carboxamide

The title compound was isolated as the HCl salt. MS: 390 (M+1); 388 (M−1). Calc'd. for $C_{22}H_{23}N_5O_2$–389.19.

EXAMPLE 164

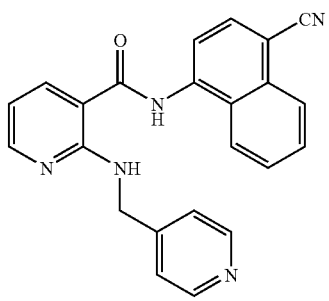

N-(4-Cyanonaphthyl){2-[(4-pyridylmethyl)amino]
(3-pyridyl)}carboxamide

The title compound was isolated as the HCl salt. MS: 380 (M+1); 378 (M−1). Calc'd. for $C_{23}H_{17}N_5O$−379.14.

EXAMPLE 165

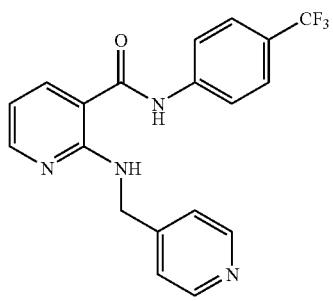

{2-[(4-Pyridylmethyl)amino](3-pyridyl)}-N-[4-(trifluoromethyl)phenyl]carboxamide The title compound was isolated as the HCl salt. MS: 373 (M+1); 371 (M−1). Calc'd. for $C_{19}H_{15}F_3N_4O$ −372.12.

EXAMPLE 166

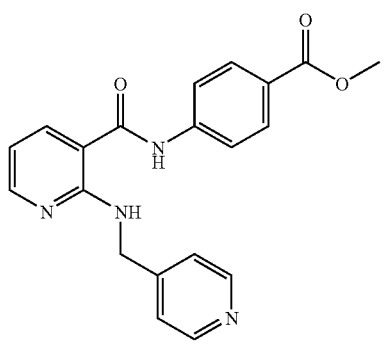

Methyl-({2-[(4-pyridylmethyl)amino]-3-pyridyl}carbonylamino)benzoate

The title compound was isolated as the HCl salt. MS: 363 (M+1); 361 (M−1). Calc'd. for $C_{20}H_{18}N_4O_3$−362.14.

The following compounds were synthesized by a procedure similar to the method described in Example 3, using an aldehyde to react with the aminopyridine core via reductive amination.

EXAMPLE 167

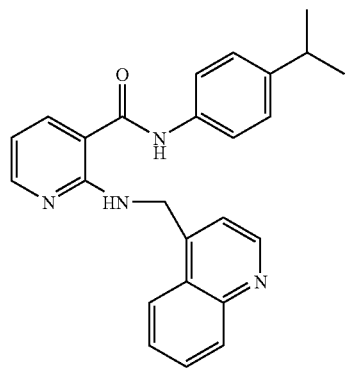

N-[4-(Isopropyl)phenyl]{2-[(4-quinolylmethyl)
amino](3-pyridyl)}carboxamide

MS: (ES+) 397 (M+H); (ES−) 395 (M−H). Calc'd. for $C_{25}H_{24}N_4O$−396.20.

EXAMPLE 168

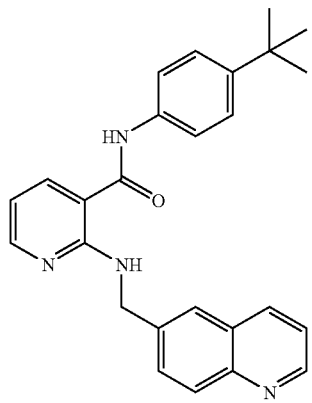

N-[4-(tert-Butyl)phenyl]{2-[(6-quinolylmethyl)
amino](3-pyridyl)}carboxamide

MS (ES+): 411 (M+H); (ES−): 409 (M−H). Calc'd. for $C_{26}H_{26}N_4O$−410.51.

EXAMPLE 169

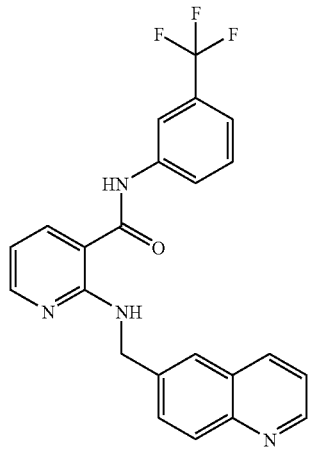

{2-[(6-Quinolylmethyl)amino](3-pyridyl)}-N-[3-(trifluoromethyl)phenyl]carboxamide MS (ES+): 423 (M+H); (ES−): 421 (M−H). Calc'd. for $C_{23}H_{17}F_3N_4O$: 422.14.

Other compounds included in this invention are set forth in Tables 3-9 below.

TABLE 3

| # | R¹ | R² | n |
|---|---|---|---|
| 170. | 2-chlorophenyl | H | 1 |
| 171. | 4-benzimidazolyl | H | 1 |
| 172. | 5-benzimidazolyl | H | 1 |
| 173. | 7-benzimidazolyl | H | 1 |
| 174. | 2-chlorophenyl | 5-Br | 1 |
| 175. | 3-isoquinolinyl | 5-Br | 1 |
| 176. | 2-quinolinyl | 5-Br | 1 |
| 177. | 2-benzthiazolyl | 5-Br | 1 |
| 178. | 2-benzimidazolyl | 5-Br | 1 |
| 179. | 4-benzimidazolyl | 5-Br | 1 |
| 180. | 5-benzimidazolyl | 5-Br | 1 |
| 181. | 6-benzimidazolyl | 5-Br | 1 |
| 182. | 7-benzimidazolyl | 5-Br | 1 |
| 183. | 4-chlorophenyl | H | 3 |
| 184. | 4-chlorophenyl | 3-pyridyl | 1 |
| 185. | 4-pyridyl | H | 1 |
| 186. | 4-pyridyl | 6-CH₃ | 1 |
| 187. | 4-chlorophenyl- | 5-Cl | 1 |
| 188. | 3,4-dichlorophenyl- | 5-Br | 1 |
| 189. | 4-fluorophenyl | 6-CH₃ | 1 |
| 190. | 3-chlorophenyl | 6-CH₃ | 1 |
| 191. | 3-fluorophenyl | 6-CH₃ | 1 |
| 192. | 3-fluoro-4-methoxyphenyl | 6-CH₃ | 1 |
| 193. | 3-fluoro-4-methylphenyl | 6-Cl | 1 |
| 194. | 4-phenoxyphenyl | H | 1 |
| 195. | 3-phenoxyphenyl | H | 1 |
| 196. | 4-biphenyl | H | 1 |
| 197. | 4-cyclohexylphenyl | H | 1 |
| 198. | 2-quinolyl | H | 1 |
| 199. | 3-isoquinolyl | H | 1 |
| 200. | 3-quinolyl | H | 1 |
| 201. | 1-isoquinolyl | H | 1 |
| 202. | 5-quinolyl | H | 1 |
| 203. | 5-isoquinolyl | H | 1 |
| 204. | 6-quinolyl | H | 1 |
| 205. | 6-isoquinolyl | H | 1 |
| 206. | 7-quinolyl | H | 1 |
| 207. | 7-isoquinolyl | H | 1 |
| 208. | 4-quinolyl | H | 1 |
| 209. | 4-isoquinolyl | H | 1 |
| 210. | 4-pyridyl | H | 1 |
| 211. | 4-pyrimidinyl | H | 1 |
| 212. | 2-pyrimidinyl | H | 1 |
| 213. | 6-pyrimidinyl | H | 1 |
| 214. | 4-pyridazinyl | H | 1 |
| 215. | 5-pyridazinyl | H | 1 |
| 216. | 4-indolyl | H | 1 |
| 217. | 5-isoindolyl | H | 1 |
| 218. | 5-naphthyridinyl | H | 1 |
| 219. | 6-quinozalinyl | H | 1 |
| 220. | 6-isoquinolyl | H | 1 |
| 221. | 4-naphthyridinyl | H | 1 |
| 222. | 5-quinozalinyl | H | 1 |
| 223. | 4-naphthyridinyl | H | 1 |

TABLE 3-continued

| # | R¹ | R² | n |
|---|---|---|---|
| 224. | 7-tetrahydroquinolinyl | H | 1 |
| 225. | 6-indazolyl | H | 1 |
| 226. | 6-isoindolyl | H | 1 |
| 227. | 5-indazolyl | H | 1 |
| 228. | 5-isoindolyl | H | 1 |
| 229. | 6-benzothienyl | H | 1 |
| 230. | 6-benzofuryl | H | 1 |
| 231. | 5-benzothienyl | H | 1 |
| 232. | 5-benzofuryl | H | 1 |
| 233. | 2-benzimidazolyl | H | 1 |
| 234. | 2-benzoxazolyl | H | 1 |
| 235. | 2-benzthiazolyl | H | 1 |
| 236. | 6-benzimidazolyl | H | 1 |
| 237. | 6-benzoxazolyl | H | 1 |
| 238. | 6-benzthiazolyl | H | 1 |
| 239. | 2-quinazolinyl | H | 1 |
| 240. | 3-(phenoxy)-6-pyridyl | H | 1 |
| 241. | 4-(phenylcarbonyl)phenyl | H | 1 |
| 242. | 4-(phenylamino)phenyl | H | 1 |
| 243. | 4-cyclohexyloxyphenyl | H | 1 |
| 244. | 4-(3-thienyl)phenyl | H | 1 |
| 245. | 4-(pyrazol-3-yl)phenyl | H | 1 |
| 246. | 4-chlorophenyl | 6-F | 2 |
| 247. | 4-pyridyl | 6-Cl | 1 |
| 248. | 3-methoxyphenyl | 6-F | 1 |
| 249. | 4-hydroxyphenyl | 6-Cl | 1 |
| 250. | 3-hydroxyphenyl | H | 1 |
| 251. | 2-hydroxyphenyl | H | 1 |
| 252. | 4-chlorophenyl | 6-F | 1 |
| 253. | 4-phenoxyphenyl | 6-F | 1 |
| 254. | 4-biphenyl | 6-phenyl | 1 |
| 255. | 4-hydroxyphenyl | 6-phenyl | 1 |
| 256. | 4-cyclohexylphenyl | 6-F | 1 |
| 257. | 3-isoquinolyl | 6-phenyl | 1 |
| 258. | 4-piperidinylmethylphenyl | H | 1 |
| 259. | 4-morpholinylmethylphenyl | H | 1 |

TABLE 4a

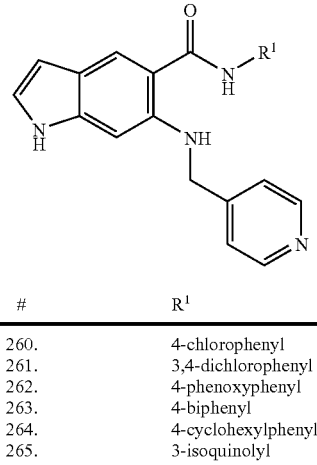

| # | R¹ |
|---|---|
| 260. | 4-chlorophenyl |
| 261. | 3,4-dichlorophenyl |
| 262. | 4-phenoxyphenyl |
| 263. | 4-biphenyl |
| 264. | 4-cyclohexylphenyl |
| 265. | 3-isoquinolyl |

TABLE 4b

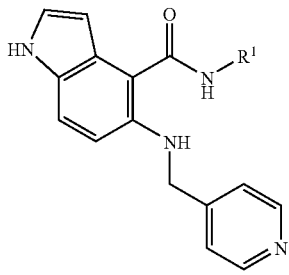

| # | R¹ |
|---|---|
| 266. | 4-chlorophenyl |
| 267. | 3,4-dichlorophenyl |
| 268. | 4-phenoxyphenyl |
| 269. | 4-biphenyl |
| 270. | 4-cyclohexylphenyl |
| 271. | 3-isoquinolyl |

TABLE 4c

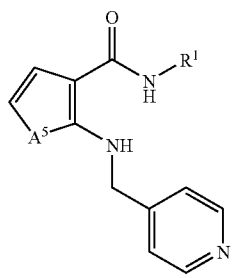

| # | R¹ | A⁵ |
|---|---|---|
| 272. | 4-chlorophenyl | NH |
| 273. | 3,4-dichlorophenyl | NH |
| 274. | 4-phenoxyphenyl | NH |
| 275. | 4-biphenyl | NH |
| 276. | 4-cyclohexylphenyl | NH |
| 277. | 3-isoquinolyl | NH |
| 278. | 4-chlorophenyl | O |
| 279. | 3,4-dichlorophenyl | O |
| 280. | 4-phenoxyphenyl | O |
| 281. | 4-biphenyl | O |
| 282. | 4-cyclohexylphenyl | O |
| 283. | 3-isoquinolyl | O |
| 284. | 3,4-dichlorophenyl | S |
| 285. | 4-phenoxyphenyl | S |
| 286. | 4-biphenyl | S |
| 287. | 4-cyclohexylphenyl | S |
| 288. | 3-isoquinolyl | S |

TABLE 4d

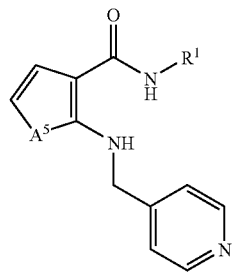

| # | R¹ | A⁵ |
|---|---|---|
| 289. | 4-chlorophenyl | NH |
| 290. | 3,4-dichlorophenyl | NH |
| 291. | 4-phenoxyphenyl | NH |
| 292. | 4-biphenyl | NH |
| 293. | 4-cyclohexylphenyl | NH |
| 294. | 3-isoquinolyl | NH |
| 295. | 4-chlorophenyl | O |
| 296. | 3,4-dichlorophenyl | O |
| 297. | 4-phenoxyphenyl | O |
| 298. | 4-biphenyl | O |
| 299. | 4-cyclohexylphenyl | O |
| 300. | 3-isoquinolyl | O |
| 301. | 3,4-dichlorophenyl | S |
| 302. | 4-phenoxyphenyl | S |
| 303. | 4-biphenyl | S |
| 304. | 4-cyclohexylphenyl | S |
| 305. | 3-isoquinolyl | S |

TABLE 4e

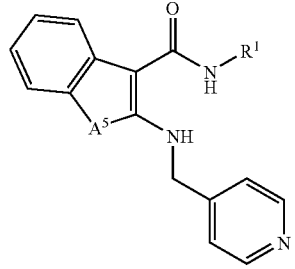

| # | R¹ | A⁵ |
|---|---|---|
| 306. | 4-chlorophenyl | NH |
| 307. | 3,4-dichlorophenyl | NH |
| 308. | 4-phenoxyphenyl | NH |
| 309. | 4-biphenyl | NH |
| 310. | 4-cyclohexylphenyl | NH |
| 311. | 3-isoquinolyl | NH |
| 312. | 4-chlorophenyl | O |
| 313. | 3,4-dichlorophenyl | O |
| 314. | 4-phenoxyphenyl | O |
| 315. | 4-biphenyl | O |
| 316. | 4-cyclohexylphenyl | O |
| 317. | 3-isoquinolyl | O |
| 318. | 3,4-dichlorophenyl | S |
| 319. | 4-phenoxyphenyl | S |
| 320. | 4-biphenyl | S |
| 321. | 4-cyclohexylphenyl | S |
| 322. | 3-isoquinolyl | S |

TABLE 4f

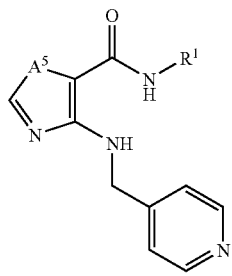

| # | R¹ | A⁵ |
|---|---|---|
| 323. | 4-chlorophenyl | NH |
| 324. | 3,4-dichlorophenyl | NH |
| 325. | 4-phenoxyphenyl | NH |
| 326. | 4-biphenyl | NH |
| 327. | 4-cyclohexylphenyl | NH |
| 328. | 3-isoquinolyl | NH |
| 329. | 4-chlorophenyl | O |
| 330. | 3,4-dichlorophenyl | O |
| 331. | 4-phenoxyphenyl | O |
| 332. | 4-biphenyl | O |
| 333. | 4-cyclohexylphenyl | O |
| 334. | 3-isoquinolyl | O |
| 335. | 3,4-dichlorophenyl | S |
| 336. | 4-phenoxyphenyl | S |
| 337. | 4-biphenyl | S |
| 338. | 4-cyclohexylphenyl | S |
| 339. | 3-isoquinolyl | S |

TABLE 4g

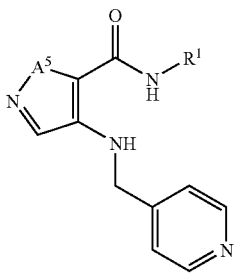

| # | R¹ | A⁵ |
|---|---|---|
| 340. | 4-chlorophenyl | NH |
| 341. | 3,4-dichlorophenyl | NH |
| 342. | 4-phenoxyphenyl | NH |
| 343. | 4-biphenyl | NH |
| 344. | 4-cyclohexylphenyl | NH |
| 345. | 3-isoquinolyl | NH |

TABLE 4g-continued

| # | R¹ | A⁵ |
|---|---|---|
| 346. | 4-chlorophenyl | O |
| 347. | 3,4-dichlorophenyl | O |
| 348. | 4-phenoxyphenyl | O |
| 349. | 4-biphenyl | O |
| 350. | 4-cyclohexylphenyl | O |
| 351. | 3-isoquinolyl | O |

TABLE 4h

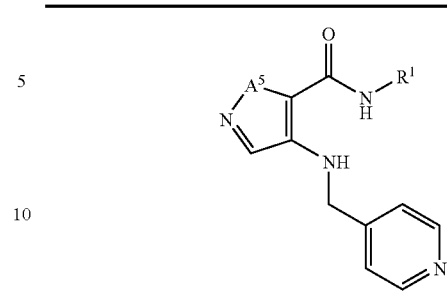

| # | R¹ | A⁵ |
|---|---|---|
| 352. | 4-chlorophenyl | NCH₃ |
| 353. | 3,4-dichlorophenyl | NCH₃ |
| 354. | 4-phenoxyphenyl | NCH₃ |
| 355. | 4-biphenyl | NH |
| 356. | 4-cyclohexylphenyl | NH |
| 357. | 4-tert-butylphenyl | NCH₃ |
| 358. | 4-chlorophenyl | O |
| 359. | 3,4-dichlorophenyl | O |
| 360. | 4-phenoxyphenyl | O |
| 361. | 4-biphenyl | O |
| 362. | 4-cyclohexylphenyl | O |
| 363. | 3-isoquinolyl | O |

TABLE 5

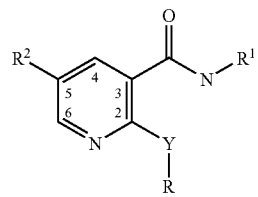

| # | R | Y | R¹ | R² |
|---|---|---|---|---|
| 364. | 4-pyridyl | —NHSO₂— | 4-chlorophenyl | H |
| 365. | 4-pyridyl | —NHSO₂— | 4-chlorophenyl | 5-Br |
| 366. | 4-pyridyl | —NHSO₂— | 3-chlorophenyl | H |
| 367. | 4-pyridyl | —NHSO₂— | 3-chlorophenyl | 5-Br |

TABLE 5-continued

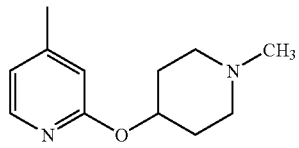

| # | R | Y | R¹ | R² |
|---|---|---|---|---|
| 368. | 4-pyridyl | —NHSO₂— | 4-phenoxyphenyl | H |
| 369. | 4-pyridyl | —NHSO₂— | 4-biphenyl | H |
| 370. | 4-pyridyl | —NHSO₂— | 3-isoquinolyl | H |
| 371. | 4-pyridyl | —NHSO₂— | 3-isoquinolyl | 5-Br |
| 372. | 5-quinolyl | —NHSO₂— | 4-chlorophenyl | H |
| 373. | 5-quinolyl | —NHSO₂— | 4-chlorophenyl | 5-Br |
| 374. | 5-quinolyl | —NHSO₂— | 3-chlorophenyl | H |
| 375. | 5-quinolyl | —NHSO₂— | 3-chlorophenyl | 5-Br |
| 376. | 5-quinolyl | —NHSO₂— | 4-phenoxyphenyl | H |
| 377. | 6-quinolyl | —NHSO₂— | 4-biphenyl | H |
| 378. | 5-quinolyl | —NHSO₂— | 3-isoquinolyl | H |
| 379. | 6-quinolyl | —NHSO₂— | 3-isoquinolyl | 5-Br |
| 380. | 4-pyridyl | —NHCH₂— | 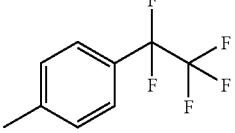 | H |
| 381. | 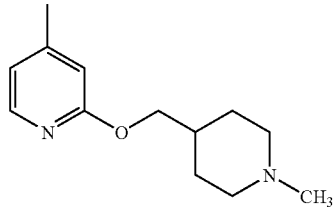 | —NHCH₂— | 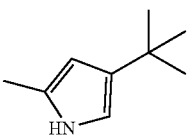 | H |
| 382. | 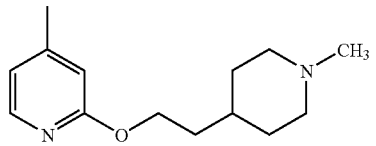 | —NHCH₂— | 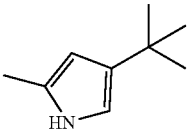 | H |
| 383. | 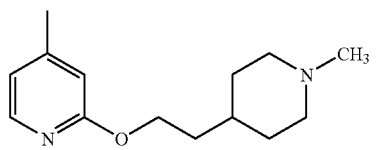 | —NHCH₂— |  | H |
| 384. | 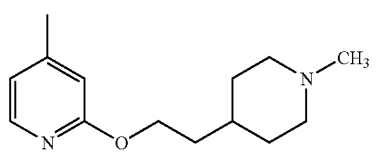 | —NHCH₂— | | H |
| 385. | | —NHCH₂— | 4-CF₃-phenyl | H |

TABLE 5-continued
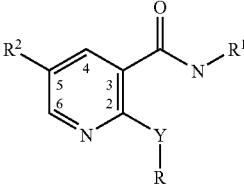
| # | R | Y | R¹ | R² |
|---|---|---|----|----|
| 386. | 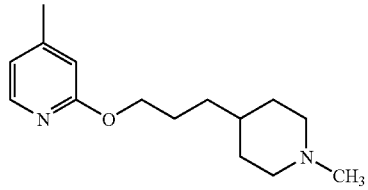 | —NHCH₂— | 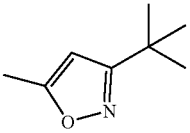 | H |
| 387. | 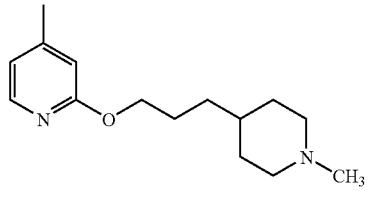 | —NHCH₂— | 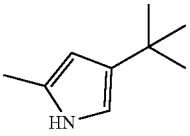 | H |
| 388. | 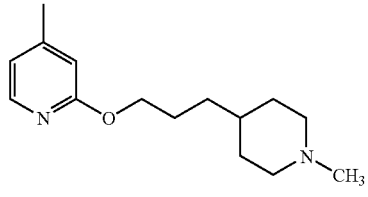 | —NHCH₂— | 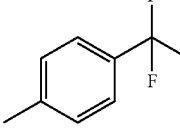 | H |
| 389. | 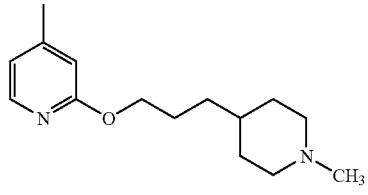 | —NHCH₂— | 3-CF₃-phenyl | H |
| 390 | 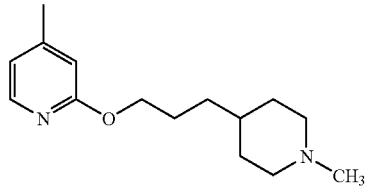 | —NHCH₂— | 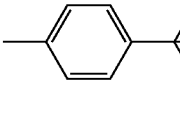 | H |
| 391. | 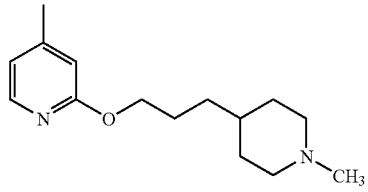 | —NHCH₂— | 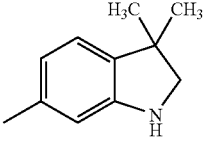 | H |

TABLE 5-continued
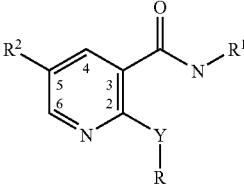
| # | R | Y | R¹ | R² |
|---|---|---|---|---|
| 392. | 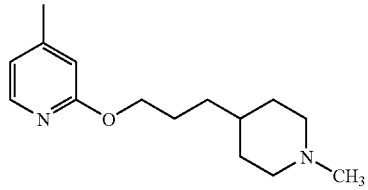 | —NHCH₂— | 4-CF₃-phenyl | H |
| 393 | 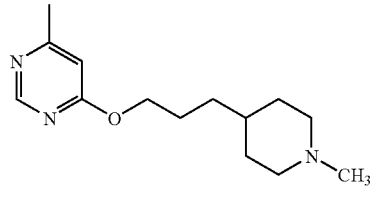 | —NHCH₂— | 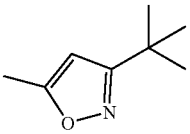 | H |
| 394 | 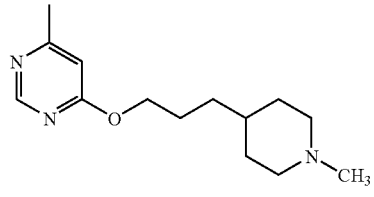 | —NHCH₂— | 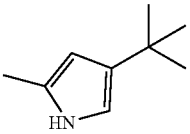 | H |
| 395. | 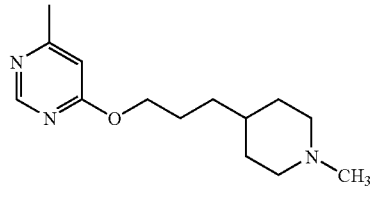 | —NHCH₂— | 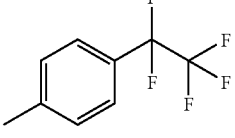 | H |
| 396. | 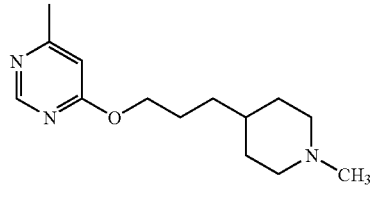 | —NHCH₂— | 3-CF₃-phenyl | H |
| 397. | 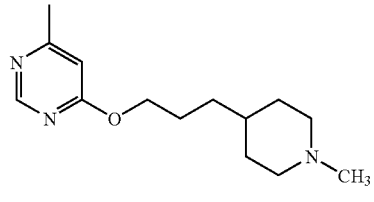 | —NHCH₂— | 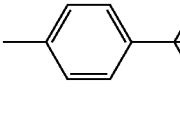 | H |

TABLE 5-continued

| # | R | Y | R¹ | R² |
|---|---|---|---|---|
| 398. | 4-methylpyrimidin-6-yl-O-(CH₂)₃-(1-methylpiperidin-4-yl) | —NHCH₂— | 3,3,6-trimethylindolin-5-yl | H |
| 399. | 4-methylpyrimidin-2-yl-O-(CH₂)₂-(1-methylpiperidin-4-yl) | —NHCH₂— | 3-tert-butyl-5-methylisoxazol-yl | H |
| 400. | 4-methylpyrimidin-6-yl-O-(CH₂)₃-(1-methylpiperidin-4-yl) | —NHCH₂— | 4-CF₃-phenyl | H |
| 401. | 4-methylpyrimidin-2-yl-O-(CH₂)₂-(1-methylpiperidin-4-yl) | —NHCH₂— | 4-tert-butyl-2-methyl-1H-pyrrol-yl | H |
| 402. | 4-methylpyrimidin-2-yl-O-(CH₂)₂-(1-methylpiperidin-4-yl) | —NHCH₂— | 4-(pentafluoroethyl)-methylphenyl | H |
| 403. | 4-methylpyrimidin-2-yl-O-(CH₂)₂-(1-methylpiperidin-4-yl) | —NHCH₂— | 3-CF₃-phenyl | H |
| 404. | 4-methylpyrimidin-2-yl-O-(CH₂)₂-(1-methylpiperidin-4-yl) | —NHCH₂— | 4-tert-butylphenyl | H |
| 405. | 4-methylpyrimidin-2-yl-O-(CH₂)₂-(1-methylpiperidin-4-yl) | —NHCH₂— | 3,3,6-trimethylindolin-5-yl | H |

TABLE 5-continued

| # | R | Y | R¹ | R² |
|---|---|---|----|----|
| 406. | 4-methyl-2-(2-(1-methylpiperidin-4-yl)ethoxy)pyrimidine | —NHCH₂— | 4-CF₃-phenyl | H |
| 407. | 6-methyl-4-(3-(1-methylpiperidin-4-yl)propoxy)pyrimidine | —NHCH₂— | 3-tert-butyl-5-methylisoxazole | H |
| 408. | 6-methyl-4-(3-(1-methylpiperidin-4-yl)propoxy)pyrimidine | —NHCH₂— | 4-tert-butyl-2-methyl-1H-pyrrole | H |
| 409. | 6-methyl-4-(3-(1-methylpiperidin-4-yl)propoxy)pyrimidine | —NHCH₂— | 4-(pentafluoroethyl)-methylphenyl | H |
| 410. | 6-methyl-4-(3-(1-methylpiperidin-4-yl)propoxy)pyrimidine | —NHCH₂— | 3-CF₃-phenyl | H |
| 411. | 6-methyl-4-(3-(1-methylpiperidin-4-yl)propoxy)pyrimidine | —NHCH₂— | 4-tert-butylphenyl | H |

TABLE 5-continued
| # | R | Y | R¹ | R² |
|---|---|---|----|----|
| 412. | 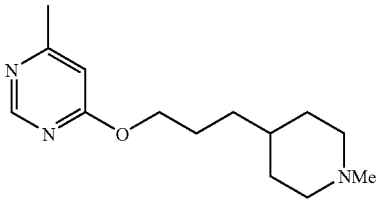 | —NHCH₂— | 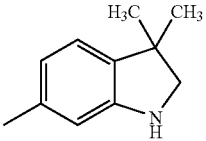 | H |
| 413. | 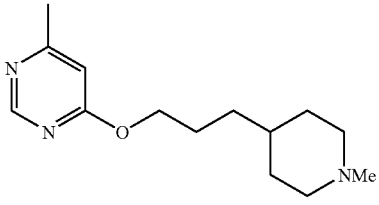 | —NHCH₂— | 4-CF₃-phenyl | H |
| 414. | 4-pyridyl | —NHCH₂— | 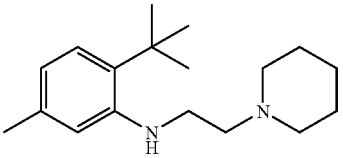 | H |
| 415. | 4-pyridyl | —NHCH₂— | 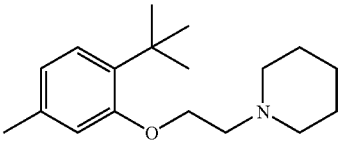 | H |
| 416. | 4-pyridyl | —NHCH₂— | 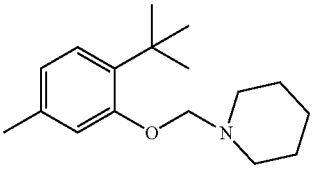 | H |
| 417. | 4-pyridyl | —NHCH₂— | 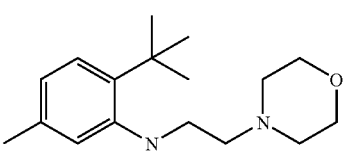 | H |
| 418. | 4-pyridyl | —NHCH₂— | 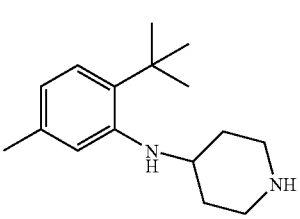 | H |

TABLE 5-continued
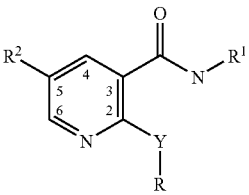
| # | R | Y | R¹ | R² |
|---|---|---|---|---|
| 419. | 4-pyrimidinyl | —NHCH₂— | | H |
| 420. | 4-pyrimidinyl | —NHCH₂— | | H |
| 421. | 4-pyrimidinyl | —NHCH₂— | | H |
| 422. | 4-pyrimidinyl | —NHCH₂— | | H |
| 423. | 4-pyrimidinyl | —NHCH₂— | | H |
| 424. | 4-pyrimidinyl | —NHCH₂— | | H |
| 425. | 4-pyrimidinyl | —NHCH₂— | | H |

TABLE 5-continued
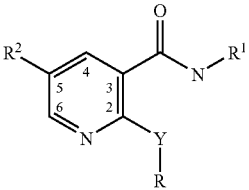
| # | R | Y | R¹ | R² |
|---|---|---|---|---|
| 426. | 4-pyrimidinyl | —NHCH₂— | 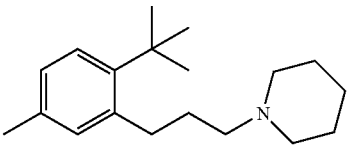 | H |
| 427. | 4-pyrimidinyl | —NHCH₂— | 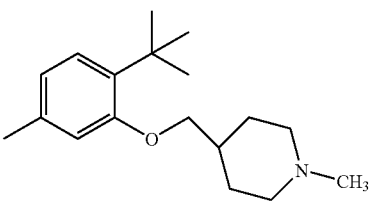 | H |
| 428. | 4-pyrimidinyl | —NHCH₂— | 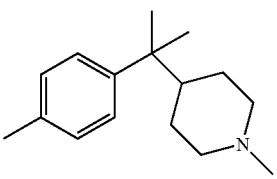 | H |
| 429. | 3-pyridyl | —NH(CH₂)₂— | 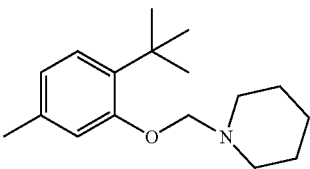 | H |
| 430. | 3-pyridyl | —NH(CH₂)₂— | 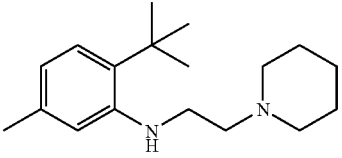 | H |
| 431. | 3-pyridyl | —NH(CH₂)₂— | 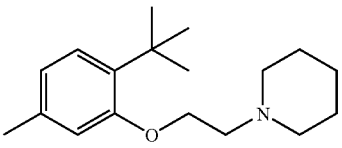 | H |
| 432. | 3-pyridyl | —NH(CH₂)₂— | 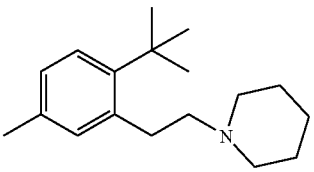 | H |

TABLE 5-continued

| # | R | Y | R¹ | R² |
|---|---|---|---|---|
| 433. | 3-pyridyl | —NH(CH₂)₂— | 2-tert-butyl-5-methylphenyl with 4-methylpiperazin-1-yl | H |
| 434. | 3-pyridyl | —NH(CH₂)₂— | 2-tert-butyl-5-methylphenyl with 3-(piperidin-1-yl)propyl | H |
| 435. | 3-pyridyl | —NH(CH₂)₂— | 2-tert-butyl-5-methylphenyl with O-CH₂-(1-methylpiperidin-4-yl) | H |
| 436. | 3-pyridyl | —NH(CH₂)₂— | 2-tert-butyl-5-methylphenyl with NH-piperidin-4-yl | H |
| 437. | 3-pyridyl | —NH(CH₂)₂— | 2-tert-butyl-5-methylphenyl with NH-CH₂CH₂-morpholino | H |
| 438. | 2-methoxy-4-methylpyridyl | —NHCH₂— | 2-tert-butyl-5-methylphenyl with NH-CH₂CH₂-morpholino | H |
| 439. | 2-methoxy-4-methylpyridyl | —NHCH₂— | 2-tert-butyl-5-methylphenyl with NH-piperidin-4-yl | H |

TABLE 5-continued
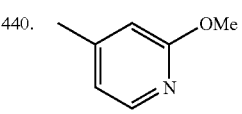
| # | R | Y | R¹ | R² |
|---|---|---|---|---|
| 440. | 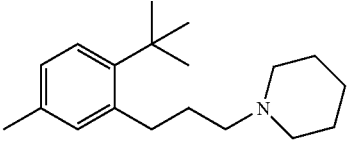 | —NHCH₂— | 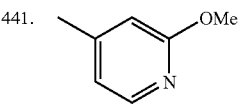 | H |
| 441. | 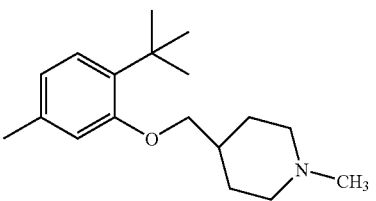 | —NHCH₂— | 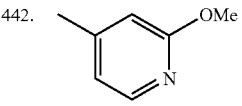 | H |
| 442. | 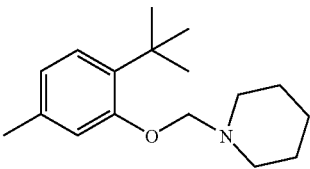 | —NHCH₂— | 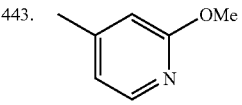 | H |
| 443. | 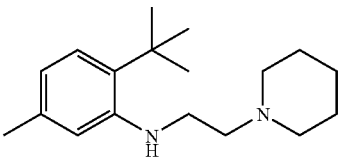 | —NHCH₂— | 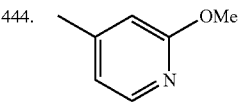 | H |
| 444. | 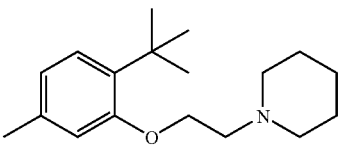 | —NHCH₂— | 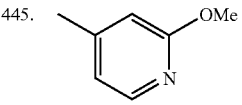 | H |
| 445. | 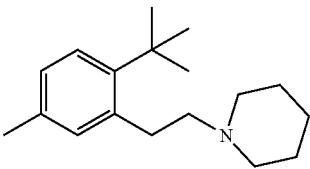 | —NHCH₂— | 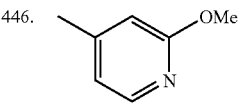 | H |
| 446. | 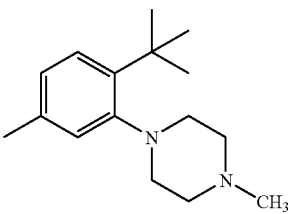 | —NHCH₂— |  | H |

TABLE 5-continued

| # | R | Y | R¹ | R² |
|---|---|---|---|---|
| 447. | 4-methyl-2-(SMe)-pyridine | —NHCH₂— | 2-tert-butyl-5-methylphenyl-O-CH₂-piperidine | H |
| 448. | 4-methyl-2-(SMe)-pyridine | —NHCH₂— | 2-tert-butyl-5-methylphenyl-NH-CH₂CH₂-piperidine | H |
| 449. | 4-methyl-2-(SMe)-pyridine | —NHCH₂— | 2-tert-butyl-5-methylphenyl-O-CH₂CH₂-piperidine | H |
| 450. | 4-methyl-2-(SMe)-pyridine | —NHCH₂— | 2-tert-butyl-5-methylphenyl-CH₂CH₂-piperidine | H |
| 451. | 4-methyl-2-(SMe)-pyridine | —NHCH₂— | 2-tert-butyl-5-methylphenyl-(4-methylpiperazin-1-yl) | H |
| 452. | 4-methyl-2-(CH₃)-pyridine | —NHCH₂— | 2-tert-butyl-5-methylphenyl-O-CH₂-piperidine | H |
| 453. | 4-methyl-2-(CH₃)-pyridine | —NHCH₂— | 2-tert-butyl-5-methylphenyl-NH-CH₂CH₂-piperidine | H |

TABLE 5-continued
| # | R | Y | R¹ | R² |
|---|---|---|----|-----|
| 454. | 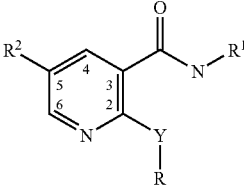 | —NHCH₂— | 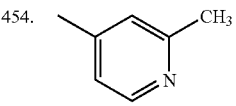 | H |
| 455. | 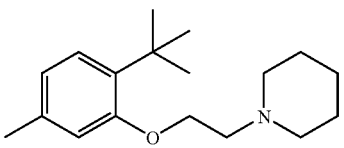 | —NHCH₂— | 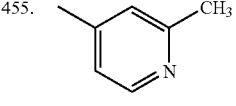 | H |
| 456. | 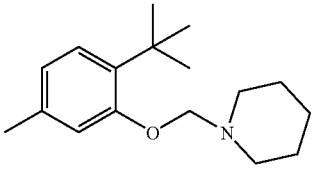 | —NHCH₂— | 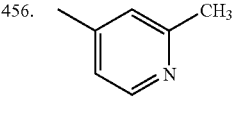 | H |
| 457. | 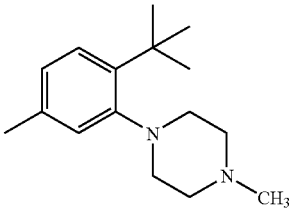 | —NHCH₂— | 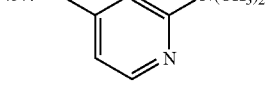 | H |
| 458. | 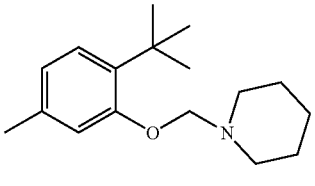 | —NHCH₂— | 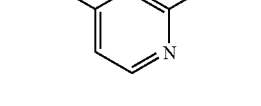 | H |
| 459. | 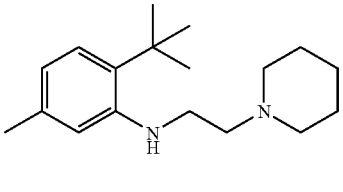 | —NHCH₂— | 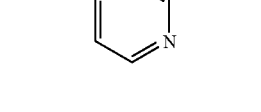 | H |
| 460. | 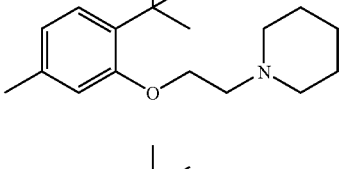 | —NHCH₂— | 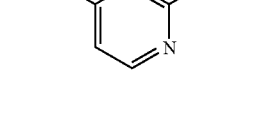 | H |

TABLE 5-continued

| # | R | Y | R¹ | R² |
|---|---|---|---|---|
| 461. | 4-(dimethylamino)pyridin-2-yl | —NHCH₂— | 2-tert-butyl-5-(4-methylpiperazin-1-yl)phenyl | H |
| 462. | 4-pyridyl | —NHCH₂— | 2-(pentafluoroethyl)-5-(4-methylpiperazin-1-yl)phenyl | H |
| 463. | 4-pyridyl | —NHCH₂— | 2-(pentafluoroethyl)-5-(morpholinomethyl)phenyl | H |
| 464. | 4-pyridyl | —NHCH₂— | 2-(pentafluoroethyl)-5-((1-methylpiperidin-4-yl)methyl)phenyl | H |
| 465. | 4-pyridyl | —NHCH₂— | 2-(pentafluoroethyl)-5-(piperazin-1-ylmethyl)phenyl | H |
| 466. | 4-pyridyl | —NHCH₂— | 2-(pentafluoroethyl)-5-(morpholinomethyl)phenyl | H |
| 467. | 4-pyridyl | —NHCH₂— | 2-(pentafluoroethyl)-5-((4-methylpiperazin-1-yl)methyl)phenyl | H |
| 468. | 4-pyridyl | —NHCH₂— | 2-(pentafluoroethyl)-5-(pyrrolidin-2-ylmethoxy)phenyl | H |

TABLE 5-continued

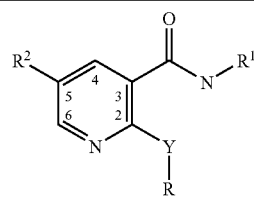

| # | R | Y | R¹ | R² |
|---|---|---|---|---|
| 469. | 4-pyridyl | —NHCH₂— | 2-CF₃, 5-methyl phenyl with O-CH₂-azetidine | H |
| 470. | 3-pyridyl | —NH(CH₂)₂— | 2-CF₂CF₃, 5-methyl phenyl with CH₂-N-methylpiperazine | H |
| 471. | 3-pyridyl | —NH(CH₂)₂— | 2-CF₂CF₃, 5-methyl phenyl with CH₂-morpholine | H |
| 472. | 3-pyridyl | —NH(CH₂)₂— | 2-CF₂CF₃, 5-methyl phenyl with CH₂-piperazine-NH | H |
| 473. | 3-pyridyl | —NH(CH₂)₂— | 2-CF₂CF₃, 5-methyl phenyl with N-methylpiperazinyl | H |
| 474. | 3-pyridyl | —NH(CH₂)₂— | 2-CF₂CF₃, 5-methyl phenyl with CH₂-morpholine | H |
| 475. | 3-pyridyl | —NH(CH₂)₂— | 2-CF₂CF₃, 5-methyl phenyl with CH₂-(N-methylpiperidinyl) | H |
| 476. | 3-pyridyl | —NH(CH₂)₂— | 4-methyl phenyl with C(CF₃)₂-O-CH₂CH₂-piperidine | H |
| 477. | 3-pyridyl | —NH(CH₂)₂— | 2-CF₂CF₃, 5-methyl phenyl with O-CH₂-pyrrolidine | H |

TABLE 5-continued

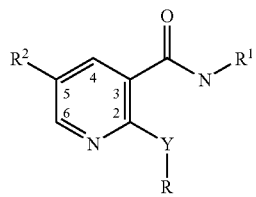

| # | R | Y | R¹ | R² |
|---|---|---|---|---|
| 478. | 3-pyridyl | —NH(CH$_2$)$_2$— | 2-CF$_3$, 5-methyl phenyl with -O-CH$_2$-(azetidin-3-yl) | H |
| 479. | 4-pyrimidinyl | —NHCH$_2$— | 2-CF$_3$, 5-methyl phenyl with -O-CH$_2$-(azetidin-3-yl) | H |
| 480. | 4-pyrimidinyl | —NHCH$_2$— | 2-CF$_2$CF$_3$, 5-methyl phenyl with -O-CH$_2$-(1-methylpiperidin-4-yl) | H |
| 481. | 4-pyrimidinyl | —NHCH$_2$— | 2-CF$_2$CF$_3$, 5-methyl phenyl with -O-CH$_2$-(1-methylpiperidin-4-yl) | H |
| 482. | 4-pyrimidinyl | —NHCH$_2$— | 2-CF$_2$CF$_3$, 5-methyl phenyl with -CH$_2$-morpholino | H |
| 483. | 4-pyrimidinyl | —NHCH$_2$— | 2-CF$_2$CF$_3$, 5-methyl phenyl with -CH$_2$-(1-methylpiperidin-4-yl) | H |
| 484. | 4-pyrimidinyl | —NHCH$_2$— | 2-CF$_2$CF$_3$, 5-methyl phenyl with -O-CH$_2$CH$_2$-piperidino | H |
| 485. | 4-pyrimidinyl | —NHCH$_2$— | 2-CF$_2$CF$_3$, 5-methyl phenyl with -O-CH$_2$-CH(OH)-CH$_2$-pyrrolidino | H |

TABLE 5-continued

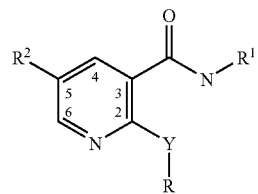

| # | R | Y | R¹ | R² |
|---|---|---|---|---|
| 486. | 4-pyrimidinyl | —NHCH₂— | (4-methylphenyl with C(CF₃)₂-O-CH₂CH₂-N(piperidine)) | H |
| 487. | 4-pyrimidinyl | —NHCH₂— | (5-methyl-2-(CF₂CF₃)phenyl-CH₂-N(piperazine)-NH) | H |
| 488. | 4-pyrimidinyl | —NHCH₂— | (5-methyl-2-(CF₂CF₃)phenyl-CH₂-N(morpholine)) | H |
| 489. | 4-pyrimidinyl | —NHCH₂— | (5-methyl-2-(CF₂CF₃)phenyl-CH₂-N(piperazine)-N-CH₃) | H |
| 490. | 4-pyrimidinyl | —NHCH₂— | (5-methyl-2-(CF₂CF₃)phenyl-O-CH₂-(pyrrolidin-2-yl)) | H |
| 491. | 4-(N(CH₃)₂)-pyridinyl | —NHCH₂— | (5-methyl-2-(CF₂CF₃)phenyl-N(piperazine)-N-CH₃) | H |
| 492. | 4-(N(CH₃)₂)-pyridinyl | —NHCH₂— | (5-methyl-2-(CF₂CF₃)phenyl-O-CH₂-(1-methylpiperidin-4-yl)) | H |
| 493. | 4-(N(CH₃)₂)-pyridinyl | —NHCH₂— | (5-methyl-2-(CF₂CF₃)phenyl-CH₂-N(morpholine)) | H |
| 494. | 4-(N(CH₃)₂)-pyridinyl | —NHCH₂— | (5-methyl-2-(CF₂CF₃)phenyl-CH₂-(1-methylpiperidin-4-yl)) | H |

TABLE 5-continued

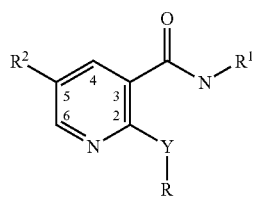

| # | R | Y | R¹ | R² |
|---|---|---|----|----|
| 495. | 4-pyridyl-N(CH₃)₂ | —NHCH₂— | phenyl with CF₂CF₃ and OCH₂CH₂-piperidine | H |
| 496. | 4-pyridyl-N(CH₃)₂ | —NHCH₂— | phenyl with CF₂CF₃ and OCH₂CH(OH)CH₂-pyrrolidine | H |
| 497. | 4-pyridyl-N(CH₃)₂ | —NHCH₂— | phenyl with C(CF₃)₂OCH₂CH₂-piperidine | H |
| 498. | 4-pyridyl-CH₃ | —NHCH₂— | phenyl with CF₂CF₃ and N-methylpiperazine | H |
| 499. | 4-pyridyl-CH₃ | —NHCH₂— | phenyl with CF₂CF₃ and OCH₂-(N-methylpiperidin-4-yl) | H |
| 500. | 4-pyridyl-CH₃ | —NHCH₂— | phenyl with CF₂CF₃ and CH₂-morpholine | H |
| 501. | 4-pyridyl-CH₃ | —NHCH₂— | phenyl with CF₂CF₃ and CH₂-(N-methylpiperidin-4-yl) | H |
| 502. | 4-pyridyl-CH₃ | —NHCH₂— | phenyl with CF₂CF₃ and OCH₂CH₂-piperidine | H |

TABLE 5-continued
| # | R | Y | R¹ | R² |
|---|---|---|----|----|
| 503. | 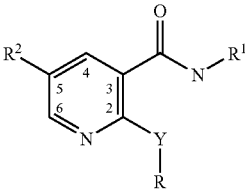 | —NHCH₂— | 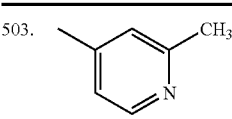 | H |
| 504. | 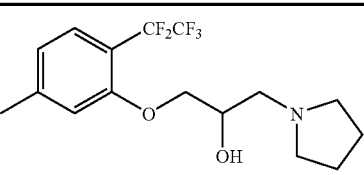 | —NHCH₂— | 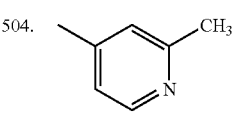 | H |
| 505. | 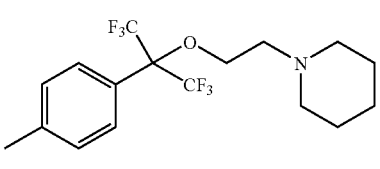 | —NHCH₂— | 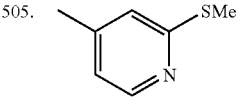 | H |
| 506. | 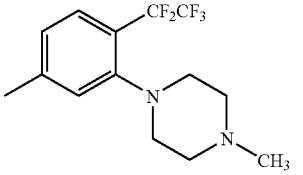 | —NHCH₂— | 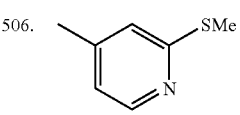 | H |
| 507. | 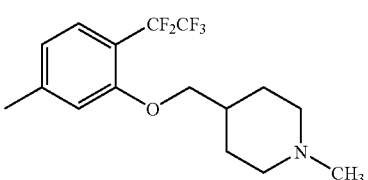 | —NHCH₂— | 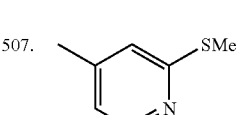 | H |
| 508. | 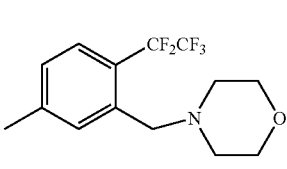 | —NHCH₂— | 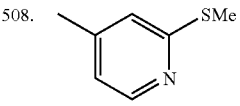 | H |
| 509. | 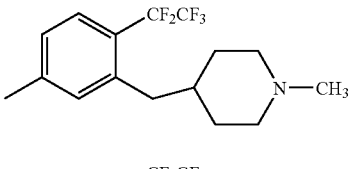 | —NHCH₂— | 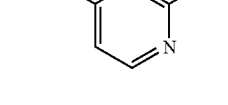 | H |
| 510. | 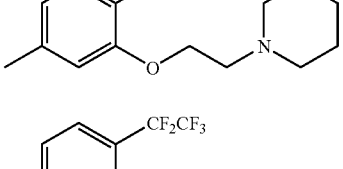 | —NHCH₂— | 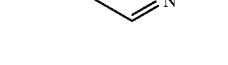 | H |

TABLE 5-continued
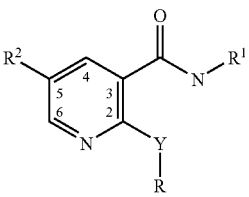
| # | R | Y | R¹ | R² |
|---|---|---|----|----|
| 511. | 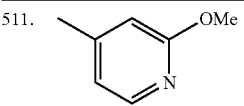 | —NHCH₂— | 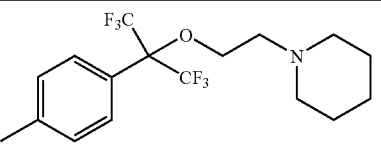 | H |
| 512. | 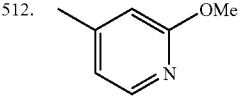 | —NHCH₂— | 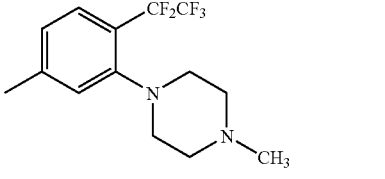 | H |
| 513. | 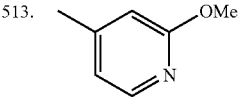 | —NHCH₂— | 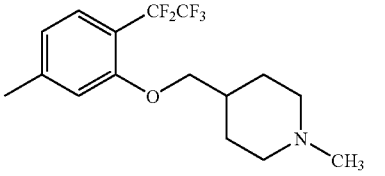 | H |
| 514. | 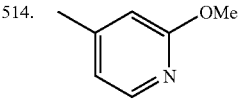 | —NHCH₂— | 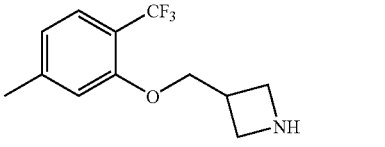 | H |
| 515. | 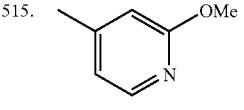 | —NHCH₂— | 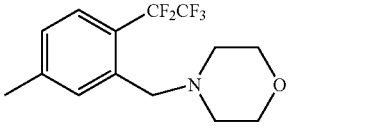 | H |
| 516. | 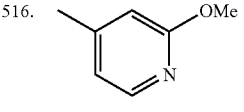 | —NHCH₂— | 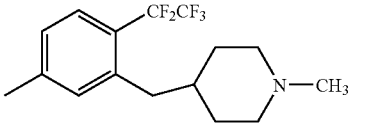 | H |
| 517. | 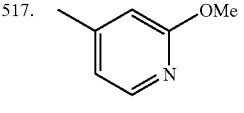 | —NHCH₂— | 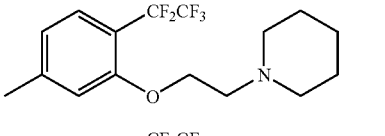 | H |
| 518. | 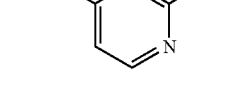 | —NHCH₂— | 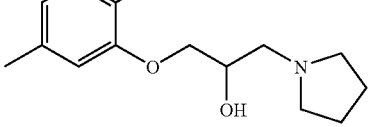 | H |
| 519. | 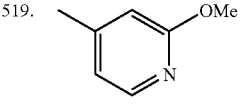 | —NHCH₂— | 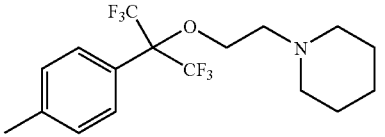 | H |

TABLE 5-continued

| # | R | Y | R¹ | R² |
|---|---|---|----|----|
| 520. | 4-methyl-2-methoxypyridyl | —NHCH₂— | 2-(pentafluoroethyl)-5-methylbenzyl-4-methylpiperazine | H |
| 521. | 4-methyl-2-methoxypyridyl | —NHCH₂— | 2-(pentafluoroethyl)-5-methylbenzyl-piperazine | H |
| 522. | 4-methyl-2-methoxypyridyl | —NHCH₂— | 2-(pentafluoroethyl)-5-methylbenzyl-morpholine | H |
| 523. | 4-methyl-2-methoxypyridyl | —NHCH₂— | 2-(pentafluoroethyl)-5-methylphenoxymethyl-pyrrolidine | H |
| 524. | 4-methyl-2-methoxypyridyl | —NHCH₂— | 3,3,6-trimethyl-2,3-dihydrobenzo[d]isothiazole 1,1-dioxide | H |
| 525. | 4-pyridyl | —NHCH₂— | 3-CF₃-phenyl | H |
| 526. | 4-pyridyl | —NHCH₂— | 3-CF₃-5-methyl-phenylpropyl-morpholine | H |
| 527. | 4-pyridyl | —NHCH₂— | 3-CF₃-5-methyl-phenylpropyl-piperidine | H |
| 528. | 4-pyridyl | —NHCH₂— | 3-CF₃-5-methyl-benzyl-4-methylpiperazine | H |

TABLE 5-continued
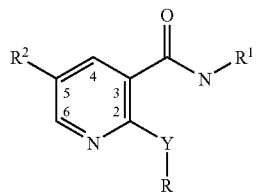
| # | R | Y | R¹ | R² |
|---|---|---|----|----|
| 529. | 4-pyridyl | —NHCH₂— | 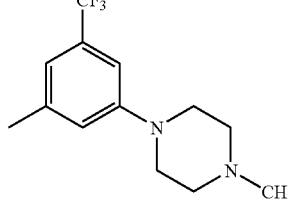 | H |
| 530. | 4-pyridyl | —NHCH₂— | 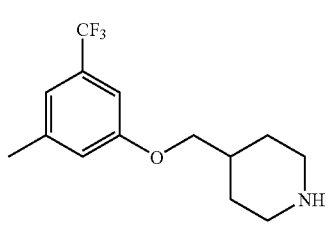 | H |
| 531. | 4-pyridyl | —NHCH₂— | 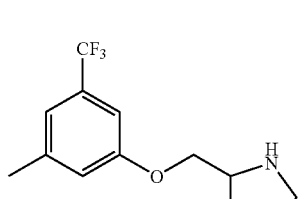 | H |
| 532. | 4-pyridyl | —NHCH₂— | 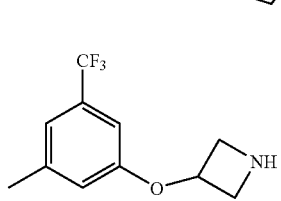 | H |
| 533. | 4-pyridyl | —NHCH₂— | 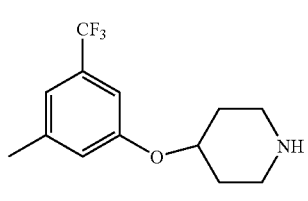 | H |
| 534. | 3-pyridyl | —NH(CH₂)₂— | 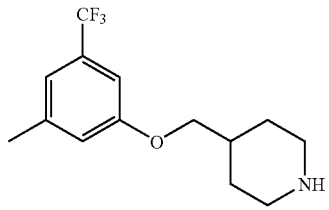 | H |

TABLE 5-continued

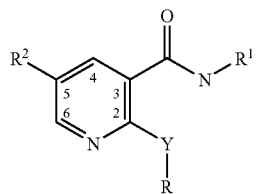

| # | R | Y | R¹ | R² |
|---|---|---|----|----|
| 535. | 3-pyridyl | —NH(CH₂)₂— | 3-CF₃-5-methyl-phenyl-O-CH₂-pyrrolidin-2-yl | H |
| 536. | 3-pyridyl | —NH(CH₂)₂— | 3-CF₃-5-methyl-phenyl-O-azetidin-3-yl | H |
| 537. | 3-pyridyl | —NH(CH₂)₂— | 3-CF₃-5-methyl-phenyl-CH₂-(4-methylpiperazin-1-yl) | H |
| 538. | 3-pyridyl | —NH(CH₂)₂— | 3-CF₃-5-methyl-phenyl-(CH₂)₃-morpholin-4-yl | H |
| 539. | 4-pyridyl | —NHCH₂— | 3-methyl-3-(hydroxymethyl)-6-methyl-3H-indol-yl | H |
| 540. | 4-pyrimidinyl | —NHCH₂— | 3-CF₃-5-methyl-phenyl-O-CH₂-piperidin-4-yl | H |
| 541. | 4-pyrimidinyl | —NHCH₂— | 3-CF₃-5-methyl-phenyl-O-CH₂-pyrrolidin-2-yl | H |

TABLE 5-continued
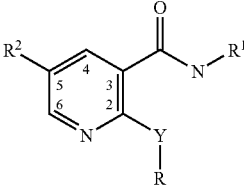
| # | R | Y | R¹ | R² |
|---|---|---|---|---|
| 542. | 4-pyrimidinyl | —NHCH₂— | 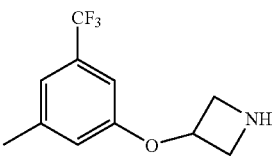 | H |
| 543. | 4-pyrimidinyl | —NHCH₂— | 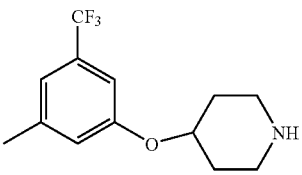 | H |
| 544. | 4-pyrimidinyl | —NHCH₂— | 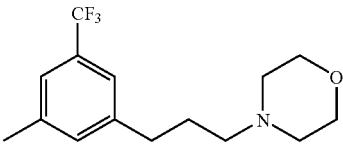 | H |
| 545. | 4-pyrimidinyl | —NHCH₂— | 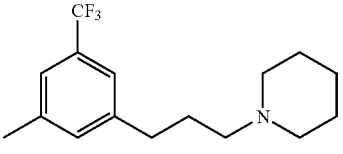 | H |
| 546. | 4-pyrimidinyl | —NHCH₂— | 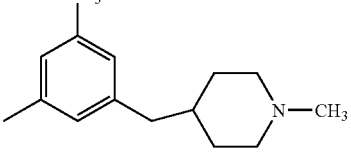 | H |
| 547. | 4-pyrimidinyl | —NHCH₂— | 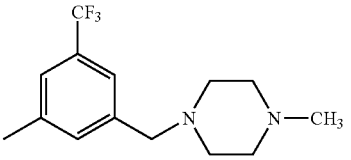 | H |
| 548. | 4-pyrimidinyl | —NHCH₂— | 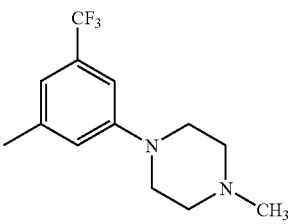 | H |

TABLE 5-continued

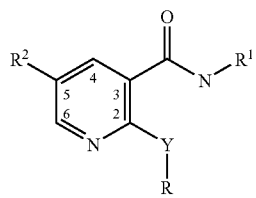

| # | R | Y | R¹ | R² |
|---|---|---|---|---|
| 549. | 4-pyrimidinyl | —NHCH₂— | 3-CF₃-5-(1-methylpiperidin-4-yl)phenyl | H |
| 550. | 4-methyl-2-(dimethylamino)pyridinyl | —NHCH₂— | 3-CF₃-phenyl | H |
| 551. | 4-methyl-2-(dimethylamino)pyridinyl | —NHCH₂— | 3-CF₃-5-(1-methylpiperidin-4-yl)phenyl | H |
| 552. | 4-methyl-2-(dimethylamino)pyridinyl | —NHCH₂— | 3-CF₃-5-(4-methylpiperazin-1-yl)phenyl | H |
| 553. | 4-methyl-2-(dimethylamino)pyridinyl | —NHCH₂— | 3-CF₃-5-((4-methylpiperazin-1-yl)methyl)phenyl | H |
| 554. | 4-methyl-2-(dimethylamino)pyridinyl | —NHCH₂— | 3-CF₃-5-((1-methylpiperidin-4-yl)methyl)phenyl | H |
| 555. | 4-methyl-2-(dimethylamino)pyridinyl | —NHCH₂— | 3-CF₃-5-(3-(piperidin-1-yl)propyl)phenyl | H |

TABLE 5-continued

| # | R | Y | R¹ | R² |
|---|---|---|---|---|
| 556. | 4-N(CH₃)₂-pyridin-2-yl (methyl at 4, N(CH₃)₂ at 2) | —NHCH₂— | 3-CF₃-5-(3-morpholinopropyl)phenyl | H |
| 557. | 2-methyl-4-pyridinyl | —NHCH₂— | 3-CF₃-phenyl | H |
| 558. | 4-methyl-2-N(CH₃)₂-pyridinyl | —NHCH₂— | 3-CF₃-5-(1-methylpiperidin-4-yl)phenyl | H |
| 559. | 4-methyl-2-N(CH₃)₂-pyridinyl | —NHCH₂— | 3-CF₃-5-(4-methylpiperazin-1-yl)phenyl | H |
| 560. | 4-methyl-2-N(CH₃)₂-pyridinyl | —NHCH₂— | 3-CF₃-5-((4-methylpiperazin-1-yl)methyl)phenyl | H |
| 561. | 4-methyl-2-N(CH₃)₂-pyridinyl | —NHCH₂— | 3-CF₃-5-((1-methylpiperidin-4-yl)methyl)phenyl | H |
| 562. | 4-methyl-2-N(CH₃)₂-pyridinyl | —NHCH₂— | 3-CF₃-5-(3-piperidin-1-ylpropyl)phenyl | H |
| 563. | 4-methyl-2-N(CH₃)₂-pyridinyl | —NHCH₂— | 3-CF₃-5-(3-morpholinopropyl)phenyl | H |

TABLE 5-continued

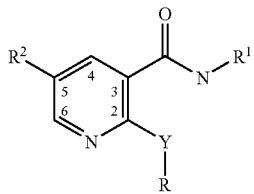

| # | R | Y | R¹ | R² |
|---|---|---|----|-----|
| 564. | 4-Me, 2-SMe pyridine | —NHCH₂— | 3-CF₃-phenyl | H |
| 565. | 4-Me, 2-SMe pyridine | —NHCH₂— | 3-CF₃-5-(1-methylpiperidin-4-yl)phenyl | H |
| 566. | 4-Me, 2-SMe pyridine | —NHCH₂— | 3-CF₃-5-(4-methylpiperazin-1-yl)phenyl | H |
| 567. | 4-Me, 2-SMe pyridine | —NHCH₂— | 3-CF₃-5-((4-methylpiperazin-1-yl)methyl)phenyl | H |
| 568. | 4-Me, 2-SMe pyridine | —NHCH₂— | 3-CF₃-5-((1-methylpiperidin-4-yl)methyl)phenyl | H |
| 569. | 4-Me, 2-SMe pyridine | —NHCH₂— | 3-CF₃-5-(3-(piperidin-1-yl)propyl)phenyl | H |
| 570. | 4-Me, 2-SMe pyridine | —NHCH₂— | 3-CF₃-5-(3-(morpholin-4-yl)propyl)phenyl | H |

TABLE 5-continued
| # | R | Y | R¹ | R² |
|---|---|---|----|----|
| 571. | 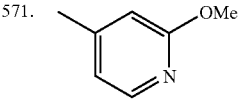 | —NHCH₂— | 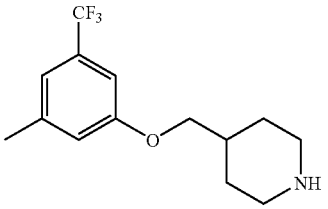 | H |
| 572. | 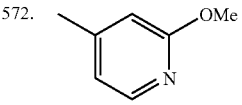 | —NHCH₂— | 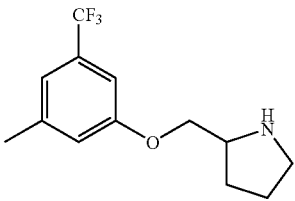 | H |
| 573. | 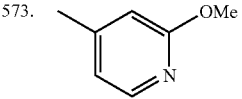 | —NHCH₂— | 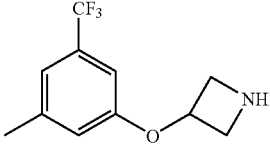 | H |
| 574. | 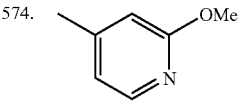 | —NHCH₂— | 3-CF₃-phenyl | H |
| 575. | 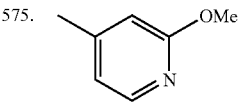 | —NHCH₂— | 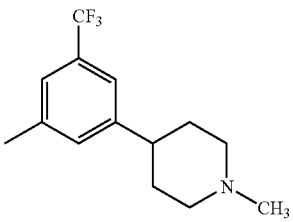 | H |
| 576. | 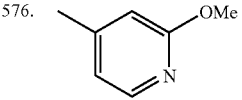 | —NHCH₂— | 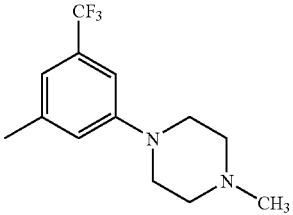 | H |
| 577. | 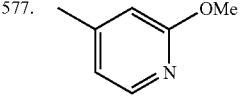 | —NHCH₂— | 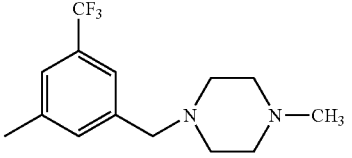 | H |

TABLE 5-continued

| # | R | Y | R¹ | R² |
|---|---|---|----|----|
| 578. | 4-methyl-2-methoxypyridinyl | —NHCH₂— | 3-(trifluoromethyl)-5-methylbenzyl-(1-methylpiperidin-4-yl)methyl | H |
| 579. | 4-methyl-2-methoxypyridinyl | —NHCH₂— | 3-(trifluoromethyl)-5-methylphenyl-3-(piperidin-1-yl)propyl | H |
| 580. | 4-methyl-2-methoxypyridinyl | —NHCH₂— | 3-(trifluoromethyl)-5-methylphenyl-3-(morpholin-4-yl)propyl | H |
| 581. | 4-pyrimidinyl | —NHCH₂— | 3,3,6-trimethyl-1-((1-methylpiperidin-4-yl)methyl)indoline | H |
| 582. | 4-pyrimidinyl | —NHCH₂— | 3,3,6-trimethyl-1-(1-methylpiperidin-4-yl)indoline | H |
| 583. | 4-pyrimidinyl | —NHCH₂— | 3,3,6-trimethylindoline | H |

TABLE 5-continued

| # | R | Y | R¹ | R² |
|---|---|---|---|---|
| 584. | 4-methyl-2-(N(CH₃)₂)-pyridine | —NHCH₂— | 3,3,6-trimethyl-1-(piperidin-4-ylmethyl)indoline | H |
| 585. | 4-methyl-2-(N(CH₃)₂)-pyridine | —NHCH₂— | 3,3,6-trimethyl-1-((1-methylpiperidin-4-yl)methyl)indoline | H |
| 586. | 4-methyl-2-(N(CH₃)₂)-pyridine | —NHCH₂— | 3,3,6-trimethyl-1-(1-methylpiperidin-4-yl)indoline | H |
| 587. | 4-methyl-2-(N(CH₃)₂)-pyridine | —NHCH₂— | 3,3,6-trimethylindoline | H |
| 588. | 4-methyl-2-methyl-pyridine | —NHCH₂— | 3,3,6-trimethyl-1-(piperidin-4-ylmethyl)indoline | H |
| 589. | 4-methyl-2-methyl-pyridine | —NHCH₂— | 3,3,6-trimethyl-1-((1-methylpiperidin-4-yl)methyl)indoline | H |

TABLE 5-continued
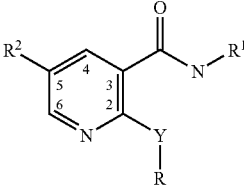
| # | R | Y | R¹ | R² |
|---|---|---|----|----|
| 590. | 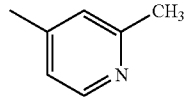 | —NHCH₂— | 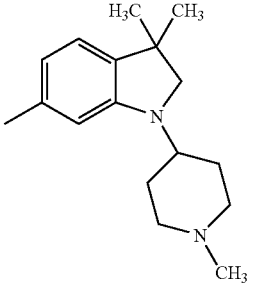 | H |
| 591. | 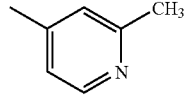 | —NHCH₂— | 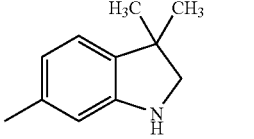 | H |
| 592. | 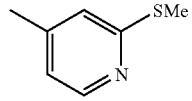 | —NHCH₂— | 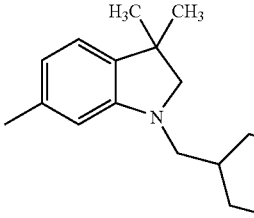 | H |
| 593. | 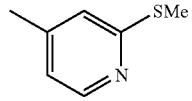 | —NHCH₂— | 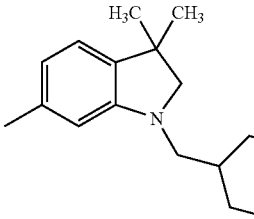 | H |
| 594. | 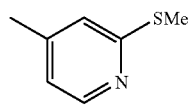 | —NHCH₂— | 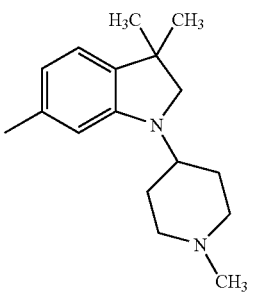 | H |

TABLE 5-continued
| # | R | Y | R¹ | R² |
|---|---|---|----|----|
| 595. | 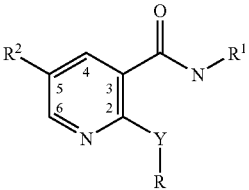 | —NHCH₂— | 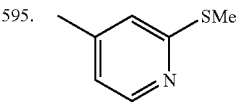 | H |
| 596. | 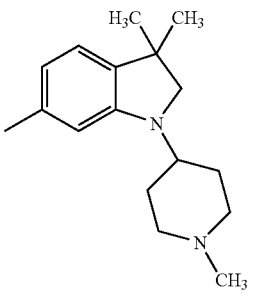 | —NHCH₂— | 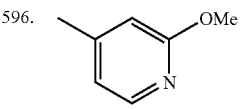 | H |
| 597. | 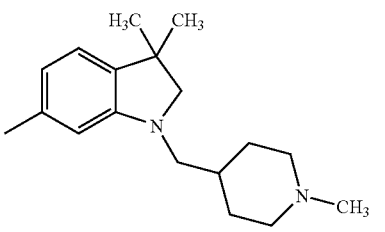 | —NHCH₂— | 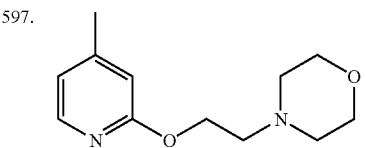 | H |
| 598. | 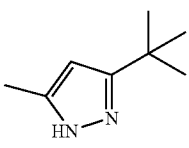 | —NHCH₂— | 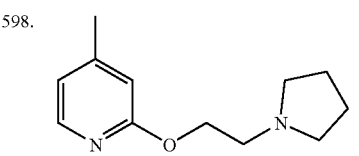 | H |
| 599. | 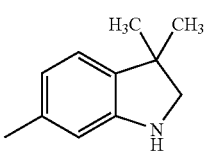 | —NHCH₂— | 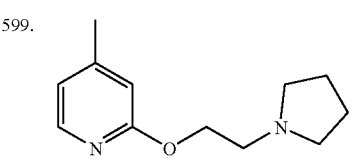 | H |
| 600. | 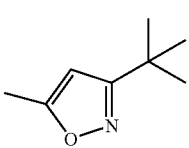 | —NHCH₂— | 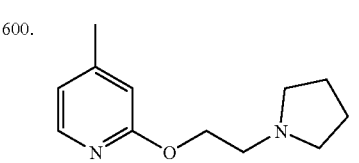 | H |
| 601. | 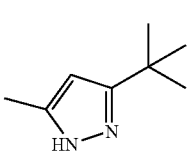 | —NHCH₂— | 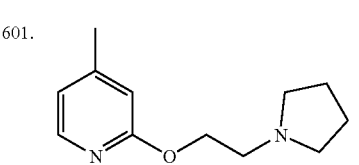 | H |

TABLE 5-continued
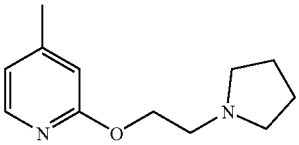
| # | R | Y | R¹ | R² |
|---|---|---|----|----|
| 602. | 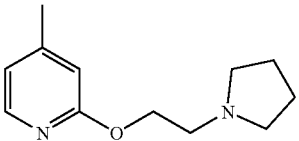 | —NHCH₂— | 3-CF₃-phenyl | H |
| 603. | 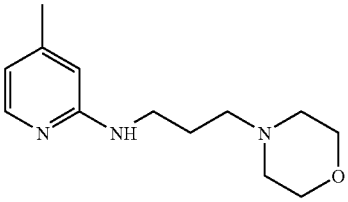 | —NHCH₂— | 4-CF₃-phenyl | H |
| 604. | 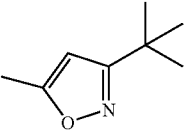 | —NHCH₂— | 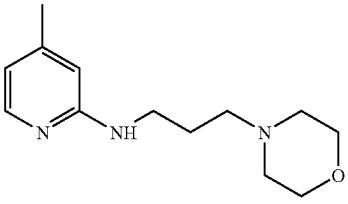 | H |
| 605. | 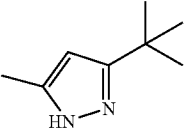 | —NHCH₂— | 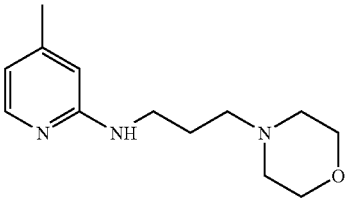 | H |
| 606. | 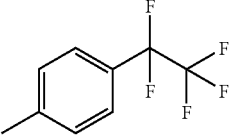 | —NHCH₂— | 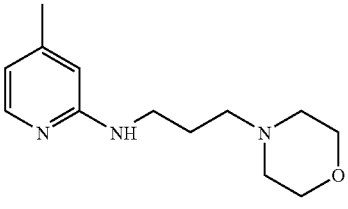 | H |
| 607. | 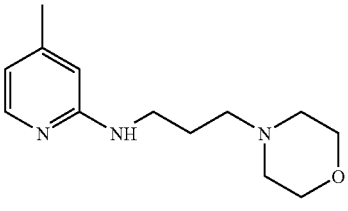 | —NHCH₂— | 3-CF₃-phenyl | H |
| 608. | 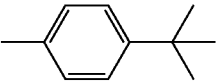 | —NHCH₂— | | H |

US 8,058,445 B2
267 268
TABLE 5-continued
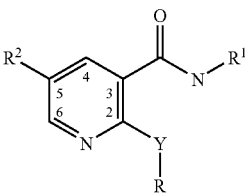
| # | R | Y | R¹ | R² |
|---|---|---|---|---|
| 609. | 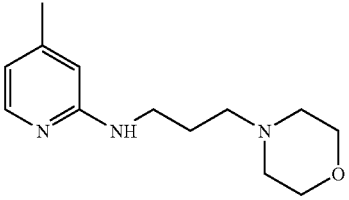 | —NHCH₂— | 4-CF₃-phenyl | H |
| 610. | 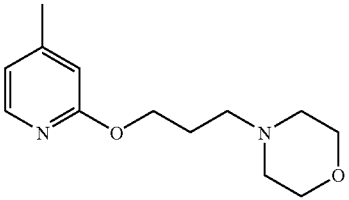 | —NHCH₂— | 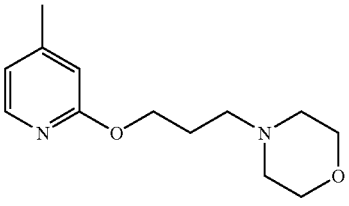 | H |
| 611. | 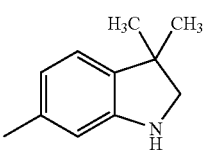 | —NHCH₂— | 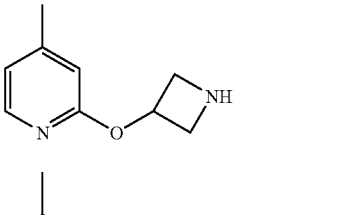 | H |
| 612. | 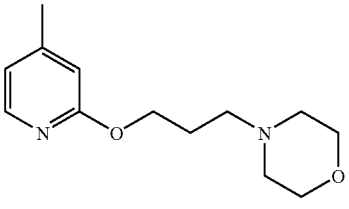 | —NHCH₂— | 3-CF₃-phenyl | H |
| 613. | 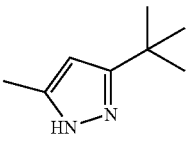 | —NHCH₂— | 4-CF₃-phenyl | H |
| 614. | 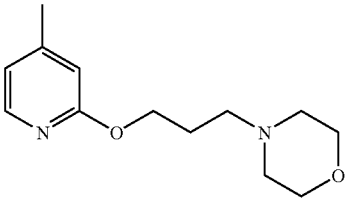 | —NHCH₂— | 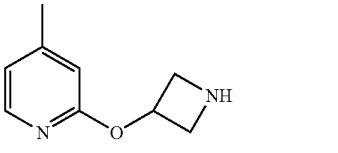 | H |
| 615. | 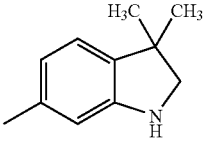 | —NHCH₂— | 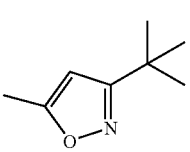 | H |

TABLE 5-continued

| # | R | Y | R¹ | R² |
|---|---|---|----|-----|
| 616. | 4-methyl-2-(azetidin-3-yloxy)pyridine | —NHCH₂— | 5-tert-butyl-1H-pyrazol-3-yl | H |
| 617. | 4-methyl-2-(azetidin-3-yloxy)pyridine | —NHCH₂— | 4-(1,1,2,2,2-pentafluoroethyl)phenyl | H |
| 618. | 4-methyl-2-(azetidin-3-yloxy)pyridine | —NHCH₂— | 3-CF₃-phenyl | H |
| 619. | 4-methyl-2-(azetidin-3-yloxy)pyridine | —NHCH₂— | 4-CF₃-phenyl | H |
| 620. | 4-methyl-2-((1-methylpyrrolidin-2-yl)methoxy)pyridine | —NHCH₂— | 3,3,6-trimethyl-2,3-dihydro-1H-indol-5-yl | H |
| 621. | 4-methyl-2-((1-methylpyrrolidin-2-yl)methoxy)pyridine | —NHCH₂— | 3-tert-butyl-5-methylisoxazol-4-yl | H |
| 622. | 4-methyl-2-((1-methylpyrrolidin-2-yl)methoxy)pyridine | —NHCH₂— | 5-tert-butyl-1H-pyrazol-3-yl | H |

271
272
TABLE 5-continued
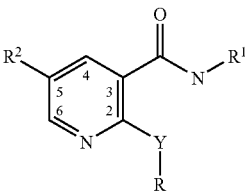
| # | R | Y | R¹ | R² |
|---|---|---|----|----|
| 623. | 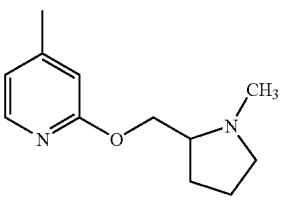 | —NHCH₂— | 3-CF₃-phenyl | H |
| 624. | 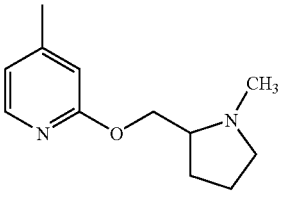 | —NHCH₂— | 4-CF₃-phenyl | H |
| 625. | 4-pyridyl | —NHCH₂— | 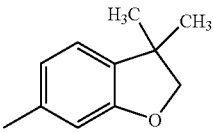 | H |
| 626. | 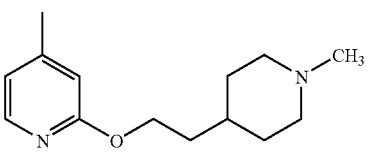 | —NHCH₂— | 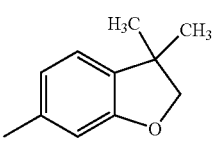 | H |
| 627. | 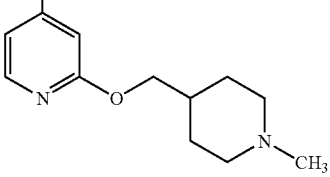 | —NHCH₂— | 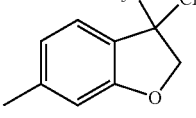 | H |
| 628. | 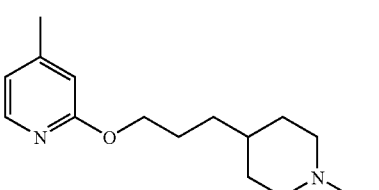 | —NHCH₂— | 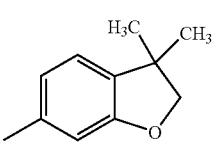 | H |
| 629. | 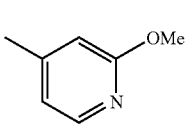 | —NHCH₂— | 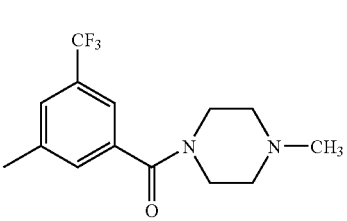 | H |

TABLE 5-continued

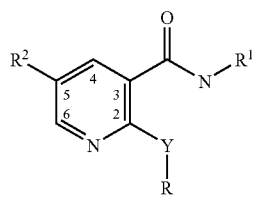

| # | R | Y | R¹ | R² |
|---|---|---|---|---|
| 630. | 4-methyl-2-methylpyridyl | —NHCH₂— | 3-CF₃-5-methyl-benzoyl-(4-methylpiperazine) | H |
| 631. | 4-methyl-2-SMe-pyridyl | —NHCH₂— | 3-CF₃-5-methyl-benzoyl-(4-methylpiperazine) | H |
| 632. | 4-methyl-2-N(CH₃)₂-pyridyl | —NHCH₂— | 3-CF₃-5-methyl-benzoyl-(4-methylpiperazine) | H |
| 633. | 3-pyridyl | —NH(CH₂)₂— | 3-CF₃-5-methyl-benzoyl-(4-methylpiperazine) | H |
| 634. | 4-pyrimidinyl | —NHCH₂— | 3-CF₃-5-methyl-benzoyl-(4-methylpiperazine) | H |
| 635. | 4-pyridyl | —NHCH₂— | 3-CF₃-5-methyl-benzoyl-(4-methylpiperazine) | H |

TABLE 6

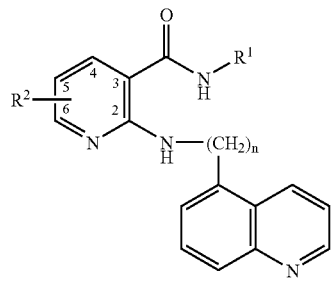

| # | R¹ | n | R² |
|---|---|---|---|
| 636. | 4-chlorophenyl | 1 | 6-F |
| 637. | 3,4-dichlorophenyl | 1 | H |
| 638. | 4-fluorophenyl | 1 | H |
| 639. | 3-chlorophenyl | 1 | H |
| 640. | 3-fluorophenyl | 1 | H |
| 641. | 3-fluoro-4-methoxyphenyl | 1 | H |
| 642. | 3-fluoro-4-methylphenyl | 2 | H |
| 643. | 4-phenoxyphenyl | 1 | H |
| 644. | 3-phenoxyphenyl | 1 | H |
| 645. | 4-biphenyl | 1 | H |
| 646. | 4-cyclohexylphenyl | 1 | H |
| 647. | 2-quinolyl | 1 | H |
| 648. | 3-isoquinolyl | 1 | H |
| 649. | 3-quinolyl | 1 | H |
| 650. | 1-isoquinolyl | 1 | H |
| 651. | 5-quinolyl | 1 | H |
| 652. | 5-isoquinolyl | 1 | H |
| 653. | 6-quinolyl | 1 | H |
| 654. | 6-isoquinolyl | 1 | H |
| 655. | 7-quinolyl | 1 | H |
| 656. | 7-isoquinolyl | 1 | H |
| 657. | 4-quinolyl | 1 | H |
| 658. | 4-isoquinolyl | 1 | H |
| 659. | 4-pyridyl | 1 | 6-F |
| 660. | 4-pyrimidinyl | 1 | H |
| 661. | 2-pyrimidinyl | 1 | H |
| 662. | 6-pyrimidinyl | 1 | H |
| 663. | 4-pyridazinyl | 1 | H |
| 664. | 5-pyridazinyl | 1 | H |
| 665. | 4-indolyl | 1 | H |
| 666. | 5-isoindolyl | 1 | H |
| 667. | 5-naphthyridinyl | 1 | H |
| 668. | 6-quinozalinyl | 1 | H |
| 669. | 6-isoquinolyl | 1 | H |
| 670. | 4-naphthyridinyl | 1 | H |
| 671. | 5-quinozalinyl | 1 | H |
| 672. | 4-naphthyridinyl | 1 | H |
| 673. | tetrahydroquinolinyl | 1 | H |
| 674. | 6-indazolyl | 1 | H |
| 675. | 6-isoindolyl | 1 | H |
| 676. | 5-indazolyl | 1 | H |
| 677. | 5-isoindolyl | 1 | H |
| 678. | 6-benzothienyl | 1 | H |
| 679. | 6-benzofuryl | 1 | H |
| 680. | 5-benzothienyl | 1 | H |
| 681. | 5-benzofuryl | 1 | H |
| 682. | 2-benzimidazolyl | 1 | H |
| 683. | 2-benzoxazolyl | 1 | H |
| 684. | 2-benzthiazolyl | 1 | H |
| 685. | 6-benzimidazolyl | 1 | H |
| 686. | 6-benzoxazolyl | 1 | H |
| 687. | 6-benzthiazolyl | 1 | H |
| 688. | 2-quinazolinyl | 1 | H |
| 689. | 3-(phenoxy)-6-pyridyl | 1 | H |
| 690. | 4-(phenylcarbonyl)phenyl | 1 | H |
| 691. | 4-(phenylamino)phenyl | 1 | H |
| 692. | cyclohexyloxyphenyl | 1 | H |
| 693. | 4-(3-thienyl)phenyl | 1 | H |
| 694. | 4-(pyrazol-3-yl)phenyl | 1 | 6-CH₃ |

TABLE 7

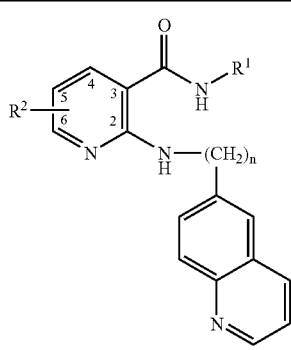

| # | R¹ | n | R² |
|---|---|---|---|
| 695. | 4-chlorophenyl | 1 | 6-Cl |
| 696. | 3,4-dichlorophenyl | 1 | 5-Cl |
| 697. | 4-fluorophenyl | 1 | H |
| 698. | 3-chlorophenyl | 1 | H |
| 699. | 3-fluorophenyl | 1 | H |
| 700. | 3-fluoro-4-methoxyphenyl | 1 | H |
| 701. | 3-fluoro-4-methylphenyl | 1 | H |
| 702. | 4-phenoxyphenyl | 1 | H |
| 703. | 3-phenoxyphenyl | 1 | H |
| 704. | 4-biphenyl | 1 | H |
| 705. | 4-cyclohexylphenyl | 1 | H |
| 706. | 2-quinolyl | 1 | H |
| 707. | 3-isoquinolyl | 1 | H |
| 708. | 3-quinolyl | 1 | H |
| 709. | 1-isoquinolyl | 1 | H |
| 710. | 5-quinolyl | 1 | H |
| 711. | 5-isoquinolyl | 1 | H |
| 712. | 6-quinolyl | 1 | H |
| 713. | 6-isoquinolyl | 1 | H |
| 714. | 7-quinolyl | 1 | H |
| 715. | 7-isoquinolyl | 1 | H |
| 716. | 4-quinolyl | 1 | H |
| 717. | 4-isoquinolyl | 1 | H |
| 718. | 4-pyridyl | 1 | H |
| 719. | 4-pyrimidinyl | 1 | H |
| 720. | 2-pyrimidinyl | 1 | H |
| 721. | 6-pyrimidinyl | 1 | H |
| 722. | 4-pyridazinyl | 1 | H |
| 723. | 5-pyridazinyl | 1 | H |
| 724. | 4-indolyl | 1 | H |
| 725. | 5-isoindolyl | 1 | H |
| 726. | 5-naphthyridinyl | 1 | H |
| 727. | 6-quinozalinyl | 1 | H |
| 728. | 6-isoquinolyl | 1 | H |
| 729. | 4-naphthyridinyl | 1 | H |
| 730. | 5-quinozalinyl | 1 | H |
| 731. | 4-naphthyridinyl | 1 | H |
| 732. | tetrahydroquinolinyl | 1 | H |
| 733. | 6-indazolyl | 1 | H |
| 734. | 6-isoindolyl | 1 | H |
| 735. | 5-indazolyl | 1 | H |
| 736. | 5-isoindolyl | 1 | H |
| 737. | 6-benzothienyl | 1 | H |
| 738. | 6-benzofuryl | 1 | H |
| 739. | 5-benzothienyl | 1 | H |
| 740. | 5-benzofuryl | 1 | H |

TABLE 8

| # | R¹ | n | R² |
|---|---|---|---|

Structure (for entries 741–755):

A nicotinamide core with R² at position 5/6, C(=O)NHR¹ at position 3, and NH—(CH₂)$_n$—(quinolin-6-yl) at position 2.

| # | R¹ | n | R² |
|---|---|---|---|
| 741. | 2-benzimidazolyl | 1 | H |
| 742. | 2-benzoxazolyl | 1 | H |
| 743. | 2-benzthiazolyl | 1 | H |
| 744. | 6-benzimidazolyl | 1 | H |
| 745. | 6-benzoxazolyl | 1 | H |
| 746. | 6-benzthiazolyl6-benzoxazolyl | 1 | H |
| 747. | 2-quinazolinyl6-benzoxazolyl | 1 | H |
| 748. | 3-(phenoxy)-6-pyridyl | 1 | H |
| 749. | 4-(phenylcarbonyl)phenyl | 1 | H |
| 750. | 4-(phenylamino)phenyl | 1 | H |
| 751. | cyclohexyloxyphenyl | 1 | H |
| 752. | 4-(3-thienyl)phenyl | 1 | H |
| 753. | 4-(pyrazol-3-yl)phenyl | 1 | H |
| 754. | 4-chlorophenyl | 1 | EtO₂CCH=CH— |
| 755. | 4-chlorophenyl | 1 | 5-Br |

Structure (for entries 756–817):

A nicotinamide core with R² at position 5/6, C(=O)NHR¹ at position 3, and NH—(CH₂)$_n$—(quinolin-4-yl) at position 2.

| # | R¹ | n | R² |
|---|---|---|---|
| 756. | 4-pyridyl | 1 | H |
| 757. | 4-pyridyl | 1 | H |
| 758. | 4-chlorophenyl | 1 | 6-F |
| 759. | 3,4-dichlorophenyl- | 1 | 6-CH₃ |
| 760. | 4-fluorophenyl | 1 | H |
| 761. | 3-chlorophenyl | 1 | H |
| 762. | 3-fluorophenyl | 1 | H |
| 763. | 3-fluoro-4-methoxyphenyl | 1 | H |
| 764. | 3-fluoro-4-methylphenyl | 1 | H |
| 765. | 4-phenoxyphenyl | 1 | H |
| 766. | 3-phenoxyphenyl | 1 | H |
| 767. | 4-biphenyl | 1 | H |
| 768. | 4-cyclohexylphenyl | 1 | H |
| 769. | 2-quinolyl | 1 | H |
| 770. | 3-isoquinolyl | 1 | H |
| 771. | 3-quinolyl | 1 | H |
| 772. | 1-isoquinolyl | 1 | H |
| 773. | 5-quinolyl | 1 | H |
| 774. | 5-isoquinolyl | 1 | H |
| 775. | 6-quinolyl | 1 | H |
| 776. | 6-isoquinolyl | 1 | H |
| 777. | 7-quinolyl | 1 | H |
| 778. | 7-isoquinolyl | 1 | H |
| 779. | 4-quinolyl | 1 | H |
| 780. | 4-isoquinolyl | 1 | H |
| 781. | 4-pyridyl | 1 | H |
| 782. | 4-pyrimidinyl | 1 | H |
| 783. | 2-pyrimidinyl | 1 | H |
| 784. | 6-pyrimidinyl | 1 | H |
| 785. | 4-pyridazinyl | 1 | H |
| 786. | 5-pyridazinyl | 1 | H |
| 787. | 4-indolyl | 1 | H |
| 788. | 5-isoindolyl | 1 | H |
| 789. | 5-naphthyridinyl | 1 | H |
| 790. | 6-quinozalinyl | 1 | H |
| 791. | 6-isoquinolyl | 1 | H |
| 792. | 4-naphthyridinyl | 1 | H |
| 793. | 5-quinozalinyl | 1 | H |
| 794. | 4-naphthyridinyl | 1 | H |
| 795. | 7-tetrahydroquinolinyl | 1 | H |
| 796. | 6-indazolyl | 1 | H |
| 797. | 6-isoindolyl | 1 | H |
| 798. | 5-indazolyl | 1 | H |
| 799. | 5-isoindolyl | 1 | H |
| 800. | 6-benzothienyl | 1 | H |
| 801. | 6-benzofuryl | 1 | H |
| 802. | 5-benzothienyl | 1 | H |
| 803. | 5-benzofuryl | 1 | H |
| 804. | 2-benzimidazolyl | 1 | H |
| 805. | 2-benzoxazolyl | 1 | H |
| 806. | 2-benzthiazolyl | 1 | H |
| 807. | 6-benzimidazolyl | 1 | H |
| 808. | 6-benzoxazolyl | 1 | H |
| 809. | 6-benzthiazolyl | 1 | H |
| 810. | 2-quinazolinyl | 1 | H |
| 811. | 3-(phenoxy)-6-pyridyl | 1 | H |
| 812. | 4-(phenylcarbonyl)phenyl | 1 | H |
| 813. | 4-(phenylamino)phenyl | 1 | H |
| 814. | 4-cyclohexyloxyphenyl | 1 | H |
| 815. | 4-(3-thienyl)phenyl | 1 | H |
| 816. | 4-(pyrazol-3-yl)phenyl | 1 | H |
| 817. | 3,4-dichlorophenyl | 1 | H |

TABLE 9

Structure: A nicotinamide core with R² at position 5/6, C(=O)NHR¹ at position 3, and NH—(CH₂)$_n$—(1,2,4-triazol-1-yl) at position 2.

| # | R¹ | n | R² |
|---|---|---|---|
| 818. | 4-chlorophenyl | 1 | 6-F |
| 819. | 3-fluoro-4-methoxyphenyl | 1 | H |
| 820. | 4-phenoxyphenyl | 1 | H |
| 821. | 4-biphenyl | 1 | H |
| 822. | 4-cyclohexyiphenyl | 1 | H |
| 823. | 2-quinolyl | 1 | H |
| 824. | 3-isoquinolyl | 1 | H |
| 825. | 3-quinolyl | 1 | H |

EXAMPLE 826

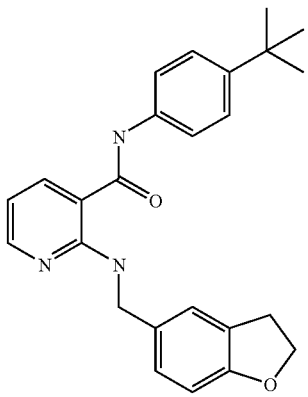

N-[4-(tert-Butyl)phenyl]{2-[(2,3-dihydrobenzo[b]furan-5-ylmethyl)amino](3-pyridyl)}carboxamide The titled compound was prepared from 2,3-dihydrobenzo[b]furan-5-ylmethylamine by the method described in Example 25. MS: (ES+) 402 (M+1)$^+$; (ES−) 400 (M−1)$^−$. Calc'd. for $C_{25}H_{27}N_3O_2$: 401.21.

EXAMPLE 827

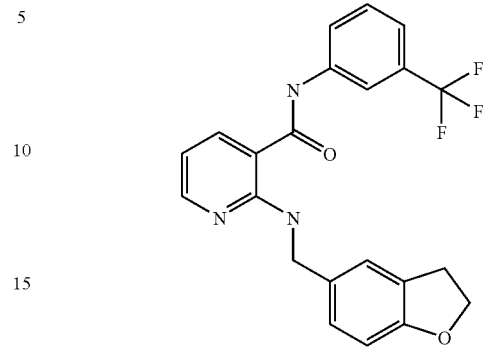

{2-[(2,3-Dihydrobenzo[b]furan-5-ylmethyl)amino](3-pyridyl)}-N-[3-(trifluoromethyl)phenyl]carboxamide The titled compound was prepared from 2,3-dihydrobenzo[b]furan-5-ylmethylamine by the method described in Example 25. MS: (ES+) 414 (M+1)$^+$; (ES−): 412 (M−1)$^−$. Calc'd. for $C_{22}H_{18}F_3N_3O_2$: 413.14.

The following compounds (Examples 828-864) were synthesized by the method described in Example 25 or Example 82 unless specifically described.

TABLE 10

| # | Y | R$^1$ | M+H | calc'd |
|---|---|---|---|---|
| 828. | —NH(CH$_2$)$_2$— | 4-tert-butylphenyl | 375 | 374.2 |
| 829. | —NH(CH$_2$)$_2$— | 4-sec-butylphenyl | 375 | 374.2 |
| 830. | —NH(CH$_2$)$_2$— | 4-phenoxyphenyl | 411 | 410.2 |
| 831. | —NH(CH$_2$)$_2$— | 3-(trifluoromethyl)phenyl | 387 | 386.1 |
| 832. | —NH(CH$_2$)$_2$— | 4-isopropylphenyl | 361 | 360.2 |

TABLE 10-continued

| # | Y | R¹ | M + H | calc'd |
|---|---|---|---|---|
| 833. | —NH(CH₂)₂— | 6-methyl-1-(1-methylpiperidin-4-yl)indoline | 457 | 456.6 |
| 834. | —NH(CH₂)₂— | 4-(1,1,2,2,2-pentafluoroethyl)phenyl | 437 | 436.4 |
| 835. | —NH(CH₂)₂— | 3,3,6-trimethyl-1-(1-methylpiperidin-4-yl)indoline | 485.3 | 484.7 |
| 836. | —NH(CH₂)₂— | 3,3,6-trimethylindoline | 388.3 | 387.5 |
| 837. | —NH(CH₂)₂— | 3,3,6-trimethyl-1-(piperidin-4-ylmethyl)indoline | 485.3 | 484.6 |
| 838. | —NH(CH₂)₂— | 3-methyl-5-(trifluoromethyl)phenyl linked via O to piperidin-4-yl | 486 | 485.5 |

TABLE 10-continued

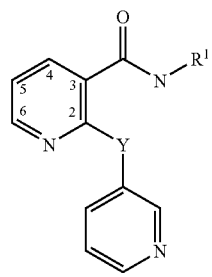

| # | Y | R¹ | M + H | calc'd |
|---|---|---|---|---|
| 839. | —NH(CH₂)₂— | 3-CF₃-5-methylphenyl-O-(1-Boc-piperidin-4-yl) | 586.4 | 585.6 |
| 840. | —NH(CH₂)₂— | 2-CF₂CF₃-5-methylphenyl-O-(CH₂)₂-piperidin-1-yl | 564 | 563.6 |
| 841. | —NH(CH₂)₂— | 2-CF₂CF₃-5-methylphenyl-O-CH₂-CH(OH)-CH₂-pyrrolidin-1-yl | 580 | 579.6 |
| 842. | —NH(CH₂)₂— | 2-CF₂CF₃-5-methylphenyl-O-CH₂-(1-methylpiperidin-4-yl) | 564 | 563.6 |
| 843. | —NH(CH₂)₂— | 3,3,6-trimethyl-1-((1-methylpiperidin-4-yl)methyl)indolin-? | 499.2 | 498.7 |
| 844. | —NH(CH₂)₂— | 3-CF₃-5-methylphenyl-(CH₂)₃-piperidin-1-yl | 512.1 | 511.6 |
| 845. | —NH(CH₂)₂— | 3-CF₃-5-methylphenyl-CH₂-(1-methylpiperidin-4-yl) | | 497.6 |
| 846. | —NHCH₂—CH(4-morpholino) | 4-methylphenyl-CF₂CF₃ | | 521.5 |

TABLE 10-continued
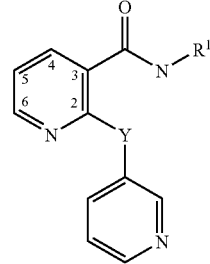
| # | Y | R¹ | M + H | calc'd |
|---|---|---|---|---|
| 847. | —NH(CH$_2$)$_2$— | 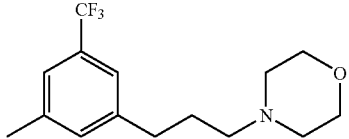 | 514 | 513.6 |
| 848. | —NH(CH$_2$)$_2$— | 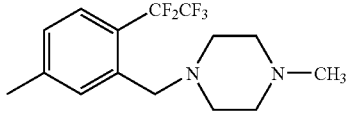 | | 548.6 |
| 849. | —NH(CH$_2$)$_2$— | 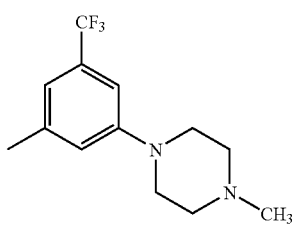 | 484.1 | 483.2 |
| 850. | —NH(CH$_2$)$_2$— | 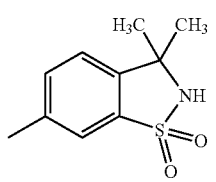 | 438 | 437 |
| 851. | —NH(CH$_2$)$_2$— | 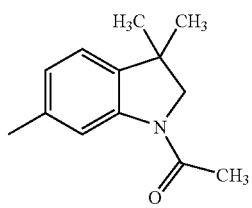 | 430.2 | 429.5 |
| 852. | —NH(CH$_2$)$_2$— | 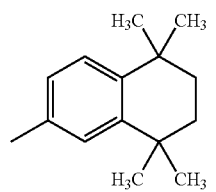 | 429 | 428.6 |

TABLE 10-continued
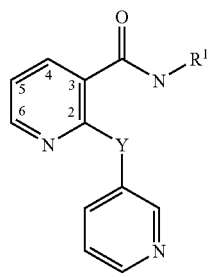
| # | Y | R¹ | M + H | calc'd |
|---|---|---|---|---|
| 853. | —NH(CH₂)₂— | 3-CF₃, 5-methyl benzoyl piperazine | | 498.5 |
| 854. | —NH(CH₂)₂— | 3-CF₃, 5-methyl benzoyl piperazine-NBOC | 599 | 598.6 |
| 855. | —NH(CH₂)₂— | 3,3,6-trimethyl-1-(piperidin-4-yl)indoline | 471.3 | 470.7 |
| 856. | —NH(CH₂)₂— | 4-methylphenyl dimethyl 1-methylpiperidin-4-yl | 458 | 457.3 |
| 857. | —NH(CH₂)₂— | 2,2,4,6-tetramethyl-3,4-dihydro-2H-benzo[b][1,4]oxazine | 418.1 | 417.2 |
| 858. | —NH(CH₂)₂— | 4,4,7-trimethyl-1,2,3,4-tetrahydroquinoline | 402 | 401.1 |

TABLE 10-continued
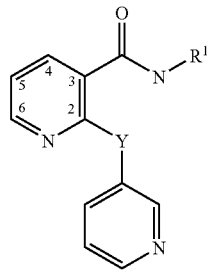
| # | Y | R¹ | M + H | calc'd |
|---|---|---|---|---|
| 859. | —NH(CH₂)₂— | | 445.9 | 445.5 |
| 860. | —NH(CH₂)₂— | | 432.1 | 431.5 |
| 861. | —NH(CH₂)₂— | | 472.0 | 471.2 |
| 862. | —NH(CH₂)₂— | | 416.3 | 415.2 |
| 863. | —NH(CH₂)₂— | | 403.1 | 402.1 |
| 864. | —NH(CH₂)₂— | | 472.1 | 471.2 |

EXAMPLE 865

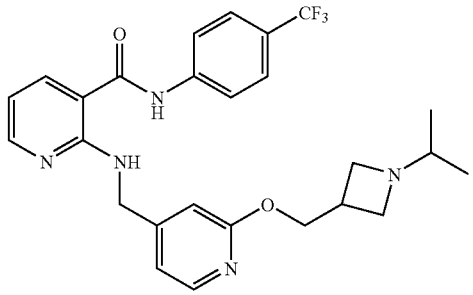

2-{[2-(1-Isopropyl-azetidin-3-ylmethoxy)-pyridin-4-ylmethyl]-amino}-N-(4-trifluoromethyl-phenyl)-nicotinamide A solution of 2-fluoro-N-(4-trifluoromethyl-phenyl)-nicotinamide (107 mg) and [2-(1-isopropyl-azetidin-3-ylmethoxy)-pyridin-4-yl]-methylamine (89 mg) and NaHCO$_3$ (95 mg) was dissolved in IpOH (10 ml) and heated to 80° C. for 18 h. After cooling to RT, the mixture was diluted with EtOAc (50 ml) forming a precipitate which was filtered. The filtrate was concentrated in vacuo. The residue was purified by silica gel column chromatography (20% (12 N NH$_3$/MeOH)/EtOAc) to give the product as a light yellow oil. M+H 500.1; Calc'd 499.2.

The following compounds (Example 866-939) were synthesized by the method described above.

866) N-(4-tert-Butyl-phenyl)-2-{[2-(1-isopropyl-azetidin-3-ylmethoxy)-pyridin-4-ylmethyl]-amino}-nicotinamide. M+H 488.1; Calc'd–487.3
867) 2-[(2,3-Dihydro-benzofuran-5-ylmethyl)-amino]-N-{4-[1-methyl-1-(1-methyl-piperidin-4-yl)-ethyl]-phenyl}-nicotinamide. M+H 485.3; Calc'd 484.6.
868) N-(1-Acetyl-3,3-dimethyl-2,3-dihydro-1H-indol-6-yl)-2-[(2,3-dihydro-benzofuran-5-ylmethyl)-amino]-nicotinamide. M+H 457.1; Calc'd 456.5.
869) 2-[(2,3-Dihydro-benzofuran-5-ylmethyl)-amino]-N-[3,3-dimethyl-1-(1-Boc-piperidin-4-ylmethyl)-2,3-dihydro-1H-indol-6-yl]-nicotinamide. M+H 612.6; Calc'd 611.8.
870) 2-[(2,3-Dihydro-benzofuran-5-ylmethyl)-amino]-N-[3,3-dimethyl-1-(1-methylpiperidin-4-ylmethyl)-2,3-dihydro-1H-indol-6-yl]-nicotinamide. M+H 526.3; Calc'd 525.7.
871) N-(1-Acetyl-3,3-dimethyl-2,3-dihydro-1H-indol-6-yl)-2-({2-[2-(1-methyl-piperidin-4-yl)-ethoxy]-pyridin-4-ylmethyl}-amino)-nicotinamide. M+H Calc'd 556.
872) 2-({2-[2-(1-Methyl-piperidin-4-yl)-ethoxy]-pyridin-4-ylmethyl}-amino)-N-(3-trifluoromethyl-phenyl)-nicotinamide. M+H Calc'd 513.
873) N-(4-tert-Butyl-phenyl)-2-{[2-ethylpyridin-4-ylmethyl]-amino}-nicotinamide.
874) N-(4-tert-Butyl-phenyl)-2-({2-[2-(1-methyl-pyrrolidin-2-yl)-ethoxy]-pyridin-4-ylmethyl}-amino)-nicotinamide. M+H Calc'd 487.
875) 2-({2-[2-(1-Methyl-pyrrolidin-2-yl)-ethoxy]-pyridin-4-ylmethyl}-amino)-N-(4-pentafluoroethyl-phenyl)-nicotinamide. M+H Calc'd 549.
876) N-(4-Pentafluoroethyl-phenyl)-2-{[2-(2-pyrrolidin-1-yl-ethoxy)-pyridin-4-ylmethyl]-amino}-nicotinamide. M+H Calc'd 535.
877) N-(4-tert-Butyl-phenyl)-2-{[2-(2-pyrrolidin-1-yl-ethoxy)-pyridin-4-ylmethyl]-amino}-nicotinamide. M+H Calc'd 473.
878) N-[3-(4-Boc-piperazin-1-ylmethyl)-5-trifluoromethyl-phenyl]-2-[(pyridin-4-ylmethyl)-amino]-nicotinamide. M+H 571.4; Calc'd 570.3.
879) N-[3-(4-Boc-piperazine-1-carbonyl)-5-trifluoromethyl-phenyl]-2-[(pyridin-4-ylmethyl)-amino]-nicotinamide. M+H Calc'd 584.
880) N-[3-(4-Boc-piperazine-1-carbonyl)-5-trifluoromethyl-phenyl]-2-(2-pyridin-4-yl-ethylamino)-nicotinamide. M+H Calc'd 598.
881) N-[3-(4-Methyl-piperazin-1-ylmethyl)-4-pentafluoroethyl-phenyl]-2-[(pyridin-4-ylmethyl)-amino]-nicotinamide. M+H Calc'd 534.
882) N-[3-(4-Boc-piperazin-1-ylmethyl)-4-pentafluoroethyl-phenyl]-2-[(pyridin-4-ylmethyl)-amino]-nicotinamide. M+H 621.4; Calc'd 620.
883) 2-{[2-(1-Methyl-piperidin-4-ylmethoxy)-pyridin-4-ylmethyl]-amino}-N-(4-trifluoromethyl-phenyl)-nicotinamide.
884) N-(4-tert-Butyl-phenyl)-2-{[2-(1-methyl-piperidin-4-ylmethoxy)-pyridin-4-ylmethyl]-amino}-nicotinamide.
885) 2-({2-[3-(1-Methyl-piperidin-4-yl)-propoxy]-pyridin-4-ylmethyl}-amino)-N-(4-pentafluoroethyl-phenyl)-nicotinamide. M+H 578.3. Calc'd 577.2.
886) N-(1-Acetyl-3,3-dimethyl-2,3-dihydro-1H-indol-6-yl)-2-[(2-methoxy-pyridin-4-ylmethyl)-amino]-nicotinamide.
887) N-[3,3-Dimethyl-1-(1-methyl-piperidin-4-yl)-2,3-dihydro-1H-indol-6-yl]-2-[(2-methoxy-pyridin-4-ylmethyl)-amino]-nicotinamide. M+H 501.2; Calc'd 500.3.
888) N-(1-Boc-3,3-dimethyl-2,3-dihydro-1H-indol-6-yl)-2-[(2-methoxy-pyridin-4-ylmethyl)-amino]-nicotinamide.
889) N-[3,3-Dimethyl-1-(1-Boc-piperidin-4-ylmethyl)-2,3-dihydro-1H-indol-6-yl]-2-[(2-methoxy-pyridin-4-ylmethyl)-amino]-nicotinamide. M+H 601.6; Calc'd 600.34.
890) N-[3,3-Dimethyl-1-(1-methyl-piperidin-4-yl)-2,3-dihydro-1H-indol-6-yl]-2-[(pyridin-4-ylmethyl)-amino]-nicotinamide.
891) N-[1-(2-Dimethylamino-acetyl)-3,3-dimethyl-2,3-dihydro-1H-indol-6-yl]-2-[(2-methoxy-pyridin-4-ylmethyl)-amino]-nicotinamide.
892) N-[1-(2-Dimethylamino-acetyl)-3,3-dimethyl-2,3-dihydro-1H-indol-6-yl]-2-[(pyridin-4-ylmethyl)-amino]-nicotinamide.
893) 2-[(2-Methoxy-pyridin-4-ylmethyl)-amino]-N-[3-(1-Boc-piperidin-4-ylmethoxy)-5-trifluoromethyl-phenyl]-nicotinamide
894) N-[3,3-Dimethyl-1-(1-Boc-pyrrolidin-2-ylmethoxy)-2,3-dihydro-1H-indol-6-yl]-2-[(2-methoxy-pyridin-4-ylmethyl)-amino]-nicotinamide.
895) N-[3,3-Dimethyl-1-(2-Boc-amino-acetyl)-2,3-dihydro-1H-indol-6-yl]-2-[(2-methoxy-pyridin-4-ylmethyl)-amino]-nicotinamide.
896) N-[3,3-Dimethyl-1-(2-Boc-amino-acetyl)-2,3-dihydro-1H-indol-6-yl]-2-[(pyridin-4-ylmethyl)-amino]-nicotinamide.
897) 2-[(2-Methoxy-pyridin-4-ylmethyl)-amino]-N-[3-(1-methyl-pyrrolidin-2-ylmethoxy)-5-trifluoromethyl-phenyl]-nicotinamide. M+H 516.1.
898) 2-[(2-Methoxy-pyridin-4-ylmethyl)-amino]-N-[3-(1-Boc-piperidin-4-ylmethyl)-5-trifluoromethyl-phenyl]-nicotinamide. M+H 501.3.
899) 2-[(2-Methoxy-pyridin-4-ylmethyl)-amino]-N-[3-(4-Boc-piperazin-1-ylmethyl)-5-trifluoromethyl-phenyl]-nicotinamide.

900) 2-{[2-(3-Morpholin-4-yl-propoxy)-pyridin-4-ylmethyl]-amino}-N-(4-pentafluoroethyl-phenyl)-nicotinamide. M+H 566.
901) (S) 2-{[2-(1-Methyl-pyrrolidin-2-ylmethoxy)-pyridin-4-ylmethyl]-amino}-N-(4-pentafluoroethyl-phenyl)-nicotinamide. M+H 536.
902) N-(3-tert-Butyl-isoxazol-5-yl)-2-{[2-(3-morpholin-4-yl-propoxy)-pyridin-4-ylmethyl]-amino}-nicotinamide. M+H 495. Calc'd 494.
903) N-(1-Acetyl-3,3-dimethyl-2,3-dihydro-1H-indol-6-yl)-2-{[2-(3-morpholin-4-yl-propylamino)-pyridin-4-ylmethyl]-amino}-nicotinamide. M+H 558; Calc'd 557.
904) N-(4-tert-Butyl-phenyl)-2-{[2-(3-morpholin-4-yl-propoxy)-pyridin-4-ylmethyl]-amino}-nicotinamide. M+H 504. Calc'd 503.
905) N-(4-tert-Butyl-phenyl)-2-{[2-(2-morpholin-4-yl-ethoxy)-pyridin-4-ylmethyl]-amino}-nicotinamide. M+H 409; Calc'd 489.
906) 2-{[2-(2-Morpholin-4-yl-ethoxy)-pyridin-4-ylmethyl]-amino}-N-(4-trifluoromethyl-phenyl)-nicotinamide. M+H 502; Calc'd 501.
907) 2-{[2-(2-Morpholin-4-yl-ethoxy)-pyridin-4-ylmethyl]-amino}-N-(3-trifluoromethyl-phenyl)-nicotinamide. M+H 502; Calc'd 501.
908) 2-{[2-(2-Morpholin-4-yl-ethoxy)-pyridin-4-ylmethyl]-amino}-N-(4-pentafluoroethyl-phenyl)-nicotinamide. M+H 552; Calc'd 551.
909) N-(3-tert-Butyl-isoxazol-5-yl)-2-{[2-(2-morpholin-4-yl-ethoxy)-pyridin-4-ylmethyl]-amino}-nicotinamide. M+H 481; Calc'd 480.
910) N-(1-Acetyl-3,3-dimethyl-2,3-dihydro-1H-indol-6-yl)-2-{[2-(2-morpholin-4-yl-ethoxy)-pyridin-4-ylmethyl]-amino}-nicotinamide. M+H 545; Calc'd 544.
911) N-(1-Acetyl-3,3-dimethyl-2,3-dihydro-1H-indol-6-yl)-2-{[2-(1-methyl-piperidin-4-yloxy)-pyridin-4-ylmethyl]-amino}-nicotinamide.
912) 2-{[2-(1-Methyl-piperidin-4-yloxy)-pyridin-4-ylmethyl]-amino}-N-(4-trifluoromethyl-phenyl)-nicotinamide.
913) 2-{[2-(1-Methyl-piperidin-4-yloxy)-pyridin-4-ylmethyl]-amino}-N-(4-pentafluoroethyl-phenyl)-nicotinamide.
914) 2-{[2-(1-Methyl-piperidin-4-yloxy)-pyridin-4-ylmethyl]-amino}-N-(4-tert-butyl-phenyl)-nicotinamide.
915) (R)N-(4-tert-Butyl-phenyl)-2-{[2-(1-methyl-pyrrolidin-2-ylmethoxy)-pyridin-4-ylmethyl]-amino}-nicotinamide. M+H 474; Calc'd 473.
916) (R)N-[3-(1-Boc-pyrrolidin-2-ylmethoxy)-5-trifluoromethyl-phenyl]-2-[(pyridin-4-ylmethyl)-amino]-nicotinamide.
917) (R)N-[3-(1-Methyl-pyrrolidin-2-ylmethoxy)-5-trifluoromethyl-phenyl]-2-[(pyridin-4-ylmethyl)-amino]-nicotinamide. M+H 486; Calc'd 485.5.
918) N-[3-(1-Methyl-piperidin-4-yloxy)-5-trifluoromethyl-phenyl]-2-[(pyridin-4-ylmethyl)-amino]-nicotinamide.
919) N-[3-(1-Methyl-piperidin-4-ylmethyl)-5-trifluoromethyl-phenyl]-2-[(pyridin-4-ylmethyl)-amino]-nicotinamide.
920) N-[4-tert-Butyl-3-(1-Boc-pyrrolidin-2-ylmethoxy)-phenyl]-2-[(pyridin-4-ylmethyl)-amino]-nicotinamide. M+H 560; Calc'd 559.
921) N-(3,3-Dimethyl-2,3-dihydro-benzofuran-6-yl)-2-{[2-(1-methyl-piperidin-4-ylmethoxy)-pyridin-4-ylmethyl]-amino}-nicotinamide.
922) 2-({2-[3-(1-Methyl-piperidin-4-yl)-propoxy]-pyridin-4-ylmethyl}-amino)-N-(4-trifluoromethyl-phenyl)-nicotinamide.
923) 2-({2-[3-(1-Methyl-piperidin-4-yl)-propoxy]-pyridin-4-ylmethyl}-amino)-N-(3-trifluoromethyl-phenyl)-nicotinamide.
924) 2-({2-[3-(1-Methyl-piperidin-4-yl)-propoxy]-pyridin-4-ylmethyl}-amino)-N-(4-tert-butyl-phenyl)-nicotinamide.
925) 2-({2-[3-(1-Methyl-piperidin-4-yl)-propoxy]-pyridin-4-ylmethyl}-amino)-N-(3-tert-butyl-isoxazol-5-yl)-nicotinamide.
926) N-(3,3-Dimethyl-2,3-dihydro-1H-indol-6-yl)-2-({2-[3-(1-methyl-piperidin-4-yl)-propoxy]-pyridin-4-ylmethyl}-amino)-nicotinamide.
927) 2-[(Pyridin-4-ylmethyl)-amino]-N-(3,9,9-trimethyl-2,3,4,4a,9,9a-hexahydro-1H-3-aza-fluoren-6-yl)-nicotinamide.
928) N-[3,3-Dimethyl-1-(1-Boc-piperidin-4-ylmethyl)-2,3-dihydro-1H-indol-6-yl]-2-[(pyridin-4-ylmethyl)-amino]-nicotinamide
929) N-[3,3-Dimethyl-1-(1-methyl-piperidin-4-ylmethyl)-2,3-dihydro-1H-indol-6-yl]-2-[(pyridin-4-ylmethyl)-amino]-nicotinamide. M+H 485.3; Calc'd 484.6.

The following compounds (Example 930-937) were synthesized by the method described above, substituting $K_2CO_3$ for $NaHCO_3$—

930) 2-{[2-(1-Methyl-piperidin-4-ylmethoxy)-pyridin-4-ylmethyl]-amino}-N-(4-pentafluoroethyl-phenyl)-nicotinamide. M+H 550.2; Calc'd 549.2.
932) N-(1-Acetyl-3,3-dimethyl-2,3-dihydro-1H-indol-6-yl)-2-{[2-(1-methyl-piperidin-4-ylmethoxy)-pyridin-4-ylmethyl]-amino}-nicotinamide. M+H 543.4; Calc'd 542.3.
933) N-(4-tert-Butyl-phenyl)-2-{[2-(3-morpholin-4-yl-propylamino)-pyrimidin-4-ylmethyl]-amino}-nicotinamide. M+H 504.3; Calc'd 503.6.
934) 2-{[2-(3-Morpholin-4-yl-propylamino)-pyrimidin-4-ylmethyl]-amino}-N-(4-pentafluoroethyl-phenyl)-nicotinamide. M+H 566.3; Calc'd 565.55.
935) 2-{[2-(3-Morpholin-4-yl-propylamino)-pyrimidin-4-ylmethyl]-amino}-N-(3-trifluoromethyl-phenyl)-nicotinamide. M+H 516.0; Calc'd 515.5.
936) N-(4-tert-Butyl-phenyl)-2-({2-[2-(1-methyl-pyrrolidin-2-yl)-ethylamino]-pyrimidin-4-ylmethyl}-amino)-nicotinamide. M+H Calc'd 487.6.
937) N-(1-Acetyl-3,3-dimethyl-2,3-dihydro-1H-indol-6-yl)-2-({2-[2-(1-methyl-pyrrolidin-2-yl)-ethylamino]-pyrimidin-4-ylmethyl}-amino)-nicotinamide. M+H Calc'd 542.69.

The following compounds (Example 938-939) were synthesized by the method described above, substituting $Cs_2CO_3$ for $NaHCO_3$—

938) 2-{[2-(1-Methyl-piperidin-4-ylmethoxy)-pyridin-4-ylmethyl]-amino}-N-[3-(1-methyl-piperidin-4-yl)-5-trifluoromethyl-phenyl]-nicotinamide. M H 597.0; Calc'd 596.7.
939) N-(3-tert-Butyl-isoxazol-5-yl)-2-{[2-(1-methyl-piperidin-4-ylmethoxy)-pyridin-4-ylmethyl]-amino}-nicotinamide. M+H 479; Calc'd 478.3.

The following compounds (Example 940-945) were synthesized by the method described above, substituting t-BuOH for IpOH.

940) N-[3-(1-Boc-azetidin-3-ylmethoxy)-5-trifluoromethyl-phenyl]-2-[(pyridin-4-ylmethyl)-amino]-nicotinamide. M+H 558.1. Calc'd 557.6.
941) 2-[(2-Methoxy-pyridin-4-ylmethyl)-amino]-N-[3-(1-Boc-azetidin-3-ylmethoxy)-5-trifluoromethyl-phenyl]-nicotinamide. M+H 588.1. Calc'd 587.2.

942) 2-[(Pyridin-4-ylmethyl)-amino]-N-(2,2,4-trimethyl-3,4-dihydro-2H-benzo[1,4]oxazin-6-yl)-nicotinamide. M+H 404.5; Calc'd 403.2.

943) N-(4-Acetyl-2,2-dimethyl-3,4-dihydro-2H-benzo[1,4]oxazin-6-yl)-2-[(pyridin-4-ylmethyl)-amino]-nicotinamide. M+H 432.1; Calc'd 431.5.

944) N-(2,2-Dimethyl-3-oxo-3,4-dihydro-2H-benzo[1,4]oxazin-6-yl)-2-[(pyridin-4-ylmethyl)-amino]-nicotinamide. M+H 404.5; Calc'd 403.2.

945) 2-{[2-(1-Benzhydryl-azetidin-3-yloxy)-pyridin-4-ylmethyl]-amino}-N-(4-tert-butyl-phenyl)-nicotinamide. M+H 598.4; Calc'd 597.3.

The following compounds (Example 946-993) were synthesized by the method described above, unless specifically described.

946) N-(4,4-Dimethyl-1-oxo-1,2,3,4-tetrahydro-isoquinolin-7-yl)-2-[(pyridin-4-ylmethyl)-amino]-nicotinamide was prepared with MeOH as the solvent at 110° C. M+H 402.3.

947) N-(4-tert-Butyl-phenyl)-2-({2-[2-(1-methyl-piperidin-4-yl)-ethoxy]-pyridin-4-ylmethyl}-amino)-nicotinamide was prepared with pentanol at 95° C. M+H Calc'd 501.

948) N-(3-tert-Butyl-isoxazol-5-yl)-2-({2-[2-(1-methyl-piperidin-4-yl)-ethoxy]-pyridin-4-ylmethyl}-amino)-nicotinamide was prepared with pyridine at 95° C. M+H Calc'd 492.

949) N-(3-trifluoromethylphenyl)-2-({2-[2-(1-methyl-piperidin-4-yl)-ethoxy]-pyridin-4-ylmethyl}-amino)-nicotinamide was prepared with pyridine at 95° C. M+H Calc'd 513.

950) 2-[(2,3-Dihydro-benzofuran-6-ylmethyl)-amino]-N-[3-(1-Boc-pyrrolidin-2-ylmethoxy)-4-pentafluoroethyl-phenyl]-nicotinamide was prepared with DIEA at 120° C. M+H 663.4; Calc'd 662.6.

951) (R)N-[3-(2-Hydroxy-3-pyrrolidin-1-yl-propoxy)-4-pentafluoroethyl-phenyl]-2-[(pyridin-4-ylmethyl)-amino]-nicotinamide was prepared with IpOH as the solvent at 135° C. M+H 566.5; Calc'd 565.5.

952) (S)N-[3-(2-Hydroxy-3-pyrrolidin-1-yl-propoxy)-4-pentafluoroethyl-phenyl]-2-[(pyridin-4-ylmethyl)-amino]-nicotinamide was prepared with IpOH as the solvent at 135° C. M+H 566.5; Calc'd 565.5.

953) N-[4-tert-Butyl-3-(1-methyl-piperidin-4-ylmethoxy)-phenyl]-2-[(pyridin-4-ylmethyl)-amino]-nicotinamide was prepared with IpOH as the solvent at 130° C. M+H 488.3; Calc'd 487.6.

954) N-[3-(1-Methyl-piperidin-4-ylmethoxy)-4-pentafluoroethyl-phenyl]-2-[(pyridin-4-ylmethyl)-amino]-nicotinamide was prepared with IpOH as the solvent at 135° C. M+H 550.2; Calc'd 549.5.

955) N-[4-Pentafluoroethyl-3-(2-piperidin-1-yl-ethoxy)-phenyl]-2-[(pyridin-4-ylmethyl)-amino]-nicotinamide was prepared with IpOH as the solvent at 130° C. M+H 550.1; Calc'd 549.5.

956) N-[4-Trifluoromethyl-3-(2-piperidin-1-yl-ethoxy)-phenyl]-2-[(pyridin-4-ylmethyl)-amino]-nicotinamide was prepared with IpOH as the solvent at 130° C. M+H 486.3; Calc'd 485.5.

957) (S)N-[3-(1-Boc-pyrrolidin-2-ylmethoxy)-4-pentafluoroethyl-phenyl]-2-[(pyridin-4-ylmethyl)-amino]-nicotinamide was prepared with DIEA at 135° C. M+H 572. Calc'd 571.6.

958) (R)N-[3-(1-Boc-pyrrolidin-2-ylmethoxy)-4-trifluoromethyl-phenyl]-2-[(pyridin-4-ylmethyl)-amino]-nicotinamide was prepared with DIEA at 130° C. M+H 622. Calc'd 621.6.

959) (R)N-[3-(1-Boc-pyrrolidin-2-ylmethoxy)-4-pentafluoroethyl-phenyl]-2-[(pyridin-4-ylmethyl)-amino]-nicotinamide was prepared with DIEA at 130° C. M+H 622.4. Calc'd 621.6.

960) N-(4-tert-Butyl-phenyl)-2-{[2-(1-methyl-piperidin-4-yloxy)-pyridin-4-ylmethyl]-amino}-nicotinamide was prepared with pyridine and TEA at 90° C. M+H 474.

961) N-(3-Trifluoromethyl-phenyl)-2-{[2-(1-methyl-piperidin-4-yloxy)-pyridin-4-ylmethyl]-amino}-nicotinamide was prepared with pyridine and TEA at 90° C. M+H 486.

962) N-(3-tert-Butyl-isoxazol-5-yl)-2-{[2-(1-methyl-piperidin-4-yloxy)-pyridin-4-ylmethyl]-amino}-nicotinamide was prepared with pyridine and TEA at 90° C. M+H 465.

963) N-[3-(3-Piperidin-1-yl-propyl)-5-trifluoromethyl-phenyl]-2-[(pyridin-4-ylmethyl)-amino]-nicotinamide was prepared with pyridine at 90° C. M+H 498; Calc'd 497.6.

964) N-[3-(3-Morpholin-4-yl-propyl)-5-trifluoromethyl-phenyl]-2-[(pyridin-4-ylmethyl)-amino]-nicotinamide was prepared at 130° C. neat. M+H 500. Calc'd 499.2.

965) 2-[(2-Methoxy-pyridin-4-ylmethyl)-amino]-N-[3-(1-Boc-piperidin-4-yloxy)-5-trifluoromethyl-phenyl]-nicotinamide was prepared at 130° C. neat. M+H 602. Calc'd for $C_{30}H_{34}F_3N_5O_5$: 601.6.

967) N-{4-tert-Butyl-3-[2-(1-Boc-piperidin-4-yl)-ethoxy]-phenyl}-2-[(pyridin-4-ylmethyl)-amino]-nicotinamide was prepared with DIEA and IpOH at 130° C. M+H 574.6.

968) N-[4-tert-Butyl-3-(1-methyl-azetidin-3-ylmethoxy)-phenyl]-2-[(pyridin-4-ylmethyl)-amino]-nicotinamide was prepared with IpOH and DIEA at 130° C. M+H 546.

969) N-(3,3-Dimethyl-1,1-dioxo-2,3-dihydro-1H-1λ-benzo[d]isothiazol-6-yl)-2-[(pyridin-4-ylmethyl)-amino]-nicotinamide was prepared neat at 130° C. M+H 424; Calc'd 423.

970) N-[1,1,4,4-Tetramethyl-1,2,3,4-tetrahydro-naphth-6-yl]-2-[(pyridin-4-ylmethyl)-amino]-nicotinamide was prepared neat at 130° C. M+H 415; Calc'd 414.

971) N-{4-[1-Methyl-1-(1-methyl-piperidin-4-yl)-ethyl]-phenyl}-2-[(pyridin-4-ylmethyl)-amino]-nicotinamide was prepared with pyridine. M+H 444; Calc'd 443.27.

972) 2-[(2-Methoxy-pyridin-4-ylmethyl)-amino]-N-{4-[1-methyl-1-(1-methyl-piperidin-4-yl)-ethyl]-phenyl}-nicotinamide was prepared with pyridine and NaHCO$_3$ at 110° C. MS: 473 (M+H), Calc'd for $C_{28}H_{35}N_5O_2$—472.6.

973) N-(3,3-Dimethyl-2,3-dihydro-benzofuran-6-yl)-2-[(pyridin-4-ylmethyl)-amino]-nicotinamide was prepared with IpOH at 120° C. M+H 375. Calc'd for $C_{27}H_{32}N_6O$: 374.

974) 2-{[2-(3-Dimethylamino-propoxy)-pyridin-4-ylmethyl]-amino}-N-(4-pentafluoroethyl-phenyl)-nicotinamide. M+H 524; Calc'd 523.2.

975) N-[3-(1-Methyl-piperidin-4-yl)-5-trifluoromethyl-phenyl]-2-[(pyridin-4-ylmethyl)-amino]-nicotinamide. M+H 470.4; Calc'd 469.21.

976) 2-{[2-(1-Methyl-piperidin-4-ylmethoxy)-pyridin-4-ylmethyl]-amino}-N-[3-(1-methyl-piperidin-4-yl)-5-trifluoromethyl-phenyl]-nicotinamide. M+H 597.0; Calc'd 596.31.

977) N-[3-(azetidin-3-ylmethoxy)-5-trifluoromethyl-phenyl]-2-[(pyridin-4-ylmethyl)-amino]-nicotinamide. M+H 458.1; Calc'd 457.2.

978) N-(3-Hydroxy-5-trifluoromethyl-phenyl)-2-[(pyridin-4-ylmethyl)-amino]-nicotinamide. M+H 388.9; Calc'd 388.11.

979) N-(2-Acetyl-4,4-dimethyl-1,2,3,4-tetrahydro-isoquinolin-7-yl)-2-[(pyridin-4-ylmethyl)-amino]-nicotinamide. M+H 430; Calc'd 429.22.

980) N-[2-(4-methoxy-benzyl)-4,4-dimethyl-1-oxo-1,2,3,4-tetrahydro-isoquinolin-7-yl]-2-[(pyridin-4-ylmethyl)-amino]-nicotinamide. M+H 522.3; Calc'd 521.24.

981) N-(2-Acetyl-4,4-dimethyl-1,2,3,4-tetrahydro-isoquinolin-7-yl)-2-[(quinolin-4-ylmethyl)-amino]-benzamide. M+H 479; Calc'd 478.24.

982) 2-[(Pyridin-4-ylmethyl)-amino]-N-[3-(2-pyrrolidin-1-yl-ethoxy)-4-trifluoromethyl-phenyl]-nicotinamide. M+H 486; Calc'd 485.

983) 2-{[2-(1-Methyl-piperidin-4-ylmethoxy)-pyridin-4-ylmethyl]-amino}-N-(3-trifluoromethyl-phenyl)-nicotinamide. M+H 500.5; Calc'd 499.5.

984) N-[3-(1-Boc-azetidin-3-ylmethoxy)-4-tert-butyl-phenyl]-2-[(pyridin-4-ylmethyl)-amino]-nicotinamide. M+H 546. Calc'd 545.

985) 2-Methyl-2-[4-({2-[(pyridin-4-ylmethyl)-amino]-pyridine-3-carbonyl}-amino)-phenyl]-propionic acid methyl ester. M+H 405; Calc'd 404.

986) N-(4-tert-Butyl-phenyl)-2-{[2-(3-morpholin-4-yl-propylamino)-pyrimidin-4-ylmethyl]-amino}-nicotinamide. M+H 504.3; Calc'd 503.

987) N-(4-pentafluoroethyl-phenyl)-2-{[2-(3-morpholin-4-yl-propylamino)-pyrimidin-4-ylmethyl]-amino}-nicotinamide. M+H 566.3; Calc'd 565.

988) N-(4-trifluoromethyl-phenyl)-2-{[2-(3-morpholin-4-yl-propylamino)-pyrimidin-4-ylmethyl]-amino}-nicotinamide. M+H 516.0; Calc'd 515.

989) N-(4-tert-Butyl-phenyl)-2-({2-[2-(1-methyl-pyrrolidin-2-yl)-ethylamino]-pyrimidin-4-ylmethyl}-amino)-nicotinamide. M+H 488.4; Calc'd 487.

990) N-(1-Acetyl-3,3-dimethyl-2,3-dihydro-1H-indol-6-yl)-2-({2-[2-(1-methyl-pyrrolidin-2-yl)-ethylamino]-pyrimidin-4-ylmethyl}-amino)-nicotinamide. M+H 543.5; Calc'd 542.

991) N-(1-Acetyl-3,3-dimethyl-2,3-dihydro-1H-indol-6-yl)-2-(2,3-dihydro-benzo[1,4]dioxin-6-ylamino)-nicotinamide. M+H 459.3.

992) 2-({2-[2-(1-Methyl-pyrrolidin-2-yl)-ethylamino]-pyrimidin-4-ylmethyl}-amino)-N-(3-trifluoromethyl-phenyl)-nicotinamide. M+H 500.4; Calc'd 499.

EXAMPLE 993

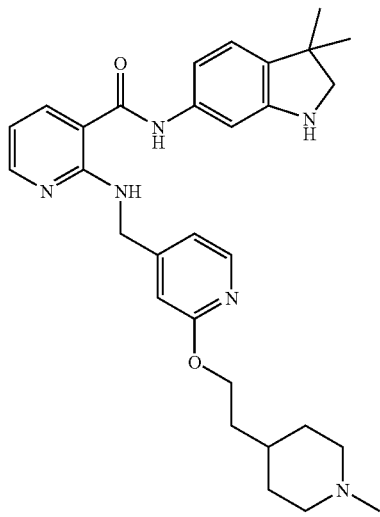

N-(3,3-Dimethyl-2,3-dihydro-1H-indol-6-yl)-2-({2-[2-(1-methyl-piperidin-4-yl)-ethoxy]-pyridin-4-ylmethyl}-amino)-nicotinamide N-(1-Acetyl-3,3-dimethyl-2,3-dihydro-1H-indol-6-yl)-2-({2-[2-(1-methyl-piperidin-4-yl)-ethoxy]-pyridin-4-ylmethyl}-amino)-nicotinamide (300 mg, Example 871) was dissolved in conc. HCl (20 ml) and EtOH (20 ml) and heated at 70° C. for 4H. The mixture was concentrated and the residue was diluted with sat'd $NaHCO_3$ and $CH_2Cl_2$. The organic layer was dried over $Na_2SO_4$ and concentrated to obtain the desired compound. M+H 515. Calc'd for $C_{30}H_{38}N_6O_2$: 514.

The following compounds (Example 995-1009) were synthesized by the method described above, unless specifically described.

995) N-(2,2-Dimethyl-3,4-dihydro-2H-benzo[1,4]oxazin-6-yl)-2-[(pyridin-4-ylmethyl)-amino]-nicotinamide. M+H 390.3; Calc'd 389.4.

996) N-(4,4-Dimethyl-1,2,3,4-tetrahydro-isoquinolin-7-yl)-2-[(pyridin-4-ylmethyl)-amino]-nicotinamide. M+H 388.3.

997) N-(3,3-Dimethyl-2,3-dihydro-1H-indol-6-yl)-2-{[2-(1-methyl-piperidin-4-ylmethoxy)-pyridin-4-ylmethyl]-amino}-nicotinamide. M+H 501.3; Calc'd 500.3.

998) N-(3,3-Dimethyl-1-piperidin-4-yl-2,3-dihydro-1H-indol-6-yl)-2-[(pyridin-4-ylmethyl)-amino]-nicotinamide was prepared with 1N HCl in ether and dioxane at RT. M+H 457.2; Calc'd 456.7.

999) N-(3,3-dimethyl-2,3-dihydro-1H-indol-6-yl)-2-({2-[2-(1-methyl-pyrrolidin-2-yl)-ethylamino]-pyrimidin-4-ylmethyl}-amino)-nicotinamide. M+H Calc'd 500.65.

1000) N-(3,3-dimethyl-2,3-dihydro-1H-indol-6-yl)-2-[(2-methoxy-pyridin-4-ylmethyl)-amino]-nicotinamide. M+H 404.3; Calc'd 403.2.

1001) N-[3,3-Dimethyl-1-(piperidin-4-ylmethyl)-2,3-dihydro-1H-indol-6-yl]-2-[(2-methoxy-pyridin-4-ylmethyl)-amino]-nicotinamide was prepared with HCl in EtOAc. M+H 501.4; Calc'd 500.3.

1002) N-(3,3-Dimethyl-1-piperidin-4-yl-2,3-dihydro-1H-indol-6-yl)-2-[(2-methoxy-pyridin-4-ylmethyl)-amino]-nicotinamide. M+H 487.4; Calc'd 486.3.

1003) 2-[(2-Methoxy-pyridin-4-ylmethyl)-amino]-N-[3-(piperidin-4-ylmethoxy)-5-trifluoromethyl-phenyl]-nicotinamide was prepared with HCl in EtOAc.

1004) N-[3,3-Dimethyl-1-(pyrrolidin-2-ylmethyl)-2,3-dihydro-1H-indol-6-yl]-2-[(2-methoxy-pyridin-4-ylmethyl)-amino]-nicotinamide was prepared with HCl in EtOAc.

1005) 2-[(2-Methoxy-pyridin-4-ylmethyl)-amino]-N-[3-(piperazin-1-ylmethyl)-5-trifluoromethyl-phenyl]-nicotinamide was prepared with HCl in EtOAc. M+H 501.3.

1006) N-(3,3-dimethyl-2,3-dihydro-1H-indol-6-yl)-2-{[2-(2-morpholin-4-yl-ethoxy)-pyridin-4-ylmethyl]-amino}-nicotinamide. M+H 503; Calc'd 502.

1007) N-(3,3-dimethyl-2,3-dihydro-1H-indol-6-yl)-2-{[2-(1-methyl-piperidin-4-yloxy)-pyridin-4-ylmethyl]-amino}-nicotinamide. M+H 529.

1008) N-(3,3-dimethyl-2,3-dihydro-1H-indol-6-yl)-2-{[2-(2-morpholin-4-yl-propylamino)-pyridin-4-ylmethyl]-amino}-nicotinamide. M+H 516; Calc'd 515.

1009) N-(3,3-dimethyl-2,3-dihydro-1H-indol-6-yl)-2-({2-[2-(1-methyl-pyrrolidin-2-yl)-ethylamino]-pyrimidin-4-ylmethyl}-amino)-nicotinamide. M+H 501.4; Calc'd 500.

EXAMPLE 1010

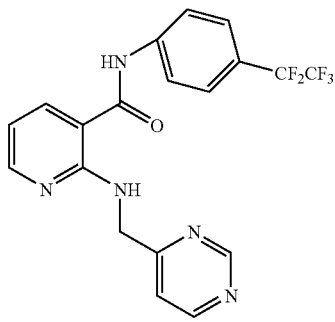

N-(4-Pentafluoroethyl-phenyl)-2-[(pyrimidin-4-ylmethyl)-amino]-nicotinamide

2-Amino-N-(4-pentafluoroethyl-phenyl)-nicotinamide (180 mg), TSOH (40 mg) and a solution of pyrimidine-4-carboxaldehyde in DMSO (10 ml) were stirred at 60 C for 6 h. Treated with NaBH$_4$ (200 mg) and stirred for 2 h at RT. MS (ES+): 566.3 (M+H)$^+$; Calc'd for $C_{26}H_{28}F_5N_7O_2$–565.

EXAMPLE 1011

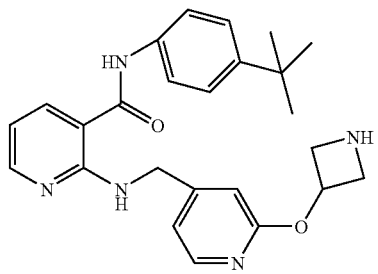

2-{[2-(Azetidin-3-yloxy)-pyridin-4-ylmethyl]-amino}-N-(4-tert-butyl-phenyl)nicotinamide 2-{[2-(1-Benzhydryl-azetidin-3-yloxy)-pyridin-4-ylmethyl]-amino}-N-(4-tert-butyl-phenyl)-nicotinamide (210 mg) was heated at reflux with Et$_3$SiH (5 ml) and TFA (15 ml) for 9 h. The mixture was concentrated, then diluted with CH$_2$Cl$_2$ (50 ml) and washed with sat'd NaHCO$_3$ (50 ml) and brine (30 ml), dried over MgSO$_4$ and purified by silica gel chromatography (10% MeOH/2M NH$_3$ 90% EtOAc) to afford the product as a yellow solid. M+H Calc'd for $C_{25}H_{29}N_5O_2$: 431.2.

EXAMPLE 1012

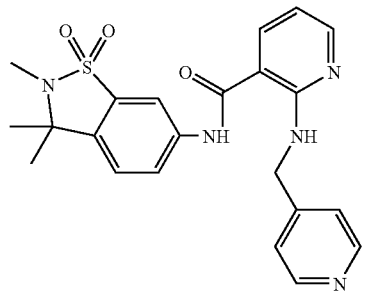

N-(2,3,3-Trimethyl-1,1-dioxo-2,3-dihydro-1H-1λ'-benzo[d]isothiazol-6-yl)-2-[(pyridin-4-ylmethyl)-amino]-benzamide N-(3,3-Dimethyl-1,1-dioxo-2,3-dihydro-1H-1λ'-benzo[d]isothiazol-6-yl)-2-[(pyridin-4-ylmethyl)-amino]-benzamide (110 mg) was dissolved in DMF and added NaH (30 mg). The mix was stirred for 15 min then MeI (18 ul) was added and stirred for 10 min. The Solvent was evaporated and purified by preparative TLC (10% MeOH/EtOAc) to give the product. M+H 438; Calc'd for $C_{22}H_{23}N_5O_3S$: 437.1.

The following compounds (Example 1013-1014) were synthesized by the method described above, unless specifically described.

1013) N-[3,3-Dimethyl-1,1-dioxo-2-(2-piperidin-1-yl-ethyl)-2,3-dihydro-1H-1λ'-benzo[d]isothiazol-6-yl]-2-[(pyridin-4-ylmethyl)-amino]-nicotinamide. M+H 535; Calc'd for $C_{28}H_{34}N_6O_3S$: 534.

1014) N-[2-(2-Dimethylamino-ethyl)-3,3-dimethyl-1,1-dioxo-2,3-dihydro-1H-1λ'-benzo[d]isothiazol-6-yl]-2-[(pyridin-4-ylmethyl)-amino]-nicotinamide. M+H 495; Calc'd 494.

EXAMPLE 1015

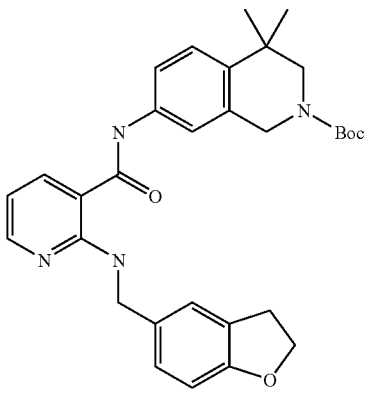

2-[(2,3-Dihydro-benzofuran-5-ylmethyl)-amino]-N-(1-Boc-4,4-dimethyl-1,2,3,4-tetrahydro-isoquinolin-7-yl)-nicotinamide M+H 529.4. Calc'd for 528.3.

EXAMPLE 1016

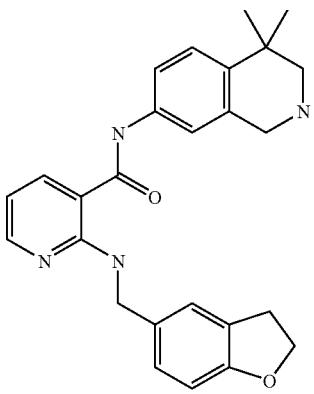

2-[(2,3-Dihydro-benzofuran-5-ylmethyl)-amino]-N-(4,4-dimethyl-1,2,3,4-tetrahydro-isoquinolin-7-yl)-nicotinamide M+H 429.2. Calc'd for 228.2.

EXAMPLE 1017

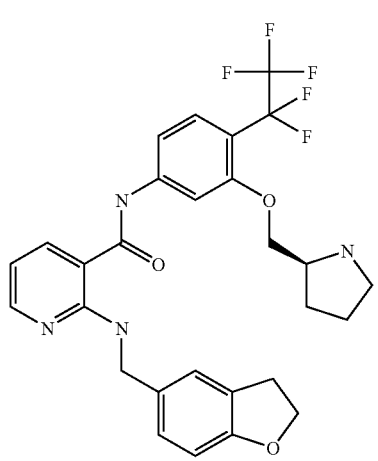

2-[(2,3-Dihydro-benzofuran-5-ylmethyl)-amino]-N-[4-pentafluoroethyl-3-(pyrrolidin-2-ylmethoxy)-phenyl]-nicotinamide M+H 663.4. Calc'd for 662.3.

EXAMPLE 1018

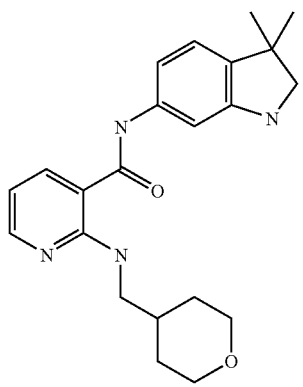

N-(3,3-Dimethyl-2,3-dihydro-1H-indol-6-yl)-2-[(tetrahydro-pyran-4-ylmethyl)-amino]-nicotinamide M+H 381.3. Calc'd for

EXAMPLE 1019

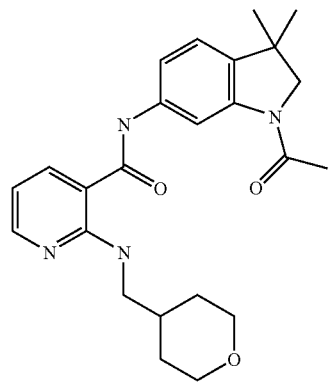

N-(1-Acetyl-3,3-dimethyl-2,3-dihydro-1H-indol-6-yl)-2-[(tetrahydro-pyran-4-ylmethyl)-amino]-nicotinamide M+H 430. Calc'd for.

EXAMPLE 1020

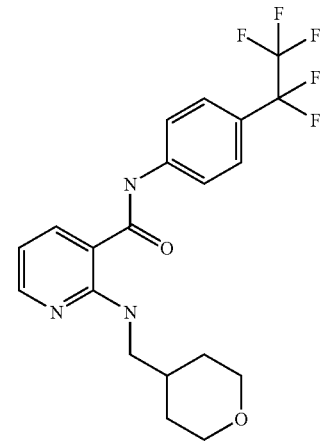

N-(4-Pentafluoroethyl-phenyl)-2-[(tetrahydro-pyran-4-ylmethyl)-amino]-nicotinamide M+H 432.2. Calc'd for Although the pharmacological properties of the compounds of Formula I-XII vary with structural change, in general, activity possessed by compounds of Formula I-XII may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention showed inhibition of KDR kinase at doses less than 50 μM.

Biological Evaluation

HUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS+ antibiotics, and spun at 1000 rpm for 10 min. Prior to centrifugation of the cells, a small amount is collected for a cell count. After centrifugation, the medium is discarded, and the cells are resuspended in the appropriate volume of DMEM+ 10% FBS+antibiotics to achieve a concentration of $3 \times 10^5$ cells/mL. Another cell count is performed to confirm the cell concentration. The cells are diluted to $3 \times 10^4$ cells/mL in DMEM+10% FBS+antibiotics, and 100 μL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 μL of each compound dilution are diluted further in a total of 1 mL DMEM+ 10% FBS+antibiotics (400× dilution). Medium containing 0.25% DMSO is also prepared for the 0 μM compound sample. At the 22-hour timepoint, the medium is removed from the cells, and 100 μL of each compound dilution is added. The cells are incubated at 37° C. for 2-3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 μL of each will be added to the cells (110 μL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50-0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. $IC_{50}$ values are then determined.

Examples 4, 7, 20-21, 25-26, 28, 33, 67, 72(f-i, n-o), 78, 82, 84, 86, 94-95, 97-100, 105, 111-112, 115-118, 130, 133, 138, 140, 151, 154-156, 158-159, 165, 167, 169, 817, 826-829, 831-838, 840-844, 845, 847-851, 853, 855-860, 862, 864, 873, 900, 904-905, 916-917, 922-924, 942-944, 946, 951-952, 954-955, 963-964, 973, 977-978, 982, 985, 991, 995, 1000 and 1008 inhibited VEGF-stimulated HUVEC proliferation at a level below 50 nm.

Angiogenesis Model

To determine the effects of the present compounds on angiogenesis in vivo, selective compounds are tested in the rat corneal neovascularization micropocket model or the angiogenesis assay of Passaniti, Lab. Invest., 67, 519-28 (1992).

Rat Corneal Neovascularization Micropocket Model

In Life Aspects: Female Sprague Dawley rats weighing approximately 250 g were randomized into one of five treatment groups. Pretreatment with the vehicle or compound was administered orally, 24 h prior to surgery and continued once a day for seven additional days. On the day of surgery, the rats were temporarily anesthetized in an Isofluorane gas chamber (delivering 2.5 liters/min oxygen+5% Isofluorane). An othoscope was then placed inside the mouth of the animal to visualize the vocal cords. A tip-blunted wire was advanced in between the vocal cords and used as a guide for the placement of an endotracheal Teflon tube (Small Parts Inc. TFE-standard Wall R-SWTT-18). A volume-controlled ventilator (Harvard Apparatus, Inc. Model 683) was connected to the endotracheal tube to deliver a mixture of oxygen and 3% Isofluorane. Upon achieving deep anesthesia, the whiskers were cut short and the eye areas and eyes gently washed with Betadine soap and rinsed with sterile saline. The corneas were irrigated with one to two drops of Proparacaine HCl ophthalmic topical anesthetic solution (0.5%) (Bausch and Lomb Pharmaceuticals, Tampa Fla.). The rat was then positioned under the dissecting microscope and the corneal surface brought into focus. A vertical incision was made on the midline of the cornea using a diamond blade knife. A pocket was created by using fine scissors to separate the connective tissue layers of the stroma, tunneling towards the limbus of the eye. The distance between the apex of the pocket and the limbus was approximately 1.5 mm. After the pocket had been made, the soaked nitrocellulose disk filter (Gelman Sciences, Ann Arbor Mich.) was inserted under the lip of the pocket. This surgical procedure was performed on both eyes. rHu-bFGF soaked disks were placed into the right eye, and the rHu-VEGF soaked disks were placed into the left eye. Vehicle soaked disks were placed in both eyes. The disk was pushed into position at the desired distance from the limbal vessels. Ophthalmic antibiotic ointment was applied to the eye to prevent drying and infection. After seven days, the rats were euthanized by $CO_2$ asphyxiation, and the eyes enucleated. The retinal hemisphere of the eye was windowed to facilitate fixation, and the eye placed into formalin overnight.

Post Mortem Aspects: After twenty-four hours in fixative, the corneal region of interest was dissected out from the eye, using fine forceps and a razorblade. The retinal hemisphere was trimmed off and the lens extracted and discarded. The corneal dome was bisected and the superfluous cornea trimmed off. The iris, conjunctiva and associated limbal glands were then carefully teased away. Final cuts were made to generate a square 3×3 mm containing the disk, the limbus, and the entire zone of neovascularization.

Gross Image Recording: The corneal specimens were digitally photographed using a Sony CatsEye DKC5000 camera (A.G. Heinz, Irvine Calif.) mounted on a Nikon SMZ-U stereo microscope (A.G. Heinz). The corneas were submerged in distilled water and photographed via trans-illumination at approximately 5.0 diameters magnification.

Image analysis: Numerical endpoints were generated using digital micrographs collected from the whole mount corneas after trimming and were used for image analysis on the Metamorph image analysis system (Universal Imaging Corporation, West Chester Pa.). Three measurements were taken: Disk placement distance from the limbus, number of vessels intersecting a 2.0 mm perpendicular line at the midpoint of the disk placement distance, and percent blood vessel area of the diffusion determined by thresholding.

General Formulations:

0.1% BSA in PBS vehicle: 0.025 g of BSA was added to 25.0 ml of sterile 1× phosphate buffered saline, gently shaken until fully dissolved, and filtered at 0.2 μm. Individual 1.0 ml samples were aliquoted into 25 single use vials, and stored at −20° C. until use. For the rHu-bFGF disks, a vial of this 0.1% BSA solution was allowed to thaw at room temperature. Once thawed, 10 μl of a 100 mM stock solution of DTT was added to the 1 ml BSA vial to yield a final concentration of 1 mM DTT in 0.1% BSA.

rHu-VEGF Dilutions:

Prior to the disk implant surgery, 23.8 μl of the 0.1% BSA vehicle above was added to a 10 μg rHu-VEGF lyophilized vial yielding a final concentration of 10 μM.

rHu-bFGF: Stock concentration of 180 ng/μl:

R&D rHu-bFGF: Added 139 μl of the appropriate vehicle above to the 25 μg vial lyophilized vial. 13.3 μl of the [180 ng/μl] stock vial and added 26.6 μl of vehicle to yield a final concentration of 3.75 μM concentration.

Nitro-cellulose disk preparation: The tip of a 20-gauge needle was cut off square and beveled with emery paper to create a punch. This tip was then used to cut out ≅0.5 mm diameter disks from a nitrocellulose filter paper sheet (Gelman Sciences). Prepared disks were then placed into Eppendorf microfuge tubes containing solutions of either 0.1% BSA in PBS vehicle, 10 μM rHu-VEGF (R&D Systems, Minneapolis, Minn.), or 3.75 μM rHu-bFGF (R&D Systems, Minneapolis, Minn.) and allowed to soak for 45-60 min before use. Each nitrocellulose filter disk absorbs approximately 0.1 μl of solution.

In the rat micropocket assay, compounds of the present invention will inhibit angiogenesis at a dose of less than 50 mg/kg/day.

Tumor Model

A431 cells (ATCC) are expanded in culture, harvested and injected subcutaneously into 5-8 week old female nude mice (CD1 nu/nu, Charles River Labs) (n=5-15). Subsequent administration of compound by oral gavage (10-200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control. Compounds of the present invention are active at doses less than 150 mpk.

Rat Adjuvant Arthritis Model

The rat adjuvant arthritis model (Pearson, Proc. Soc. Exp. Biol. 91, 95-101 (1956)) is used to test the anti-arthritic activity of compounds of the formula I, or salts thereof. Adjuvant Arthritis can be treated using two different dosing schedules: either (i) starting time of immunization with adjuvant (prophylactic dosing); or from day 15 when the arthritic response is already established (therapeutic dosing). Preferably a therapeutic dosing schedule is used.

Rat Carrageenan-induced Analgesia Test

The rat carrageenan analgesia test was performed with materials, reagents and procedures essentially as described by Hargreaves, et al., (Pain, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined.

Formulations

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg or 5 to 1000 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.1 and about 50 mg/kg, and more preferably about 0.1 and about 20 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:

1. A method of treating cancer in a subject, said method comprising administering an effective amount of a compound wherein said compound is N-(3,3-dimethylindolin-6-yl){2-[(4-pyridylmethyl) amino](3-pyridyl)}carboxamide and pharmaceutically acceptable salts thereof; wherein said cancer is selected from non-small cell lung cancer, thyroid cancer and breast cancer.

2. The method of claim 1 wherein the cancer is non-small cell lung cancer.

3. The method of claim 1 wherein the cancer is breast cancer.

4. The method of claim 1 wherein the cancer is thyroid cancer.

* * * * *